(12) United States Patent
Caldwell et al.

(10) Patent No.: US 8,597,916 B2
(45) Date of Patent: Dec. 3, 2013

(54) MULTIMERIC OXIDOREDUCTASES

(71) Applicant: Danisco US Inc., Palo Alto, CA (US)

(72) Inventors: Robert M. Caldwell, Belmont, CA (US); M. Harunur Rashid, Sunnyvale, CA (US); Fernando Valle, Burlingame, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/706,649

(22) Filed: Dec. 6, 2012

(65) Prior Publication Data

US 2013/0203135 A1   Aug. 8, 2013

Related U.S. Application Data

(63) Continuation of application No. 13/228,758, filed on Sep. 9, 2011, now Pat. No. 8,349,599, which is a continuation of application No. 12/857,480, filed on Aug. 16, 2010, now Pat. No. 8,034,593, which is a continuation of application No. 11/872,890, filed on Oct. 16, 2007, now Pat. No. 7,803,591, which is a continuation of application No. 10/899,557, filed on Jul. 27, 2004, now abandoned.

(60) Provisional application No. 60/491,151, filed on Jul. 30, 2003.

(51) Int. Cl.
| | |
|---|---|
| C12N 9/02 | (2006.01) |
| C12N 1/20 | (2006.01) |
| C12N 15/00 | (2006.01) |
| C12P 7/00 | (2006.01) |
| C07H 21/04 | (2006.01) |

(52) U.S. Cl.
USPC ............. 435/132; 435/252.3; 435/320.1; 435/440; 435/189; 435/252.33; 435/252.34; 536/23.2

(58) Field of Classification Search
None
See application file for complete search history.

(56) References Cited

U.S. PATENT DOCUMENTS

| | | |
|---|---|---|
| 3,790,444 A | 2/1974 | Sato et al. |
| 3,922,194 A | 11/1975 | Sonoyama et al. |
| 3,956,076 A | 5/1976 | Powell et al. |
| 3,998,697 A | 12/1976 | Sonoyama et al. |
| 4,245,049 A | 1/1981 | Kita et al. |
| 4,757,012 A | 7/1988 | Estell et al. |
| 4,758,514 A | 7/1988 | Light et al. |
| 5,004,690 A | 4/1991 | Light et al. |
| 5,008,193 A | 4/1991 | Anderson et al. |
| 5,032,514 A | 7/1991 | Anderson et al. |
| 5,376,544 A | 12/1994 | Lazarus et al. |
| 5,583,025 A | 12/1996 | Lazarus et al. |
| 5,795,761 A | 8/1998 | Powers et al. |

FOREIGN PATENT DOCUMENTS

WO    WO 02/073181 A    9/2002

OTHER PUBLICATIONS

Adachi et al., "Crystallization and Characterization of NADP-Dependent D-Glucose Dehydrogenase from Gluconobacter suboxydans," Agric. Biol. Chem., 44:301-308, 1980.
Altschul et al., "Basic Local Alignment Search Tool," J. Mol. Biol., 215:403-410, 1990.
Altschul et al., "Gapped BLAST and PSI-BLAST: a new generation of protein database search programs," Nucl. Acids Res., 25(17):3389-3402, 1997.
Amann et al., "Vectors Bearing a hybrid trp-lac promoter useful for regulated expression of cloned genes in Escherichia coli," Gene 25: 167-178, 1983.
Ambler, R.P., "Sequence variability in bacterial cytochromes c," Biochimica et Biophysica Acta, 1058: 42-47, 1991.
Ameyama et al., "D-Glucose Dehydrogenase of Gluconobacter suboxydans: Solubilization, Purification and Characterization," Agric. Biol. Chem., 45(4):851-861, 1981.
Amore et al, "The fermentation of xylose—an analysis of the expression of Bacillus and Actinoplanes xylose isomerase genes in yeast," Appl. Microbiol. Biotech, 30:351-357, 1989.
Anderson et al., "Production of 2-Keto-L-Gulonate, an Intermediate in L-Ascorbate Synthesis, by a Genetically Modified Erwinia herbicola," Science, 230(11): 144-149, 1985.
Arnold et al. "Optimizing industrial enzymes by directed evolution," in Scheper, T. et al. (eds.) New Enzymes for Organic Synthesis: Screening, Supply and Engineering, Berlin, Germany: Springer-Verlag, 1997, pp. 1-14.
Bittker et al., Nucleic acid evolution and minimization, 2002, Nat. Biotech. 20:1024-1029, 2002.
Branden, C. et al. "Prediction, Engineering, and Design of Protein Structures," in Introduction to Protein Structure, New York: Garland Publishing, 1991, p. 247.
Brosius et al., "Spacing of the —10 and 35 Regions in the tac Promoter," J. Biol. Chem. 260(6): 3539-3541, 1985.
Bui-Nguyen, M., J., "Application of High-performance liquid chromatograpy to the separation of ascorbic acid from isoascorbic acid," J. Chrom., 196:163-165, 1980.
Bunton et al., "The Determination of Ascorbic and Erythorbic Acids in Meat Products", J. Assoc. Pub. Analysts 17:105-110, 1979.
Crawford et al., "Synthesis of L-Ascorbic Acid", Advances in Carbohydrate Chemistry and Biochemistry 37: 79-155, 1980.
Datsenko et al., "One-step inactivation of chromosomal genes in Escherichia coli K-12 using PCR products," PNAS, 97(12): 6640-6645, 2000.
Deuschle et al., "Promoters of Escherichia coli: a hierarchy of in vivo strength indicates alternate structures," Embo J. 5(11): 2987-2994, 1986.
Devereux et al., "A comprehensive set of sequence analysis programs for the VAX," Nucl. Acid Res., 12(1):387-395, 1984.

(Continued)

Primary Examiner — Yong Pak
(74) Attorney, Agent, or Firm — Danisco US Inc.

(57) ABSTRACT

The present invention concerns multimeric oxidoreductase complexes which function in the enzymatic conversion of a carbon substrate, said complexes having a dehydrogenase subunit and a cytochrome C subunit. The invention further relates to polynucleotides coding for the multimeric complexes and methods of use thereof.

10 Claims, 60 Drawing Sheets

(56) References Cited

OTHER PUBLICATIONS

Dunham et al., Bacterial Cloning Systems in Birren et al. (eds.) Cloning Systems (Genome Analysis: A Laboratory Manual Series, vol. 3), Cold Spring Harbor, N.Y.: Cold Spring Harbor Laboratory Press, 1999, pp. 1-57.

Feng et al., "Progressive Sequence Alignment as a Prerequisite to Correct Phylogenetic Trees," J. Mol. Evol., 35:351-360, 1987.

Frey et al., "Replication and copy number control of the broad-host-range plasmid RSF1010," Gene 113:101-106, 1992.

Higgins et al., "Fast and Sensitive Multiple Sequence Alignments on a Microcomputer," CABIOS Communications, 5(2):151-153, 1989.

International Search Report published Aug. 27, 2007 in PCT/US2004/024204, filed Jul. 27, 2004, 4 pgs.

Karlin et al., "Applications and statistics for multiple high-scoring segments in molecular sequences," PNAS, 90:5873-5787, 1993.

Kulbe et al. "Enzyme-Catalyzed Production of Mannitol and Gluconic Acid," Ann. N.Y. Acad Sci 6:552-568, 1987.

Lerner et al., "Low copy number plasmids for requlated low-level expression of cloned genes in *Excherichia coli* with blue/white insert screening capability," Nucleic Acid Res., 18(15): 4631, 1990.

Mathews, F. S., "The Structure, Function and Evolution of Cytochromes," Prog. Biophys. Mol. Biol., 45:1-56, 1985.

Matsushita et al., "Membrane-Bound D-Glucate from *Pseudomonas aeruginosa*", J. Biochem. 85:1173-1181, 1979.

Matsushita et al., D-Gluconate Dehydrogenase from Bacteria, 2-Keto-D-Gluconate-Yielding, Membrane-Bound, Methods in Enzymology, 89: 187-193, 1982.

McIntire et al.,"Identification of the covalently bound flavins of D-gluconate dehydrogenases from *Pseudomonas aeruginosa* and *Pseudomonas fluorescens* and of 2-keto-D-gluconate dehydrogenase from Gluconbacter melanogenus," Biochem. J., 231:651-654, 1985.

Miller at al., "A Novel Suicide Vector and Its Use in Construction of Insertion Mutations: Osmoregulation of Outer Membrane Proteins and Virulence Determinants in *Vibrio cholerae* Requires toxR," J. Bacterial. 170, 2575-2583, 1988.

Mulligan et al., Characterization in Vitro of the Effect of Spacer Length on the Activity of *Escherichia coli* RNA Polymerase at the TAC Promoter, J. Biol. Chem., 260(6): 3529-3538, 1985.

Needleman et al., "A General Method Applicable to the Search for Similarities in the Amino Acid Sequence of Two Proteins," J. Mol. Biol., 48: 443-453, 1970.

Neijssel et al, "Physiological Significance and Bioenergetic Aspests of Glucose Dehydrogenase," Antonie Van Leauvenhoek 56(1):51-61, 1989.

Nordling et al., Medium-chain dehydrogenases/reductases (MDR) Family characterizations including genome comparisons and active site modeling, Eur. J. Biochem., 269:4267-4276, 2002.

Pachla et al., "Determination of Ascorbic Acid in Foodstuffs, Pharmaceuticals, and Body Fluids by Liquid Chromatography with Electrochemical Detection," Anal. Chem., 48(2): 364, 1976.

Palmeros et al., "A family of removable cassettes designed to obtain antibiotic-resistance-free genomic modifications of *Escherichia coli* and other bacteria," Gene, 247: 255-264, 2000.

Pearson et al., "Improved tools for biological sequence comparison," Proc. Natl. Acad. Sci., 85:2444-2448, 1988.

Potter, H., "Electroporation in Biology: Methods, Applications, and Instrumentation," Anal. Biochem., 174:361-373, 1988.

Pujol et al., "Genetic and Biochemical Characterization of the Pathway in *Pantoea citrea* Leading to Pink Disease of Pineapple", J. Bacteriol. 182(8),:2230-2237, 2000.

Reichstein and Grussner, Eine ergiebige Synthese der I-Ascorbinsaure (C-Vitamin)2) Helv. Chem. Acta., 17: 311-328 1934.

Russell et al., "Construction and analysis of in vivo activity of *E. coli* promoter hybrids and promoter mutants that alter the −35 to −10 spacing," Gene, 20: 231-243, 1982.

Saito et al., Cloning of Genes Coding for L-Sorbose and L-Sorbosone Dehydrogenases from Gluconobacter oxydans and Microbial Production of 2-Keto-L-Gulonate, a Precursor of L-Ascorbic Acid, in a Recombinant G. oxydans Strain, Appl. Environ. Microbiol., 63(2):454-460, 1997.

Shao et al., "Random-priming in vitro recombination: an effective tool for directed evolution," Nucleic Acids Res. 26(2): 681-683, 1998.

Shinagawa et al., "2-Keto-D-gluconate Dehydrogenase from Gluconobacter melanogenus, Membrane-Bound," Methods in Enzymology, 89: 194-198, 1982.

Shinagawa et al., "Distribution and Solubilization of Particulate Gluconate Dehydrogenase and particulate 2-Ketogluconate Dehydrogenase in Acetic Acid Bacteria," Agric. Biol. Chem., 40:475-483, 1976.

Shinagawa et al., "Distribution of Gluconate Dehydrogenase and Ketogluconate Reductases in Aerobic Bacteria,", Agric. Biol. Chem., 42(5):1055-1057, 1978.

Shinagawa et al., "Purification and Characterization of 2-Keto-D-gluconate Dehydorgenase from Gluconbacter melanogenus,"Agric. Biol. Chem., 45:1079-1085, 1981.

Smith et al., "Comparison of Biosequences, " Advances in Applied Mathematics, 2: 482-489, 1981.

Smith et al., "Purification and characterization of glucose dehydrogenase from the thermoacidophilic archaebacterium *Thermoplasma acidophilum*," Biochem. J., 261:973-977, 1989.

Sommer et al., "T4 early promoter strength probed in vivo with unribosylated and ADP-ribosylated *Escherichia coli* RNA polymerase: a mutation analysis," Microbiol., 146:2643-2653, 2000.

Stemmer W.P.C., "Rapid evolution of a protein in vitro by DNA shuffling," (1994) Nature 370:389-391.

Stemmer W.P.C., "DNA shuffling by randon fragmentation and reassembly: in vitro recombination for molecular evolution," PNAS 91:10747-10751, 1994.

Stroshane et al., "Fermentation of Glucose by Acetobacter melanogeuns," Biotechnol. BioEng., 9: 459-465, 1977.

Sugisawa et al. "Microbial Production of 2-Keto-L-Gulonic Acid from L-Sorbose and D-Sorbitol by Gluconobacter melanogenus," Agric. Biol. Chem., 54(5):1201-1209, 1990.

Thompson et al., Clustal W: improving the sensitivity of progressive multiple sequence alignment through sequence weighting, position-specific gap penalties and weight matrix choice, Nucleic Acid Research 22(22): 4673-4680, 1994.

Truesdell et al., "Pathways for Metabolism of Ketoaldonic Acids in an *Erwinia* sp.," J. Bacteriol. 173(21):6651-6656, 1991.

Wang et al., "Two-Stage PCR Protocol Allowing Introduction of Multiple Mutations, Deletions and Insertions Using QuikChange Site-Directed Mutagenesis," Biotechniques , 26(4): 680-682, 1999.

Wells et al., "Cassette mutagenesis: an efficient method for generation for multiple mutations at defined sites," Gene, 34: 315-323, 1985.

Yum et al, Cloning and Expression of a Gene Cluster Encoding Three Subunits of Membrane-Bound Gluconate Dehydrogenase from Erwinia Cypripedii ATCC 29267 in *Escherichia coli*, J. of Bacteriol. 179(21):6566-6572, 1997.

Zhao et al., "Directed evolution converts subtilisin E into afunctional equivalent of thermitase," Protein Eng., 12(1): 47-53, 1999.

FIGURE 2A

SEQ ID NO.1 - Orf 765

MAQITKKEVDVVVCGFGWAGSLMSIELAMAGLTVRALEKGPERDYEAFAYPKPADEYAYA
VRNKVMTTPADSAVTVRYTMQDTALPTRKWGAFVPGGGVGGAGMHWTGVLLRPTPTDIKL
KTYADEAYKPGVLQEDMRVRDFPFTWNEIEPWFEKFEHICGLSGNTGNLRGQIMEGGDPF
EGPRANPMPLPALENTLNNVMFGDTVKKMGYHPFTIPSAAASRVWTNPYGNTIAPCNYCG
YCSKYPCLNYSKASPQTAVLDSLKQMDNFSYEVNAEVLRVVLHDDKKTAKGVIYIDEQGN
ECFQPAKIVILSSFQFYNVRLMLLSGIGQPYNPVTEEGVVGRNYAFLSNGSATLFFKDKN
FNPFVSSGPTGMQFNDISPGNFDGPGLGIIGGAKIQSAQSTGTPISTALPPGTPSWGAGW
KEGLENWYGHSMKVGITTSCMSYRDVYLDLDPTYKDRHGQPLLRMTFNWKHNELQLQQYL
KGIVGNIVKEMNPDSFSMSFLPMGADFDLTKYVSTHNVGGAIMGDDPKTSALNRYLQSWD
VHNVFVPGGNAFPQNFQSNPTNTIGAITLMAANAIKEQYLKNPGPMVQV

SEQ ID NO.2 - Orf 2909

MKITNEPVDVVIVGLGWTGAIQGIELARTGLKIRALERGADRTSAEFAYPVPADELAYTK
RHKIMQSPAVAAFTTRHNLNEVALPMRELGSFRLGDGVGGADLHWTAMITRPTPVDLKLA
TYAREKFEKSQLDKELRIYDFPVSWSEIEPHMDFFDQVCGSSGQAGNVRGQILPGGDPFE
GPRSSPFPNPPLIDTLNSSMFRQAATEMGYHPYSIPSAAVSQAFTNPYGQQIAPCNYCGY
CQFYSCLNYSKASPQTAILDRLKQYDNFDYKTHANVIRVEKHADGKTATGVTYIDENDNE
VFQPAKIVILASFGLNNVRLLLNSKIGQPYNPVTEEGVVGRNYTHQYGGGITLYFNQLEF
NPFATAGPTGVVITDFGTGNINTADLGFIGGAKIYSSQPTGTPMGAPVIDSAAKWGSRWK
KGLKQSYGHSMAIKLEGSNMATQTNYLDLDPNYKDKFGMPLLRVTYDYVQNDLRMLQFMR
EKMVGIAEHLKPDHYSVGMLKMDSHFASSPAYANTHNAGGAIMGDNPKTSVVNRYLQSWD
VHNVFVMGACVFPQNVYANPTALVAGLTYWSAKAIRETYLNNPGPLVQA

SEQ ID NO.3 - Orf 3688

MATTKKPAADIVIVGFGWTGSLMARELADSGLKIVALERGEQRDTYPDFAYPRITDELTY
GIRLKLFQNAARETVTVRHTSSQTALPYRRFGSFLPGNGVGGAGVHWNGMLWRPLAADLK
MHSTLVEKYGANFIPQDMTVQDYPFTYEEMEPFFDKFEKICGASGQAGNLNGEIQSGGNP
FEQPRQNPYPTKPLQRLYAGDVFAKAAEKMGYHPFPCPAANCTEAWTNPYKVQLGVCNYC
GFCERFGCFNYSKGSPQSCVIPSLKAYDNFELRTNAQVIRVNTDNTGKQATGVTYIDGSG
NEVEQPASLVILSAFQLHNVRLLLLSKIGKPYDPQTGEGVVGRNYAYQMTGGSKLFFGPD
QDFKPFAATGTTATFIDNFNAENFDHSSLGFVGGSTISAAFSGGRPIQQTLLPSDAPRWG
SGWKTAIKTHYAHTMSIGASGSVMPYRQCYLDLDPTYHDVNGQPLLRMTFDWQPNELKMT
EFIGGKVEEIIKVINPPHYEMGFMNMNSHYDVRPYQSTHTTGGAVMGDSPRTSVVNKYLQ
SWDVPNLFVLGACCFPQNLAYNPTGIVCATALFSAHAIKTRYLAAPGPLVTI

SEQ ID NO.4 - Orf 2036

MTIKKDPVDVVIVGFGWTGSVMAMELAETGLKIVALERGEQRDTYPDFAYPRIVDELTYG
VRLKLFQNLSNETVTVRHAPGDLALPYRKMGSFLPGDGVGGAGVHWNGLLWRPLETDLRL
KSTITEKYGAAFIPQDMTLQDYPFTYAEMEPFFTRFEKICGASGQAGNINGEIQQGGNPF
EAPRSGAYPTSALKSQYSGELFGKVAKEHGYSPFPGPAAICTESYQNPYGVQLGVCNYCG
FCERFGCFNYSKASPQTCVIPALRQHTNFELRTHSVIRVNKDSTGKKATGVTYIDANGQ
EVEQPAALVVLGAFQLHNVRLLLLSGIGQPYDPRTGEGVVGRNYAYQVNGGVKLFYDKDQ
YFNNFAATGCSGTYIDNFNGENFDHSSLGFIGGGTISAHATGGRPIQQTELPSGSPKWGT
GWKKAMKDNYLHSMSVGSASSVMPYKQCYLDLDPTYTDGYGLPLLRMTFDWQENDLRVTQ
FVAGKTEELVKALKPRSYDMGFKKLNTHYDVRPYQSTHTTGGAVMGDNPRTSVVNKYLQS
WDVPNVFVLGACCFPQNIAYNPTGIVGATTLFAAHAIKTQYLRNPGPLVQA

FIGURE 2B

SEQ ID NO.5 - Orf 1841
MAIVKNKTDVVIVGMGWTGAIMAKEMTDAGLSVVALERGADRDTEPDFAYPGVVDELQGS
VHRRYLQSLHQETVTVRHNTGSVAVPYRQMGSFKPGTGVGGAGSHWSGCHFRPLPEDLRL
RSNLEERYGKSFIPSDMTIDDFPVSYDELEPHLDMFEKVCGTSGKAGVIRGVVQAGGNPF
EGSRSGEYPLGPNPNYLGAEWFYKAAREKGYHPYPIPASNAAGPYINPYGCQMGPCNACG
FCSDYGCLNYSKASPNICIMPVLRQRKNFELRTHAQVLKVNLSSDGKKATGVTYLDSNGQ
ETEQPADLVLLCAFSLYNVHLMLLSQIGKPYDPVSNEGTVGRNYSYQNLNRVMMFYDQSV
QANGFIGIGGSGTTMDDLNGNQLDNAQAGFVGGGIIWARQPGNGPVRGVAVPKGTPGWGS
AWKKAVSESFRHSFYYEVQGACMSYQQNYLSLDPTWKDAFGRPLLRMTFDWQPNEVKASQ
FLVGKAVDMCQVLNPKSISSDAKKDGAHYDITKYQSTHTCGGAVMGSDPKKSALNRYLQS
WDVPNVFAIGANAFPQNNGYNPTGLVGGLAYWAATAIREQYLKNPGPLVQA

SEQ ID NO.6 - Orf 3652
MASVMKKTDAVIVGFGWAGAIMAKELTEAGLNVVALERGPQRDTYPDGAYPQSIDELTYN
IRKKLFQDLSKSTVTVRHNPSQTAVPYRQLNAFLPGTGTGGAGLHWSGVHFRVDPAELRL
RSHYEERYGKDFIPQGMTIQDFGVSYDELEPFFDQAEKVFGTSGTAWTVKGELVGKGKGG
NPFAPDRSSDFPLKAQKRTYSAQLFAEAAESVGYHPYDMPSANTSGPYTNTYGAQMGPCN
FCGYCSGYACYMYSKASPNVNILPALRQEPKFELRNDSYVLRVNLTDDKKRATGVTYVDA
SGREFEQPADLVILSAFQFHNVHLMLLSGIGKPYNPVTNEGVVGRNFAYQNISTLKALFD
KNITTNPFIGAGGAGVGVDDFNADNFDHGPHGFVGGSPLWVNQAGVKPISGLPTPTGTPA
WGSEWKAAVADTYTHHVSMDAHGAHQSYRTNYLDLDPNYKDVHGQPLLRMTFDWQENDIK
MSQFMVSKMHNIAQAMNPKMIMGGPKTAGTHFDTTVYQTTHMNGGAIMGEDPKTSAINRY
LQSWDVSNVFVPGASAFPQGLGYNPTGMVAALTYWSAKTIREVYLKNPGPLVQA

SEQ ID NO.7 - Orf 1952
MTKKLPATDVVIVGLGWAGSILAKELCDQGLNVIGLERGPWRDTAKDFNVATAPDELRYN
AREELMLRPAQNTCTMRNNPSETALPMRFWGSFHPGNGTGGAGNHWAGITFRYQPADFRL
ASHLRERYGKEVDPALTLQDWGITWEEMEPFYDSFERVAGISGKAGNIKGSIIEGGNPFE
GPRARDYPNPPNIQTIAQTFFAKTATEMGYKPFNVPSALASQGYTNQYGVTMGPCTYCGF
CTNYGCANYSKASAIVNVLPAVVSMPNFEARTNCEVMEVLKDSSGKKATGVVYIDSNGER
YEQPASIVIVAAFTFENVRLMLLSNVGVPYDPVTGKGTTGRNYCYQTANGVRLFFKDQIF
NPFIGGGAIGMGIDEFNNDNFDHSGLGFVGGGSTRVTPIGAAPIASRPVPPGTPRWGSAW
KKATVEHYLTNMSIGCEASSYPQRTNYLSLDPNYTDPHGRPLLRITFDFPDNDMRMAQYV
TNKVGEIALRMNPVQIQKQPRTAPWANNDYQSSHVVGGFVMGADPSTSAVNKFCQVWDIP
NLFVVGGSAVPNNPGYNPTGTVGALAFRTAHYIRTQYLKQPGEMMV

SEQ ID NO.8 - Orf 1749
MSKIRPKADAVIVGLGWAGSLMANELTQAGLNVVAIERGSWRDTSTDFPTSIDTDELRFV
SRRAIMQPTAVETMTFRNNPLQQALPLREFNTYQFGMNVGGAGTHWNAMTWRFLPNDFQT
YTNTVERYGKNKFLEGMQVQDWGVTYDDLEPFYDKFERFAGTSGKAGNIKGEKIDGGNVF
EGPRSRDYPLPPLKRTQLSMIFDKATREMGLHPFAVPAGNTSGAYTNTLGINMAPCTYCG
FCEFFGCGNWSKSSPNACILPAVMQRSNFSVITESEVLRVNKAADGKTATGVTFIGSDGV
EWEQPADIVIISAYQFDNVRLMLLSGIGEPYNYKTGTVVGRNYAYQTISGAGVFFENEN
LNPFIGAGALAQAVDDYNSDNFDHSNLDFIGGGVALVHSSNGRPIALSGAVPPGTPKWGS
KWKQAAQQSYQNYNSVYVMGNSYPHRDVFLDLDPEYKDRHGQPLLRVTFDWIENDKRSGH
FMADRSVEIGHAMGAKTVVRQEPTARNFSPMDNLSSHTTGGACMGDDPKTSAVNRYLQSW
DVHNVFVCGASAFANNGGYNPTGTVGALTLWAAEAIKNQYLKSPGPLVRI

SEQ ID NO.9 - Orf 2633
MNNIRPKADVVIVGLGWCGSLIAEELTRAGMNVVAIERGPWWETSTDFPPSIDTDELRWD
TRRSMLLPPAVETTTFRNNTSQQALPSRDWNLNELGYNVGGSGTHWAGMAWRFTPFDFQP
YSQTVARYGKQQIVPGLILQDWGVSYDELEPFYDRFEKIAGVSGKAGKSNGNVVPEGNPF
EGNRSSEYPLPPLESTRLTDLFEQGAKSLGLNPFMVPAGQASRAYVNPLGVRMGPCTYCG

FIGURE 2C

YCLYYGCGNFSKSSPNACVIPALMQRENFTVLTDSAVVKVNKAEDGKTATGVTFIDKNNK
QWEQPADIVILSAFQMQNVRLLLLSQIGQPYNPQTKQGVVGRAYSFQTVSGASLFFKDEY
LNQYIGAGALSQQVDDFNGDNFDHTGKGFIGGAGILVVARGARPIGNADTLPPGTPRWGK
EWKQAYTHAFQNATFIFGQGTSYSHEDYYLDLDPEYKDKYGLPLLRVTFDYNDNDRRSAK
FVEQRSVEIGKAMGAERVFGTNSASGHYSPYNFASDHTIGGAVMGTDPRTSVLNRYQQSW
DVHNVFVLGASSFPNNAGYNPTGTIGALSLWTAKAIIEQYRKNPGPLVKV

SEQ ID NO.10 - Orf 3052
MNYTRPKADAVIIGLGWAGSLMAEELTRAGLNVVAIERGPWEQTQSNFSPAIAADELRYG
VRREILKPPRVETLTFRNDSSQKALPARDWNAFQMGYSVGGAGKHWAANAWRFNPSDFEM
ATRHKERYNNMPLADGLILQDWGVSYAELEPFYDRVEKIAGISGKAGVLNGSTQEGGNPF
EGNRTSEYPTPPLIRSHWNDTFHNITTKMGYHPFPIPAGTIGAAFTNPLGINLAPCTYCG
YCGFYGCGNWSKSSPNICVVPALMDRTNFTLLTECTALYINKADDEKTVTGVTFRDSDGN
TGFQPADIVCLSAYQLDNVRLLLLSKIGKAYDHATGEGTLGRAYNYQTMSMGYLYYENEY
MNPFISTGALSTQIDDFNGDNFDHTGLGFLGGAGIQALSDQGTPLSMTDRLPAGSKMWGS
AWKKAFRHSYQNYAKIQGQGTSYSHRDSYLSLDPNYTDENGQPLLRLTFDYNQNDRLMAR
FIRDRIEDICKVSGASSWITEAFPDSHNSPFRAYDSSHTIGGAVMGLDPKTSVLNRYQQH
WDAHNLFVLGASSYPNNGGYNPTITLSALTLWTAHHIVNDYLKNPGSLVR

FIGURE 3A

SEQ ID NO.11 - Orf 3818
MSQNNVDAEVIIIGSGVMGGLLATQLSAAGKSVIIVEAGPRVTRQQIVDRFRNSPFKMSL
TNMKLQGVGSPYPDLPHVPSTYGNYLQQVGPVKYPTKYLRVVGGTTWHFGSALWRMIPND
FKLKTLYGHGRDWPFGYDELEPWYCEAEHALGVSGVDGQDESGHGGKPWPPRSKPFPMPG
LPTSYMFDRLSELLGKGGYNPVLEPNGRATRPWGNRPVCAGNNNCNPVCPIGAKYDGSMH
IDQAERLGAKLLDNSVVYKIEADDNGKITRIWYKKPDGSEHSLTANLFIVAAYGIESPKL
LLMSTSEKYPNGIANSSDQVGRNLMGHTGISMNFMMAEDVWPGQGPTELLVYLNNRDGEF
RKTFPSYKIKVRNTVPTADYASGLISKGVLGSELDEQLRKLSARSLNFAIDFETVPLPEN
RVVPSKTKTDAIGIPLPEISYSVTDYWQAGKEAGLKDFANFAKLLGGDVLKIDTNYQDRQ
HIMGTTIMGDDPKNSVVNSDCRTHDHPNLYIAGTSVMPSASCMNPTLTGAALSLRLANHIL
LKNVLV

SEQ ID NO.12 - Orf 2448
MANTTLDFDYVIVGSGVTGALIAWQLSRHGKRVCMIEAGDHIQRWKAIEHYRSLPDKSIA
NNSPYPNLEWAPNPIGGHYLEQKGPVNYATTYIRMVGGTTWHWDSATWRLLPSDFELKTR
YGVGRDWPIGYEVLEPWYQKAEEQLGVNGWDTEDQSGQGKDHYPPRSQPYPTPGHPFSWG
QQVVAGKLEAAGYSAIHEPNARLSVATAERPACAGNNTCDPICPIGAKYTADFHVQKALD
HGCTLLSNSVVYRVEAGDDGKITAVHFRRPDKSTGTVSGKVFVIAANAIETPKLLLMSVS
ERYPQGIANTSGQVGRNLMDHTGLGFNLVTEDEVWPGTGPNALLVMLNAREGKFRAERAS
YKTKFRNTAVNFAVTKSLIKQGIMGNELYRQIKYQSARQLSIAVDLETLPNPQNRIVPSK
DRTDSLGIPVPEIHYDVDDYWNKGRDAAIADVQNIAKILNAKIVATDTNKQNREHILGTM
IMGNSPTDSVVDKNCRTHDHPNLYIAGTSVFPAVGCVNPTLTGAALALRIADTLLQDPVT

SEQ ID NO.13 - Orf 3042
MKTTHSATVVIIGSGIAGSQIAQKLQKAGIDTLMLEAGSRIERWKIVENYRNSPFKTDFQ
SPYPPTRHAPHPQYSPEDNGYFIQYGPEPYKAGYLRVAGGTTWHWSAQAWRLLPNDMRLK
TLYGVGRDWPISYDDLEPYYYESEVEMGVGGPEDTGSPRSKPYPHPPLPLSDFDKAFKNV
VDKNGYHLITEPAARNTEPFDGRPACCGNSNCMPICPIEAQYTGETAVRKAERAGSLLVP
DAVVYKIEHDAKGNITSVLYKDPNGESFRVTGKIFVLAANAIETPKLMLISRSDKYPNGI
GNTTDNVGRHLMDHPGTSVYFLSKEPMWPGRGPMRLSCINNLRDGDFRSEHSAMKINLGN
YSPTLAVSNYLLSKGVSGKDLPAMVRDYASRWVAVNTFFDILPDRDNRIVAVDSQKDAMG
IPKPGVHYHINDYINKARDVAHQHFDHIAGLFGGTEVRHDDKYFNNNHIMGTLIMGNDPN
DSVVDADLRTHDHQNLFVASSGVMASAGTVNCTLTLSALAMRLADKLIAECQHL

SEQ ID NO.14 - Orf 1983
MATEFDADVIVVGSGACGSNLANELAVKGKSVILLEAGANVPRWKILENFRNSGRHYDRN
NAYPNNPWSPTSNTPGYIENVGEFREQPGMLKLVGGTTWHWGGATWRYIPNDFKLKTMYG
VGRDWPISYSDLEPFYTRAEYAIGVAGSDTEDQSGQNPGISFPPRSKAYPVDPEADIYSN
AKLKAALLPHGHSVVHEPTVRIHRPYDGRPGCCQGNNNCDQVCPIGTLYNGSVHADKAVRN
GAKLITDAVVHKITKGEQGKITSVSYLTPAGEEHTLTAKYFVLAAHSFETSKLMLMNDIG
NSSDMVGRNLMDHIGLSMNFLADEPMWAGRGPVQQATIMTWRDGDFRSKYSANKHSLANN
NPQIDIAQRAINEGLMGKELDARILDWSSRWMSIYSFLEPLPNPANRVQPNPAWKDSLGL
PGIKVTFDVDDYTKLGAKHMVEQYKQIAGLMNGQIIDLNTAFENHDHLMGTMIMGDNPKD
SVVNHECRSHDHPNLFIASVGVIPAAGVVNPTLTGVALAIRSADIIAKEV

SEQ ID NO.15 - Orf 3399
MSDSLSADVVVIGAGIAGSLAALKMAKAGASVLILESGPEIKRDEAVNYFRNSPFKGDFT
EPYPPEPWAPQPKFIPTDNNYLIQKGPDPYRAQYLRGIGGTTWHWAGQAFRLLPNDMKIN
TLYGVGRDWPISYEDLEPYYSDAEYQMGVSGDDDLNSPRSRPYPLPGIPLPYGFERLKQR
LSPLGYQVGIGPQARNSIPYQGRPACCGNNNCMPVCPIDAQYHGGISARKAVDAGVKIIA
NAVVYRIEADDHGVIQAVHYLDQNKATHRVTGKQFVLTANGVESPKILLLSTSDRYPNGI
ANSSGMVGRNLMDHPGTSVEFYADEPIWFGRGPMRPGSINNMRDGSWRSERSALRIDLAN

FIGURE 3B

TSPVRYLTERLVRQGYYGKALNDKLAFQAERFVQLKCLLEMLPDPENRLVLSKTEKDAWG
IPRLEVYYKFPEYVHAGYDQSMSDFRKIVQQMGGTEPLYSQRGVYDNNQHITGTMIMGSD
PKNSVVDGNCRTHDHPNLFIAGTGIMPSASTVNSTLTGTALALRMADYVLKSL

SEQ ID NO.16 - Orf 1955
MSEQYSADVVVVGGGICGGTVAKELAEAGLSVLVLDAGPRWERGEVVENWRNLPPVNKSE
SDYATPYPAEPWAVHPQLYPYNNYPEVSGPDASAFRQGMIKGVGGTTWHWAASCWRFLPA
DMQLQTTYGVGRDWVVTYDEMEDYYYRAEVLIGVNGPNDTSLKYVAPRKKPFPMEPMPYG
PADRRFTEVVATAGYENTPVPQGRNSRPYDGRPQCCGNNNCMPICPIGAMFNGIHSIIKA
EKAGAKVLPNAVVYKFDTDENNNITALYYYDPDKNSHRVTARTFVLAGNGIETPKLLLMA
ANDRNPNGIANSSGMVGRNMMDHPGILMSFQSAEPIWTGGGSVQMSSITNYRDGDFRREH
SAIQIGMNNTSQNHKAGVKALQMGLVGKKLDEEIRRRAACGMDIYVNHDILANPDNRLTL
STVHKDKLGIPYPHVTYDVGDYVRKAAVSSREHLMTIAKLFGATEIEMTPYFNPNNHIMG
GTIGGHDPKDSVVDKWMRTHDHQNLYIASGGVMAAAGTVNSTLSMVALSLRATDSIKRDL
QHG

SEQ ID NO.17 - Orf 3675
MNADVIVVGTGVVGCLIAEQLLDSGHSVVMLEAGPRVERWQIVENYRNLPPVSRLHFNAP
YPPEPWAPHLMSATPEQAAEYLQLEGPNARAYQQGYVRYAGGATWHWAGICWRLTPEDMQ
LKTLYGVGRDWAFDYATLEPYYTRAEYALGVCGPSEPELQWPPVRSKPYPMGRLPFGPGE
QRFTDAAASIGLTNLPSAQARNSGIAYGDRPACCGNNNCIPVCPIGAKYDAATSLTRIES
KGGKIQPNAVVYKIETGADNKVQAVHYFDNNKQTHRVTGSVFVIACNGIETPKLLLMSAD
SRNPHGVANSSDQVGRNMMDQPKLVVELELAEPAWTGVGPVQGSSIMETSQGSFRSEYCG
ALFRFNNMARSRIGAMAALEKGLVGKALDTEIRRLSACTTEIAIEHELMPDANNRLTLSA
KKDWLGLPKPNIYYDVGDYVRQGSQRHSLPIARQLAKAMGATKVDISTEYTNSDHIMGGC
IMGTDPAVSVVDVDCRAHDHENLFLPGGAAMTTGGCGNSTLTMSALALKAADAIHAQLGK
A

SEQ ID NO.18 - Orf 1220
MSETISTDIVVIGSGVVGSLTARKLALAGRKVLMLEAGPRIQRDQIVSNFRHSARKDDFI
APYPNSEIAPFPDYKPEDNGYLDQTGPKDYKPEYLRVVGGTSWHWAAQAWRLVPNDFRLK
SQYGVGRDWPISYEDLEPYYYEAEILWGVSGPAEMAKYSPRKHPYPMEGVKMSYLEQRVT
ARLAPKYEVLTNTTGRNSVPYDGRPQCCGNNNCMPICPIDAQYHGGIAAAAAEIAGVKLI
PQAVVYKLEHNSHGKITALHYYDWNKQSHRVEAEIFVMAANAVETPRILMLSADDKNPNG
LCNNYDQLGRNLMDHPSNSATFYVDEPLWPGRGPMSPSSIQQLRDGAFRSESAAFRIDIS
NSSRVAGVTAGAIKEGLTGADLDSAILYRASHELSIKNVLEQLPDPKNRTMLSTRKKDAL
GLPVPAFSYSFDEYIEKGMQHSLEVYADIARMLGATNVRYSTPGVYSNNQHITGTLAMGT
DEKTSVTDHVGKAWEYDNLYMVSTGVMPTVATANSTLTACALGLRTADAILGKI

SEQ ID NO.19 - Orf 2419
MMMKKPEFTPGGDASADIVIVGSGIVGGLIADRLVSQGYSVLILEAGLRISRAQAVENWRNMPF
ANRAGSDFQGLYPQSPLAPAPLYFPPNNYVNVTGPSAGSFQQGYLRTVGGTTWHWAASCWRHHP
SDFVMKSKYGVGRDWPISYDEMEPWYCEAEYEIGVAGPSDPSMQSPSERSRPYPMDMVPFAHGD
TYFASVVNPHGYNLVPIPQGRSTRPWEGRPVCCGNNNCQPICPIGAMYNGIHHIERAESKGAVV
LAESVVYKIDTDDNNRVTAVHWLDNQGASHKATGKAFALACNGIETPRLLLQAANKANPTGIAN
SSDMVGRNMMDHSGFHCSFLTEEPVWLGRGPAQSSCMVGPRDGAFRSEYSANKMILNNISRVVP
ATKQALAKGLVGKALDEEIRYRSIHGVDLSISLEPLPDPENRLTLSKTRKDPHGLACPDIHYDV
GDYVRKGATAAHEQLQHIGSLFNGKEFNITTALNANNHIMGGTIMGKSAKDAVVDGNCRTFDHE
NLWLPGGGAIPSASVVNSTLSMAALGLKAAHDISLRMKEFA

FIGURE 4A

SEQ ID NO.20 - Orf 766
MKKMTFKRLLLANTVVLACGLAGAVQAADAPNQDQLVKQGEYLARLGDCMACHTTSGRPD
YSGGLAIKSDLGTIYSTNITPDKQYGIGNYTEQQFADAVRKGVRPDGSFLYPAMPYPDYA
KTSDADIHALYSYFMHGVTASNSQPPQTDLSFPFSQRWGMRFWNMVFTSDKPFQPIGGAS
EQVNRGAYIVESLGHCSSCHTPRGVAMEEKALDSSDSNFLSGGNLNGWDVPSLRGIARWS
PDEIVDYLQSGRNDKAGVAGEMTSVVKNSTSHMTDADLQAIAAYLKFLGGNPPLQAYDQQ
KNQATTAKLTAAVDLTEGQTLYLNNCGACHFVNGLDAARAFPQLDQASVVNAKDPQGLIH
IILQGAQLPATEKSPSMLKMPGFGHRLSDDQVAKLATFVRQGWSNDASAVTADQVKKVRE
GLEQH

SEQ ID NO.21 - Orf 2908
MKTIFVKLLPLAIMSVIGVIGLKQAYADSNDSADLIKQGAYLARAGDCTACHTEAGGKPF
AGGLAIRSPMGVIYSTNITPDKNAGIGSYTEQQFAEAVRKGVRRDGSNLYPAMPYPDYSG
ITDKDIHALYVYFMHGVAPVSVKAPQTSLTFPFSLRWGMKFWNIAFASGNSYPPAPTTQS
DSADAQALSRGRYLVDTLGHCSSCHTPRGIGMQEKALNDSDSRFLSSGMLNDWTVPSLRN
PDGWSVNDIAEYLSTGRNDFASVGGEMTGVVQHSMQHMNQADLHAIALYLKSLPASTKQQ
HNVKPDLQNDTQKTVDTLTLGKNLNSGQMLYLNNCEACHLTDGGGAKKIFPRLNGASIVL
ADNPTGLISVMLKGAQTPSTANAPSVQFMPGFEQRLNDQQIAELASFVRSGWGNNAPPVS
AADVAKVRASLNTSQK

SEQ ID NO.22 - Orf 2035
MKKITLLYSAVLAGLLGCTVAQADDSGGQLVARGEYLATAGDCVACHTASGPAFTGGLKM
TTPVGAIYSTNITPDKQTGIGDYTYDDFARALRQGIARDGRHLYPAMPYTEYAKVNDDDM
HALYAYFMHGVTAVHQPNKPSDIPWPLNMRWPLAVWNKLFLDNTPFKNDPAQSAEWNRGA
YLVQGLEHCGACHTPRGIAFQEKASDEKGADFLTGGTLEGWHAPDLTGNVKSGLGRWSTG
DLQTFLKTGRNDQSAAFGSMSEAIGHSTQHLTDADLHAMAVYIKSLKSSDPEAQPPATTD
STTAALIRGDLSQTGAEEYMDNCAACHRLDGKGYAKTFPTLAGNPVLLSDDPSSLISIVL
TGGKMPVTQQSVTGLTMPDFGWRLSDQQVADVVSFIRSSWGNNAGKVEAKQVADIRKLMP
VPNQADNPQVKAEKPDPAKK

SEQ ID NO.23 - Orf 1840
MKAIKGIIVVILVLVIILLAYALWPTKTASLSPLPADNSPQLASLVSQGQYLATAGDCAA
CHTQPGGKPLAGGLPIRSPIGVIYTTNITPDKQTGIGNYSLDDFERAVRHGILPNGDTLY
PAMPYPSYAKISDDDVRALYAWFMHGVQPVSQQNRASDIPWPLSMRLPLAVWRKMFAPDP
ANTGFTADKYQSASLARGAYLVQGLGHCGTCHTPRAGTLQEKALDDSGQQYLAGGQVIDG
WLAVNLRGDKADGLGNWTEQDIIDTLRTGHNVSHTVVGQPMAEVVAKSTSHMSDADLAAI
AAYIKSLPAGQGSKASYTESSQTADMLARGENPTGAQLYVDNCSACHQTSGKGVQHIFP
AMADNPTILADNPVSVIHLILDGSRLPATPQSPSALAMPGFGWRLSDKQVADLSNFIRNS
WGNKATEVTEQQVKQVRADYPPKGENKDP

SEQ ID NO.24 - Orf 3651
MKKSILALVFGSLAFSAMAEDNSGQDLVKRGEYLARAGDCVACHTSEGGQPFAGGLPMAT
PIGKIYSTNITPDKTYGIGDYTDDFQKAVRHGVAKNGETLYPAMPYPSYAVVSDDDMHA
LYAYFMQGVKPVSQPNHATDIPWPLSMRWPLAIWRGMFAPAVKPATAQPGEDPVLARGRY
LVEGLGHCGACHTPRSITMQEKALNNSEGTDYLSGSSAPIDGWTAINLRGDDRDGLGRWS
TSDIAQFLRYGRNDRTAVFGGMTDVVQHSLQYLSDDDINAIARYLKSLSPRDSHQPVFKA
DDSVSQALWKGNDQRTGAAEYVDSCAACHKTDGSGYTRFFPALKGNPVVLAEDPTSLIHI
VLTGDTLPGVQGAPSAITMPAFGWRLNDQQVANVVNFIRSSWGNTSTAAVSADQVAKLRK
SADVQGKMGDASVEKLPKQP

FIGURE 4B

SEQ ID NO.25 - Orf 3053
MAKKTRRVISVVAAVVIAGALGYTAYEQYGIHKNYPQTVSLETGPALQDQIKRGEYIARL
SDCTACHTAEGGQPFAGGYALQTPFGKILSSNITSDRETGIGGWTQEQFDKAVRHGVGSH
GYLYAAMPYPAYSRLTDADLTDLWAYIRNLPAVNHKVVENQLPFPFNQRWTLAGWNMLFF
KDAAFTPNPQASEQVNRGQYLVDGPGHCASCHTAKNMLGGDSSAYLQGGALQGWYAPDLT
PDPHSGLGNWSNADIVSYLRSGSNRITASSGPMTEAVENSTQYMNDNDLNAIAAYLKSIP
ASHPQVPTALTADDQQMVSGKKVFESQCSACHVSDGAGIRNMIPALAGNPQVNSADPSSL
LNVVLNGSEGPFTHANPTAAGMPSFGWKLSDANIAEALTYIRNSWGNAAPAVTADQVSAA
RKATGAKSWLGDSIASQDSGK

SEQ ID NO.26 - Orf 2632
MKKTTIAIAVAGIVVVGALAALWMNGSTRADDVAGDQVQTSQPVSAEDSAAVKRGEYIAV
AGDCVACHTAPGSKTPFSGGYGIDTPFGTIYASNITPDNQTGIGQWTERDFYRAVRHGIG
RQGENLYPAMPYNAYVKVSDQDMHDLWMYMRTVKPVNQQPPETHLPFPYNIRLAMRGWNL
LFFKNSGFDANSSQSAEWNRGAYLVQGLEHCAACHTPKNMLGGDTSAYLQGSSLGQWHAP
EITGNTYTGIGQWSEQQVVDYLKSGSNQVAVASGPMAEAVTNSTQHLTDADLRAIAVYLK
SQPGSANQKPAALAATSPLMQQGANVYQANCSACHNSDGRGIPQLAAGLRDNPGIMAADS
SSVITTILEGGRGAVTLNNPTSGAMPSFAWKLSDQQIAAVSSYIRNSWQNAAPAVTSQQV
AAMRKQLKLTPQLPDNGEPAH

SEQ ID NO.27 - Orf 1750
MTIKKYIASVVGVAVVAGLGFTGWKCWHNAHQDHSFVAPASAGDTGSTAIARGKYLATAG
DCVACHTAPGGKPYAGGLGLNTPFGTIYATNITPDKETGIGGWTDQQFMNAVRNGKGANG
ENLYPAMPYNVYAQVSDQDLKDIKAYLDSVPAVHYTGPKTDLPFPYNIRLMMMGWNLLFL
NTAAFKADPAQSAQWNRGAYLVEGLGHCTSCHTPKNMLGADKMGVHLQGGELEGWLAPEI
TGNTRQGIGGWSDDELVHYLKTGANDKTVAAGPMAEAVHNSLQHLNDQDLTAMATYLKSL
PGSEDKSVALSGMDDVMARGQSIYQANCSACHQSDGAGVRDMVPALRGNNGLQAFEPTNV
LHVVLMIGAQGAATASNPTSAAMPEFGWKLTDQQMADVSTYVRNSWGNKAPAVTASQAAAA
RKLLSGSPALHNPAAN

SEQ ID NO.28 - Orf 1953
MMKKLMLTAGSLLLLTAGYAHADSGGDSWDLVSKGRYIAQLGDCTACHTEPGHPLFSGGV
AIETPFGKLVGANITPDPETGIGKWTFEDFQNAMRKGHSRDGQLLYGAMPFTAYTKVTTD
DNRALWSYLQTVQPVNRVVNTNQLPFPFNIRTSLHVWDMLNFTEGEYKPDPKQSAEWNRG
AYLVQGLGHCSTCHTPKNMLGGDKDSKFLQGGSLGVWFAPDITANTHSGIGQWTQQEIVE
YLKTGANKYDIASGPMAEAVEHSTQYWKDEDLNAAAVYLKSLKNDSSQPQPLAADNGQMV
NGKAIYADRCSACHVSQGQGVSHLFPQLANAPLVNAVDPASLIHVVLAGSRAGGTAAAPT
APAMPAFGWNMTDQNVADVLTYIRNSWGNAAPSVTASDVKNMRSTLEK

SEQ ID NO.29 - Orf 3687
MQKLRVFTPLAIMLAGFCGSVYADNSPASSDSTSLSRGEYLARAGDCVACHTAEGGKPFAGGLK
MTTPVGAIYSTNITPDKDTGIGNYSYDDFVKAVRQGVSKSGSTLYPAMPYASFTRISDQDMHDL
YNYFMQQVKPVSQQNKASDIPWPLSMRWPLAFWRWTFTDDKRFQPVEGKSAEWQRGAYLVEGLE
HCGACHTPRGIAFQEKALDQSDPVYLTGNTLEGWYAPDLTGTQSDGLGRWSQQDIVSFLKNGVT
AQSSAFGSMSEVVHDSTSYLTDSDLQAIAVYLKSLPAAHQTQAPASNNATAQALFKGDVSATGA
QVYLDNCSACHRSDGKGYDKTFPSLAGNSAVLNSDPSSVIHIILQGGQRAVTPDMPTGLTMPDF
GWRLSDQQVADVATFIRQGWGNNAAAVTASQVADIRKLIPKPASQAAK

FIGURE 5A

SEQ ID NO.30 - Orf 3820
MSRSVKVRPTSLALIIGLSVFSGKAVQAADTPSASTIIEQGKYLSVAADCGACHNSPTSG
AAMAGGYAIASPMGNIIASNITPSVTAGIGNYTEQQFARAVREGVNAQGDHLYPAMPYTS
YSKMTDSDIHALYQYFMHGVQPVDTPAPATKLPFPFSIRSSMALWNMLFASQQRFTPDSQ
KSAQLNRGDYLVNVLEHCDACHTPRNFLMGQKNDLALSGGQVGSWYAPNITSDKTAGIGS
WSDDQLFQYLKTGHVAGKAQAAGPMAEAIENSLQHLSDDDLHAIVAWLKQVPASGATATE
SRFTQGAPSDSEAAMRATDHPDAGWVVFSNSCANCHQANGEGSQFYPSLFHNSATGAAQP
DNLIATILFGVRRHADGQYVAMPAFGPAASFVDRLNDQQVADVANYVLKNYGNASLTVTA
DQVKTVREGGPVPAIAYLSNPAVLAIGALIVLVILGLIVTAVRRRGKK

SEQ ID NO.31 - Orf 1956
MKQQHKLNAHKAAGFRRKLLSLCLGLSALSAVPVMAAEQVPVSQPSVDNSADALLKQGHY
LAIAADCAACHTDPQTKKTFAGGYAIHSPMGVIYSTNITPSRQYGIGSYSEAQFEQAVRH
GIRGDGSHLYPAMPYTSYSGLTDQDIHALYYYFTHGVQPVEQANRPTELSFPFNIREAMW
GWNLLFLKQKPFRDDPSQSPQWNRGKYLVANLEHCGECHTPRNTLMGSETGSAQYSGAAL
GSWFAPNLTSDQQSGLGSWQRDQLITYLKTGHVAGKAQAAGPMAEAVTNSLQYLSDDDIG
AIVTYLQSLPPVSEPDQAKATGDFGSSAGNSSDSEVRGTQPMGSVLPDDITGKALYDTTC
ASCHQSSGAGTTDNFYPSLFHNTATGGNTPNNLVSAILFGVQREVNGKQVLMPAFGPGSD
VQSLNDEQVAKLSNYIFKQFGNPQLSVTADQVKTLREGGPQPFLAKYAASGSAVGGVILL
LIIVLIIVRISRKRR

SEQ ID NO.32 - Orf 2446
MKCAYLSLLISTLLYAGFSPATQAETPATAETLLAQGKYLSVAADCSACHDSPDHHVMAG
GNSINSPLGKIVASNITPSVHYGIGSYTEQQFSDAVRKGINAQGENLYPAMPYTSYSQLT
DSDIHALYYYFMHGVTAVDRAAGATQLPFPFNLRISMKLWNALYADNKPFRPSSSQTDQV
NRGNYLIYGLAHCDTCHTPRNALMAEKSDQSLSGGSLGQWYAPNITSDKSSGIGNWSDQQ
LYQYLKTGHAVGKAQAAGPMAEAIEHSLQYLSDDDLHAIVASLRLTRPVNTASADRGMQG
KAISDENSIRGTKVASGEPVSGPMSGAILYSGNCAACHTPSGAGSYSQNYPSLVHNTTVG
STDPTNLIATLLFGVHRTVDQQSITMPAFGPQGYTDRLSFAEIATLATYVRQTYGAGGEA
VSEQQVEQVYQGGPKPLIGWLADGRIQALIVVLLLLAGLIITVVRKGRKA

SEQ ID NO.33 - Orf 3674
MKKHAIKFSLSLMFAGSMLWAGSAAAATGDAAAAISRGEYLATASDCAACHTDKGGLPFA
GGLKIESPVGTIIASNITPSLTAGIGHYTEQQFADAVRKGIRADGANLYPAMPYTAYSVM
TDQDIHDLYQYFMQGVKPVDHPAAETELPFPMNIRMMMKAWNLLFLNDKPFSPDASQSAA
WNRGKYLVTGAAHCSTCHTPRGPLMEEESSQFLSGGQVGAWYAPNITSDPQSGIGRWSQA
DIVQYLRTGNLPGKAQAAGSMGEAVEHSFQHLTDDDLNAIATYIRTVKPVATPENAGSRF
MQGDSHDATGKIRGLSQQQVTDAKQQGLALFQGNCASCHEAGGQGSRDSYYPSLFHNSVT
GAENSNNLIATILNGVNRTTRDGQVFMPGFGHHPNDINNLTDEQIASLANYVLTTYGKPS
KPVTAAMVATVRQGGPGSSLVLLARFGIAAGVVVVLILLGFWVVRRKKNVRDPS

SEQ ID NO.34 - Orf 1221
MKKLLSLCIAGALAGIMLNSAAMAEDSNAQSLIAKGQYLSVAGDCAACHTTSGGKPFAGG
LAIATPIGKIFSTNITPSKTSGIGDYSLQEFEKAVRQGVRKDGANLYPAMPYTSYAKISD
EDMQALYAYFMHGVAPVDEKGPQTALPFPFNIRLSMAGWNLIFAGDKPFTPDSNQSAEWN
RGAYLVQGLAHCSTCHTPRNALMAEESGQALAGASLGTWFAPNITPDAHAGIGKWSASDL
ATYLSTGRSPNGSQAGGPMLEAIDKSFSKLSQSDINAIVTYVRSVKPQSANAAPGQVPAS
APVVSDFALMNGTASDGAKLYEAHCSTCHQASGQGSNGLPALYGNAALHRPVADNAVMAI
LDGLTPTQGQAMPSFKTAMNDQQIATLTNYLFKTFGDAGVQTTADRVKVLREGGAPSPLL
AIAKGGMIAAVIVVLLLIVGGVMVKSRRKRR

FIGURE 5B

SEQ ID NO.35 - Orf 1984
MKKYSALLTLSAAFLFSPLALAATSSNSDLVSRGEYLARAGDCTACHTAAGGAEYAGGYK
FNMPMGTIVAPNITSSVQYGIGNWSEADFAKAVRQGVRPDGSHLYPAMPYTSYATVTDED
MQALYAFFKTVPAVDKAPADKNDLKFPFNLPGLMGIWNALFASDAPFKADPALTAEQNRG
KYLAEGLAHCSTCHSPRNQMMAEDTHQLLAGNHVDGWLAPNITSDAVSGIGGWSQQELTE
YLKTGHVEGKAQAGGPMADAIEHSFSHLSDSDLASIATWLKTVPAIRTPGQTQPSWAAAP
ASKVDWTSYQTGGGKNNSPAYRDSSTTDGAVLFDSSCAACHQSSGQGSDDHYFPSLTHNS
AVGAADPSNLVMAIVDGIHRKTPEGEAVMPAFSSETQAIHSWLNNDQIAAVTNYVTEKFG
HGNAGLTGADVEKIRNGNSNVPFLIKNAGGLTIGGIVIVVIIIALLAARSRKKRR

SEQ ID No.36 - Orf 3400
MKAVIIRSAIALALMHGSLALAADDNADLIKRGEYLATASDCTACHTAPGGPAYGGGYPV
ATPFGKIWGSNISSDKQFGIGSWTDDQFVAAVRQGVGKNGEQLYPAMPYDAFTKMKRDDV
LAIKAYLMSLPAVHKAAPETSLPFPFNQRWGMRFWKMFNLTEGELKNDPQQSPQWNNGRY
LVEALAHCTTCHTPRNLTMGMDTSKPLSGGDLGDWIAFNITPGKSGIGDWSSQDIVTYLK
TGYLAGKASASGPMAEAIEHSLQYLPDSDLQDIATYLKSVKPVDDEKQSVPRDSQGQPSD
AIIRLRGADAATLQSQPGAVVFEGNCSTCHGAEGAGSGQGFHAYPSLFHHSSTGAIDPKN
VVSVILNGVNRHMQQGDIFMPSFAPQLNDQQVADVANFVMQKFGNPAAEKVDTSQVSKAR
KNASLPLPPTFADGANP

SEQ ID NO.37 - Orf 3041
MIRSSFKRSRNFLPLAGLLFCAAGYAQTGSAQPDPVATQPTPTQPAAAAGTQGTTLIQQG
EYLAKAADCEVCHTATGGQTFAGGLGFKTPFGTIFSSNITPDKTHGIGQWSEKQFSDALR
YGIRADGKNLYPAMPYTSYSKLTDADIHAMYAFFMSLKPVATDPPENKMGFPYNQRIALK
GWNLINFHYQPFKQDPDQSAEWNRGHYLATALGHCEECHTPRNLAMGLSDKSYAGAMVDG
WEAFNISSDNTSGIGRWSHADLMQYLKTGSVPGVATTGGGMADVISHSLRFLSNDDLSAL
ATYIKSVPPQKTASQNRSGYGDNVQSDITQAVRGMPIDDSAPSGAVLFNGNCASCHGTKG
QGIGENRYYPSLSNNSVVGADKANNLVQVILYGIDRTNGKGEHIVMPGFGDELTDSQIAT
LTNYLRTNFGTNPAPVDAAQVKALRENNVMVIPGYLLILGGVIGVIILVAIIMYFRRRKA
ARNHAG

SEQ ID No.38 - Orf 2420
MKRFSRVKLTLLGLLCGGLTSLAANAADIDQALLQQGEQVATASDCQACHTAPGSKTAF
SGGYAIASPMGAIYSTNITPDPATGIGKYTEQQFIEAVRHGVRADGAQLYPAMPYTSYR
MMTDSDIHALYYYFMHGVKPVDQQNTETQLSFPFNMRFSMKFWNLLYADTKTFQQDPQK
SAEWNRGNYLVNGLAHCDTCHTPRGFMMNEQTDQPLAGAPLGSWYAPNITSDKVSGIGG
WSNDEIVQYLKTGRAAGKNQAAGGMAEAVEHSLQYLPDSDLQAIATYLKQTTPIRTPGE
TQAAYSYGSSSTNVDDQVRGMAPNNARDSLTSGAALFSGSCASCHQPDGAGSKNQTYPS
LFNNTATGMIHPQNLIATILFGVQRNTKDHQVLMPGFGASTSYVDSLTDQQIADISNYV
LHNYGNPAVTVKAGDVAWVRKGGHPPALVALQPYMIPAIAVGVIIIILLLVAFRLRRSR
RKS

FIGURE 6A

SEQ ID NO.39 - Orf 3653
MSEQNKGQSRRDFLLKTITLAPAMAVGSTAIGSLALSPAVQAADTQTSGPQKARDYQPNW
FTKEEFAFITAAVAKLIPADSRGPGALEAGVPEYIDRQMDTPYATGSNWYMQGPFAPDTP
KELGYQLPLVPRQIYRLGLADADNFCKQQYGHVFAELSDDQQVTALKAFESGQAKFTQLP
ATLFFSYLLQNTREGFFSDPIHGGNQGMAGWKLIGFPGARADFMDWVERGEHYPFPPVSI
RGERA

SEQ ID NO.40 - Orf 3689
MKNTPRSKDSTGRRLFLQRSLSLIPLVAATGTPFATSQAAEKKTPAVTQDYVPQFFDPQQ
WAFINAAVDRLIPEDQNGAGAVSEGVPVYIDRQMELPYGYGHLWYMQPPFASHSDPTLGY
QSPLVPRELYRQGIALTEHYCQQTFHKSFAQLTTDQQDQVLQLLEKNTLTDNNLSGSLFF
EQLLDNTKEGYLADPVHGGNQTLASWKLIGYPGARADYTDTVAQPNVPYPLGPVSISGKR
SV

SEQ ID NO.41 - Orf 1842
MSDKPSHSRRDFLLKSLTLIPAVSVGGAITSGIAGPGNAQAAETSATAATAQTPYSPVFF
KPDEWAFVKAACARLIPADDMGSGALEAGVPEFLDRHLQTPYANGSVWYTQGPFVEAGPE
FGYQGRKTLSEIIRSGIRGVIGWTQSNKQQTFDALTHAEQEEILVALEKGKIHLEEMDAK
TFFDYFLGEVRNGFFADPSYGGNKGMVGWKLIGFPGMRADYIDFITVRDKPYPLGPVDLA
GNRG

SEQ ID NO.42 - Orf 2037
MKENSQPPAASRRKFLQTALAIIPSTALATSVVPAALAAEQTKNPTRDYVPVFFKDDEWR
FIIAATDVLIPGDEYGPGAVSEGVPVFIDRQMEMPYGYGQLWYMKPPFQEGSPLLGYQKN
LTPRDIYRRGIAALNKACQTTYQHPFASLATADKVQVMEDLESGKLVTEDVDGKLFFAQL
LENTKEGYLADPIHGGNQTMASWKMIGFPGARADYVQVMDNPGKPYLPGPVSISGKYGA

SEQ ID NO.43 - Orf 2910
MKQSGIGRRPFIIGSLIGIASLGMKCGVSSVFAAVTSPLDELNSYQPVFFKPEEWQFIMA
ACDRLIPQDEEGPGALETHVPVFIDKQMLTPYGKGEDWYMEGPFNAHASTLFGYQLPFPL
QVMYQRGIKATNSYTRLHFNQDFAALTAAQQDAVLSALEENKITFSEFSEPDLSASYFFT
RLLENTKEGYLSDPKYGGNKGMAAWVMINFPGARASFPTWIKIHNVKYPLGPVALNGDVA
QSS

SEQ ID NO.44 - Orf 1951
MSDPSSKGISRRRLLSGSAAGLTVAAVSSANATTITGIPRWMLFDHNSPITPTSPGLKFL
TQEEATEVDAIVSQLIPADELSVSGKDAGCTVFIDRQLAGSYGDASRNYMRGPFREGTPA
QGDQSPLVPRERYRLGLAGLSDYCQQKYQKLFSQLDSATRDEVLTGLEQGKINLTGISGK
MFFDQVLTNTMEGFFSDPVYGGNRNMVSWKMIGFPGARYDYRDYLTKTDQKLDLVPISIM
GSTAWNAKV

SEQ ID NO.45 - Orf 2634
MKRREFLSSMAAFGAASAIPLTNAAEISGGQPWPPGQVSLPPGLPRKGGLQFFTRHQLET
VGATAERFIPADELSISGKEAGCAIFIDRQLAGDFGQAVTVYRLGRFVKGTPEQGPQSPL
TPADQYRLGLNALDSYCQQQFHHNFTELTGDQQDQVLQGMETGKISLAENFDSKVFFELL
LQNVREGFLSDPLYGGNKDMASWKMIGFPGARYDFRDVIAKKGQKLNIIPTSLIDNNL

SEQ ID NO.46 - Orf 764
MLLQKNTTRRKFLLGSLMALPLTELVLKGLTAAQAADMAAPELTSYKPAFFTADEWQFIL
AATDRIIPAGGPGKAPGALETNVPIFIDQQLHDEHFGKEIYMEGPFNPHAPATMGYQVPL
YPQQIYQTGIRLTNQWSQQNLQKPFHQLSEADKDKVLTGLQKNTLDFAALGENTLKGSLF
FSQLLGETKHGYLADPMYGGNKGMKAWIAIGFPGARASYLEWVKQHNVKYPLGPVSLLGE
TA

FIGURE 6B

SEQ ID NO.47 - Orf 3051
MQRRKFIKTGLILAGTGTAASVFKPAGAAARDNILNGGKLWKAKETPPPTPADPTKRLYL
TEQEYAQITAIFNRLIPADELTVSASDAGCVVFIDNQLAGNYGKASWRYNVGPFENGTPS
QGNQQPYTPAQIYRIGLAEIEKDCQSKFSKSFSELTNDQQDKYLEQMEADQIKYPTLSSK
DVFSQFLSNVQEGFLADPIYGGNRNMIGWKMIGFPGARYDYRDYAPLKGTKLNIEPVSII
QLLKA

SEQ ID NO.48 - Orf 1748
MKRRRFLASLGVLLISTALKVKAKIISGGMPWVVHAVKPPQPVVAGEWQFFTPEEVAIIE
AIADRIIPQDELSIGGKEAGCALFLDRQLAGDYGKAVSIYRLGPFIQNGLPEAGPQYKDV
PAERYRLGLASVNEISQAKYNGKKFNEISEEQQDDLLGKIESGVLPLTGVDGKLFFDQLV
INMREGFFADPLYGGNKDMAGWKMLGFPGAQYDFRDVIDKRGEELNIKPVSMVTNNDQS

FIGURE 7

SEQ ID NO.49 - Orf 3819
MTANNRHPSGVSRRRLLQGMGILSVAGLCGSLFPSFRAAAAELQDSGFIPLSEFLVNRRV
NPILAQRYYDALHRHDEKFDQKLALLKQDIQPGKYQNIDDFLQKNAVGTDLRQAAGQVIS
AWYTGVVGNDEKLELIAYADAMMYVPTSGVLVVPTYGSGPISWAAVDNKPAHQGPAV

SEQ ID NO.50 - Orf 2447
MKLTDTISTDRRKLIKSLSLLTVFSVSGLRLVTCPAFAGGLPASADFHEFSTFVIGRPVDPVL
SGRYFAALQAADGHFIQQLNQAMVASVPFRSQGIDTMLASLPHDSDIFNTLKKITSAWYLGIV
GEGAGATLIAFHDALMFQPTREYVFVPGYGGGPDSWVSLKHPDLLSEDTEQEQKNG

SEQ ID NO.51 - Orf 3676
MKNEIIRDDSPAEYNLSRRKVLLGGLILLGSSYLGPSLPAWADTLNDQATIDQFMQLSQL
LVNHQLDPVTGQRLAAAMISGNMITRQQITSLLAVAQARQAKVVEDFFSDIPQGELKNAA
LSIISAWYKGVLIDAPGAEVFAYEKALMYQPTIDVMTIPTYAITGPNGWSSHAAPLADMPDF

SEQ ID NO.52 - Orf 1219
MIDMLNMISRRRILQGMGALAATTLLPSGILPAFADTPANSDFNDISRLLTGRNTLSAEF
SSALFSAFTKIDSRFPQQLARLKQWITANSVPAADLQKRLTADSSVADLAGLPALILTGW
YLGIAGSGDKAVCVTYVDALANQEVASVLNPPTYAYGAYGSWATKPF

SEQ ID NO.53 - Orf 1957
MNNHNAPETQPELSEEGLRRRKLFGQTGGLVASFAIGSAIAGSTLSNGANAATTSAGPDT
QTLNQFMKTSRLLTGHQNLDLTLGQRLYVAFSEKDPQFITQLSALNQWIADKQPADVEAL
DSQLSGQPLHALMMSVIKGWYLGVIDDSHHAKVYAYQNALMYQVPRDGMVIPTYAHNGPD
YWTADPPPVDRLLNF

SEQ ID NO.54 - Orf 3043
MNKATPVSPGERRRFIKLLAASTVAGTVSSLLPGQIAWAIDAGQPAVAGFPAFMTVSEII
CGYPTLDNALGKRIFSLISAEHGDASQSIAELQKQLNADMSSAEMQAALKTLDTPAQQLF
SEILRGWQIGIVGSGKQSQVVAYEYALMYAPISDVVVLPTFARGEPHYWAYPPVIKTGKL

SEQ ID NO.55 - Orf 1982
MKFVIDQESDTGEISASRRSFLIKITALLASFTLIPAHAVITTPADVGASVISQLQTTAQ
FLTESQQDPQLIIRAANALLKVNSNFAGDLQQLSSLIADNHIANLKDLKTSNLFEGKPQQ
TAKDILSALYLGYAGTPVMLSSEDNVVFVAYAQARTYQLTKDFTPVPSYSRWKSGYWAHLPAGV

SEQ ID NO.56 - Orf 3398
MNLTRRRLLTGSAGLIVAGVLSQTLSGRYALASPPLASAVAPSAGFNTLSVLITGQDKPD
ALLAQRLYSWLAAHTSGLDSQLETLSSLLQQHSDANGSTLLSLMKSQPENINTLYQSLVS
GWYLGVVGPLPRPDCIAFENIVSYQLLKQSVLPPSYAPGQPGFWVQPPAGRVHV

SEQ ID NO.57 - Orf 2418
MKQIFEQSHTDLPENGTGSSRRGFIKSALVLTASGLVASLPLRSFASSVVHGGDTTQDFI
SVSQAITEHKHINPQLAAHFLSAFIKRDNQFSSKITRLAQLYQTGDTAIVFKNKAVAAGL
GDFLQQILTAWYTGTIGDDYKGTLVAYKEALMYDTVSDGLVVPTYCGNGPLWWTVPVPDP
LDPELINNL

FIGURE 8

SEQ ID NO.58 - Orf 3397

MKTKTLLAAALLLTTGYAATAGAATLTNSQANHVIENAESTIKAQNSTGCAVVVDNDGMLLSFQ
RLDGATPGCIDAAIGKARTSALYHAPSVKFMQRLQSGETTVLAIPHAVPLGGGYPLTLQGEVVG
AVGVSTPKQDLDNQASETAAKSLK

FIGURE 9A

SEQ ID NO.59 - Orf 765

ATGGCTCAGATAACTAAGAAAGAAGTCGACGTCGTGGTTTGCGGATTCGGCTGGGCCGGT
TCACTGATGAGTATTGAACTGGCCATGGCAGGACTGACAGTGCGTGCACTGGAAAAAGGT
CCTGAACGTGATTATGAAGCGTTTGCCTATCCTAAACCGGCAGACGAATATGCCTATGCG
GTTCGTAACAAGGTGATGACCACCCCCGCAGATTCTGCGGTGACCGTGCGTTACACCATG
CAGGACACCGCACTGCCAACCCGTAAGTGGGGCGCCTTTGTGCCTGGCGGCGGTGTGGGT
GGTGCCGGTATGCACTGGACCGGTGTGTTACTGCGTCCGACCCCGACCGATATTAAACTC
AAAACCTATGCCGATGAGGCCTACAAACCGGGTGTATTACAGGAAGATATGCGGGTGCGT
GATTTCCCGTTTACCTGGAATGAGATTGAGCCATGGTTTGAAAAATTTGAGCATATCTGC
GGATTATCCGGTAACACCGGTAACCTGCGCGGCCAGATAATGGAAGGCGGAGATCCGTTT
GAAGGGCCCCGTGCCAATCCGATGCCATTGCCGGCACTGGAAAATACGCTCAATAACGTG
ATGTTTGGCGATACCGTGAAAAAAATGGGTTATCACCCGTTCACCATTCCGTCGGCTGCC
GCTTCCCGTGTCTGGACCAACCCTTACGGAAACACTATTGCTCCGTGTAACTATTGCGGT
TACTGCTCTAAATATCCGTGCCTCAACTACTCCAAAGCCTCACCCCAGACCGCAGTGCTG
GATTCACTGAAGCAGATGGATAACTTCTCTTATGAAGTAAACGCGGAAGTGTTGAGAGTG
GTGCTGCATGATGATAAGAAAACCGCCAAAGGGGTTATCTATATCGATGAGCAGGGTAAC
GAATGCTTTCAGCCGGCAAAAATTGTCATCCTCAGCAGCTTCCAGTTCTATAACGTGCGT
CTGATGCTGCTGTCCGGTATTGGCCAGCCTTACAACCCGGTCACCGAAGAAGGGGTAGTC
GGACGTAACTATGCGTTCCTGAGTAATGGTTCTGCGACTCTGTTTTTCAAAGATAAAAAC
TTTAACCCGTTTGTCAGCTCCGGACCGACCGGTATGCAGTTCAACGATATCTCTCCGGGC
AACTTCGACGGTCCGGGACTTGGCATTATCGGCGGAGCAAAAATTCAGAGTGCCCAGTCG
ACCGGAACCCCAATCAGCACCGCGCTGCCGCCGGGTACTCCCTCCTGGGGAGCGGGCTGG
AAAGAGGGGCTGGAAAACTGGTACGGCCATTCAATGAAGGTGGGGATCACCACTTCCTGT
ATGTCGTACCGTGACGTTTACCTGGATCTGGACCCGACCTATAAAGATCGCCACGGTCAG
CCATTATTGCGCATGACCTTTAACTGGAAGCACAACGAACTGCAGTTACAGCAGTACCTG
AAAGGCATTGTCGGCAATATCGTCAAAGAGATGAACCCTGACAGTTTCAGCATGAGTTTC
CTGCCGATGGGCGCTGACTTTGATCTGACCAAGTATGTCTCTACCCATAACGTGGGCGGG
GCTATTATGGGCGATGATCCGAAAACATCGGCCCTGAACCGTTACCTGCAAAGCTGGGAT
GTTCATAACGTATTTGTGCCGGGAGGTAATGCGTTCCGCAGAACTTCCAGTCCAACCCG
ACCAACACTATCGGTGCAATTACGCTGATGGCAGCTAATGCCATTAAAGAACAGTATCTG
AAAAATCCGGGCCCAATGGTACAGGTG

FIGURE 9B

SEQ ID NO.60 - Orf 2909

ATGAAAATTACCAATGAACCTGTTGATGTGGTCATCGTCGGTCTGGGTTGGACCGGTGCT
ATTCAGGGTATTGAGTTAGCCAGGACAGGATTAAAGATACGAGCACTTGAGCGTGGGGCC
GATCGTACCAGCGCCGAATTTGCATACCCGGTTCCGGCAGATGAACTGGCTTACACCAAG
CGCCACAAAATAATGCAAAGCCCGGCGGTTGCCGCATTCACCACACGACATAATCTGAAT
GAAGTTGCGTTGCCAATGCGAGAACTGGGTTCTTTTAGGCTTGGAGATGGTGTCGGAGGC
GCAGATTTACACTGGACAGCCATGATTACCCGGCCAACTCCGGTTGACCTGAAACTGGCA
ACCTATGCCCGAGAAAAATTTGAAAATCTCAGCTGGATAAAGAACTGAGGATTTATGAC
TTTCCGGTAAGTTGGTCTGAGATTGAACCTCATATGGACTTTTTTGATCAGGTTTGCGGA
TCATCAGGTCAGGCAGGCAATGTCCGCGGCCAAATCCTGCCAGGGGGTGACCCTTTTGAA
GGTCCTCGCTCCAGTCCATTTCCAAATCCACCACTGATCGATACACTGAATAGCAGTATG
TTTCGCCAGGCGGCCACTGAAATGGATATCATCCCTATTCAATCCCTTCCGCTGCCGTT
TCTCAGGCATTCACTAACCCCTATGGCCAGCAGATTGCTCCTTGTAACTACTGTGGTTAC
TGTCAGTTTTATTCCTGCCTTAATTACTCAAAGGCCTCACCTCAGACGGCAATTCTGGAT
CGCCTGAAGCAGTATGATAATTTTGACTACAAAACTCATGCCAACGTTATCCGTGTAGAA
AAACATGCAGATGGCAAAACTGCAACAGGGGTAACCTATATCGATGAAAACGATAATGAA
GTTTTTCAGCCAGCAAAAATCGTCATTCTGGCCAGTTTTGGGCTGAACAACGTACGTTTG
CTGCTAAATTCTAAAATTGGTCAGCCGTACAATCCAGTGACCGAAGAAGGGGTGGTTGGA
CGTAACTATACCCACCAGTATGGTGGTGGTATCACGCTTTACTTTAATCAACTTGAATTT
AATCCATTTGCAACTGCAGGACCGACCGGAGTCGTTATTACCGATTTTGGTACCGGAAAC
ATCAATACTGCAGACCTTGGTTTTATCGGTGGTGCCAAAATCTATAGTTCGCAGCCGACG
GGAACCCCGATGGGCGCGCCGGTGATTGATTCCGCCGCTAAGTGGGGAAGTCGCTGGAAG
AAAGGCCTGAAACAAAGCTACGGACATTCAATGGCCATTAAGCTGGAAGGCTCCAATATG
GCCACTCAGACCAATTATCTTGATCTGGATCCTAACTATAAAGATAAATTCGGTATGCCT
TTGCTACGCGTCACTTATGACTATGTGCAAAATGATTTACGCATGCTGCAATTTATGCGC
GAGAAAATGGTTGGTATCGCTGAACATCTAAAACCAGACCATTATTCCGTTGGAATGCTA
AAAATGGATAGCCATTTTGCCAGTTCTCCGGCTTATGCTAATACCCATAATGCAGGTGGT
GCAATCATGGGAGATAACCCGAAAACCTCAGTCGTAAATCGCTATTTGCAAAGCTGGGAT
GTGCATAACGTATTTGTCATGGGTGCCTGTGTGTTTCCACAAAATGTCTATGCTAATCCG
ACAGCATTGGTTGCAGGGCTGACTTACTGGTCAGCTAAGGCCATTCGTGAAACGTATCTA
AATAACCCCGGTCCGCTGGTTCAGGCA

FIGURE 9C

SEQ ID NO.61 - Orf 3688

ATGGCAACAACTAAAAAACCGGCAGCCGACATCGTCATTGTTGGCTTTGGCTGGACAGGT
TCTCTGATGGCCCGTGAATTAGCAGATTCCGGATTAAAGATCGTCGCGCTGGAACGAGGT
GAACAACGAGATACTTATCCGGATTTTGCTTATCCACGTATAACCGATGAACTCACCTAT
GGCATTCGTCTGAAATTATTTCAGAACGCAGCACGGGAAACCGTCACCGTCCGTCATACT
TCGTCCCAGACAGCACTGCCTTATCGGCGTTTTGGGTCCTTTCTGCCAGGTAATGGTGTG
GGTGGCGCAGGTGTCCACTGGAATGGCATGTTGTGGCGTCCACTGGCCGCCGATTTAAAA
ATGCACTCAACTCTGGTTGAGAAATATGGCGCGAATTTTATTCCGCAGGATATGACCGTC
CAGGACTATCCTTTCACTTATGAAGAGATGGAACCTTTTTTCGACAAATTCGAAAAAATA
TGTGGTGCTTCCGGACAAGCTGGCAATCTGAATGGTGAAATTCAGTCAGGCGGAAACCCG
TTTGAACAGCCCAGACAAAACCCCTACCCGACCAAACCACTGCAACGCTTGTATGCCGGT
GATGTGTTCGCCAAAGCGGCAGAAAAAATGGGTTATCACCCATTCCCTTGCCCTGCTGCT
AACTGTACCGAAGCCTGGACCAACCCTTATAAAGTGCAACTGGGAGTATGTAACTATTGT
GGTTTCTGTGAACGCTTTGGTTGTTTCAATTATTCCAAAGGCTCTCCACAAAGTTGCGTA
ATTCCGTCACTCAAGGCCTATGATAATTTCGAACTGCGAACGAACGCCCAGGTGATTCGG
GTCAATACCGATAATACGGGTAAACAAGCTACCGGAGTGACCTATATTGATGGCAGCGGT
AATGAAGTGGAACAACCTGCATCCCTGGTGATTCTTAGTGCTTTCCAGCTGCATAATGTC
CGGTTGTTATTACTCTCTAAAATCGGTAAGCCCTATGATCCGCAAACCGGCGAAGGTGTT
GTCGGGCGAAATTATGCTTACCAGATGACAGGAGGTTCAAAACTGTTTTTTGGACCTGAT
CAGGATTTTAAACCGTTCGCGGCTACAGGTACCACAGCAACCTTTATCGACAACTTTAAT
GCCGAAAACTTCGACCATTCATCGCTTGGATTTGTCGGCGGCTCAACAATTTCTGCAGCA
TTCAGTGGTGGCCGTCCTATTCAACAGACACTGCTACCCTCTGACGCTCCCCGTTGGGGA
AGTGGCTGGAAAACCGCAATAAAAACCCACTATGCACATACCATGTCTATTGGTGCTTCA
GGTTCGGTAATGCCCTACCGGCAATGTTATCTCGATCTGGACCCGACTTATCATGATGTT
AACGGACAACCATTACTGAGAATGACGTTCGACTGGCAACCTAATGAACTGAAAATGACT
GAGTTTATTGGCGGAAAAGTTGAAGAGATCATCAAGGTCATTAATCCGCCACACTATGAA
ATGGGCTTTATGAACATGAACAGTCACTATGATGTTCGCCCTTATCAGTCAACACATACT
ACCGGCGGTGCAGTCATGGGCGACTCCCCCGCACCAGCGTCGTCAACAAATACCTGCAA
AGCTGGGATGTTCCTAACCTGTTTGTCCTTGGAGCCTGCTGTTTCCCGCAAAACCTGGCC
TACAACCCGACAGGTATTGTCTGTGCTACAGCATTGTTCTCGGCACATGCGATTAAAACC
CGCTATCTGGCTGCACCTGGCCCGCTGGTTACAATA

FIGURE 9D

SEQ ID NO.62 - Orf 2036
ATGACAATTAAAAAAGATCCGGTAGATGTAGTTATTGTTGGTTTTGGCTGGACAGGCTCT
GTGATGGCAATGGAACTGGCCGAAACCGGCCTGAAAATTGTTGCACTGGAACGTGGTGAA
CAGCGGGATACCTATCCTGATTTTGCCTATCCACGAATTGTGGATGAGCTGACTTACGGT
GTCCGGTTAAAACTATTCCAGAACCTGTCTAACGAAACGGTGACGGTGCGTCATGCACCG
GGCGATCTGGCTCTGCCTTATCGGAAATGGGGTCTTTCCTGCCAGGTGACGGGGTAGGC
GGCGCAGGTGTTCACTGGAATGGCCTGCTGTGGCGCCCTCTGGAAACCGATCTGCGACTG
AAATCAACGATCACCGAAAAGTACGGAGCCGCGTTTATTCCACAGGACATGACGTTACAG
GATTATCCGTTTACCTATGCTGAAATGGAGCCGTTCTTTACCCGTTTTGAAAAAATCTGT
GGTGCTTCCGGCCAGGCCGGCAATATTAACGGTGAAATTCAGCAGGGGGGTAACCCGTTT
GAAGCCCCGCGCAGTGGTGCCTATCCGACCAGCGCCCTGAAAAGCCAGTATTCCGGAGAA
CTGTTTGGCAAAGTCGCCAAAGAGCATGGTTATAGTCCGTTCCCGGGGCCTGCGGCAATC
TGTACCGAATCGTATCAGAATCCGTACGGGGTCCAGTTAGGGGTGTGTAACTACTGCGGT
TTCTGTGAGCGTTTTGGTTGTTTCAACTACTCGAAAGCTTCTCCGCAAACCTGTGTTATC
CCTGCGTTGCGCCAGCATACTAATTTTGAATTGCGCACTCATTCTCATGTAATTCGTGTT
AACAAAGACAGCACAGGGAAAAAAGCGACCGGAGTTACCTATATTGATGCCAATGGCCAG
GAAGTGGAGCAACCGGCGGCCCTGGTGGTCCTCGGAGCGTTCCAGCTGCACAATGTTCGT
CTGCTGTTGCTGTCAGGGATAGGTCAGCCGTATGACCCTCGTACCGGCGAAGGTGTGGTC
GGCCGAAATTATGCCTACCAGGTCAATGGTGGTGTGAAATTGTTTTATGACAAAGACCAG
TATTTTAATAATTTTGCCGCGACCGGGTGCTCAGGAACCTATATCGATAACTTTAACGGT
GAGAATTTCGACCACTCCTCACTCGGGTTTATTGGTGGAGGCACTATTTCCGCACATGCC
ACCGGCGGCCGTCCTATTCAGCAGACAGAACTGCCTTCCGGCAGCCCTAAATGGGGTACC
GGCTGGAAAAAAGCGATGAAAGATAATTATCTGCACAGTATGAGTGTTGGTTCAGCTTCC
TCAGTGATGCCTTATAAGCAGTGTTATCTGGATCTGGATCCTACCTATACCGACGGCTAC
GGTTTGCCTTTGCTGAGAATGACGTTTGACTGGCAGGAGAATGATCTGCGTGTGACACAG
TTTGTTGCCGGTAAAACCGAGGAACTGGTCAAAGCGCTAAAACCTCGCAGTTATGATATG
GGATTCAAGAAGCTCAATACTCACTATGATGTCCGTCCTTATCAGTCCACGCATACCACC
GGCGGTGCGGTGATGGGGGATAACCCTCGTACCAGTGTAGTGAATAAATATCTGCAAAGC
TGGGATGTGCCAAATGTGTTTGTCCTTGGTGCCTGCTGCTTCCCGCAGAATATTGCCTAC
AACCCCACCGGCATCGTAGGGGCAACCACACTGTTTGCCGCGCATGCGATTAAAACTCAG
TATCTCCGTAACCCGGGACCACTGGTACAGGCC

SEQ ID NO.63 - Orf 1841
ATGGCTATTGTAAAAAATAAGACCGATGTAGTGATCGTGGGGATGGGTTGGACCGGTGCC
ATTATGGCGAAAGAGATGACAGATGCCGGGCTTTCGGTAGTCGCTCTCGAACGCGGAGCT

FIGURE 9E

GATCGGGATACGGAACCAGATTTTGCTTATCCTGGAGTCGTAGACGAATTACAGGGTTCG
GTGCACCGCCGCTATCTGCAAAGCCTGCACCAGGAAACGGTTACTGTGCGTCATAACACG
GGTTCTGTGGCGGTTCCTTACCGTCAGATGGGCTCATTTAAGCCTGGCACCGGAGTGGGA
GGCGCCGGCAGCCACTGGTCAGGATGCCATTTTCGTCCGCTGCCTGAAGATTTACGCCTG
CGTAGTAACCTGGAGGAACGTTACGGCAAATCTTTTATTCCGTCAGATATGACTATCGAC
GATTTTCCGGTCAGCTACGATGAACTGGAACCGCATCTCGATATGTTTGAAAAGGTTTGT
GGTACCTCAGGCAAGGCCGGAGTGATCCGTGGAGTTGTTCAGGCGGGAGGAAATCCGTTC
GAAGGCTCGCGTAGCGGAGAGTATCCACTGGGCCCTAACCCCAACTATCTGGGTGCCGAG
TGGTTTTATAAAGCCGCCAGGGAAAAGGGCTATCACCCCTATCCTATCCCGGCCTCCAAT
GCCGCCGGCCCTTACATTAACCCTTATGGCTGTCAGATGGGCCCCTGTAATGCCTGTGGT
TTTTGCAGTGATTACGGTTGTCTTAATTATTCAAAAGCGAGTCCGAACATCTGTATTATG
CCGGTTTTGCGTCAGCGTAAAAATTTTGAATTACGCACCCATGCTCAGGTTCTGAAAGTA
AATCTGAGCAGCGACGGCAAAAAAGCTACCGGAGTAACCTATCTGGACAGTAATGGTCAG
GAAACCGAACAACCGGCTGACCTGGTGCTGTTATGCGCCTTCTCACTCTATAACGTCCAT
CTGATGCTGCTGTCACAAATTGGCAAGCCTTACGACCCTGTCAGTAATGAAGGAACCGTA
GGCCGCAACTACTCCTACCAGAACCTTAACCGCGTGATGATGTTCTATGATCAAAGCGTA
CAGGCCAACGGCTTTATTGGAATCGGTGGTTCCGGAACCACAATGGATGATCTGAACGGC
AATCAGCTGGACAATGCGCAGGCCGGGTTTGTCGGCGGCGGAATCATCTGGGCAAGGCAG
CCAGGCAATGGTCCGGTGCGCGGCGTTGCTGTGCCAAAAGGTACCCCGGGTTGGGGATCG
GCCTGGAAAAAGCAGTTTCAGAAAGCTTCCGTCATTCGTTCTATTACGAAGTCCAGGGA
GCCTGCATGTCTTATCAGCAAAACTATCTGAGCCTGGACCCTACCTGGAAGATGCTTTT
GGCCGTCCTCTGTTACGGATGACTTTTGACTGGCAGCCTAACGAAGTTAAGGCTTCACAG
TTTCTGGTCGGGAAAGCGGTGGATATGTGTCAGGTACTCAATCCGAAATCTATCTCCAGC
GATGCCAAAAAGACGGCGCTCATTACGATATCACCAAATATCAGAGTACCCACACCTGT
GGCGGTGCGGTAATGGGCAGCGACCCGAAAAAATCGGCACTGAACCGTTATCTGCAATCC
TGGGATGTGCCAAACGTGTTTGCTATCGGGGCGAATGCCTTTCCACAGAATAATGGATAC
AACCCTACCGGTCTGGTGGGCGGGCTGGCCTACTGGGCTGCCACCGCTATTCGTGAACAA
TACCTGAAAAACCCGGGCCCGTTGGTCCAGGCA

SEQ ID NO.64 - 3652
ATGGCCAGTGTAATGAAAAAACAGATGCAGTGATTGTCGGTTTCGGCTGGGCCGGGGCT
ATCATGGCAAAGAGCTGACAGAAGCCGGGCTGAATGTTGTTGCGCTGGAACGTGGACCA
CAGCGTGATACTTATCCGGACGGTGCTTACCCGCAGTCTATTGATGAGCTGACTTACAAC
ATCCGTAAGAAGCTGTTCCAGGATTTATCAAAAGTACGGTCACTGTTCGCCACAATCCA
TCACAGACCGCCGTGCCTTATCGCCAGTTAAATGCGTTCCTGCCTGGAACCGGTACCGGA

FIGURE 9F

GCGCCGGGCTGCACTGGTCAGGGGTTCATTTTCGTGTTGATCCGGCTGAACTTCGCCTG
CGTAGCCACTATGAAGAGCGCTATGGTAAAGACTTTATCCCTCAGGGGATGACCATCCAG
GATTTTGGTGTCAGTTACGATGAACTGGAGCCATTCTTTGATCAGGCAGAAAAGGTCTTT
GGTACATCCGGAACCGCCTGGACAGTGAAAGGTGAGTTGGTCGGGAAAGGTAAAGGGGGC
AACCCGTTTGCACCTGATCGTTCCAGTGACTTTCCTCTGAAAGCACAGAAACGTACTTAT
TCAGCGCAATTGTTTGCAGAGGCTGCGGAGTCTGTAGGCTATCATCCGTATGATATGCCG
TCTGCTAACACTTCTGGTCCTTACACCAATACTTATGGTGCTCAGATGGGGCCGTGTAAT
TTCTGCGGATATTGCAGTGGTTATGCCTGCTATATGTACTCGAAGGCTTCGCCAAACGTC
AATATATTGCCAGCCTTACGTCAGGAACCTAAATTTGAATTGCGCAATGATTCCTATGTG
CTGCGGGTTAATCTGACCGATGATAAGAAACGCGCTACCGGAGTCACCTATGTCGATGCC
AGCGGTCGTGAGTTTGAACAGCCTGCTGACCTGGTCATTCTGTCTGCGTTCCAGTTTCAC
AATGTCCATCTGATGCTGCTTTCCGGTATCGGTAAACCCTATAACCCGGTGACTAATGAA
GGGGTTGTTGGGCGTAACTTTGCTTACCAGAACATTTCTACTCTGAAGGCTTTGTTCGAC
AAAAATATCACAACCAATCCGTTTATCGGTGCGGGTGGTGCGGGTGTCGGGGTGGATGAT
TTCAATGCCGATAACTTTGACCATGGTCCGCACGGTTTTGTCGGCGGATCGCCGTTATGG
GTAAACCAGGCCGGTGTTAAACCAATCTCCGGACTGCCGACTCCTACCGGAACTCCGGCC
TGGGGTAGCGAATGGAAAGCCGCTGTCGCAGACACTTATACCCATCATGTATCGATGGAT
GCGCACGGTGCTCACCAGTCTTACCGTACTAACTATCTCGATCTTGACCCTAACTACAAG
GATGTCCACGGACAACCCTTGCTGCGCATGACTTTTGACTGGCAAGAGAACGACATCAAA
ATGTCGCAGTTTATGGTGTCGAAAATGCACAACATCGCACAGGCCATGAACCCGAAAATG
ATCATGGGTGGGCCAAAGACCGCCGGTACGCATTTTGATACCACCGTGTATCAGACCACT
CATATGAATGGCGGCGCCATTATGGGTGAAGATCCGAAAACCAGTGCGATCAACCGCTAT
CTGCAGAGTTGGGATGTGTCGAATGTGTTTGTACCAGGGGCTTCTGCGTTCCCGCAGGGG
TTGGGTTATAACCCGACCGGGATGGTCGCTGCACTGACCTATTGGTCAGCAAAAACCATC
CGGGAAGTTTACCTGAAAAATCCGGGTCCGTTGGTACAGGCA

SEQ ID NO.65 - Orf 1952
ATGACAAAAAAACTCCCTGCCACTGATGTGGTGATTGTTGGCCTCGGCTGGGCCGGTTCA
ATTTTAGCCAAAGAACTCTGCGATCAGGGTCTGAATGTGATTGGTCTGGAACGTGGCCCG
TGGCGCGATACTGCCAAAGATTTTAACGTAGCCACCGCGCCGGATGAATTGCGTTACAAC
GCCCGCGAGGAACTGATGCTCCGGCCGGCACAGAACACCTGTACCATGCGTAATAACCCT
TCAGAAACTGCACTGCCAATGCGGTTCTGGGGCTCTTTCCACCCGGGTAACGGTACCGGT
GGCGCCGGTAACCACTGGGCGGGTATTACTTTCCGCTATCAGCCTGCCGATTTCCGGCTG
GCGAGCCATCTGCGTGAGCGCTACGGCAAGAAGTTGATCCGGCTCTGACCTTACAGGAC
TGGGGGATCACCTGGGAAGAGATGGAACCCTTTTATGACTCTTTTGAACGGGTTGCCGGA

FIGURE 9G

ATTTCAGGGAAAGCCGGTAACATCAAAGGCAGTATTATCGAAGGCGGAAACCCGTTCGAA
GGTCCGCGCGCCCGTGATTATCCAAATCCGCCAAATATTCAGACCATTGCGCAAACATTC
TTTGCCAAAACTGCCACCGAAATGGGTTACAAACCTTTTAACGTTCCTTCTGCACTGGCC
TCTCAGGGTTATACCAACCAGTATGGTGTGACGATGGGCCCTTGTACCTATTGTGGTTTC
TGTACCAACTACGGCTGCGCCAACTATTCGAAAGCCAGTGCTATCGTTAACGTTTTACCG
GCAGTAGTCAGCATGCCCAACTTTGAAGCACGCACCAACTGTGAAGTCATGGAAGTTCTG
AAAGACAGCAGCGGCAAAAAGGCTACCGGAGTGGTGTATATCGACAGTAATGGCGAACGT
TATGAACAGCCAGCGTCTATCGTGATTGTGGCCGCCTTTACTTTTGAAAACGTGCGTCTG
ATGCTGCTGTCGAATGTTGGTGTGCCTTATGACCCTGTCACCGGCAAAGGAACTACCGGC
CGTAACTACTGTTACCAGACAGCGAATGGTGTCCGTCTGTTCTTCAAAGATCAAATCTTC
AACCCGTTTATCGGCGGTGGCGCCATCGGGATGGGAATCGACGAATTCAACAACGACAAC
TTTGATCACTCCGGATTAGGGTTTGTTGGCGGTGGTTCTACCCGGGTGACACCTATCGGT
GCTGCACCTATTGCTTCGCGTCCGGTGCCGCCGGGCACTCCGCGCTGGGGATCGGCCTGG
AAGAAGCAACCGTGGAACATTATCTGACCAATATGAGTATTGGTTGCGAGGCCAGCAGC
TATCCGCAGCGCACCAACTATCTGTCGCTCGATCCAAACTATACCGACCCGCATGGCCGG
CCGTTATTACGGATAACGTTTGATTTCCCGGACAATGATATGCGGATGGCACAGTATGTC
ACCAATAAAGTTGGTGAAATTGCCTTACGTATGAATCCGGTGCAAATCCAGAAACAACCA
CGTACTGCCCCGTGGGCCAACAACGACTACCAGTCATCTCACGTGGTTGGCGGCTTTGTG
ATGGGCGCTGACCCGTCTACCAGTGCGGTCAATAAGTTTTGCCAGGTCTGGGATATTCCA
AATCTGTTCGTGGTGGGTGGTTCTGCGGTTCCAAATAACCCCGGGTATAACCCGACCGGT
ACTGTTGGCGCCCTTGCCTTCCGTACCGCTCACTATATCCGTACTCAGTACCTCAAACAG
CCCGGGGAGATGATGGTA

SEQ ID NO.66 - Orf 1749

ATGAGCAAAATCAGGCCAAAGGCCGACGCAGTGATTGTGGGCCTGGGATGGGCAGGATCG
TTAATGGCAAATGAACTGACCCAGGCCGGGTTAAATGTTGTTGCCATTGAAAGGGGGTCA
TGGCGTGACACCAGTACCGATTTCCCAACCTCAATTGATACTGACGAATTACGTTTCGTC
AGCCGCAGAGCAATAATGCAGCCCACTGCTGTAGAAACTATGACCTTCAGGAATAATCCT
CTGCAGCAGGCTCTTCCACTGCGTGAGTTTAATACCTATCAGTTTGGTATGAATGTCGGC
GGTGCCGGTACACACTGGAACGCCATGACATGGCGCTTTTTACCTAATGACTTCCAGACA
TACACCAATACTGTTGAACGTTACGGTAAAAACAAATTCTGGAAGGGATGCAGGTTCAG
GACTGGGGCGTGACCTATGATGACCTTGAACCTTTTTATGATAAATTTGAGCGCTTTGCA
GGAACTTCAGGAAAAGCCGGAAATATTAAAGGCGAAAAAATCGACGGCGGAAATGTATTT

FIGURE 9H

GAAGGACCGCGCAGCAGGGACTATCCGTTGCCACCACTGAAACGCACTCAGTTATCGATG
ATATTTGACAAAGCGACCCGCGAAATGGGGCTACACCCGTTTGCGGTACCTGCCGGAAAT
ACTTCAGGGGCTTATACCAATACTCTGGGCATTAATATGGCCCCTTGTACTTATTGTGGG
TTCTGTGAATTTTTCGGTTGTGGTAACTGGTCGAAAAGTAGTCCGAACGCCTGTATTTTG
CCAGCAGTGATGCAACGCAGTAATTTCTCAGTGATCACCGAGTCGGAAGTGTTACGGGTG
AATAAAGCGGCAGACGGCAAGACCGCCACCGGTGTCACTTTTATCGGAAGCGATGGTGTT
GAGTGGGAACAACCTGCCGATATCGTGATCATTTCTGCCTACCAGTTTGATAATGTCCGT
CTGATGTTACTGTCAGGAATTGGCGAGCCTTATAACTATAAAACCGGCACTGGTGTGGTT
GGCCGTAATTACGCTTATCAGACTATCTCTGGTGCAGGTGTATTCTTTGAAAATGAAAAT
CTGAATCCATTTATTGGTGCTGGTGCACTGGCTCAGGCAGTGGATGATTACAACAGCGAT
AACTTCGATCACTCAAACCTGGACTTTATCGGAGGCGGTGTGGCCCTGGTTCACTCCAGC
AATGGTCGCCCGATTGCATTATCCGGTGCGGTGCCTCCGGGAACACCAAAATGGGGTTCT
AAATGGAAGCAGGCTGCTCAGCAGAGTTACCAGAATTACAACTCCGTCTATGTGATGGGC
AACAGCTATCCACATCGTGATGTTTTCCTCGATCTCGACCCCGAATATAAAGACCGCCAC
GGACAACCGCTGCTCCGGGTTACCTTCGACTGGATCGAAAATGATAAGCGCTCAGGCCAC
TTTATGGCCGATCGCTCGGTAGAAATTGGCCATGCGATGGGAGCAAAAACCGTAGTACGT
CAGGAACCTACGGCCCGTAATTTCTCGCCAATGGACAATCTTTCTTCGCATACCACCGGA
GGCGCCTGCATGGGAGATGATCCTAAGACCAGTGCGGTTAACCGTTACCTCCAAAGCTGG
GATGTGCATAACGTTTTTGTCTGTGGTGCCTCTGCTTTCGCGAATAATGGCGGTTACAAC
CCAACCGGTACCGTAGGCGCGTTAACTTTATGGGCTGCTGAAGCCATCAAAAATCAGTAC
CTCAAATCTCCCGGCCCGCTGGTGAGGATC

SEQ ID NO.67 - RZP 2633
ATGAATAATATTCGTCCAAAAGCTGATGTTGTTATTGTCGGTCTGGGATGGTGCGGCTCT
TTAATTGCTGAAGAACTCACCCGGGCCGGAATGAATGTGGTGGCTATAGAACGTGGACCC
TGGTGGGAAACCAGCACCGACTTCCCGCCATCCATTGATACTGATGAGCTGCGCTGGGAC
ACCCGTCGTTCCATGTTGTTACCCCGGCGGTCGAAACGACAACTTTCCGGAATAATACT
TCACAGCAAGCCTTACCTTCCCGTGACTGGAACCTGAATGAACTTGGCTATAACGTCGGT
GGATCCGGTACTCACTGGGCGGGAATGGCGTGGCGTTTTACGCCGTTTGATTTCCAGCCC
TATTCGCAAACCGTGGCGCGTTACGGTAAGCAGCAGATTGTTCCGGGGCTGATTCTGCAG
GACTGGGGGGTGAGTTATGATGAACTGGAGCCTTTCTATGATCGGTTTGAGAAAATAGCC
GGAGTTTCCGGAAAGGCCGGTAAGTCAAATGGCAACGTGGTGCCGGAAGGTAATCCGTTT
GAGGGTAACCGGAGCAGTGAGTATCCACTGCCGCCGCTGGAAAGTACCCGGCTAACCGAT

FIGURE 9I

CTGTTTGAGCAGGGGGCAAAATCTCTCGGGCTCAATCCGTTTATGGTTCCTGCCGGTCAG
GCTTCCCGTGCCTATGTTAACCCGTTAGGGGTTCGCATGGGGCCGTGCACCTATTGTGGT
TATTGTTTGTACTATGGCTGCGGGAACTTCTCTAAATCCAGCCCGAATGCCTGTGTTATT
CCCGCACTGATGCAGCGCGAAAACTTTACTGTGCTTACTGATTCTGCCGTTGTGAAGGTT
AATAAGGCAGAGGACGGTAAGACGGCTACCGGTGTGACGTTTATTGATAAAAACAATAAG
CAGTGGGAGCAACCGGCAGACATTGTCATCCTGTCCGCATTCCAGATGCAGAATGTGCGG
TTGCTGTTGCTGTCTCAGATTGGTCAGCCTTATAACCCGCAGACAAAGCAAGGGGTGGTA
GGGCGGGCTTACAGCTTCCAGACTGTCTCAGGAGCCAGCCTGTTCTTCAAAGATGAGTAC
CTGAATCAGTACATCGGTGCCGGAGCGCTTTCACAGCAGGTTGATGACTTTAACGGTGAT
AATTTTGACCATACCGGTAAAGGGTTTATCGGCGGTGCCGGGATTCTGGTCGTTGCCCGT
GGAGCCAGGCCAATAGGTAATGCCGATACTCTGCCACCGGGAACTCCTCGCTGGGGGAAA
GAATGGAAGCAGGCATATACCCATGCCTTCCAGAATGCGACCTTTATCTTTGGTCAGGGC
ACCAGTTATTCCCATGAAGATTATTATCTGGACCTGGATCCGGAATACAAAGATAAGTAC
GGATTGCCGTTACTTCGGGTGACGTTTGACTACAACGATAATGACCGGCGTTCGGCCAAA
TTTGTCGAACAGCGCAGTGTGGAAATCGGTAAAGCGATGGGAGCTGAGCGGGTTTTTGGC
ACTAACTCCGCTTCCGGCCATTACTCACCGTACAATTTCGCCAGCGATCACACTATCGGC
GGAGCCGTCATGGGAACCGATCCCCGGACCAGTGTGTTAAATCGCTACCAGCAGAGCTGG
GATGTGCACAATGTGTTCGTGCTGGGTGCTTCTTCTTTCCCGAATAATGCCGGATATAAC
CCGACAGGCACCATCGGTGCTCTTAGCTTATGGACTGCGAAAGCGATTATTGAGCAGTAC
AGAAAGAATCCTGGCCCGCTGGTGAAGGTG

SEQ ID NO.68 - Orf 3052
ATGAATTACACCAGACCTAAAGCAGATGCCGTTATTATCGGCCTCGGCTGGGCCGGCTCT
TTGATGGCCGAAGAACTGACCCGCGCCGGATTAAATGTGGTTGCGATTGAACGCGGCCCC
TGGGAACAGACCCAGAGCAATTTCTCCCCCGCCATTGCTGCCGATGAACTACGTTATGGC
GTACGCCGCGAAATACTGAAACCGCCCCGTGTAGAAACCCTGACTTTTCGTAACGACAGC
AGCCAGAAAGCACTGCCAGCCCGCGACTGGAATGCCTTTCAGATGGGCTACAGTGTAGGT
GGTGCCGGTAAACACTGGGCAGCCAATGCCTGGCGTTTTAACCCTTCTGATTTCGAGATG
GCGACCCGTCACAAAGAGCGCTATAACAATATGCCGCTGGCCGACGGCCTGATCCTTCAG
GACTGGGGGGTTAGCTATGCAGAGCTGGAACCTTTCTATGATCGTGTGGAAAAAATTGCC
GGTATTTCCGGTAAAGCAGGTGTGCTTAACGGCTCCACTCAGGAAGGCGGAAATCCGTTT
GAAGGCAACCGTACCAGTGAGTACCCGACACCGCCATTAATCCGTTCGCACTGGAACGAT
ACCTTCCATAATATCACCACTAAAATGGGCTACCACCCGTTCCCTATTCCGGCAGGAACC

FIGURE 9J

ATCGGTGCAGCGTTTACCAACCCGTTAGGCATTAACCTGGCCCCTTGTACCTATTGCGGC
TATTGCGGTTTTTACGGATGTGGTAACTGGTCTAAATCTTCACCGAATATCTGTGTGGTT
CCGGCACTGATGGATCGCACCAACTTTACCCTGCTGACCGAATGTACCGCGCTGTACATT
AATAAAGCTGACGATGAAAAAACCGTCACCGGTGTGACCTTCCGTGATTCTGATGGTAAC
ACCGGCTTCCAGCCGGCAGACATCGTTTGCCTGTCGGCGTATCAGTTAGACAACGTGCGC
CTGCTGTTACTGTCGAAAATCGGTAAAGCCTACGACCACGCCACAGGCGAAGGTACACTC
GGTCGCGCCTATAACTACCAGACCATGTCGATGGGATATCTGTATTACGAAAATGAATAC
ATGAACCCGTTCATCTCTACCGGCGCGTTATCCACCCAGATTGATGATTTCAATGGCGAT
AACTTCGACCACACCGGGCTTGGATTCCTGGGAGGTGCCGGAATTCAGGCGCTGTCAGAT
CAGGGGACTCCGTTAAGTATGACTGACCGCCTGCCTGCCGGCAGCAAAATGTGGGGCTCG
GCGTGGAAAAAAGCGTTCCGCCACAGTTATCAGAACTATGCCAAAATTCAGGGCCAGGGA
ACCTCGTATTCACACCGTGATTCCTATCTGTCACTGGACCCGAATTACACTGACGAGAAC
GGACAGCCTCTGCTGCGTCTGACCTTCGACTACAACCAGAATGATCGTCTGATGGCGCGT
TTTATTCGTGACCGGATTGAAGATATCTGTAAAGTCTCCGGCGCCAGCAGCTGGATAACC
GAAGCGTTCCCTGACTCCCACAACTCACCGTTCCGTGCCTATGACAGTTCTCATACCATT
GGCGGTGCCGTGATGGGGCTTGATCCGAAAACCTCGGTACTGAATCGCTACCAGCAACAC
TGGGATGCACACAATCTGTTTGTGCTCGGGGCCTCATCTTACCCGAATAATGGCGGTTAT
AACCCGACCATCACTCTCAGTGCCCTGACGTTATGGACTGCGCACCATATCGTTAATGAC
TACCTGAAAAATCCGGGTTCGCTGGTACGA

FIGURE 10A

SEQ ID NO.69 - Orf 3818

ATGAGTCAGAATAACGTAGATGCAGAAGTAATTATTATTGGTTCCGGAGTGATGGGCGGG
CTACTGGCGACTCAGCTGTCTGCTGCCGGAAAATCAGTGATTATTGTTGAGGCGGGCCCA
CGTGTTACACGCCAGCAAATCGTTGACCGTTTCAGAAACTCACCGTTCAAGATGTCACTC
ACTAATATGAAATTGCAGGGTGTCGGCTCGCCGTATCCTGATTTACCTCATGTACCTTCC
ACTTACGGCAACTACCTGCAACAGGTCGGGCCGGTAAAATACCCGACTAAATACCTGCGT
GTCGTTGGCGGAACCACATGGCACTTTGGTTCCGCTTTGTGGCGGATGATTCCAAACGAT
TTTAAATTGAAGACGTTGTACGGACATGGCAGAGACTGGCCGTTTGGTTACGACGAACTG
GAACCCTGGTATTGCGAAGCAGAGCATGCACTGGGAGTGTCAGGAGTCCATGGACAGGAC
GAGAGCGGGCACGGTGGTAAACCCTGGCCTCCACGCTCTAAACCTTTCCCGATGCCGGGC
TTACCTACCAGTTATATGTTTGACCGGCTGAGCGAGTTGCTTGGTAAAGGCGGTTATAAC
CCGGTGCTGGAACCAAATGGCAGGGCGACCCGCCCTGGGGCAATCGTCCGGTATGTGCA
GGCAATAATAACTGCAACCCGGTGTGCCCGATTGGTGCCAAATATGATGGTTCAATGCAT
ATCGATCAGGCAGAACGGCTGGGTGCTAAGCTGCTGGACAATTCGGTGGTGTATAAAATA
GAAGCGGATGACAACGGTAAAATCACCCGTATCTGGTATAAAAAGCCTGATGGTTCTGAG
CATTCCCTGACAGCAAATCTGTTTATTGTGGCTGCCTATGGGATTGAATCACCGAAATTA
TTGCTGATGTCTACCTCAGAAAAATATCCGAATGGTATTGCCAACTCTTCTGATCAGGTC
GGCCGTAATCTGATGGGTCACACCGGCATTAGTATGAACTTTATGATGGCCGAGGATGTC
TGGCCGGGGCAGGGACCAACAGAATTACTGGTCTATCTAAACAACCGTGATGGTGAGTTC
AGAAAAACGTTCCCGAGCTATAAAATCAAAGTGCGTAATACCGTGCCAACCGCTGATTAT
GCTTCCGGGCTGATTAGTAAAGGGGTATTAGGTTCAGAACTGGATGAGCAACTGCGTAAG
CTGTCAGCCCGTTCGCTGAACTTCGCCATTGATTTTGAGACAGTGCCATTGCCGGAAAAC
CGGGTCGTTCCCAGTAAAACCAAAACTGATGCAATTGGAATTCCGCTACCGGAAATATCG
TACAGCGTGACCGATTACTGGCAGGCAGGGAAAGAAGCAGGGCTGAAAGATTTTGCGAAT
TTTGCAAAATTACTGGGGGGCGATGTGCTGAAAATCGACACCAATTATCAGGATCGCCAG
CATATTATGGGAACCACCATCATGGGCGATGACCCGAAAAATTCGGTGGTGAATTCTGAT
TGCCGGACCCATGATCACCCGAACCTGTACATTGCCGGAACCAGCGTGATGCCTTCGGCA
TCCTGTATGAATCCAACTCTCACCGGGGCTGCGTTAAGTTTGCGGCTGGCAAATCATCTG
TTGAAAAACGTACTGGTT

SEQ ID NO.70 - Orf 2448

ATGGCTAATACTACTTTAGATTTCGACTACGTTATCGTCGGCTCAGGCGTTACCGGAGCA
CTGATTGCCTGGCAATTGTCCCGTCATGGTAAACGGGTTTGTATGATTGAGGCCGGCGAT

FIGURE 10B

CACATTCAACGCTGGAAAGCGATAGAGCATTACCGCAGTTTGCCGGATAAAAGCATCGCC
AATAATTCACCCTACCCTAATCTGGAGTGGGCACCCAATCCCATTGGCGGGCATTATCTG
GAACAAAAGGGCCCGGTAAATTATGCGACGACTTATATCAGAATGGTGGGGGGAACTACC
TGGCACTGGGACTCTGCGACCTGGAGACTGTTACCGTCAGATTTTGAACTTAAAACCCGC
TATGGCGTAGGCCGCGACTGGCCGATTGGTTACGAAGTGCTGGAACCCTGGTATCAGAAA
GCTGAAGAGCAACTGGGGGTCAATGGCTGGGATACTGAAGATCAGAGTGGCCAGGGCAAA
GATCATTACCCTCCACGTTCACAACCCTATCCTACTCCGGGCCACCCGTTCAGTTGGGGA
CAACAGGTTGTTGCCGGTAAACTTGAGGCGGCGGGTTACTCTGCCATTCATGAACCCAAT
GCCAGGCTTTCTGTGGCTACCGCCGAACGTCCGGCCTGTGCCGGAAATAATACCTGTGAC
CCTATTTGCCCCATCGGCGCTAAATATACCGCTGACTTTCATGTGCAAAAAGCGCTCGAC
CATGGCTGTACATTGCTTTCTAACTCGGTGGTTTACCGTGTCGAGGCCGGAGATGATGGT
AAAATTACCGCTGTGCATTTCCGTCGGCCGGATAAGTCAACGGGAACAGTTAGCGGGAAA
GTTTTTGTGATTGCTGCTAATGCAATTGAGACGCCTAAATTGCTGCTGATGTCCGTATCG
GAGCGCTATCCTCAGGGTATTGCTAATACATCAGGTCAGGTCGGGCGAAATCTGATGGAT
CACACCGGACTGGGCTTTAATCTGGTGACCGAAGATGAAGTCTGGCCAGGTACCGGGCCT
AATGCCTTGCTGGTGATGCTCAATGCCCGTGAAGGGAAATTCAGAGCCGAAAGAGCGTCT
TATAAAACTAAATTTCGTAATACCGCCGTCAATTTTGCCGTCACTAAGTCCCTGATTAAA
CAGGGAATCATGGGTAATGAGCTCTACCGGCAAATTAAATATCAGTCTGCCCGTCAGTTA
TCTATTGCCGTCGATCTGGAAACTTTGCCTAACCCGCAGAATCGTATTGTCCCAAGTAAA
GATCGGACTGACAGCCTGGGGATCCCTGTCCCGGAAATCCACTACGATGTGGATGATTAC
TGGAATAAAGGGCGCGATGCTGCTATCGCTGACGTACAAAATATCGCAAAAATTCTGAAC
GCAAAGATTGTGGCAACGGATACCAATAAACAAACCGCGAACATATTTTGGGAACCATG
ATTATGGGTAACTCACCCACTGATTCGGTGGTGGATAAAAATTGCCGGACTCACGATCAT
CCCAATTTATATATCGCCGGACCAGTGTCTTTCCGGCCGTCGGCTGTGTTAATCCGACC
CTGACAGGTGCAGCATTAGCTTTACGCATTGCCGACACGTTGTTACAGGATCCAGTGACT

SEQ ID NO.71 - Orf 3042
ATGAAAACCACACATTCTGCCACCGTTGTTATCATCGGTTCAGGCATCGCAGGCTCACAG
ATAGCCCAAAAATTACAAAAAGCTGGCATTGATACTCTGATGCTGGAAGCAGGTTCACGG
ATTGAGCGCTGGAAAATTGTAGAAAACTACCGTAATTCGCCATTTAAAACTGATTTTCAG
TCACCGTATCCACCGACCCGTCATGCGCCACACCCGCAATACTCGCCGGAAGATAACGGC
TACTTTATTCAGTATGGTCCGGAGCCTTATAAAGCGGGCTACCTGCGTGTCGCTGGTGGA
ACCACCTGGCACTGGTCTGCTCAGGCCTGGCGTTTACTGCCAAATGATATGCGTCTGAAA
ACACTGTATGGCGTCGGGCGTGACTGGCCGATCAGTTATGACGATCTGGAACCGTATTAC

FIGURE 10C

TATGAATCTGAAGTTGAAATGGGTGTTGGCGGCCCGGAAGACACCGGTTCACCACGGAGT
AAACCTTATCCACATCCGCCGTTGCCTTTGTCTGATTTTGACAAGGCCTTCAAAAATGTG
GTGGATAAAAACGGCTATCACCTGATTACCGAACCGGCAGCCCGTAATACTGAACCGTTT
GACGGTCGCCCGGCCTGCTGTGGCAACAGTAACTGCATGCCTATTTGTCCTATTGAAGCG
CAGTACACCGGTGAAACCGCGGTTCGTAAAGCTGAACGTGCCGGATCTCTGCTGGTTCCG
GATGCCGTGGTCTATAAAATAGAGCACGATGCCAAAGGCAATATCACTTCTGTTCTGTAT
AAAGATCCAAACGGGGAAAGTTTCCGTGTCACAGGGAAAATCTTCGTACTGGCGGCTAAT
GCCATCGAAACTCCGAAGCTGATGCTGATTTCCCGATCTGACAAATATCCAAATGGTATT
GGCAACACGACTGATAACGTTGGCCGTCACCTGATGGATCATCCTGGAACTTCAGTTTAC
TTCCTGAGTAAAGAACCGATGTGGCCGGGCCGTGGGCCTATGCGTTTAAGTTGCATTAAC
AACCTGCGCGATGGTGATTTCCGTTCAGAACATTCGGCGATGAAAATCAACCTGGGCAAC
TATTCTCCAACGCTGGCGGTGAGTAATTACCTGCTGAGTAAAGGGGTTTCCGGCAAAGAT
CTGCCGGCGATGGTGCGTGATTATGCGTCACGCTGGGTAGCAGTGAATACCTTCTTCGAT
ATCCTGCCTGACAGAGATAACCGGATTGTGGCGGTAGACTCGCAAAAAGATGCAATGGGT
ATTCCTAAACCAGGCGTGCATTACCACATCAACGATTACATTAATAAAGCGCGTGATGTC
GCCCACCAGCACTTCGACCATATTGCCGGTCTGTTTGGCGGTACGGAAGTGCGTCATGAT
GATAAGTACTTCAACAATAACCACATCATGGGCACCCTAATTATGGGTAATGATCCCAAC
GACTCCGTGGTGGATGCTGATTTACGTACCCACGATCACCAGAATCTGTTTGTGGCGTCC
AGTGGTGTTATGGCCAGTGCCGGAACCGTTAACTGCACCCTGACATTATCAGCGCTGGCG
ATGAGACTGGCAGACAAATTAATCGCGGAGTGCCAACATTTA

SEQ ID NO.72 - Orf 1983

TTGGCTACAGAATTTGATGCAGATGTGATTGTCGTAGGGTCAGGAGCCTGTGGCTCTAAC
CTGGCAAACGAACTGGCGGTAAAAGGGAAATCGGTGATTCTGCTGGAAGCAGGTGCCAAT
GTGCCGCGCTGGAAAATCCTCGAAAACTTCCGTAATTCAGGCCGCCATTATGACCGGAAT
AATGCATACCCAAATAATCCGTGGTCTCCGACCAGTAATACCCCGGCTATATAGAGAAC
GTTGGTGAATTTCGTGAACAGCCTGGCATGCTAAAACTGGTGGGTGGCACCACATGGCAC
TGGGGTGGCGCCACCTGGCGGTACATTCCAAATGATTTTAAACTGAAGACTATGTACGGT
GTGGGTCGCGACTGGCCGATCAGTTACAGCGATCTGGAACCCTTCTATACCCGTGCCGAA
TATGCTATCGGGGTTGCCGGCTCAGACACAGAAGACCAGTCAGGTCAGAACCCGGGGATC
TCTTTTCCTCCACGTTCCAAAGCTTACCCTGTAGATCCGGAAGCTGATATCTACAGTAAC
GCCAAACTTAAAGCAGCACTGTTACCGCATGGCCATAGCGTAGTACACGAACCCACAGTG
CGTATCCATCGCCCTTATGATGGTCGTCCGGGATGCCAGGGGAATAATAACTGTGACCAG

FIGURE 10D

GTCTGTCCAATAGGTACCTTGTATAACGGTTCAGTTCATGCAGATAAAGCCGTGCGTAAC
GGCGCAAAACTGATTACCGATGCGGTAGTACACAAAATTACCAAGGGTGAACAAGGTAAA
ATCACTTCTGTCAGTTACCTGACCCCTGCTGGTGAAGAACACACGCTGACTGCTAAATAT
TTTGTTCTGGCGGCACACAGTTTCGAAACTTCAAAGCTGATGCTGATGAACGATATCGGT
AACTCCTCTGATATGGTGGGTCGTAATCTGATGGACCATATTGGCCTGAGTATGAATTTC
CTTGCCGATGAACCAATGTGGGCAGGACGCGGCCCGGTGCAGCAGGCGACTATTATGACC
TGGCGTGACGGTGATTTTCGTTCCAAATATTCAGCCAACAAGCACTCTTTAGCCAATAAC
AACCCACAAATCGATATCGCCCAACGTGCTATTAACGAGGGATTGATGGGTAAAGAGCTG
GATGCTCGTATCCTTGACTGGTCATCCCGCTGGATGTCGATCTATAGCTTTCTGGAACCA
TTGCCTAATCCGGCTAACCGTGTACAGCCGAACCCGGCCTGGAAAGACAGCCTTGGTTTA
CCTGGTATCAAAGTGACCTTTGATGTCGATGACTATACCAAACTGGGTGCTAAGCACATG
GTCGAACAATATAAGCAGATTGCCGGGCTGATGAACGGTCAAATCATTGATTTAAATACT
GCGTTCGAAAACCATGACCACCTGATGGGCACCATGATTATGGGTGATAATCCTAAGGAC
TCCGTGGTTAACCATGAATGCCGCAGCCACGACCATCCGAACCTGTTTATTGCATCAGTT
GGCGTAATCCCTGCTGCCGGTGTCGTTAACCCGACACTGACCGGTGTGGCTCTGGCAATC
CGTTCTGCTGACATCATTGCAAAGGAGGTG

SEQ ID NO.73 - Orf 3399
ATGTCTGATTCATTAAGCGCCGACGTTGTTGTTATCGGAGCCGGGATTGCCGGTTCACTG
GCAGCACTAAAAATGGCTAAAGCGGGTGCCTCTGTCTTAATCCTTGAATCCGGTCCGGAA
ATTAAGCGTGACGAAGCGGTGAACTATTTTCGCAACTCGCCATTTAAAGGCGATTTTACC
GAACCGTATCCGCCGGAACCCTGGGCACCTCAGCCTAAATTTATTCCGACTGATAACAAT
TATCTGATCCAGAAAGGTCCGGACCCTTATCGTGCCCAGTATTTACGTGGCATCGGTGGT
ACCACCTGGCACTGGGCCGGTCAGGCGTTTCGTCTGCTGCCAAACGATATGAAGATCAAT
ACCCTGTACGGTGTTGGTCGTGACTGGCCAATCAGCTATGAGGACTTAGAGCCTTACTAC
AGCGATGCGGAATACCAGATGGAGTTTCCGGTGATGATGATTTAAATTCGCCGCGCTCA
CGTCCTTACCCGTTACCAGGCATTCCGTTACCTTACGGTTTTGAGCGCCTGAAACAGCGC
CTTAGCCCGCTTGGCTATCAGGTGGGTATCGGTCCGCAGGCACGTAACAGTATTCCTTAT
CAGGGACGCCCGGCCTGCTGTGGTAATAACAACTGTATGCCTGTTTGTCCTATCGATGCT
CAGTACCACGGCGGGATCTCTGCCCGCAAAGCAGTGGATGCCGGGGTAAAAATTATCGCC
AATGCCGTGGTTTACCGCATCGAAGCAGATGATCATGGCGTGATCCAGGCTGTACATTAT
CTGGATCAAAACAAAGCGACTCACCGCGTGACCGGTAAACAGTTTGTTCTGACCGCAAAC
GGCGTTGAAAGCCCGAAAATTCTGCTGCTGTCGACCTCAGATCGCTATCCAAACGGTATT

FIGURE 10E

GCTAACAGCTCCGGGATGGTAGGACGTAACCTGATGGACCACCCGGGCACCTCCGTCGAG
TTTTATGCTGACGAGCCAATCTGGTTTGGTCGTGGTCCGATGCGTCCGGGCAGTATCAAC
AACATGCGTGACGGTAGCTGGCGTAGCGAGCGTTCCGCATTGCGTATCGACCTGGCTAAC
ACCTCGCCGGTGCGTTATCTGACCGAGCGTCTGGTACGTCAGGGTTATTACGGCAAAGCG
CTGAACGACAAACTGGCCTTCCAGGCCGAGCGTTTTGTACAGCTGAAATGCCTGCTGGAA
ATGCTGCCGGATCCGGAAAACCGCTTAGTCCTCAGCAAAACTGAGAAAGATGCCTGGGGT
ATCCCGCGTCTTGAGGTGTATTACAAATTCCCTGAATACGTGCATGCCGGTTATGACCAG
TCTATGTCTGACTTCCGGAAAATTGTTCAGCAGATGGGTGGAACCGAGCCGCTATATAGC
CAGCGTGGTGTCTACGACAACAACCAGCATATCACCGGCACCATGATTATGGGCAGCGAT
CCTAAGAACTCCGTCGTTGACGGTAACTGTCGTACCCATGACCATCCGAACCTGTTTATT
GCCGGTACCGGAATCATGCCTTCGGCGTCAACCGTTAACTCCACTTTAACGGGGACGGCT
CTGGCGTTGCGTATGGCCGACTATGTGCTGAAAAGCCTG

SEQ ID NO.74 - Orf 1955
ATGTCTGAACAATATAGCGCAGATGTGGTAGTTGTTGGTGGCGGTATTTGTGGTGGAACC
GTGGCAAAAGAGCTGGCAGAAGCTGGTTTATCCGTACTGGTACTGGATGCAGGCCCTCGC
TGGGAAAGAGGGGAAGTGGTAGAGAACTGGCGAAATCTGCCGCCAGTGAATAAATCTGAA
TCTGATTACGCAACGCCATATCCGGCGGAACCGTGGGCAGTTCATCCGCAGCTCTATCCA
TATAATAATTATCCGGAAGTTTCCGGTCCGGATGCTTCTGCATTTCGTCAGGGTATGATC
AAAGGCGTCGGCGGGACAACCTGGCACTGGGCAGCTTCCTGCTGGCGTTTCCTGCCTGCA
GATATGCAGCTCCAGACCACTTATGGTGTGGGCCGTGACTGGGTGGTGACTTATGACGAA
ATGGAAGATTATTACTATCGTGCCGAGGTGCTGATTGGTGTTAATGGCCCTAACGACACA
TCACTGAAGTACGTTGCTCCACGTAAAAAGCCATTCCCGATGGAGCCAATGCCATACGGT
CCGGCCGATCGTCGGTTTACCGAAGTCGTGGCAACTGCCGGTTATGAAAACACCCCGGTA
CCCCAGGGACGTAACAGCCGGCCATATGACGGGCGTCCGCAGTGCTGCGGTAACAATAAC
TGTATGCCTATCTGTCCAATCGGCGCCATGTTCAATGGTATTCACAGTATTATTAAAGCC
GAAAAAGCAGGTGCTAAGGTTCTGCCAAATGCGGTGGTCTATAAGTTTGATACCGACGAA
AACAACAACATTACAGCGTTGTACTACTACGATCCGGACAAAAACTCGCACCGCGTAACA
GCACGGACTTTTGTGCTGGCAGGTAACGGTATCGAAACACCGAAACTGCTGCTAATGGCG
GCTAATGACCGTAACCCGAATGGTATCGCGAACAGTTCAGGAATGGTGGGCGGAATATG
ATGGATCACCCGGGTATTCTGATGAGCTTCCAGTCAGCAGAGCCTATCTGGACCGGCGGT
GGTTCGGTACAGATGAGTTCAATCACTAACTATCGTGATGGTGATTTCCGTCGTGAGCAT
TCGGCAATTCAGATCGGGATGAACAATACTTCTCAGAACCATAAAGCCGGGGTGAAAGCG
CTGCAAATGGGGCTGGTAGGTAAGAAACTGGATGAGGAGATTCGTCGCCGGGCCGCCTGT

FIGURE 10F

GGAATGGATATCTATGTTAACCACGATATTCTGGCCAATCCGGACAACCGTCTGACACTC
AGCACCGTGCATAAAGATAAACTGGGTATCCCATACCCGCATGTTACCTATGATGTGGGT
GATTATGTGCGTAAGGCCGCGGTTTCATCCCGTGAGCATCTGATGACTATTGCCAAACTG
TTTGGCGCGACCGAAATCGAAATGACTCCGTATTTTAACCCGAACAACCACATTATGGGC
GGGACTATCGGGGACATGATCCGAAAGATTCAGTGGTCGATAAATGGATGCGAACCCAC
GATCATCAGAACCTGTATATCGCTTCCGGTGGTGTGATGGCAGCCGCAGGGACTGTTAAC
TCAACCCTGAGTATGGTGGCGTTATCTTTGCGCGCTACTGACAGTATCAAACGCGATCTG
CAACACGGT

SEQ ID NO.75 - Orf 3675
ATGAATGCAGATGTGATTGTGGTTGGCACCGGGGTTGTCGGTTGCCTGATTGCTGAACAG
TTACTCGATAGTGGCCACTCCGTTGTGATGCTGGAAGCTGGCCCGCGGGTCGAACGTTGG
CAGATTGTCGAAAACTACCGAAATTTACCACCGGTTTCCCGGTTACATTTTAATGCCCCT
TATCCACCGGAGCCCTGGGCTCCTCATCTGATGTCGGCCACGCCTGAGCAGGCCGCTGAA
TATCTGCAACTGGAAGGTCCTAATGCCCGGGCCTATCAGCAGGGATATGTTCGTTATGCC
GGCGGAGCAACATGGCACTGGGCTGGAATTTGTTGGCGGTTAACTCCGGAAGATATGCAG
CTAAAAACGCTCTACGGTGTTGGCCGTGACTGGGCTTTTGATTATGCCACCCTGGAACCT
TATTACACCCGTGCCGAATATGCTCTTGGGTCTGTGGACCTTCTGAGCCGGAACTGCAA
TGGCCCCCGGTTCGTTCCAAACCTTATCCGATGGGCCGTCTGCCTTTCGGGCCGGGTGAG
CAACGCTTTACCGACGCGGCTGCCTCTATTGGCCTGACAAATCTGCCTTCAGCTCAGGCG
CGTAATAGCGGTATTGCTTACGGGGATCGTCCTGCCTGTTGCGGTAATAATAACTGCATT
CCGGTCTGCCCGATTGGTGCGAAGTACGATGCAGCAACTTCACTGACACGTATTGAATCC
AAAGGCGGCAAAATTCAGCCAAATGCGGTGGTCTATAAAATAGAAACCGGTGCGGATAAT
AAAGTCCAGGCAGTTCACTATTTTGACAATAACAAACAGACTCACCGGGTGACCGGGTCT
GTCTTTGTTATTGCCTGTAACGGTATTGAAACTCCGAAACTACTACTGATGTCTGCGGAC
AGCAGAAACCCGCACGGTGTAGCAAACAGCTCAGATCAGGTGGGACGCAATATGATGGAC
CAACCGAAGCTGGTAGTAGAACTTGAGCTGGCTGAACCCGCCTGGACCGGCGTTGGACCG
GTGCAGGGAAGCAGTATTATGGAAACCTCTCAGGGCAGTTTCCGTTCTGAATATTGCGGG
GCGTTGTTCCGTTTCAACAATATGGCTCGCAGCCGGATTGGTGCTATGGCGGCGCTGGAA
AAAGGTCTGGTGGGTAAAGCACTGGATACTGAAATTCGTCGTCTGTCAGCCTGTACCACC
GAAATTGCTATTGAACATGAGCTGATGCCGGATGCCAATAACCGCTTAACTTTATCGGCT
AAAAAAGACTGGCTGGGATTACCTAAACCCAACATTTACTACGATGTCGGTGACTATGTA
CGCCAGGGATCGCAGCGCCATTCTTTACCTATCGCCCGCCAACTGGCAAAAGCGATGGGA
GCGACCAAAGTAGATATTTCGACCGAATATACCAACAGTGACCATATTATGGGCGGCTGC

FIGURE 10G

ATTATGGGGACCGATCCTGCAGTCTCGGTGGTGGATGTGGATTGCCGGGCTCATGACCAT
GAAAACCTGTTTTTACCGGGTGGAGCTGCGATGACTACCGGAGGATGTGGTAACAGTACC
CTGACAATGTCTGCCTTAGCACTGAAAGCCGCAGATGCCATTCATGCACAATTAGGGAAA
GCA

SEQ ID NO.76 - Orf 1220
ATGTCTGAGACTATTTCTACTGACATCGTCGTGATTGGTTCCGGCGTTGTAGGTTCGTTA
ACAGCCAGAAAACTGGCTTTGGCAGGACGTAAAGTTCTGATGCTGGAAGCAGGTCCGCGT
ATTCAGCGTGACCAGATTGTCAGCAATTTTCGCCATTCGGCACGTAAAGACGATTTTATC
GCCCCGTACCCAAACTCTGAAATCGCACCATTTCCTGACTATAAGCCGGAAGATAACGGC
TATTTAGACCAGACAGGGCCTAAAGATTACAAGCCGGAATATTTGCGTGTTGTCGGTGGC
ACCAGCTGGCACTGGGCAGCTCAGGCCTGGCGCCTGGTTCCGAATGATTTTCGACTGAAA
TCACAGTATGGCGTGGGTCGTGACTGGCCGATCAGTTATGAAGATCTGGAACCCTATTAT
TATGAAGCCGAGATTTTGTGGGGTGTTTCCGGTCCTGCAGAAATGGCTAAATACTCGCCG
CGCAAGCATCCCTATCCGATGGAAGGGGTGAAAATGTCTTATCTTGAACAACGGGTCACC
GCGCGACTGGCACCCAAATATGAAGTTCTGACCAACACCACCGGTCGTAACTCCGTTCCT
TATGACGGTCGTCCACAGTGTTGCGGCAATAATAACTGTATGCCAATCTGCCCGATTGAT
GCACAGTATCACGGCGGTATTGCTGCTGCTGCCGCTGAGATTGCCGGGGTTAAACTGATC
CCTCAGGCAGTTGTTTATAAGCTTGAACATAACAGTCACGGTAAAATTACTGCTCTGCAC
TACTATGACTGGAATAAACAATCGCATCGTGTCGAAGCTGAAATCTTCGTGATGGCGGCT
AACGCTGTCGAAACCCCACGTATTCTGATGCTGTCAGCCGATGATAAAAACCCGAATGGG
TTATGCAATAACTATGATCAGCTGGGACGTAATCTGATGGATCACCCGTCGAATTCCGCA
ACTTTCTACGTAGACGAGCCTCTCTGGCCAGGTCGTGGACCGATGAGCCCTTCATCTATC
CAGCAATTGCGTGATGGTGCATTCCGTTCAGAGTCAGCGGCTTTCCGTATTGATATCTCT
AACTCCTCACGGGTTGCCGGTGTTACTGCCGGAGCGATTAAAGAAGGCCTGACCGGAGCC
GATCTGGACAGCGCTATTCTGTATCGCGCCTCACATGAACTGAGCATTAAAAACGTTCTG
GAGCAGTTACCTGATCCGAAAAACCGCACCATGCTGAGCACCCGTAAAAAGATGCCCTC
GGTCTGCCGGTTCCTGCGTTCTCGTACTCTTTTGATGAATATATCGAGAAAGGCATGCAG
CACTCGCTGGAAGTCTATGCCGATATCGCCCGCATGCTGGGTGCCACGAATGTCCGTTAT
TCGACTCCGGGTGTGTATAGCAACAACCAACACATCACCGGAACCCTGGCAATGGGCACC
GATGAAAAAACCTCAGTGACCGACCATGTGGGTAAAGCCTGGGAATACGACAACCTGTAT
ATGGTGTCTACCGGGGTGATGCCAACAGTGGCCACTGCTAACTCCACGCTGACCGCCTGT
GCTCTGGGCTTACGCACCGCTGACGCCATTCTTGGCAAAATC

FIGURE 10H

SEQ ID NO.77 - Orf 2419

ATGATGATGAAAAAACCAGAATTTACTCCGGGTGGCGATGCCTCCGCGGATATTGTTATT
GTGGGCTCCGGTATTGTTGGTGGACTGATTGCAGACAGACTGGTCAGTCAGGGATATTCC
GTACTGATACTTGAAGCAGGGTTACGAATCAGCCGTGCACAGGCAGTAGAAAACTGGCGT
AATATGCCGTTTGCTAACCGTGCCGGTTCAGATTTTCAGGGCTTATATCCGCAGTCACCA
CTGGCGCCTGCCCCGCTCTATTTTCCGCCGAACAACTATGTCAATGTCACCGGACCAAGC
GCCGGCAGCTTCCAGCAAGGCTATCTGCGAACTGTCGGAGGCACCACCTGGCACTGGGCG
GCTTCCTGCTGGCGCCACCATCCAAGTGACTTTGTGATGAAAAGCAAATACGGTGTCGGC
CGCGACTGGCCTATCTCTTATGACGAGATGGAGCCATGGTATTGTGAAGCCGAATATGAA
ATTGGTGTGGCCGGCCCGAGCGACCCGTCCATGCAGTCACCGAGTGAACGTAGCCGTCCT
TATCCGATGGATATGGTGCCATTTGCTCACGGTGATACTTATTTTGCCAGCGTGGTTAAC
CCGCATGGTTATAACCTGGTGCCAATCCCGCAGGGTCGTAGTACCCGTCCGTGGGAAGGA
CGCCCGGTTTGCTGCGGTAACAATAACTGCCAGCCTATCTGCCCAATCGGTGCAATGTAT
AACGGTATCCACCATATAGAGCGTGCTGAAAGCAAAGGTGCGGTGGTTCTGGCAGAATCA
GTGGTCTACAAGATTGATACTGATGATAATAACCGTGTTACTGCGGTGCACTGGCTGGAC
AACCAGGGCGCATCACACAAAGCGACCGGTAAAGCGTTCGCACTGGCCTGTAACGGGATT
GAAACCCCGCGTCTGCTATTACAAGCAGCCAATAAGGCTAACCCGACCGGGATTGCCAAC
AGCTCAGACATGGTTGGCCGTAACATGATGGACCACTCCGGCTTCCATTGCAGCTTCCTG
ACCGAAGAGCCTGTGTGGCTGGGTCGTGGCCCGGCTCAGAGTAGCTGTATGGTCGGCCCG
CGTGACGGTGCCTTCCGTAGCGAATATTCGGCTAACAAAATGATCCTGAATAATATTTCA
CGGGTTGTTCCAGCCACCAAACAGGCTCTGGCTAAAGGACTGGTCGGCAAAGCTCTGGAC
GAAGAGATTCGTTATCGTTCTATTCATGGTGTCGATCTTTCCATCAGTCTGGAACCGTTA
CCAGACCCGGAAAACCGTCTGACTCTCAGCAAGACTCGTAAAGATCCACATGGCCTGGCC
TGTCCGGATATTCATTACGACGTGGGAGATTATGTGCGTAAAGGGGCGACTGCGGCTCAT
GAACAACTGCAACACATCGGTTCTCTGTTTAATGGTAAAGAGTTCAATATCACGACTGCC
CTGAACGCCAATAACCACATTATGGGCGGAACCATCATGGGTAAAAGCGCCAAAGATGCC
GTGGTCGATGGTAACTGCCGGACCTTTGACCATGAGAATTTATGGTTGCCTGGCGGCGGA
GCCATTCCTTCAGCCAGTGTGGTGAACAGTACTCTGAGCATGGCAGCACTGGGCCTGAAA
GCTGCACACGATATTTCTCTGCGCATGAAGGAGTTCGCA

FIGURE 11A

SEQ-ID NO.78 - Orf 766

ATGAAAAAGATGACATTTAAGCGCCTGTTACTGGCGAATACTGTAGTTCTGGCCTGCGGG
CTGGCTGGCGCGGTACAGGCGGCCGATGCACCGAATCAGGATCAACTGGTAAAACAGGGT
GAATATCTGGCACGGCTGGGAGATTGTATGGCTTGCCATACGACCTCCGGGCGGCCTGAT
TATTCGGGCGGTCTGGCGATAAAATCGGATCTCGGGACTATTTACTCCACCAATATCACC
CCGGACAAACAGTACGGGATAGGTAATTACACCGAGCAACAGTTTGCCGATGCAGTGCGC
AAAGGGGTGCGTCCGGATGGCAGTTTCCTCTATCCGGCCATGCCTTATCCGGATTATGCC
AAAACCAGTGATGCGGATATTCATGCCCTGTACAGCTACTTTATGCACGGTGTGACCGCC
AGCAACAGTCAGCCGCCGCAGACCGACCTCAGCTTCCCGTTCAGTCAGCGTTGGGGCATG
CGTTTCTGGAACATGGTGTTTACCTCCGATAAGCCATTCCAGCCGATTGGCGGAGCTTCA
GAGCAGGTTAACCGTGGGCTTATATTGTTGAGTCTCTGGGCCACTGTAGCAGCTGCCAT
ACGCCGCGTGGTGTGGCAATGGAAGAGAAAGCGCTGGACAGCAGTGACAGCAACTTCCTT
TCTGGCGGCAACCTCAATGGCTGGGATGTCCCTTCATTACGGGTATTGCCCGCTGGAGC
CCGGATGAGATTGTCGATTACCTGCAAAGCGGACGTAACGACAAGGCCGGTGTCGCCGGT
GAGATGACCTCGGTCGTGAAAAATTCGACCTCGCACATGACCGATGCCGACCTGCAGGCG
ATTGCCGCCTATCTGAAATTCCTTGGTGGCAACCCGCCATTGCAGGCTTATGATCAGCAG
AAAAATCAGGCCACTACCGCTAAACTGACCGCGGCGGTGGATCTGACTGAAGGCCAGACG
CTCTACCTGAACAACTGTGGTGCCTGCCATTTTGTTAACGGGCTGGATGCTGCACGGGCA
TTCCCACAGTTGGATCAGGCATCGGTTGTTAATGCCAAAGATCCGCAGGGGCTGATCCAT
ATCATCCTGCAGGGTGCGCAGTTACCGGCAACTGAGAAGTCGCCATCAATGCTGAAAATG
CCTGGCTTCGGACACCGTTTATCTGACGACCAGGTGGCTAAACTGGCAACCTTCGTACGA
CAGGGCTGGAGTAACGATGCATCGGCAGTGACTGCTGATCAGGTGAAAAAGTTCGTGAG
GGGCTGGAGCAGCAC

SEQ ID NO.79 - Orf 2908

ATGAAAACAATTTTTGTGAAACTTCTGCCTCTTGCCATAATGTCAGTTATTGGCGTTATC
GGGCTGAAGCAGGCTTATGCTGACAGCAATGATAGTGCAGACCTGATAAAACAAGGTGCA
TACCTGGCTCGCGCCGGAGACTGTACAGCCTGCCATACTGAAGCTGGCGGCAAACCCTTT
GCCGGTGGTCTGGCTATCAGGAGTCCGATGGGAGTCATTTACTCAACTAATATCACTCCG
GATAAAAATGCCGGAATCGGCAGTTACACCGAACAACAGTTTGCAGAGGCGGTTCGTAAA
GGAGTCCGTCGGGATGGCAGTAATCTGTACCCGGCAATGCCTTATCCTGACTATAGCGGT
ATTACCGATAAAGACATTCATGCCCTGTATGTGTACTTTATGCACGGTGTAGCCCCGGTG

FIGURE 11B

```
AGTGTAAAAGCACCACAAACCTCCCTGACTTTCCCGTTCAGCCTGCGGTGGGGAATGAAA
TTCTGGAATATTGCCTTCGCGTCCGGAAACAGCTATCCACCAGCTCCAACAACTCAGTCA
GACAGTGCTGATGCTCAGGCATTAAGCCGGGGCAGATATCTGGTCGATACTTTAGGTCAC
TGTAGCAGTTGTCATACTCCACGAGGTATCGGGATGCAGGAAAAAGCGTTGAACGACAGT
GATAGTCGCTTTCTGTCTAGCGGCATGCTTAATGACTGGACAGTGCCTTCGTTGAGAAAT
CCTGACGGATGGTCTGTGAATGATATTGCAGAATACCTGTCTACAGGGCGCAATGACTTC
GCCAGTGTCGGTGGTGAAATGACGGGCGTGGTGCAACACAGCATGCAACATATGAACCAG
GCCGATTTACATGCCATTGCTCTGTACCTTAAATCATTACCTGCCAGTACTAAACAGCAG
CATAATGTGAAACCCGATCTGCAGAATGACACTCAGAAAACGGTGGATACTCTGACGCTC
GGCAAAAATCTCAACTCTGGTCAGATGCTTTACCTGAACAACTGTGAAGCATGTCACCTG
ACCGATGGCGGAGGAGCTAAAAAGATTTTCCCACGTCTGAATGGGGCCAGTATAGTGCTT
GCTGATAACCCGACAGGGCTGATATCGGTGATGCTTAAAGGTGCGCAGACCCCTTCTACG
GCAAATGCACCGTCAGTACAGTTTATGCCCGGATTTGAGCAACGGCTCAATGATCAGCAA
ATTGCTGAGCTCGCCAGTTTTGTCCGCAGCGGCTGGGGAAATAATGCGCCACCAGTATCA
GCAGCAGATGTGGCTAAGGTCCGTGCCAGTCTTAATACCAGTCAGAAA

SEQ ID NO.80 - Orf 2035
ATGAAAAAAATAACATTATTGTACTCAGCCGTGCTGGCGGGTCTGCTGGGCTGTACCGTG
GCACAGGCTGATGACAGTGGCGGACAACTGGTCGCCCGGGGAGAATATCTGGCGACTGCG
GGAGATTGTGTGGCCTGCCATACCGCCAGCGGTCCGGCTTTTACCGGAGGGTTGAAAATG
ACCACTCCGGTCGGCGCTATCTATTCGACCAATATTACCCCGGATAAACAGACCGGAATT
GGTGATTACACCTATGATGACTTTGCCCGCGCATTACGCCAGGGTATTGCCCGCGATGGC
CGTCATCTGTATCCGGCAATGCCTTATACGGAATATGCGAAGGTCAATGATGACGATATG
CATGCCCTGTATGCATACTTTATGCATGGTGTTACCGCGGTACATCAGCCAAATAAACCG
TCAGATATTCCCTGGCCGTTAAATATGCGCTGGCCACTGGCGGTCTGGAATAAGTTGTTC
CTCGACAATACTCCGTTCAAAAACGACCCGGCACAAAGTGCTGAGTGGAACCGTGGGGCT
TACCTGGTCCAGGGGCTTGAGCACTGTGGTGCCTGTCATACACCGCGTGGTATTGCATTT
CAGGAAAAGGCTTCAGATGAGAAGGGAGCTGACTTCTTAACCGGTGGAACACTGGAAGGC
TGGCATGCGCCGGATCTGACCGGAAATGTAAAATCCGGATTAGGGCGCTGGAGCACCGGG
GATTTGCAGACGTTCCTGAAAACCGGGCGCAATGACCAGAGCGCGGCATTTGGTTCGATG
AGTGAAGCCATCGGGCACAGTACCCAGCACCTGACCGATGCGGATTTACATGCTATGGCG
```

FIGURE 11C

GTCTATATTAAATCGCTAAAATCTTCTGATCCAGAGGCACAGCCTCCGGCGACCACCGAC
AGCACTACGGCGGCGTTAATCAGAGGAGATCTGAGCCAGACCGGTGCGGAAGAATATATG
GATAACTGTGCAGCCTGCCACCGTCTGGATGGCAAAGGGTATGCCAAAACCTTCCCGACA
CTGGCCGGTAACCCGGTATTACTGAGTGATGATCCTTCCTCACTGATTAGCATTGTCCTG
ACAGGCGGAAAGATGCCGGTGACTCAGCAATCGGTGACCGGACTGACCATGCCTGATTTC
GGCTGGCGGCTCAGTGACCAGCAGGTCGCTGATGTGGTCAGCTTTATCCGCAGCAGTTGG
GGTAATAATGCCGGTAAAGTAGAGGCTAAGCAGGTAGCAGACATTCGCAAGCTAATGCCG
GTACCGAATCAGGCAGATAATCCGCAGGTAAAGGCCGAAAAGCCGGATCCCGCTAAGAAA

SEQ ID NO.81 - Orf 1840
ATGAAAGCTATTAAAGGAATCATCGTTGTGATACTGGTGTTGGTCATTATCCTTCTGGCC
TACGCTCTGTGGCCGACCAAAACAGCATCGCTTTCGCCGTTACCTGCGGATAACTCCCCT
CAGTTGGCCTCACTGGTCAGCCAGGGTCAGTATCTTGCGACTGCCGGTGACTGTGCGGCC
TGCCATACTCAGCCGGGCGGTAAACCGTTGGCCGGGGACTGCCGATTCGCAGCCCGATT
GGGGTTATTTACACCACTAATATCACTCCGGATAAACAGACGGGGATAGGTAATTACTCT
CTGGATGATTTTGAACGCGCAGTACGCCACGGCATTTTGCCAAATGGCGACACCTTGTAT
CCGGCCATGCCTTATCCGTCCTATGCAAAAATCAGCGATGATGATGTACGGGCCTTGTAT
GCCTGGTTTATGCATGGGGTCCAACCGGTCAGCCAGCAGAACCGTGCCAGCGACATCCCG
TGGCCACTCTCGATGCGCCTGCCACTGGCGGTGTGGCGCAAGATGTTTGCGCCGGATCCG
GCTAACACCGGTTTTACAGCAGATAAATACCAGAGCGCCAGCCTGGCTCGCGGCGCTTAT
CTGGTTCAGGGCCTTGGCCATTGCGGTACCTGCCATACTCCTCGCGCCGGCACCTTGCAG
GAAAAAGCGCTGGATGATTCCGGACAGCAGTATCTTGCGGGTGGTCAGGTGATTGACGGC
TGGCTGGCGGTAAATCTGCGCGGTGATAAAGCCGACGGTCTGGGTAACTGGACAGAACAG
GATATTATCGACACCCTGCGCACCGGGCATAACGTCAGCCATACTGTGGTGGGGCAGCCA
ATGGCAGAGGTTGTGGCTAAAGCACCAGTCATATGAGTGATGCCGATTTGGCGGCCATT
GCCGCATATATCAAATCACTGCCTGCAGGCCAGGGTTCAAAAGCATCGTACACGGAATCA
TCACAAACAGCAGACATGCTGGCCCGTGGTGAAAACCCTACCCCGGGTGCGCAGTTGTAT
GTAGATAACTGTTCTGCCTGTCATCAGACCAGCGGTAAAGGTGTTCAGCATATCTTCCCT
GCGATGGCCGATAACCCGACAATACTGGCCGACAATCCGGTGTCGGTGATTCATCTGATT
CTTGACGGTAGCCGCCTGCCAGCCACACCTCAGTCCCCGTCAGCACTGGCAATGCCTGGC
TTCGGCTGGCGTTTGTCAGATAAACAGGTCGCCGATTTAAGTAACTTTATTCGCAACAGT

FIGURE 11D

TGGGGTAATAAAGCGACAGAAGTGACCGAACAGCAGGTGAAACAGGTCCGGGCAGATTAT
CCGCCGAAAGGCGAGAATAAGGATCCG

SEQ ID NO.82 - Orf 3651
ATGAAAAAAAGCATATTAGCGCTGGTGTTTGGTTCACTGGCTTTTTCTGCCATGGCCGAG
GATAACAGTGGTCAGGATTTAGTGAAGCGGGGCGAGTATCTGGCGCGGGCAGGTGACTGT
GTTGCCTGCCATACCAGCGAAGGCGGTCAGCCTTTTGCCGGTGGATTGCCGATGGCAACA
CCTATCGGAAAGATCTATTCGACCAATATTACTCCCGATAAGACTTACGGCATCGGAGAT
TATACTTATGACGATTTCCAGAAAGCGGTACGCCACGGGGTAGCGAAAAATGGTGAGACA
TTGTATCCGGCAATGCCTTATCCGTCGTACGCAGTGGTCAGTGATGACGACATGCACGCT
CTCTACGCCTATTTTATGCAGGGTGTGAAACCTGTCAGCCAGCCTAATCACGCCACTGAT
ATTCCATGGCCTCTGTCAATGCGTTGGCCGCTGGCTATCTGGCGGGAATGTTTGCTCCG
GCAGTAAAACCTGCCACAGCACAGCCAGGAGAAGATCCGGTGCTGGCGCGTGGACGCTAT
CTGGTTGAAGGGTTAGGCCACTGTGGTGCTTGCCATACTCCTCGTAGCATCACCATGCAG
GAGAAGGCGCTTAACAATAGCGAAGGTACCGATTATCTGTCTGGCAGCAGTGCTCCGATT
GATGGCTGGACAGCCATTAATCTGCGCGGCGACGATCGTGATGGTCTGGGCCGCTGGTCG
ACCAGCGATATTGCACAATTCCTGCGTTATGGACGAAATGATCGGACCGCCGTATTTGGT
GGCATGACCGATGTGGTACAGCATAGCCTGCAATACCTGAGTGATGACGATATTAACGCG
ATAGCACGTTACCTTAAGTCTCTGTCACCACGGGATAGCCATCAGCCGGTATTTAAGGCG
GATGATTCTGTCTCGCAGGCATTATGGAAAGGTAATGATCAGCGAACCGGGGCTGCTGAG
TATGTTGACAGTTGTGCAGCCTGCCATAAGACCGATGGTAGCGGGTACACCCGCTTCTTC
CCGGCGCTGAAAGGCAACCCGGTGGTACTGGCAGAAGATCCAACCTCACTTATCCATATT
GTTCTGACAGGGGATACGTTACCCGGAGTTCAGGGCGCGCCATCGGCGATCACTATGCCG
GCATTTGGCTGGCGGCTTAATGATCAGCAGGTAGCAAATGTCGTGAACTTTATCCGTAGC
AGTTGGGGAAATACCAGCACTGCGGCGGTATCGGCAGATCAGGTGGCTAAGTTGAGAAAA
TCAGCCGATGTGCAGGGAAAAATGGGTGATGCATCAGTAGAGAAATTACCTAAACAGCCT

SEQ ID NO.83 - Orf 3053
ATGGCTAAAAAAACACGACGCGTTATCTCCGTGGTCGCTGCGGTAGTCATTGCCGGTGCA
CTCGGTTATACCGCCTATGAACAGTACGGTATTCATAAAAACTATCCACAAACCGTCAGC

FIGURE 11E

CTGGAGACGGGCCCGGCACTGCAGGACCAGATTAAACGGGGCGAATATATTGCCCGTCTT
TCTGACTGTACGGCCTGTCATACCGCTGAAGGTGGCCAGCCATTTGCCGGGGGCTATGCT
CTGCAAACGCCGTTCGGGAAAATTCTGTCATCAAACATCACCTCTGACCGGGAAACCGGT
ATTGGTGGATGGACTCAGGAACAGTTTGATAAAGCTGTTCGTCATGGTGTTGGTTCTCAC
GGCTATCTGTATGCAGCCATGCCTTATCCGGCGTACTCACGGCTGACCGATGCAGACCTG
ACCGATTTATGGGCCTATATCCGTAACCTGCCAGCGGTTAACCATAAAGTGGTAGAAAAC
CAGCTGCCATTCCCGTTCAATCAGCGCTGGACGCTGGCGGGCTGGAATATGCTGTTCTTT
AAAGATGCGGCATTTACCCCTAATCCACAGGCCAGCGAACAGGTTAACCGTGGCCAGTAT
CTGGTCGATGGACCAGGGCACTGTGCTTCCTGCCATACTGCCAAAAATATGCTGGGCGGT
GACAGCTCTGCTTATCTGCAGGGCGGAGCATTGCAGGGTTGGTATGCACCGGACCTGACG
CCGGATCCTCATTCCGGTTTAGGCAACTGGAGTAATGCCGATATTGTCAGCTACCTGCGT
TCCGGCAGTAACCGTATCACCGCCTCCTCAGGCCCGATGACCGAAGCGGTAGAGAATTCA
ACGCAGTATATGAATGATAATGATTTGAACGCGATTGCGGCTTATCTGAAATCTATTCCT
GCCTCTCACCCACAGGTTCCGACAGCTCTGACGGCTGATGACCAGCAAATGGTCTCCGGC
AAGAAAGTGTTTGAATCTCAGTGCAGTGCCTGTCACGTTTCTGATGGTGCAGGGATTCGC
AACATGATCCCGGCACTGGCAGGCAATCCACAGGTAAATTCTGCAGATCCGTCCAGCCTG
CTAAACGTGGTACTGAATGGCAGCGAGGGACCGTTTACCCATGCGAATCCGACGGCTGCA
GGTATGCCATCGTTCGGCTGGAAACTGTCTGACGCTAATATTGCAGAGGCCCTGACCTAT
ATCCGTAACAGCTGGGGCAACGCCGCTCCGGCCGTCACGGCTGACCAGGTGAGCGCAGCC
CGTAAAGCAACCGGAGCAAAAAGCTGGCTGGGAGATTCCATCGCCTCTCAGGACAGCGGT
AAA

SEQ ID NO.84 - Orf 2632
ATGAAAAAGACAACAATAGCCATTGCTGTTGCGGGGATCGTCGTGGTCGGCGCACTCGCT
GCATTATGGATGAACGGCAGCACGCGGGCAGACGATGTAGCCGGAGACCAGGTGCAGACC
AGCCAGCCGGTGTCTGCAGAAGACAGTGCGGCGGTGAAACGGGGTGAATACATCGCAGTA
GCCGGTGACTGTGTCGCCTGCCATACTGCCCCGGGAAGTAAAACCCCGTTCAGTGGCGGA
TATGGATTGATACGCCGTTTGGGACCATTTATGCCAGTAATATCACGCCTGATAACCAG
ACCGGAATTGGCCAGTGGACCGAACGTGATTTCTACCGGGCAGTTCGTCACGGTATTGGC
CGGCAGGGCGAAAATCTCTACCCGGCGATGCCCTATAATGCCTACGTGAAGGTCAGTGAT
CAGGATATGCATGATCTGTGGATGTATATGCGTACGGTTAAACCGGTGAATCAGCAGCCG
CCGGAAACTCACCTGCCGTTCCCTTATAATATCCGACTGGCAATGCGTGGCTGGAATCTG

FIGURE 11F

CTGTTTTTTAAAAATAGTGGATTTGATGCGAATAGCAGTCAGTCAGCAGAGTGGAACCGC
GGGGCTTATCTGGTTCAGGGGCTTGAGCACTGTGCTGCCTGCCACACGCCGAAAAATATG
CTGGGTGGAGATACGTCAGCGTATCTGCAAGGTAGCAGCCTCGGACAGTGGCATGCACCG
GAAATTACCGGCAACACCTATACCGGTATTGGCCAGTGGAGTGAGCAACAGGTGGTTGAT
TACCTGAAAAGCGGCAGCAATCAGGTTGCAGTAGCTTCCGGACCGATGGCCGAAGCGGTG
ACCAATTCGACTCAACATCTGACGGATGCTGATCTGCGGGCCATTGCAGTCTATCTGAAA
TCCCAGCCGGGTTCGGCAAACCAAAAGCCAGCGGCTTTGGCAGCAACCAGCCCGTTGATG
CAACAGGGAGCGAATGTTTATCAGGCAAACTGTAGTGCCTGTCATAACAGCGATGGCCGG
GGAATACCTCAGCTGGCTGCCGGGTTGCGGGATAACCCGGGAATAATGGCGGCCGACAGC
TCATCGGTCATTACTACTATTCTTGAAGGCGGGCGCGGCGCGGTGACCCTGAACAATCCG
ACCAGTGGTGCTATGCCCTCGTTCGCATGGAAACTGTCTGATCAGCAAATTGCCGCGGTA
TCTTCCTATATTCGCAACAGCTGGCAAAATGCGGCCCCGGCAGTGACTTCACAACAGGTG
GCTGCAATGCGTAAGCAACTGAAACTGACCCCTCAGTTACCAGATAACGGAGAGCCGGCA
CAT

SEQ ID NO.85 - Orf 1750
ATGACGATTAAAAAATATATTGCTTCAGTTGTCGGAGTGGCTGTAGTGGCCGGACTCGGA
TTCACTGGCTGGAAATGCTGGCATAACGCTCATCAGGATCACAGTTTTGTAGCCCCTGCA
TCTGCCGGGGATACCGGCAGCACGGCGATTGCACGTGGTAAATATCTGGCCACGGCCGGG
GATTGTGTTGCCTGTCACACTGCGCCTGGCGGTAAGCCTTATGCGGGTGGACTGGGACTC
AATACGCCGTTTGGTACCATCTATGCGACCAATATCACCCCGGATAAAGAGACCGGAATT
GGCGGCTGGACTGATCAGCAGTTTATGAACGCTGTTCGTAACGGTAAAGGTGCTAACGGT
GAGAATCTCTATCCGGCAATGCCTTATAATGTTTATGCTCAGGTCAGCGATCAGGATCTG
AAAGATATTAAAGCCTATCTGGACAGCGTACCGGCAGTACATTACACCGGACCAAAAACA
GATTTACCATTTCCGTATAATATCCGGCTGATGATGATGGGCTGGAACCTGCTGTTCCTG
AATACCGCAGCGTTCAAAGCTGACCCTGCACAATCTGCCCAGTGGAACCGTGGCGCTTAC
TTAGTTGAAGGGCTCGGGCATTGTACTTCCTGTCACACACCAAAGAATATGCTGGGTGCG
GATAAAATGGGGGTTCATCTGCAAGGTGGTGAGCTGGAAGGGTGGCTGGCTCCGGAAATT
ACCGGCAACACGCGTCAGGGAATCGGTGGCTGGAGTGATGATGAATTAGTGCATTACCTG
AAAACCGGAGCAAACGATAAAACGGTTGCTGCAGGTCCAATGGCTGAAGCGGTTCATAAT
TCACTGCAACATTTGAACGATCAGGACTTAACGGCAATGGCAACTTACCTGAAAAGCTTG

FIGURE 11G

CCAGGCAGTGAAGACAAATCAGTTGCTCTGAGTGGAATGGATGATGTGATGGCCCGCGGA
CAGAGTATTTATCAGGCGAACTGCTCTGCCTGCCATCAGTCGGATGGTGCTGGTGTCCGG
GATATGGTGCCGGCGTTAAGGGGTAACAACGGGCTACAGGCATTTGAACCGACCAACGTG
TTGCATGTACTGATGATTGGGGCACAGGGCGCAGCCACCGCCAGCAATCCTACCAGCGCG
GCGATGCCAGAGTTTGGCTGGAAACTGACTGACCAGCAAATGGCAGATGTCAGTACTTAT
GTCCGTAACAGTTGGGGAAATAAGGCGCCAGCTGTCACCGCATCACAGGCGGCGGCTGCA
CGGAAACTGCTGTCAGGTTCACCGGCATTGCATAATCCAGCGGCAAAC

SEQ ID NO.86 - Orf 1953
ATGATGAAAAAGTTAATGCTGACTGCCGGCAGTTTACTGTTGCTGACAGCCGGTTACGCA
CATGCTGACAGCGGTGGCGATTCCTGGGACCTGGTAAGTAAAGGCCGTTACATTGCGCAA
CTGGGTGACTGTACCGCCTGTCATACAGAGCCGGGACATCCTCTGTTTTCCGGCGGGGTC
GCGATTGAGACACCTTTTGGAAAACTGGTAGGCGCGAATATTACCCCTGATCCGGAAACC
GGCATTGGTAAATGGACCTTTGAAGACTTCCAGAACGCGATGCGTAAAGGCCACAGCCGT
GACGGTCAGTTGCTTTACGGTGCCATGCCTTTCACGGCCTACACCAAAGTAACTACCGAC
GATAACCGGGCACTGTGGTCTTATCTGCAAACTGTTCAGCCGGTAAACCGGGTGGTTAAC
ACCAACCAGTTGCCATTCCCGTTCAATATCCGTACTTCACTGCATGTCTGGGATATGCTG
AATTTTACCGAAGGTGAATATAAGCCGGACCCTAAACAATCAGCCGAATGGAACCGGGGC
GCTTATCTGGTTCAGGGTCTGGGGCATTGCAGTACCTGCCATACACCTAAAAATATGCTG
GGTGGTGATAAAGACAGCAAGTTCCTGCAAGGCGGCTCACTGGGTGTCTGGTTTGCTCCG
GATATTACCGCCAATACCCACAGCGGTATTGGTCAGTGGACCCAGCAGGAAATTGTCGAA
TACCTGAAAACCGGTGCTAATAAATACGATATCGCTTCAGGTCCGATGGCTGAAGCTGTA
GAGCATTCGACTCAGTACTGGAAAGATGAAGACCTGAATGCGGCTGCGGTGTACCTGAAA
TCGCTGAAAAACGATAGTAGCCAACCACAACCTCTGGCGGCGGATAATGGCCAGATGGTG
AATGGTAAAGCGATTTACGCGGACCGTTGCAGTGCCTGCCATGTGTCACAAGGTCAGGGA
GTCTCACATCTGTTCCCGCAACTGGCTAATGCACCACTGGTTAATGCAGTCGACCCTGCA
TCACTGATTCATGTAGTGCTGGCGGGCAGTCGCGCCGGAGGGACCGCTGCGGCTCCAACG
GCTCCTGCTATGCCTGCATTTGGCTGGAACATGACGGATCAGAACGTCGCCGATGTGCTG
ACCTATATTCGTAACAGTTGGGGGAATGCAGCACCGTCTGTCACCGCCAGCGATGTGAAG
AATATGCGCAGTACTTTAGAGAAG

FIGURE 11H

SEQ ID NO.87 - Orf 3687
ATGCAGAAATTAAGGGTGTTTACCCCGTTGGCTATTATGCTGGCTGGGTTTTGTGGCTCTGTTTA
CGCTGATAACAGTCCTGCCTCGTCAGACAGCACATCGCTTTCCCGCGGAGAATATCTGGCCAGAG
CCGGCGACTGTGTTGCCTGCCATACAGCAGAAGGAGGCAAACCTTTTGCCGGTGGATTGAAAATG
ACGACGCCGGTAGGGGCCATCTATTCAACAAATATCACTCCGGATAAAGATACCGGGATCGGTAA
TTACAGTTACGATGACTTTGTCAAAGCTGTACGCCAGGGAGTCAGTAAATCCGGATCAACCCTCT
ATCCGGCGATGCCGTATGCTTCTTTTACCAGGATATCAGACCAGGATATGCATGATCTGTATAAC
TATTTTATGCAGCAGGTTAAACCGGTCAGCCAGCAGAATAAAGCCTCTGATATCCCCTGGCCTTT
GAGTATGCGCTGGCCACTGGCATTCTGGCGCTGGACATTTACCGATGATAAGCGTTTTCAGCCTG
TCGAAGGTAAATCGGCAGAATGGCAACGGGGGCGTATCTGGTCGAGGGGCTGGAACATTGCGGA
GCCTGCCACACTCCGAGAGGTATAGCATTCCAGGAGAAAGCACTTGATCAAAGTGATCCGGTTTA
TCTGACGGGTAACACACTGGAAGGATGGTATGCACCGGATCTCACCGGCACGCAATCTGATGGTC
TGGGTCGCTGGTCACAACAGGACATTGTCAGTTTCCTGAAAAATGGTGTAACGGCACAAAGCTCT
GCCTTTGGTTCCATGTCAGAGGTGGTTCATGACAGTACCAGCTATCTTACCGACAGTGATCTTCA
GGCAATTGCAGTCTATCTGAAATCGCTGCCTGCGGCACACCAGACGCAGGCGCCAGCCAGTAATA
ATGCTACCGCTCAGGCACTTTTTAAAGGCGATGTTTCTGCTACGGGTGCACAGGTTTATCTGGAT
AACTGTTCTGCCTGTCATCGCTCGGATGGTAAAGGGTATGATAAAACGTTCCCGTCACTGGCAGG
CAATTCCGCAGTACTGAACAGTGACCCTTCATCAGTGATTCATATTATCTTGCAGGGGGGACAAC
GCGCAGTGACACCAGATATGCCGACCGGATTAACCATGCCGGACTTTGGTTGGCGGTTATCGGAT
CAGCAGGTCGCGGATGTCGCCACCTTTATCCGTCAGGGATGGGGGAATAATGCTGCTGCGGTCAC
AGCCAGTCAGGTTGCCGATATCCGCAAGCTAATCCCGAAACCCGCTTCTCAGGCTGCTAAGTAGC

FIGURE 12A

SEQ ID NO.88 - Orf 3820
ATGAGCAGGAGTGTAAAAGTGAGACCAACGAGTCTGGCTTTAATTATCGGGCTCTCGGTG
TTCTCGGGGAAAGCTGTGCAGGCTGCAGACACCCCTTCAGCATCGACGATAATTGAGCAA
GGAAAATATTTATCAGTGGCCGCGGACTGTGGAGCCTGTCATAACTCCCCGACAAGCGGA
GCTGCTATGGCGGGGGGCTATGCGATTGCCTCACCAATGGGCAATATTATCGCCAGCAAC
ATTACCCCGTCAGTGACAGCCGGCATTGGTAATTATACCGAACAACAATTTGCCCGGGCG
GTCAGAGAGGGAGTTAACGCACAGGGCGACCATCTTTATCCGGCAATGCCTTATACCTCG
TACAGTAAAATGACTGACAGTGATATTCATGCGCTGTATCAGTATTTTATGCACGGGGTT
CAGCCGGTTGATACTCCGGCTCCGGCCACAAAGCTTCCGTTTCCGTTCTCAATTCGTAGC
AGTATGGCGTTGTGGAATATGCTGTTTGCCAGCCAGCAGCGTTTCACTCCGGATAGCCAG
AAATCAGCTCAGCTAAACCGGGGTGATTACCTGGTCAATGTGCTGGAGCACTGTGATGCC
TGCCATACTCCTCGTAATTTCCTGATGGGTCAGAAAATGACCTGGCTTTATCCGGCGGG
CAGGTGGGTAGCTGGTATGCTCCTAATATCACTTCTGATAAAACTGCCGGTATTGGTAGC
TGGAGCGATGACCAGCTGTTTCAGTACCTGAAAACAGGTCATGTTGCCGGTAAAGCTCAG
GCCGCGGGCCCTATGGCAGAAGCCATTGAGAACAGCCTGCAACACCTTAGCGATGATGAT
TTGCATGCCATTGTTGCCTGGCTGAAACAGGTTCCCGCCTCGGGCGCCACAGCTACGGAA
TCACGTTTTACTCAGGGTGCGCCTTCAGACAGTGAGGCCGCCATGCGCGCGACCGATCAT
CCGGATGCCGGCTGGGTCGTGTTCAGTAACAGCTGTGCTAACTGCCACCAGGCCAACGGT
GAAGGCAGCCAGTTTTATCCTTCGTTATTCCACAACAGTGCAACCGGTGCCGCACAGCCG
GACAACCTGATTGCGACCATTCTGTTTGGTGTCCGCCGTCACGCCGACGGCCAGTATGTT
GCGATGCCAGCATTCGGACCTGCAGCTTCGTTTGTTGACCGGCTCAATGATCAGCAAGTT
GCAGATGTGGCTAACTATGTCTTAAAAAATTACGGAAATGCCTCACTGACTGTCACTGCC
GATCAGGTGAAAACAGTTCGTGAAGGCGGGCCTGTACCGGCCATTGCTTATCTGTCAAAT
CCGGCAGTGTTAGCTATCGGTGCATTGATTGTGCTGGTGATTCTGGGCCTGATCGTGACT
GCAGTTCGCAGAAGGGGGAAAAAA

SEQ ID NO.89 - Orf 1956
GTGAAACAACAACACAAGCTAAACGCGCATAAAGCCGCAGGTTTCCGCCGAAAGCTACTG
AGTCTTTGTCTGGGACTGAGTGCATTAAGCGCGGTTCCTGTGATGGCAGCTGAGCAGGTG
CCGGTCAGTCAGCCTTCTGTGGATAACAGTGCTGATGCATTGTTGAAACAGGGGCATTAT
CTGGCCATTGCTGCTGACTGTGCCGCCTGTCATACCGATCCTCAAACCAAAAGACTTTC

FIGURE 12B

GCCGGTGGTTACGCCATTCACTCTCCAATGGGGGTGATTTATTCCACCAACATCACTCCT
TCACGGCAGTATGGTATCGGTTCCTACAGCGAAGCTCAGTTTGAACAGGCAGTTCGCCAT
GGTATTCGCGGTGACGGGAGCCACCTGTATCCGGCCATGCCATACACTTCCTATTCGGGT
CTGACCGATCAGGATATTCATGCGTTGTATTACTATTTCACTCACGGCGTACAACCGGTA
GAACAGGCTAATCGTCCGACAGAACTCAGCTTTCCGTTTAATATCCGCGAAGCTATGTGG
GGCTGGAATTTACTGTTCCTGAAACAAAACCTTTCCGTGACGACCCCTCCCAAAGCCCG
CAATGGAACCGTGGTAAGTATCTGGTCGCGAACCTTGAACACTGTGGAGAGTGTCACACC
CCACGTAATACATTGATGGGCAGCGAAACCGGGTCGGCACAGTATAGCGGTGCAGCCCTG
GGAAGCTGGTTTGCACCAAATCTGACTTCTGACCAGCAGAGCGGTCTGGGCAGCTGGCAA
CGTGATCAGCTCATCACCTATCTGAAAACAGGTCATGTTGCCGGTAAAGCTCAGGCTGCC
GGACCGATGGCGGAAGCTGTCACCAATAGCCTGCAATATCTGAGTGATGATGATATCGGG
GCCATTGTGACGTATTTGCAAAGTCTGCCACCGGTCAGTGAACCAGACCAGGCGAAAGCT
ACCGGTGATTTCGGCAGTTCCGCTGGTAACAGTTCAGATTCTGAGGTTCGTGGTACTCAG
CCTATGGGATCTGTACTGCCGGACGACATTACCGGTAAAGCCCTTTACGACACAACCTGT
GCCAGCTGCCATCAGTCTTCCGGAGCGGGTACTACGGATAATTTCTATCCATCACTGTTC
CACAACACTGCCACCGGCGGAAATACCCCGAACAATCTGGTCTCCGCGATTCTGTTTGGT
GTGCAACGTGAAGTGAACGGCAAGCAGGTACTGATGCCAGCCTTTGGTCCGGGATCAGAC
GTGCAATCGCTGAATGATGAGCAGGTAGCAAAACTTAGTAATTACATCTTCAAACAATTC
GGCAATCCACAACTGTCGGTGACTGCTGATCAGGTAAAAACACTACGTGAAGGCGGCCCA
CAGCCGTTCCTCGCCAAATACGCTGCATCAGGATCGGCAGTGGGTGGTGTGATCCTGTTA
CTGATTATTGTGCTGATTATTGTCCGCATTTCGCGCAAACGTCGC

SEQ ID NO.90 - Orf 2446
ATGAAATGCGCTTATTTATCTTTACTGATAAGTACGCTGCTGTATGCCGGTTTTTCGCCC
GCCACTCAGGCTGAAACACCCGCGACAGCAGAAACTCTGCTTGCACAAGGAAAATATTTA
TCTGTGGCTGCAGACTGTAGCGCCTGCCATGACAGTCCCGATCACCATGTCATGGCTGGC
GGAAACAGTATAAATTCCCCACTGGGCAAGATTGTTGCCAGTAACATTACCCCGTCAGTG
CACTATGGCATTGGCAGTTATACCGAGCAGCAATTTTCGGATGCGGTCGAAAAGGTATT
AATGCTCAGGGCGAAAACCTCTACCCTGCAATGCCTTACACCTCTTACAGCCAGCTCACC
GACAGCGATATCCACGCGTTGTATTACTATTTTATGCATGGTGTAACTGCTGTCGATCGC
GCCGCTGGGGCCACACAGCTGCCCTTTCCGTTTAACCTGCGTATCAGCATGAAACTGTGG
AATGCTCTGTATGCGGACAACAAGCCGTTCCGTCCTTCATCCTCGCAAACCGATCAGGTT

FIGURE 12C

AACCGCGGCAACTATCTGATTTACGGGTTGGCTCATTGTGATACCTGCCATACACCGCGA
AATGCCCTGATGGCCGAAAAATCTGACCAGTCTCTCTCCGGGGGATCACTCGGCCAATGG
TATGCACCCAATATCACCTCAGATAAGTCCTCTGGTATCGGTAACTGGAGCGATCAGCAA
CTGTACCAGTATCTGAAGACCGGACATGCTGTCGGCAAAGCCCAGGCTGCCGGGCCAATG
GCAGAAGCTATTGAACACAGCCTGCAATACCTGTCTGATGATGACCTGCATGCGATTGTA
GCCAGCCTTCGTCTAACCAGACCGGTGAATACTGCATCCGCAGATCGCGGGATGCAGGGT
AAAGCAATATCTGATGAAAACAGTATCCGTGGTACCAAAGTTGCCAGCGGAGAGCCGGTT
TCCGGCCCAATGTCAGGGCAATTCTGTACTCAGGTAACTGTGCTGCCTGCCATACGCCT
TCCGGTGCCGGATCCTACAGCCAGAATTATCCGTCACTGGTACACAACACCACTGTAGGG
AGCACCGATCCCACTAATCTGATTGCCACTCTGTTATTTGGCGTTCACCGTACCGTTGAT
CAACAAAGCATCACAATGCCCGCCTTTGGGCCACAAGGCTATACCGACCGTCTTAGCTTT
GCAGAGATTGCCACACTGGCGACCTATGTCCGGCAGACTTATGGCGCCGGAGGTGAAGCT
GTCAGCGAACAACAGGTAGAGCAGGTTTACCAGGGTGGGCCTAAGCCGCTGATTGGCTGG
CTGGCCGACGGAAGAATACAGGCTTTAATCGTTGTAGTGCTGTTGCTGTTGGCTGGCCTG
ATTATCACCGTAGTGCGCAAAGGGAGAAAAGCA

SEQ ID NO.91 - Orf 3674
ATGAAAAAACATGCCATAAAGTTTTCCCTGTCGCTAATGTTTGCCGGAAGCATGTTGTGG
GCTGGTTCCGCTGCAGCCGCAACTGGCGATGCCGCGGCGGCCATTAGCCGTGGTGAATAT
CTGGCGACGGCTTCGGACTGTGCTGCCTGTCATACTGATAAAGGCGGTCTGCCGTTTGCC
GGTGGATTAAAAATTGAATCCCCGGTCGGGACGATTATTGCCAGTAATATTACTCCCTCC
TTAACCGCTGGGATTGGTCATTATACTGAACAGCAGTTTGCGGATGCGGTGCGTAAAGGG
ATTCGTGCCGATGGTGCTAACCTTTACCCGGCCATGCCTTATACAGCGTACTCGGTGATG
ACAGATCAGGATATTCATGATCTGTACCAGTACTTTATGCAGGGCGTAAAACCGGTGGAT
CATCCGGCCGCGGAGACTGAGTTACCGTTCCCGATGAACATCCGCATGATGATGAAGGCC
TGGAATTTACTGTTCCTCAACGATAAACCATTCAGCCCGGATGCATCACAAAGCGCTGCG
TGGAACCGGGGTAAATATCTGGTAACTGGTGCAGCGCACTGTAGTACCTGTCATACACCC
AGAGGGCCACTGATGGAAGAGGAAAGCAGTCAGTTCCTGAGCGGTGGTCAGGTCGGGGCA
TGGTACGCGCCAAATATTACTTCGGATCCACAGTCAGGGATTGGCCGCTGGAGCCAGGCT
GATATTGTACAGTATCTGCGCACTGGTAATCTGCCAGGTAAAGCCCAGGCTGCCGGTAGT
ATGGGAGAAGCGGTAGAGCATAGCTTCCAGCATCTGACAGATGATGACCTGAATGCGATT
GCTACCTATATTCGTACCGTGAAGCCAGTGGCAACGCCCGAAAACGCCGGTTCAAGATTT

FIGURE 12D

ATGCAGGGTGACAGCCACGATGCTACCGGAAAAATTCGTGGTCTGAGTCAGCAACAGGTC
ACTGATGCTAAACAGCAAGGGCTGGCGTTGTTCCAGGGCAATTGTGCCTCCTGTCATGAA
GCTGGCGGGCAGGGAAGCAGGGATAGTTATTATCCGAGCCTGTTCCACAATTCAGTGACC
GGCGCAGAGAACAGTAATAACCTGATTGCTACCATTCTGAATGGCGTTAACCGTACCACC
CGGGACGGTCAGGTATTTATGCCAGGTTTTGGTCATCATCCAAATGATATCAATAATCTG
ACTGACGAGCAGATAGCGTCGCTGGCAAACTATGTGCTCACAACCTATGGTAAACCGTCG
AAACCGGTGACTGCGGCGATGGTTGCCACCGTACGCCAGGGAGGGCCGGGTTCCAGTCTG
GTGCTTCTCGCCCGGTTTGGAATAGCTGCCGGAGTGGTAGTTGTTTTGATTCTGCTGGGA
TTCTGGGTGGTTCGCCGCAAAAAAAACGTCAGGGATCCGTCG

SEQ ID NO.92 - Orf 1221
ATGAAAAAACTGCTTTCCCTGTGTATCGCGGGTGCCCTGGCCGGGATCATGCTGAATAGT
GCCGCCATGGCTGAAGACAGCAATGCTCAGAGCCTGATCGCAAAAGGACAGTATCTTTCG
GTAGCCGGTGACTGTGCTGCCTGTCATACCACCAGCGGAGGAAAACCTTTTGCCGGCGGT
CTGGCTATTGCCACACCGATTGGCAAGATATTCTCCACCAATATCACTCCGTCAAAAACC
TCCGGCATTGGCGATTACTCGCTGCAGGAGTTTGAAAAGCGGTTCGTCAGGGAGTAAGA
AAAGACGGCGCCAATCTCTATCCGGCGATGCCTTACACTTCTTATGCCAAAATTTCCGAT
GAGGATATGCAGGCTCTGTATGCTTATTTCATGCATGGCGTTGCGCCTGTGGATGAGAAA
GGCCCGCAAACTGCCCTGCCATTCCCGTTCAATATTCGTCTGTCGATGGCGGGCTGGAAC
CTGATTTTTGCCGGAGACAAACCATTTACGCCAGACAGTAACCAGTCAGCAGAATGGAAC
CGCGGCGCTTATCTGGTTCAGGGTCTGGCTCACTGCTCCACCTGCCATACCCCGCGTAAT
GCTTTGATGGCTGAAGAGTCTGGCCAGGCGCTGGCTGGTGCTTCTCGGTACCTGGTTT
GCACCAAATATTACCCCGGATGCCCATGCAGGGATTGGCAAATGGTCAGCCAGTGATTTA
GCCACTTATCTGTCTACCGGTCGTTCACCGAACGGTTCTCAGGCTGGCGGCCCGATGCTG
GAAGCTATCGATAAAAGCTTTAGTAAACTTTCTCAGTCAGATATTAATGCGATAGTGACC
TATGTGCGTTCCGTGAAGCCTCAGTCAGCCAATGCCGCTCCGGGCCAGGTACCTGCCAGT
GCCCCGGTAGTGTCCGATTTTGCGCTGATGAATGGAACAGCTTCTGATGGCGCGAAGCTG
TATGAAGCTCACTGCTCCACCTGCCACCAGGCCTCTGGTCAGGGCAGCAATGGCTTACCG
GCTTTATATGGTAACGCCGCGCTGCATCGTCCGGTAGCGGATAACGCAGTCATGGCTATC
CTGGACGGCCTGACTCCGACTCAGGGCCAGGCTATGCCGTCGTTTAAAACTGCCATGAAT
GATCAACAGATTGCCACCCTGACCAACTACCTGTTTAAAACCTTTGGCGATGCCGGTGTT
CAGACCACCGCAGACAGAGTTAAGGTATTACGGGAAGGTGGAGCACCATCTCCGTTACTG

FIGURE 12E

GCGATTGCCAAAGGCGGGATGATAGCTGCGGTGATCGTGGTATTACTGCTGATAGTGGGC
GGAGTGATGGTTAAATCGCGGCGTAAACGCCGT

SEQ ID NO.93 - Orf 1984
ATGAAAAAATACTCAGCTCTTCTGACTTTGTCAGCTGCATTCCTGTTCTCCCCCCTCGCT
CTGGCGGCCACCAGCAGCAATAGCGATTTAGTCAGTCGCGGTGAATATCTGGCGCGGGCC
GGTGACTGTACTGCATGCCACACTGCCGCAGGTGGTGCCGAATATGCCGGCGGGTATAAA
TTTAATATGCCTATGGGCACTATCGTAGCACCGAATATTACCTCTTCAGTGCAATACGGT
ATTGGTAACTGGTCTGAAGCCGATTTTGCCAAAGCAGTAAGGCAAGGGGTACGCCCTGAT
GGTTCTCATCTCTATCCGGCAATGCCATATACCTCTTACGCCACAGTTACCGATGAAGAT
ATGCAGGCGTTATATGCTTTCTTCAAAACCGTTCCGGCAGTAGATAAAGCCCCGGCAGAT
AAAAACGACCTGAAATTTCCGTTTAACCTGCCAGGCCTGATGGGGATCTGGAATGCTTTG
TTTGCCAGTGATGCGCCATTTAAAGCCGATCCGGCATTAACTGCTGAGCAAAACCGGGGG
AAATATCTGGCCGAAGGGCTGGCTCACTGTTCAACCTGTCACAGTCCACGCAATCAGATG
ATGGCCGAGGATACTCATCAGTTGCTTGCAGGCAATCATGTGGATGGCTGGCTGGCACCA
AACATAACCTCTGATGCTGTCAGCGGCATCGGTGGCTGGAGCCAGCAGGAACTGACCGAA
TATCTGAAAACCGGCCATGTGGAAGGGAAAGCTCAGGCCGGTGGTCCTATGGCTGATGCC
ATCGAGCACAGTTTCAGTCACTTATCAGACAGTGATTTAGCCAGTATTGCCACATGGCTG
AAAACAGTACCAGCCATCCGCACTCCGGGCCAGACACAACCTTCATGGGCTGCCGCGCCA
GCCAGTAAGGTAGACTGGACAAGTTATCAAACCGGGGGCGGGAAGAATAATTCTCCGGCG
TACCGTGACTCGTCCACTACCGACGGAGCCGTACTGTTTGACAGCAGTTGTGCGGCCTGC
CATCAATCGAGTGGCCAGGGTTCAGACGACCATTACTTCCCGTCTCTGACCCATAACAGT
GCGGTTGGTGCAGCGGACCCGTCAAATCTGGTTATGGCGATTGTTGATGGTATTCACCGT
AAAACCCCGGAGGGTGAAGCGGTTATGCCAGCGTTCTCTTCAGAAACTCAGGCCATTCAC
TCATGGCTGAATAATGATCAGATTGCGGCAGTGACTAACTACGTCACCGAAAAATTTGGT
CACGGAAATGCCGGTCTGACCGGTGCCGATGTTGAGAAAATCCGTAACGGCAACAGCAAT
GTTCCGTTCCTGATTAAAAATGCAGGCGGCCTGACCATTGGCGGGATAGTGATTGTCGTT
ATTATCATTATTGCGTTACTGGCGGCACGCAGCCGTAAAAAACGTCGA

SEQ ID NO.94 - Orf 3400
ATGAAAGCTGTGATAATTCGATCGGCCATCGCGTTAGCTCTGATGCATGGCAGCCTGGCA

FIGURE 12F

CTGGCGGCAGATGATAATGCTGACTTAATTAAACGCGGAGAATATCTGGCAACTGCCAGT
GACTGTACCGCTTGTCATACGGCCCCTGGTGGTCCGGCATATGGCGGTGGTTACCCGGTA
GCGACTCCGTTCGGTAAAATCTGGGGAAGTAATATCTCCTCAGATAAACAATTTGGTATT
GGTAGCTGGACCGACGATCAGTTTGTCGCGGCGGTCCGTCAGGGTGTCGGTAAAAACGGC
GAGCAGCTGTATCCGGCGATGCCGTATGACGCATTTACCAAGATGAAACGCGACGATGTT
CTGGCCATCAAAGCCTACCTGATGTCATTACCGGCTGTGCATAAAGCCGCACCAGAAACC
TCTCTGCCGTTCCCGTTCAACCAGCGTTGGGGGATGCGTTTCTGGAAAATGTTTAACCTG
ACTGAAGGCGAACTGAAAAATGACCCTCAGCAGAGCCCACAATGGAACAATGGTCGTTAC
CTGGTAGAGGCACTGGCACACTGTACCACCTGCCATACACCGCGTAATCTGACCATGGGA
ATGGATACCAGCAAACCGCTATCCGGCGGGGATTTAGGCGACTGGATTGCCTTTAATATT
ACCCCGGGTAAATCAGGAATCGGCGACTGGTCGAGTCAGGATATCGTGACCTACCTGAAA
ACCGGTTACCTGGCAGGCAAAGCCTCAGCATCAGGCCCGATGGCCGAAGCGATTGAGCAC
AGCCTGCAATATCTGCCGGATTCAGATTTGCAGGATATAGCCACTTACCTGAAATCGGTA
AAACCGGTGGATGATGAGAAGCAGAGCGTGCCACGGGACAGCCAGGGACAGCCGTCGGAT
GCCATTATCCGCCTGCGGGGTGCTGATGCAGCCACTCTACAGTCACAACCCGGCGCTGTG
GTATTTGAAGGCAACTGTTCGACCTGTCACGGTGCTGAAGGTGCCGGATCAGGCCAGGGA
TTCCACGCCTATCCGTCACTGTTCCACCACTCCAGCACCGGAGCCATCGATCCTAAAAAC
GTGGTATCGGTGATACTGAACGGTGTTAACCGCCATATGCAACAGGGTGATATTTTTATG
CCATCCTTTGCTCCGCAGTTAAACGATCAGCAGGTGGCTGATGTGGCGAACTTTGTGATG
CAGAAATTTGGCAATCCGGCGGCTGAAAAGTAGACACCAGCCAGGTTTCCAAAGCACGG
AAAAATGCCAGTCTGCCGTTACCGCCAACCTTTGCAGACGGTGCTAATCCG

SEQ ID NO.95 - Orf 3041
ATGATTCGTTCATCTTTTAAGCGCTCACGGAATTTTCTGCCGTTGGCCGGGCTGTTGTTT
TGTGCTGCGGGCTATGCGCAAACCGGATCAGCTCAACCTGATCCGGTGGCAACACAACCC
ACTCCGACTCAGCCAGCGGCCGCTGCCGGTACGCAGGGAACGACCCTGATTCAGCAGGGT
GAGTATCTGGCGAAAGCCGCGGACTGTGAAGTTTGTCATACGGCTACCGGCGGGCAGACC
TTCGCTGGTGGGCTTGGGTTTAAAACCCCGTTTGGCACCATTTTTTCATCGAACATCACC
CCGGATAAAACCCACGGGATTGGTCAGTGGAGTGAGAAGCAGTTCAGTGATGCGCTACGT
TATGGCATCCGTGCTGATGGCAAGAATCTGTACCCGGCAATGCCTTATACCTCTTATTCT
AAGCTGACGGATGCAGACATACATGCCATGTATGCCTTCTTTATGTCGCTGAAACCGGTC
GCCACCGATCCCCCGGAAAATAAGATGGGCTTCCCGTACAATCAGCGTATTGCCCTGAAA

FIGURE 12G

```
GGCTGGAATCTGATCAATTTCCATTACCAGCCGTTTAAGCAGGATCCTGATCAGTCGGCC
GAATGGAACCGGGGTCACTACCTGGCAACGGCGCTGGGACACTGTGAAGAGTGCCATACT
CCACGTAACCTGGCGATGGGCCTGAGCGATAAGTCCTATGCCGGTGCGATGGTGGATGGC
TGGGAAGCATTTAACATCTCTTCGGATAATACTTCCGGGATTGGTCGTTGGAGCCACGCT
GATCTGATGCAGTACCTGAAAACCGGTTCTGTACCAGGTGTGGCTACCACGGGCGGAGGT
ATGGCTGATGTTATTTCTCACAGTCTGCGTTTCCTGAGCAATGATGACCTCAGTGCACTG
GCAACCTATATCAAGAGTGTTCCGCCGCAGAAAACTGCGTCACAAAACCGCTCCGGATAC
GGCGACAATGTTCAGAGTGATATTACTCAGGCGGTTCGCGGCATGCCAATTGATGATTCC
GCACCTTCTGGTGCCGTATTATTTAACGGCAACTGTGCCAGCTGTCACGGGACCAAAGGT
CAGGGGATAGGTGAAAACCGTTACTATCCGTCACTGTCAAATAACAGTGTGGTCGGTGCG
GATAAAGCCAATAACCTGGTTCAGGTGATTCTGTATGGTATCGATCGTACCAACGGCAAA
GGCGAACATATCGTGATGCCTGGCTTTGGTGACGAACTGACCGACAGTCAGATTGCGACC
CTGACTAACTATCTGCGCACCAATTTCGGCACTAATCCTGCGCCGGTTGATGCCGCACAG
GTGAAAGCGCTGCGGGAAAATAACGTGATGGTTATTCCGGGCTACCTGCTGATTTTGGGC
GGAGTCATCGGTGTCATCATCCTTGTTGCCATCATTATGTACTTCGTCGCAGAAAAGCT
GCGCGCAACCACGCGGGC
```

SEQ ID NO.96 - Orf 2420
```
ATGAAACGATTCTCGCGGGTAAAGCTTACCTTACTGGGGTTGTTGTGCGGCGGTCTGACT
TCACTGGCGGCAAATGCAGCTGACATTGACCAGGCGCTATTGCAACAAGGTGAACAGGTG
GCAACAGCCTCTGACTGTCAGGCTTGTCACACCGCACCAGGCAGTAAAACCGCATTCAGT
GGTGGTTATGCAATTGCTTCTCCGATGGGAGCAATATATTCAACCAACATCACTCCGGAT
CCGGCAACAGGTATCGGCAAATACACCGAGCAGCAGTTTATCGAGGCGGTTCGTCATGGT
GTTCGGGCCGATGGTGCCCAACTGTATCCGGCCATGCCTTATACTTCGTACCGGATGATG
ACTGACAGTGACATCCATGCGCTGTATTACTACTTTATGCATGGTGTGAAACCGGTCGAC
CAGCAGAATACAGAAACTCAGCTCTCCTTCCCGTTCAACATGCGTTTTAGCATGAAGTTC
TGGAATCTGCTCTATGCCGACACTAAGACTTTCCAACAGGATCCGCAAAAGAGCGCGGAA
TGGAATCGCGGAAATTATCTGGTCAATGGCCTTGCGCACTGTGACACCTGTCATACACCA
CGTGGCTTTATGATGAATGAACAGACCGACCAGCCGCTGGCAGGTGCTCCTCTGGGAAGC
TGGTATGCACCGAACATTACTTCAGATAAGGTCAGTGGTATTGGCGGCTGGAGTAACGAT
GAGATAGTTCAGTACCTGAAAACTGGCCGTGCAGCAGGTAAAAACCAGGCGGCTGGCGGG
```

FIGURE 12H

ATGGCAGAAGCCGTGGAACACAGTCTGCAATATCTGCCGGACAGTGATTTACAGGCTATT
GCCACTTATCTGAAGCAAACCACACCGATCCGCACCCCGGGCGAGACTCAGGCGGCATAC
AGCTATGGCTCGTCTTCGACCAATGTTGATGATCAGGTCCGTGGAATGGCACCAAATAAT
GCCCGTGACTCATTAACCAGCGGAGCTGCTTTATTCAGCGGAAGCTGTGCCAGCTGTCAC
CAGCCAGACGGTGCAGGAAGCAAGAATCAGACTTATCCTTCGCTGTTCAATAACACGGCG
ACCGGCATGATTCACCCGCAAAACCTGATTGCAACTATCCTGTTTGGTGTCCAACGTAAC
ACTAAAGACCATCAGGTGCTGATGCCAGGTTTCGGTGCTTCAACCTCCTATGTGGATAGC
CTGACCGATCAACAGATTGCGGATATCAGTAACTATGTACTGCATAATTACGGTAATCCT
GCGGTTACAGTGAAAGCAGGCGATGTGGCGTGGGTTCGTAAAGGCGGGCATCCGCCGGCA
CTGGTTGCGCTGCAGCCTTATATGATTCCGGCAATTGCGGTCGGGGTCATTATCATTATC
CTGCTGCTGGTAGCATTCAGACTTCGTCGTAGCCGACGCAAAAGT

Figure 13A

SEQ ID NO. 97 - Orf 3653
ATGTCAGAACAGAACAAAGGGCAGTCTCGCAGGGATTTTTTACTAAAAACGATCACTTTA
GCACCTGCAATGGCTGTCGGAAGCACCGCTATAGGTTCACTTGCTCTTAGCCCGGCAGTA
CAGGCCGCCGATACTCAAACCAGCGGCCCGCAAAAGGCCCGGGATTATCAGCCAAACTGG
TTTACCAAAGAAGAGTTTGCATTTATCACTGCTGCTGTGGCGAAACTGATTCCAGCAGAT
TCCCGTGGCCCGGGAGCCCTTGAGGCGGGTGTACCTGAATACATCGACCGGCAAATGGAT
ACTCCTTATGCCACTGGTTCAAACTGGTATATGCAAGGCCCGTTTGCCCCCGATACGCCG
AAAGAACTGGGTTATCAGTTACCGCTGGTGCCGCGGCAAATTTATCGTCTGGGACTGGCC
GATGCAGATAATTTCTGCAAACAACAATATGGTCACGTGTTTGCTGAGCTCAGCGATGAT
CAGCAGGTCACTGCACTGAAAGCTTTTGAATCTGGTCAGGCTAAATTCACTCAGCTTCCT
GCCACACTGTTTTTTTCCTATTTACTACAGAACACCCGCGAAGGTTTCTTCAGCGATCCG
ATCCACGGCGGCAATCAGGGTATGGCTGGCTGGAAACTGATTGGTTTCCCTGGTGCCCGG
GCTGACTTTATGGACTGGGTCGAACGTGGTGAACATTATCCGTTCCCACCAGTATCAATT
CGCGGAGAAAGGGCA

SEQ ID NO. 98 - Orf 3689
ATGAAAAATACGCCCCGGAGTAAGGACTCCACCGGCAGACGACTTTTTTTACAACGTTCT
CTATCGCTAATCCCTTTAGTTGCAGCCACAGGTACTCCTTTTGCCACCAGCCAGGCTGCC
GAAAAAAAACTCCGGCAGTCACTCAGGATTACGTACCGCAATTTTTTGACCCTCAGCAA
TGGGCGTTTATTAATGCCGCAGTTGATCGGCTAATTCCGGAAGATCAGAACGGGGCGGGA
GCTGTCAGTGAAGGTGTTCCGGTCTACATCGATCGTCAGATGGAACTCCCTTATGGTTAC
GGACACCTCTGGTATATGCAGCCCCCTTTCGCATCCCACAGCGACCCGACCCTGGGCTAC
CAGTCCCCTCTGGTGCCTCGTGAGCTTTATCGCCAGGGGATTGCACTCACTGAGCACTAC
TGCCAGCAAACATTTCATAAGTCGTTTGCTCAACTCACCACCGACCAGCAGGATCAGGTA
TTACAGTTACTCGAAAAGAATACCCTGACGGATAACAATCTGAGTGGTTCGTTATTTTTT
GAGCAACTGCTGGATAACACCAAGGAAGGCTACCTTGCAGACCCGGTACATGGAGGCAAT
CAGACTTTGGCTTCATGGAAACTGATTGGTTACCCGGGGGCTCGTGCAGATTATACCGAC
ACCGTAGCACAGCCAAATGTCCCATACCCGTTGGGCCCTGTGAGTATTTCCGGTAAAAGG
AGTGTC

SEQ ID NO. 99 - Orf 1842
ATGTCAGATAAACCTTCCCATTCCAGGCGTGATTTCCTGCTGAAATCACTCACTCTGATC
CCTGCGGTTTCCGTAGGAGGTGCTATTACCAGCGGTATCGCAGGACCGGGCAATGCTCAG
GCGGCCGAAACCTCTGCTACAGCCGCGACAGCGCAGACTCCCTATTCCCCCGTATTTTTC

FIGURE 13B

AAACCTGACGAGTGGGCATTTGTGAAAGCAGCCTGCGCCCGGCTGATACCTGCCGATGAT
ATGGGGTCTGGCGCGTTGGAGGCCGGGGTGCCTGAATTTCTCGATCGTCACCTGCAGACC
CCTTATGCCAACGGTTCTGTCTGGTATACCCAGGGGCCATTTGTTGAGGCAGGACCGGAA
TTTGGCTATCAGGGTCGTAAAACGCTGAGTGAGATCATTCGTTCAGGGATCCGTGGTGTT
ATCGGCTGGACGCAGAGCAATAAACAGCAGACGTTCGATGCCCTGACCCATGCAGAACAG
GAAGAAATATTGGTGGCATTGGAAAAAGGCAAGATCCATCTGGAAGAGATGGATGCCAAA
ACCTTCTTCGACTACTTCCTGGGTGAAGTGCGCAATGGCTTCTTTGCTGATCCTTCCTAC
GGAGGCAACAAAGGGATGGTTGGCTGGAAGCTGATCGGCTTCCCGGGCATGCGTGCCGAT
TACATAGATTTCATTACCGTCCGCGATAAACCTTATCCGCTCGGACCGGTAGATTTGGCA
GGGAACAGGGGT

SEQ ID NO. 100 - Orf 2037
ATGAAAGAAAATTCTCAACCGCCGGCAGCATCGCGGCGAAAATTTTTACAGACAGCCCTG
GCCATTATTCCTTCTACCGCTCTGGCCACCAGTGTCGTGCCTGCTGCTCTGGCGGCCGAA
CAGACCAAAAATCCCACCCGTGATTATGTGCCGGTCTTTTTTAAAGACGATGAGTGGCGG
TTTATTATCGCGGCCACCGATGTGCTGATCCCGGGGGATGAATATGGCCCTGGCGCCGTG
AGTGAAGGAGTTCCGGTGTTTATCGACCGGCAGATGGAAATGCCTTATGGCTACGGTCAG
TTGTGGTACATGAAACCGCCTTTTCAGGAAGGATCTCCACTGCTGGGTTACCAGAAAAAC
CTGACTCCACGGGATATCTATCGACGGGGGATCGCCGCCCTGAATAAAGCCTGCCAGACC
ACTTATCAGCATCCGTTCGCCTCACTGGCGACAGCAGATAAAGTTCAGGTAATGGAAGAT
TTGGAATCCGGAAAGCTGGTGACCGAAGACGTTGACGGCAAACTGTTTTTTGCACAGTTA
CTGGAAAATACCAAAGAAGGATACCTTGCCGATCCGATTCACGGGGGCAATCAGACAATG
GCCTCCTGGAAAATGATTGGTTTCCCTGGCGCCCGCGCCGATTACGTTCAGGTCATGGAT
AATCCCGGAAAACCTTATCTTCCGGGCCCGGTCAGTATTTCCGGTAAATATGGTGCT

SEQ ID NO. 101 - Orf 2910
ATGAAACAAAGTGGTATCGGGAGGCGTCCGTTTATTATCGGATCTCTGATTGGTATTGCT
TCATTAGGCATGAAGTGTGGTGTAAGTAGTGTTTTTGCAGCTGTCACCTCCCCACTGGAT
GAACTTAACAGTTATCAGCCCGTTTTTTTTAAACCCGAAGAGTGGCAATTCATCATGGCT
GCCTGCGATCGTCTCATCCCACAGGATGAGGAAGGGCCTGGCGCACTTGAAACACATGTA
CCTGTTTTTATTGATAAACAGATGCTAACACCTTACGGGAAAGGTGAGGACTGGTATATG
GAAGGCCCTTTTAATGCGCATGCCAGCACATTATTTGGCTACCAGTTACCTTTTCCATTG
CAGGTTATGTATCAAAGAGGAATTAAAGCCACCAACAGCTATACCCGCCTCCATTTCAAT
CAGGATTTTGCAGCATTAACTGCGGCACAGCAGGATGCTGTCTTATCAGCACTGGAAGAA

FIGURE 13C

AATAAGATCACTTTCTCAGAGTTTTCAGAGCCTGACTTATCAGCCTCATATTTCTTTACC
CGGTTGCTGGAAAATACCAAAGAAGGTTATCTGTCTGATCCTAAATATGGTGGAAATAAA
GGCATGGCAGCCTGGGTAATGATCAACTTCCCTGGTGCCCGCGCCAGTTTCCCTACATGG
ATAAAAATTCACAACGTCAAATATCCATTAGGACCGGTAGCTTTGAATGGTGATGTTGCC
CAATCCTCT

SEQ ID NO. 102 - Orf 1951
ATGTCTGATCCTTCATCGAAAGGGATTAGCCGGCGACGGCTGCTCTCTGGCTCTGCCGCA
GGTTTAACCGTTGCCGCGGTAAGCAGTGCTAATGCCACCACTATCACCGGCATCCCTCGC
TGGATGCTGTTTGACCATAACAGCCCCATCACTCCCACCAGCCCCGGCCTTAAGTTCCTG
ACTCAGGAAGAAGCGACTGAAGTGGATGCTATCGTCAGTCAGTTGATCCCTGCGGATGAG
TTGTCGGTGAGCGGTAAAGATGCCGGTTGTACGGTATTTATCGACCGGCAACTGGCTGGC
AGCTATGGCGATGCCAGCCGCAACTATATGCGTGGCCCTTTCCGGGAAGGAACTCCGGCC
CAGGGTGATCAGTCTCCGTTAGTACCCCGCGAGCGTTACCGTCTTGGACTGGCGGGCTTG
AGTGACTATTGCCAGCAAAAATACCAGAAACTGTTCAGCCAACTGGACAGCGCAACCCGG
GATGAAGTGTTGACCGGACTGGAACAGGGAAAAATCAATCTTACCGGCATCAGCGGCAAG
ATGTTTTTTGATCAGGTTCTAACCAACACCATGGAGGGCTTCTTCTCCGATCCGGTGTAT
GGCGGCAACCGCAATATGGTCAGCTGGAAAATGATTGGTTTCCCTGGCGCTCGTTATGAC
TATCGCGACTATCTGACCAAAACCGATCAGAAACTGGATTTAGTCCCGATTTCCATCATG
GGCAGCACCGCCTGGAACGCGAAGGTA

SEQ ID NO. 103 - Orf 2634
ATGAAGCGAAGAGAGTTTCTGTCATCAATGGCTGCGTTTGGTGCTGCCTCGGCGATCCCG
CTGACCAATGCTGCCGAAATCTCTGGCGGCCAGCCCTGGCCGCCTGGTCAGGTGAGCCTG
CCTCCGGGCTTGCCGAGAAAAGGCGGATTACAGTTTTTTACCCGCCATCAACTGGAAACC
GTCGGAGCAATTGCTGAGCGGTTTATTCCCGCCGATGAATTAAGTATCAGTGGTAAAGAG
GCCGGCTGCGCAATTTTTATCGATCGCCAACTGGCAGGGGATTTTGGCCAGGCTGTCACG
GTGTACCGGCTGGGCCGGTTTGTTAAAGGCACTCCTGAGCAGGGGCCACAGTCACCTCTC
ACCCCGGCAGATCAATATCGTCTGGGCCTGAATGCGCTGGACAGCTATTGCCAGCAGCAG
TTTCACCATAACTTTACTGAGTTGACCGGTGATCAGCAGGACCAGGTTTTGCAGGGCATG
GAAACCGGGAAAATCAGCCTGGCTGAAAACTTTGACAGTAAGGTGTTTTTTGAACTGTTA
CTGCAAAACGTCCGTGAAGGTTTTCTGTCCGATCCCCTGTATGGCGGCAACAAAGATATG
GCCAGCTGGAAAATGATTGGTTTTCCCGGTGCCCGTTATGACTTCCGCGATGTTATCGCC
AAAAAAGGCCAAAAATTAAACATTATTCCTACCAGCCTGATTGATAACAACCTT

FIGURE 13D

SEQ ID NO. 104 - Orf 764
ATGCTTTTGCAAAAAAACACCACGCGCCGCAAATTCCTGCTCGGTTCGCTGATGGCTTTG
CCACTCACCGAACTGGTGCTTAAGGGTCTGACTGCGGCACAGGCAGCCGATATGGCTGCA
CCTGAACTTACCAGCTATAAACCGGCCTTTTTCACCGCTGACGAATGGCAGTTTATTCTG
GCTGCGACCGACCGCATTATTCCTGCGGGCGGACCGGGTAAAGCCCCGGGCGCGCTGGAA
ACTAATGTGCCGATATTTATCGACCAGCAACTCCATGATGAGCATTTCGGTAAGGAAATC
TACATGGAAGGGCCGTTTAACCCGCATGCCCCGGCCACTATGGGGTATCAGGTGCCTCTC
TATCCACAACAGATTTATCAGACCGGTATCCGGCTGACTAATCAGTGGAGCCAGCAAAAC
CTGCAGAAACCTTTCCATCAGTTATCGGAAGCAGATAAAGACAAGGTGCTGACGGGATTA
CAGAAAAACACTCTCGACTTCGCAGCCCTGGGTGAAAACACCCTGAAGGGCTCGTTGTTC
TTCAGTCAGTTGCTCGGAGAAACCAAACACGGTTATCTCGCCGACCCGATGTATGGCGGC
AATAAAGGGATGAAAGCGTGGATTGCGATTGGTTTTCCCGGGCCCGCGCCAGTTATCTG
GAATGGGTAAAACAACATAATGTGAAGTATCCCCTCGGGCCGGTCAGCCTGCTGGGCGAG
ACTGCG

SEQ ID NO. 105 - Orf 3051
ATGCAACGTCGTAAATTTATCAAGACCGGATTAATCCTGGCAGGGACCGGAACTGCAGCA
TCAGTATTTAAACCAGCGGGTGCTGCGGCGCGCGATAATATACTGAATGGCGGAAAACTG
TGGAAAGCTAAAGAAACACCACCGCCGACTCCGGCTGATCCAACCAAACGTCTCTATCTG
ACCGAACAGGAATATGCCCAGATCACCGCGATTTTTAACCGGCTGATCCCTGCAGATGAA
CTGACTGTCAGCGCCTCCGATGCGGGCTGTGTTGTTTTATCGATAACCAGTTAGCCGGA
AATTATGGTAAAGCCAGCTGGCGCTATAATGTTGGCCCGTTTGAAAATGGTACGCCTTCC
CAGGGTAACCAGCAGCCTTACACTCCGGCTCAGATTTACCGTATTGGTTTGGCCGAAATA
GAAAAAGACTGTCAGAGTAAATTTTCAAAATCCTTCAGCGAACTAACTAATGATCAGCAG
GATAAATATCTGGAACAGATGGAAGCCGACCAGATTAAATACCCTACCCTGTCATCCAAA
GATGTATTTAGTCAGTTCTTATCCAATGTACAGGAAGGTTTTCTTGCCGACCCGATATAT
GGTGGTAACCGCAATATGATTGGCTGGAAAATGATTGGTTTCCCGGGAGCACGTTATGAC
TATCGTGATTATGCCCCACTGAAAGGAACTAAATTAAATATCGAACCGGTCAGCATTATT
CAACTCCTGAAAGCA

SEQ ID NO. 106 - Orf 1748
GTGAAGCGCAGGCGTTTTTTGGCTTCTCTCGGAGTATTGCTTATCAGCACTGCTCTGAAA
GTTAAAGCAAAGATTATTTCCGGCGGTATGCCGTGGGTCGTGCATGCTGTTAAGCCACCG

FIGURE 13E

CAACCAGTAGTCGCGGGGGAATGGCAGTTTTTTACACCAGAAGAAGTGGCGATAATTGAA
GCTATTGCTGACCGGATAATCCCTCAGGATGAACTGAGTATTGGCGGAAAAGAAGCGGGT
TGCGCATTATTTCTCGACCGCCAGTTAGCGGGAGATTACGGCAAAGCAGTCAGTATATAT
CGTCTTGGACCGTTTATTCAGAATGGTTTACCGGAGGCGGGCCCGCAATATAAAGATGTC
CCTGCAGAACGTTACCGGTTGGGTCTGGCGTCAGTAAATGAAATCAGCCAGGCCAAATAC
AATGGTAAAAGTTCAATGAAATCAGTGAAGAACAACAGGATGATTTACTGGGTAAAATC
GAATCGGGAGTATTACCACTCACCGGAGTCGACGGTAAGTTATTTTTTGATCAGTTGGTC
ATAAATATGCGTGAAGGATTTTTTGCCGATCCATTATATGGCGGAAATAAAGATATGGCT
GGCTGGAAAATGCTCGGTTTTCCCGGCGCGCAATATGATTTCCGTGATGTGATTGATAAA
CGAGGCGAAGAATTGAATATCAAGCCGGTCAGCATGGTAACTAACAACGATCAATCT

Figure 14A

SEQ ID NO. 107 - Orf 3819
ATGACAGCAAATAATCGCCATCCTTCCGGGGTTTCACGCCGTCGTCTGCTGCAGGGTATG
GGCATTCTGTCGGTTGCCGGGTTATGTGGTTCACTGTTTCCTTCTTTTCGTGCAGCAGCA
GCAGAACTGCAGGACAGTGGTTTTATCCCGTTATCTGAATTTCTGGTTAATCGCCGGGTG
AACCCAATTCTGGCTCAGCGTTACTACGATGCATTGCATCGCCATGATGAAAAATTTGAT
CAGAAGCTGGCATTGCTTAAACAGGATATTCAGCCAGGAAAGTATCAAAACATTGATGAT
TTTCTTCAAAAAAATGCCGTCGGAACAGATTTACGACAGGCAGCAGGTCAGGTCATTTCT
GCCTGGTACACCGGAGTGGTAGGCAACGACGAGAAACTGGAACTTATCGCATATGCAGAC
GCGATGATGTATGTGCCCACCAGTGGCGTTCTTGTGGTTCCAACCTATGGCAGTGGCCCG
ATTTCCTGGGCTGCCGTTGACAATAAACCCGCACACCAGGGGCCGGCTGTA

SEQ ID NO. 108 - Orf 2447
ATGAAACTCACAGATACTATTTCGACAGATCGCCGAAAACTGATTAAGTCATTATCGTTG
CTGACCGTATTCTCTGTGAGTGGGTTACGTCTGGTGACCTGTCCGGCATTTGCTGGCGGT
TTGCCTGCCAGTGCGGATTTTCATGAATTCTCAACCTTTGTTATTGGCCGGCCAGTAGAT
CCTGTTTTATCAGGCCGTTATTTTGCCGCATTGCAGGCTGCAGACGGACATTTCATTCAA
CAACTGAATCAGGCGATGGTTGCCAGTGTCCCGTTTCGCAGTCAGGGGATTGATACGATG
CTGGCATCACTCCCTCACGACAGTGACATCTTTAATACCCTTAAAAAAATCACCTCAGCC
TGGTATCTGGGAATCGTCGGCGAAGGCGCCGGGGCGACTCTGATCGCCTTCCATGACGCA
CTGATGTTCCAGCCAACCCGTGAATACGTTTTTGTTCCCGGTTATGGCGGGGGCCCTGAC
AGTTGGGTCTCACTTAAACATCCCGACTTACTGAGCGAAGATACCGAGCAGGAACAGAAA
AATGGC

SEQ ID NO. 109 - Orf 3676
ATGAAAAATGAAATTATTCGGGATGACTCTCCTGCTGAATACAATTTGTCCCGCAGAAAG
GTGCTGCTTGGTGGTCTTATTTTATTAGGCAGTAGTTATCTGGGCCCATCGCTTCCGGCC
TGGGCAGATACGTTAAATGACCAGGCTACCATCGACCAGTTTATGCAGTTATCACAATTA
CTTGTTAATCATCAGCTTGATCCGGTAACAGGGCAGCGTCTGGCTGCTGCGATGATCAGT
GGCAACATGATTACACGGCAACAGATAACCAGTCTGCTGGCTGTAGCTCAGGCCCGTCAG
GCAAAAGTGGTTGAGGATTTTTTCTCAGATATTCCACAGGGTGAGCTGAAAAATGCGGCT
CTCAGCATTATCTCTGCCTGGTATAAAGGTGTACTGATTGATGCACCCGGGGCTGAGGTG
TTTGCTTATGAAAAAGCCTTAATGTATCAGCCGACTATCGATGTGATGACCATTCCGACC
TATGCCATTACCGGCCCTAATGGCTGGAGCTCCCATGCAGCTCCGCTGGCCGATATGCCG
GACTTC

FIGURE 14B

SEQ ID NO. 110 - Orf 1219
ATGATTGATATGTTAAATATGATATCGCGCAGGCGCATATTGCAGGGGATGGGGGCATTG
GCCGCCACAACATTACTTCCGTCTGGTATTTTACCGGCATTCGCGGATACTCCTGCAAAC
AGCGACTTTAACGATATATCCAGGTTGTTAACCGGCCGCAATACTTTATCGGCTGAATTT
AGTAGCGCGCTTTTTTCTGCCTTCACGAAAATTGATAGCCGCTTCCCACAGCAACTGGCT
CGCCTGAAACAGTGGATCACTGCTAATTCCGTCCCGGCAGCTGACCTGCAGAAACGTCTG
ACCGCCGACAGCTCTGTCGCGGATCTGGCCGGATTACCGGCACTGATTCTGACCGGCTGG
TATCTGGGTATTGCCGGCAGCGGCGACAAAGCTGTCTGCGTCACCTATGTCGATGCTCTG
GCAAATCAGGAAGTTGCATCGGTGCTGAACCCGCCTACCTACGCCTATGGCGCCTATGGC
AGTTGGGCCACAAAACCTTTT

SEQ ID NO. 111 - Orf 1957
ATGAATAACCATAATGCACCTGAAACACAGCCTGAGCTGAGTGAAGAGGGGTTGCGTCGC
CGAAAGCTGTTCGGACAGACGGGCGGGTTGGTGGCTTCCTTCGCCATTGGCTCCGCAATA
GCTGGCAGCACACTCAGTAATGGTGCCAATGCAGCAACCACTTCTGCCGGGCCTGATACT
CAGACCCTGAATCAGTTTATGAAAACCTCCCGTCTTCTTACCGGCCATCAGAACCTCGAT
CTTACCCTGGGTCAACGTCTGTACGTGGCATTCAGCGAGAAGGACCCACAGTTCATTACC
CAGCTGTCAGCCTTGAATCAGTGGATTGCCGATAAACAACCGGCAGATGTAGAGGCCCTT
GACAGCCAGTTGTCAGGACAGCCGCTGCATGCCCTGATGATGTCGGTGATTAAAGGCTGG
TATCTCGGAGTCATTGATGACAGTCACCATGCCAAAGTCTATGCCTATCAGAATGCCCTG
ATGTACCAGGTACCGCGTGATGGCATGGTCATCCCTACCTATGCGCATAACGGACCGGAC
TACTGGACTGCAGATCCACCACCGGTCGATCGACTTCTGAACTTC

SEQ ID NO.112 - Orf 3043
ATGAATAAGGCTACACCTGTCAGCCCCGGTGAAAGACGACGCTTTATTAAGTTGTTAGCA
GCATCAACGGTGGCGGGAACAGTCAGCAGTTTATTGCCGGGCCAGATAGCCTGGGCAATT
GATGCCGGGCAGCCGGCGGTCGCCGGTTTTCCGGCATTTATGACGGTATCTGAAATTATT
TGCGGCTATCCGACTCTGGATAATGCACTGGGCAAACGTATTTTCAGCCTGATCAGTGCT
GAGCACGGTGATGCTTCTCAGAGTATTGCCGAGCTGCAAAAGCAACTGAATGCAGATATG
TCCTCTGCCGAAATGCAGGCGGCGTTGAAAACACTGGATACCCGGCACAACAGCTGTTC
AGTGAAATTTTGCGCGGCTGGCAAATTGGTATTGTCGGTAGCGGTAAGCAATCACAGGTC
GTGGCTTATGAGTACGCACTGATGTACGCGCCGATTTCAGATGTTGTCGTCCTGCCGACG
TTTGCCCGTGGTGAACCCCATTACTGGGCATACCCTCCTGTGATTAAGACCGGAAAGCTG

FIGURE 14C

SEQ ID NO. 113 - Orf 1982
ATGAAATTTGTTATAGATCAGGAATCTGATACAGGGGAAATCTCTGCATCACGCCGTAGT
TTCCTGATAAAAATAACTGCATTATTAGCCTCATTCACCTTGATTCCGGCACATGCTGTT
ATTACCACTCCAGCTGACGTTGGTGCATCAGTGATATCGCAGTTACAGACAACCGCTCAA
TTCTTAACCGAAAGCCAGCAGGATCCTCAACTGATTATCCGTGCAGCTAACGCCCTGCTA
AAAGTTAACAGTAATTTTGCCGGTGATCTGCAACAGCTTTCTTCATTGATTGCAGACAAT
CACATAGCCAACTTAAAAGACCTCAAAACCTCAAATCTTTTTGAGGGCAAACCACAGCAA
ACCGCGAAAGACATTTTGTCTGCCTTATATCTTGGCTATGCCGGAACACCGGTGATGTTG
TCATCGGAAGATAATGTCGTGTTTGTTGCCTATGCCCAGGCACGCACGTATCAGCTCACC
AAAGATTTCACCCCGGTCCCCAGCTACTCCCGCTGGAAAAGTGGCTACTGGGCGCATTTG
CCGGCAGGCGTT

SEQ ID NO. 114 - Orf 3398
ATGAATCTTACACGCCGCCGGTTGCTGACCGGCTCGGCGGGGCTGATAGTGGCTGGCGTA
TTGTCGCAGACTCTGTCAGGCCGCTATGCGCTGGCCAGTCCGCCACTGGCTTCCGCAGTC
GCCCCCTCCGCCGGATTTAACACATTATCGGTACTGATTACCGGTCAGGATAAGCCCGAT
GCCCTGCTGGCGCAGCGCCTGTACAGCTGGTTAGCAGCCCATACTTCCGGTCTGGACAGT
CAGTTGGAGACGCTGAGCTCACTGCTGCAACAACACTCTGATGCTAATGGCAGCACCCTG
CTTAGCCTGATGAAATCGCAGCCAGAAAATATTAATACACTCTATCAGTCACTGGTGTCT
GGCTGGTATCTCGGTGTTGTCGGGCCACTGCCGCGTCCGGACTGCATCGCCTTCGAAAAT
ATTGTCAGCTACCAACTGCTCAAACAATCTGTGTTACCGCCAAGCTACGCGCCGGGCCAA
CCAGGATTCTGGGTGCAGCCACCTGCGGGGAGAGTACATGTC

SEQ ID NO. 115 - Orf 2418
ATGAAGCAAATATTTGAGCAAAGTCATACCGATCTACCGGAAAATGGAACCGGTTCCAGT
CGCAGAGGATTTATTAAGTCCGCTCTGGTATTAACTGCCAGTGGTCTGGTCGCGTCTCTG
CCATTGCGTAGTTTCGCCAGCAGTGTGGTTCATGGTGGCGATACCACTCAGGACTTTATC
AGTGTTTCGCAGGCAATCACCGAACACAAACATATCAACCCACAGTTAGCCGCTCATTTC
CTGAGTGCGTTTATCAAAAGGGATAATCAGTTCAGCAGCAAAATTACCCGACTTGCGCAG
CTCTACCAGACGGGTGATACAGCTATTGTATTTAAAAACAAAGCGGTAGCCGCCGGGCTT
GGCGATTTTCTGCAGCAGATCCTGACCGCCTGGTATACCGGAACGATTGGTGATGACTAC
AAAGGCACTCTGGTCGCTTACAAAGAAGCGCTGATGTACGACACCGTGAGCGATGGCTTA
GTGGTCCCGACCTATTGCGGCAATGGCCCGCTTTGGTGGACAGTGCCGGTCCCCGACCCA
CTCGATCCTGAACTGATCAACAACCTG

Heme-binding site 3
FIGURE 16B

SEQUENCE LISTING

<160> NUMBER OF SEQ ID NOS: 182

<210> SEQ ID NO 1
<211> LENGTH: 589
<212> TYPE: PRT
<213> ORGANISM: Pantoea citrea

<400> SEQUENCE: 1

```
Met Ala Gln Ile Thr Lys Lys Glu Val Asp Val Val Cys Gly Phe
 1               5                  10                  15

Gly Trp Ala Gly Ser Leu Met Ser Ile Glu Leu Ala Met Ala Gly Leu
                20                  25                  30

Thr Val Arg Ala Leu Glu Lys Gly Pro Glu Arg Asp Tyr Glu Ala Phe
            35                  40                  45

Ala Thr Pro Lys Pro Ala Asp Glu Tyr Ala Tyr Ala Val Arg Asn Lys
        50                  55                  60

Val Met Thr Thr Pro Ala Asp Ser Ala Val Thr Val Arg Tyr Thr Met
65                  70                  75                  80

Gln Asp Thr Ala Leu Pro Thr Arg Lys Trp Gly Ala Phe Val Pro Gly
                85                  90                  95

Gly Gly Val Gly Gly Ala Gly Met His Trp Thr Gly Val Leu Leu Arg
            100                 105                 110

Pro Thr Pro Thr Asp Ile Lys Leu Lys Thr Tyr Ala Asp Glu Ala Tyr
        115                 120                 125

Lys Pro Gly Val Leu Gln Glu Asp Met Arg Val Arg Asp Phe Pro Phe
    130                 135                 140

Thr Trp Asn Glu Ile Glu Pro Trp Phe Glu Lys Phe Glu His Ile Cys
145                 150                 155                 160

Gly Leu Ser Gly Asn Thr Gly Asn Leu Arg Gly Gln Ile Met Glu Gly
                165                 170                 175

Gly Asp Pro Phe Glu Gly Pro Arg Ala Asn Pro Met Pro Leu Pro Ala
            180                 185                 190

Leu Glu Asn Thr Leu Asn Asn Val Met Phe Gly Asp Thr Val Lys Lys
        195                 200                 205

Met Gly Tyr His Pro Phe Thr Ile Pro Ser Ala Ala Ala Ser Arg Val
    210                 215                 220
```

-continued

```
Trp Thr Asn Pro Tyr Gly Asn Thr Ile Ala Pro Cys Asn Tyr Cys Gly
225                 230                 235                 240

Tyr Cys Ser Lys Tyr Pro Cys Leu Asn Tyr Ser Lys Ala Ser Pro Gln
            245                 250                 255

Thr Ala Val Leu Asp Ser Leu Lys Gln Met Asp Asn Phe Ser Tyr Glu
        260                 265                 270

Val Asn Ala Glu Val Leu Arg Val Leu His Asp Lys Lys Thr
    275                 280                 285

Ala Lys Gly Val Ile Tyr Ile Asp Glu Gln Gly Asn Glu Cys Phe Gln
290                 295                 300

Pro Ala Lys Ile Val Ile Leu Ser Ser Phe Gln Phe Tyr Asn Val Arg
305                 310                 315                 320

Leu Met Leu Leu Ser Gly Ile Gly Gln Pro Tyr Asn Pro Val Thr Glu
                325                 330                 335

Glu Gly Val Val Gly Arg Asn Tyr Ala Phe Leu Ser Asn Gly Ser Ala
            340                 345                 350

Thr Leu Phe Phe Lys Asp Lys Asn Phe Asn Pro Phe Val Ser Ser Gly
        355                 360                 365

Pro Thr Gly Met Gln Phe Asn Asp Ile Ser Pro Gly Asn Phe Asp Gly
    370                 375                 380

Pro Gly Leu Gly Ile Ile Gly Gly Ala Lys Ile Gln Ser Ala Gln Ser
385                 390                 395                 400

Thr Gly Thr Pro Ile Ser Thr Ala Leu Pro Pro Gly Thr Pro Ser Trp
                405                 410                 415

Gly Ala Gly Trp Lys Glu Gly Leu Glu Asn Trp Tyr Gly His Ser Met
            420                 425                 430

Lys Val Gly Ile Thr Thr Ser Cys Met Ser Tyr Arg Asp Val Tyr Leu
        435                 440                 445

Asp Leu Asp Pro Thr Tyr Lys Asp Arg His Gly Gln Pro Leu Leu Arg
    450                 455                 460

Met Thr Phe Asn Trp Lys His Asn Glu Leu Gln Leu Gln Gln Tyr Leu
465                 470                 475                 480

Lys Gly Ile Val Gly Asn Ile Val Lys Glu Met Asn Pro Asp Ser Phe
                485                 490                 495

Ser Met Ser Phe Leu Pro Met Gly Ala Asp Phe Asp Leu Thr Lys Tyr
            500                 505                 510

Val Ser Thr His Asn Val Gly Gly Ala Ile Met Gly Asp Asp Pro Lys
        515                 520                 525

Thr Ser Ala Leu Asn Arg Tyr Leu Gln Ser Trp Asp Val His Asn Val
    530                 535                 540

Phe Val Pro Gly Gly Asn Ala Phe Pro Gln Asn Phe Gln Ser Asn Pro
545                 550                 555                 560

Thr Asn Thr Ile Gly Ala Ile Thr Leu Met Ala Ala Asn Ala Ile Lys
                565                 570                 575

Glu Gln Tyr Leu Lys Asn Pro Gly Pro Met Val Gln Val
            580                 585

<210> SEQ ID NO 2
<211> LENGTH: 589
<212> TYPE: PRT
<213> ORGANISM: Pantoea citrea

<400> SEQUENCE: 2

Met Lys Ile Thr Asn Glu Pro Val Asp Val Ile Val Gly Leu Gly
1               5                   10                  15
```

-continued

```
Trp Thr Gly Ala Ile Gln Gly Ile Glu Leu Ala Arg Thr Gly Leu Lys
            20                  25                  30

Ile Arg Ala Leu Glu Arg Gly Ala Asp Arg Thr Ser Ala Glu Phe Ala
        35                  40                  45

Tyr Pro Val Pro Ala Asp Glu Leu Ala Tyr Thr Lys Arg His Lys Ile
50                  55                  60

Met Gln Ser Pro Ala Val Ala Ala Phe Thr Thr Arg His Asn Leu Asn
65                  70                  75                  80

Glu Val Ala Leu Pro Met Arg Glu Leu Gly Ser Phe Arg Leu Gly Asp
                85                  90                  95

Gly Val Gly Gly Ala Asp Leu His Trp Thr Ala Met Ile Thr Arg Pro
                100                 105                 110

Thr Pro Val Asp Leu Lys Leu Ala Thr Tyr Ala Arg Glu Lys Phe Glu
            115                 120                 125

Lys Ser Gln Leu Asp Lys Glu Leu Arg Ile Tyr Asp Phe Pro Val Ser
        130                 135                 140

Trp Ser Glu Ile Glu Pro His Met Asp Phe Phe Asp Gln Val Cys Gly
145                 150                 155                 160

Ser Ser Gly Gln Ala Gly Asn Val Arg Gly Gln Ile Leu Pro Gly Gly
                165                 170                 175

Asp Pro Phe Glu Gly Pro Arg Ser Ser Pro Phe Pro Asn Pro Pro Leu
            180                 185                 190

Ile Asp Thr Leu Asn Ser Ser Met Phe Arg Gln Ala Ala Thr Glu Met
        195                 200                 205

Gly Tyr His Pro Tyr Ser Ile Pro Ser Ala Ala Val Ser Gln Ala Phe
210                 215                 220

Thr Asn Pro Tyr Gly Gln Gln Ile Ala Pro Cys Asn Tyr Cys Gly Tyr
225                 230                 235                 240

Cys Gln Phe Tyr Ser Cys Leu Asn Tyr Ser Lys Ala Ser Pro Gln Thr
                245                 250                 255

Ala Ile Leu Asp Arg Leu Lys Gln Tyr Asp Asn Phe Asp Tyr Lys Thr
            260                 265                 270

His Ala Asn Val Ile Arg Val Glu Lys His Ala Asp Gly Lys Thr Ala
        275                 280                 285

Thr Gly Val Thr Tyr Ile Asp Glu Asn Asp Asn Glu Val Phe Gln Pro
290                 295                 300

Ala Lys Ile Val Ile Leu Ala Ser Phe Gly Leu Asn Asn Val Arg Leu
305                 310                 315                 320

Leu Leu Asn Ser Lys Ile Gly Gln Pro Tyr Asn Pro Val Thr Glu Glu
                325                 330                 335

Gly Val Val Gly Arg Asn Tyr Thr His Gln Tyr Gly Gly Gly Ile Thr
            340                 345                 350

Leu Tyr Phe Asn Gln Leu Glu Phe Asn Pro Phe Ala Thr Ala Gly Pro
        355                 360                 365

Thr Gly Val Val Ile Thr Asp Phe Gly Thr Gly Asn Ile Asn Thr Ala
370                 375                 380

Asp Leu Gly Phe Ile Gly Gly Ala Lys Ile Tyr Ser Ser Gln Pro Thr
385                 390                 395                 400

Gly Thr Pro Met Gly Ala Pro Val Ile Asp Ser Ala Ala Lys Trp Gly
                405                 410                 415

Ser Arg Trp Lys Lys Gly Leu Lys Gln Ser Tyr Gly His Ser Met Ala
            420                 425                 430

Ile Lys Leu Glu Gly Ser Asn Met Ala Thr Gln Thr Asn Tyr Leu Asp
        435                 440                 445
```

```
Leu Asp Pro Asn Tyr Lys Asp Lys Phe Gly Met Pro Leu Leu Arg Val
    450                 455                 460

Thr Tyr Asp Tyr Val Gln Asn Asp Leu Arg Met Leu Gln Phe Met Arg
465                 470                 475                 480

Glu Lys Met Val Gly Ile Ala Glu His Leu Lys Pro Asp His Tyr Ser
                485                 490                 495

Val Gly Met Leu Lys Met Asp Ser His Phe Ala Ser Ser Pro Ala Tyr
            500                 505                 510

Ala Asn Thr His Asn Ala Gly Ala Ile Met Gly Asp Asn Pro Lys
        515                 520                 525

Thr Ser Val Val Asn Arg Tyr Leu Gln Ser Trp Asp Val His Asn Val
    530                 535                 540

Phe Val Met Gly Ala Cys Val Phe Pro Gln Asn Val Tyr Ala Asn Pro
545                 550                 555                 560

Thr Ala Leu Val Ala Gly Leu Thr Tyr Trp Ser Ala Lys Ala Ile Arg
                565                 570                 575

Glu Thr Tyr Leu Asn Asn Pro Gly Pro Leu Val Gln Ala
            580                 585

<210> SEQ ID NO 3
<211> LENGTH: 592
<212> TYPE: PRT
<213> ORGANISM: Pantoea citrea

<400> SEQUENCE: 3

Met Ala Thr Thr Lys Lys Pro Ala Ala Asp Ile Val Ile Val Gly Phe
1               5                   10                  15

Gly Trp Thr Gly Ser Leu Met Ala Arg Glu Leu Ala Asp Ser Gly Leu
            20                  25                  30

Lys Ile Val Ala Leu Glu Arg Gly Glu Gln Arg Asp Thr Tyr Pro Asp
        35                  40                  45

Phe Ala Tyr Pro Arg Ile Thr Asp Glu Leu Thr Tyr Gly Ile Arg Leu
    50                  55                  60

Lys Leu Phe Gln Asn Ala Ala Arg Glu Thr Val Thr Val Arg His Thr
65                  70                  75                  80

Ser Ser Gln Thr Ala Leu Pro Tyr Arg Arg Phe Gly Ser Phe Leu Pro
                85                  90                  95

Gly Asn Gly Val Gly Gly Ala Gly Val His Trp Asn Gly Met Leu Trp
            100                 105                 110

Arg Pro Leu Ala Ala Asp Leu Lys Met His Ser Thr Leu Val Glu Lys
        115                 120                 125

Tyr Gly Ala Asn Phe Ile Pro Gln Asp Met Thr Val Gln Asp Tyr Pro
    130                 135                 140

Phe Thr Tyr Glu Glu Met Glu Pro Phe Phe Asp Lys Phe Glu Lys Ile
145                 150                 155                 160

Cys Gly Ala Ser Gly Gln Ala Gly Asn Leu Asn Gly Glu Ile Gln Ser
                165                 170                 175

Gly Gly Asn Pro Phe Glu Gln Pro Arg Gln Asn Pro Tyr Pro Thr Lys
            180                 185                 190

Pro Leu Gln Arg Leu Tyr Ala Gly Asp Val Phe Ala Lys Ala Ala Glu
        195                 200                 205

Lys Met Gly Tyr His Pro Phe Pro Cys Pro Ala Ala Asn Cys Thr Glu
    210                 215                 220

Ala Trp Thr Asn Pro Tyr Lys Val Gln Leu Gly Val Cys Asn Tyr Cys
225                 230                 235                 240
```

Gly Phe Cys Glu Arg Phe Gly Cys Phe Asn Tyr Ser Lys Gly Ser Pro
                245                 250                 255

Gln Ser Cys Val Ile Pro Ser Leu Lys Ala Tyr Asp Asn Phe Glu Leu
            260                 265                 270

Arg Thr Asn Ala Gln Val Ile Arg Val Asn Thr Asp Asn Thr Gly Lys
        275                 280                 285

Gln Ala Thr Gly Val Thr Tyr Ile Asp Gly Ser Gly Asn Glu Val Glu
    290                 295                 300

Gln Pro Ala Ser Leu Val Ile Leu Ser Ala Phe Gln Leu His Asn Val
305                 310                 315                 320

Arg Leu Leu Leu Ser Lys Ile Gly Lys Pro Tyr Asp Pro Gln Thr
                325                 330                 335

Gly Glu Gly Val Val Gly Arg Asn Tyr Ala Tyr Gln Met Thr Gly Gly
                340                 345                 350

Ser Lys Leu Phe Phe Gly Pro Asp Gln Asp Phe Lys Pro Phe Ala Ala
            355                 360                 365

Thr Gly Thr Thr Ala Thr Phe Ile Asp Asn Phe Asn Ala Glu Asn Phe
        370                 375                 380

Asp His Ser Ser Leu Gly Phe Val Gly Gly Ser Thr Ile Ser Ala Ala
385                 390                 395                 400

Phe Ser Gly Gly Arg Pro Ile Gln Gln Thr Leu Leu Pro Ser Asp Ala
                405                 410                 415

Pro Arg Trp Gly Ser Gly Trp Lys Thr Ala Ile Lys Thr His Tyr Ala
                420                 425                 430

His Thr Met Ser Ile Gly Ala Ser Gly Ser Val Met Pro Tyr Arg Gln
            435                 440                 445

Cys Tyr Leu Asp Leu Asp Pro Thr Tyr His Asp Val Asn Gly Gln Pro
        450                 455                 460

Leu Leu Arg Met Thr Phe Asp Trp Gln Pro Asn Glu Leu Lys Met Thr
465                 470                 475                 480

Glu Phe Ile Gly Gly Lys Val Glu Ile Ile Lys Val Ile Asn Pro
                485                 490                 495

Pro His Tyr Glu Met Gly Phe Met Asn Met Asn Ser His Tyr Asp Val
            500                 505                 510

Arg Pro Tyr Gln Ser Thr His Thr Thr Gly Gly Ala Val Met Gly Asp
        515                 520                 525

Ser Pro Arg Thr Ser Val Val Asn Lys Tyr Leu Gln Ser Trp Asp Val
    530                 535                 540

Pro Asn Leu Phe Val Leu Gly Ala Cys Cys Phe Pro Gln Asn Leu Ala
545                 550                 555                 560

Tyr Asn Pro Thr Gly Ile Val Cys Ala Thr Ala Leu Phe Ser Ala His
                565                 570                 575

Ala Ile Lys Thr Arg Tyr Leu Ala Pro Gly Pro Leu Val Thr Ile
            580                 585                 590

<210> SEQ ID NO 4
<211> LENGTH: 591
<212> TYPE: PRT
<213> ORGANISM: Pantoea citrea

<400> SEQUENCE: 4

Met Thr Ile Lys Lys Asp Pro Val Asp Val Ile Val Gly Phe Gly
1               5                   10                  15

Trp Thr Gly Ser Val Met Ala Met Glu Leu Ala Glu Thr Gly Leu Lys
                20                  25                  30

Ile Val Ala Leu Glu Arg Gly Glu Gln Arg Asp Thr Tyr Pro Asp Phe
              35                  40                  45

Ala Tyr Pro Arg Ile Val Asp Glu Leu Thr Tyr Gly Val Arg Leu Lys
         50                  55                  60

Leu Phe Gln Asn Leu Ser Asn Glu Thr Val Thr Val Arg His Ala Pro
65                  70                  75                  80

Gly Asp Leu Ala Leu Pro Tyr Arg Lys Met Gly Ser Phe Leu Pro Gly
                 85                  90                  95

Asp Gly Val Gly Gly Ala Gly Val His Trp Asn Gly Leu Leu Trp Arg
             100                 105                 110

Pro Leu Glu Thr Asp Leu Arg Leu Lys Ser Thr Ile Thr Glu Lys Tyr
         115                 120                 125

Gly Ala Ala Phe Ile Pro Gln Asp Met Thr Leu Gln Asp Tyr Pro Phe
             130                 135                 140

Thr Tyr Ala Glu Met Glu Pro Phe Phe Thr Arg Phe Glu Lys Ile Cys
145                 150                 155                 160

Gly Ala Ser Gly Gln Ala Gly Asn Ile Asn Gly Glu Ile Gln Gln Gly
                 165                 170                 175

Gly Asn Pro Phe Glu Ala Pro Arg Ser Gly Ala Tyr Pro Thr Ser Ala
             180                 185                 190

Leu Lys Ser Gln Tyr Ser Gly Glu Leu Phe Gly Lys Val Ala Lys Glu
         195                 200                 205

His Gly Tyr Ser Pro Phe Pro Gly Pro Ala Ala Ile Cys Thr Glu Ser
             210                 215                 220

Tyr Gln Asn Pro Tyr Gly Val Gln Leu Gly Val Cys Asn Tyr Cys Gly
225                 230                 235                 240

Phe Cys Glu Arg Phe Gly Cys Phe Asn Tyr Ser Lys Ala Ser Pro Gln
                 245                 250                 255

Thr Cys Val Ile Pro Ala Leu Arg Gln His Thr Asn Phe Glu Leu Arg
             260                 265                 270

Thr His Ser His Val Ile Arg Val Asn Lys Asp Ser Thr Gly Lys Lys
         275                 280                 285

Ala Thr Gly Val Thr Tyr Ile Asp Ala Asn Gly Gln Glu Val Glu Gln
         290                 295                 300

Pro Ala Ala Leu Val Val Leu Gly Ala Phe Gln Leu His Asn Val Arg
305                 310                 315                 320

Leu Leu Leu Leu Ser Gly Ile Gly Gln Pro Tyr Asp Pro Arg Thr Gly
                 325                 330                 335

Glu Gly Val Val Gly Arg Asn Tyr Ala Tyr Gln Val Asn Gly Gly Val
             340                 345                 350

Lys Leu Phe Tyr Asp Lys Asp Gln Tyr Phe Asn Asn Phe Ala Ala Thr
         355                 360                 365

Gly Cys Ser Gly Thr Tyr Ile Asp Asn Phe Asn Gly Glu Asn Phe Asp
             370                 375                 380

His Ser Ser Leu Gly Phe Ile Gly Gly Thr Ile Ser Ala His Ala
385                 390                 395                 400

Thr Gly Gly Arg Pro Ile Gln Gln Thr Glu Leu Pro Ser Gly Ser Pro
             405                 410                 415

Lys Trp Gly Thr Gly Trp Lys Lys Ala Met Lys Asp Asn Tyr Leu His
         420                 425                 430

Ser Met Ser Val Gly Ser Ala Ser Val Met Pro Tyr Lys Gln Cys
435                 440                 445

Tyr Leu Asp Leu Asp Pro Thr Tyr Thr Asp Gly Tyr Gly Leu Pro Leu

```
              450                 455                 460
Leu Arg Met Thr Phe Asp Trp Gln Glu Asn Asp Leu Arg Val Thr Gln
465                 470                 475                 480

Phe Val Ala Gly Lys Thr Glu Glu Leu Val Lys Ala Leu Lys Pro Arg
                485                 490                 495

Ser Tyr Asp Met Gly Phe Lys Lys Leu Asn Thr His Tyr Asp Val Arg
                500                 505                 510

Pro Tyr Gln Ser Thr His Thr Thr Gly Gly Ala Val Met Gly Asp Asn
                515                 520                 525

Pro Arg Thr Ser Val Val Asn Lys Tyr Leu Gln Ser Trp Asp Val Pro
                530                 535                 540

Asn Val Phe Val Leu Gly Ala Cys Cys Phe Pro Gln Asn Ile Ala Tyr
545                 550                 555                 560

Asn Pro Thr Gly Ile Val Gly Ala Thr Thr Leu Phe Ala Ala His Ala
                565                 570                 575

Ile Lys Thr Gln Tyr Leu Arg Asn Pro Gly Pro Leu Val Gln Ala
                580                 585                 590

<210> SEQ ID NO 5
<211> LENGTH: 591
<212> TYPE: PRT
<213> ORGANISM: Pantoea citrea

<400> SEQUENCE: 5

Met Ala Ile Val Lys Asn Lys Thr Asp Val Ile Val Gly Met Gly
1               5                   10                  15

Trp Thr Gly Ala Ile Met Ala Lys Glu Met Thr Asp Ala Gly Leu Ser
                20                  25                  30

Val Val Ala Leu Glu Arg Gly Ala Asp Arg Asp Thr Glu Pro Asp Phe
            35                  40                  45

Ala Tyr Pro Gly Val Val Asp Glu Leu Gln Gly Ser Val His Arg Arg
        50                  55                  60

Tyr Leu Gln Ser Leu His Gln Glu Thr Val Thr Val Arg His Asn Thr
65              70                  75                  80

Gly Ser Val Ala Val Pro Tyr Arg Gln Met Gly Ser Phe Lys Pro Gly
                85                  90                  95

Thr Gly Val Gly Gly Ala Gly Ser His Trp Ser Gly Cys His Phe Arg
            100                 105                 110

Pro Leu Pro Glu Asp Leu Arg Leu Arg Ser Asn Leu Glu Glu Arg Tyr
        115                 120                 125

Gly Lys Ser Phe Ile Pro Ser Asp Met Thr Ile Asp Asp Phe Pro Val
    130                 135                 140

Ser Tyr Asp Glu Leu Glu Pro His Leu Asp Met Phe Glu Lys Val Cys
145                 150                 155                 160

Gly Thr Ser Gly Lys Ala Gly Val Ile Arg Gly Val Val Gln Ala Gly
                165                 170                 175

Gly Asn Pro Phe Glu Gly Ser Arg Ser Gly Glu Tyr Pro Leu Gly Pro
            180                 185                 190

Asn Pro Asn Tyr Leu Gly Ala Glu Trp Phe Tyr Lys Ala Ala Arg Glu
        195                 200                 205

Lys Gly Tyr His Pro Tyr Ile Pro Ala Ser Asn Ala Ala Gly Pro
    210                 215                 220

Tyr Ile Asn Pro Tyr Gly Cys Gln Met Gly Pro Cys Asn Ala Cys Gly
225                 230                 235                 240

Phe Cys Ser Asp Tyr Gly Cys Leu Asn Tyr Ser Lys Ala Ser Pro Asn
```

```
                    245                 250                 255
Ile Cys Ile Met Pro Val Leu Arg Gln Arg Lys Asn Phe Glu Leu Arg
                260                 265                 270

Thr His Ala Gln Val Leu Lys Val Asn Leu Ser Ser Asp Gly Lys Lys
            275                 280                 285

Ala Thr Gly Val Thr Tyr Leu Asp Ser Asn Gly Gln Glu Thr Glu Gln
        290                 295                 300

Pro Ala Asp Leu Val Leu Leu Cys Ala Phe Ser Leu Tyr Asn Val His
305                 310                 315                 320

Leu Met Leu Leu Ser Gln Ile Gly Lys Pro Tyr Asp Pro Val Ser Asn
                325                 330                 335

Glu Gly Thr Val Gly Arg Asn Tyr Ser Tyr Gln Asn Leu Asn Arg Val
            340                 345                 350

Met Met Phe Tyr Asp Gln Ser Val Gln Ala Asn Gly Phe Ile Gly Ile
        355                 360                 365

Gly Gly Ser Gly Thr Thr Met Asp Asp Leu Asn Gly Asn Gln Leu Asp
    370                 375                 380

Asn Ala Gln Ala Gly Phe Val Gly Gly Ile Ile Trp Ala Arg Gln
385                 390                 395                 400

Pro Gly Asn Gly Pro Val Arg Gly Val Ala Val Pro Lys Gly Thr Pro
                405                 410                 415

Gly Trp Gly Ser Ala Trp Lys Lys Val Ser Glu Ser Phe Arg His
            420                 425                 430

Ser Phe Tyr Tyr Glu Val Gln Gly Ala Cys Met Ser Tyr Gln Gln Asn
        435                 440                 445

Tyr Leu Ser Leu Asp Pro Thr Trp Lys Asp Ala Phe Gly Arg Pro Leu
    450                 455                 460

Leu Arg Met Thr Phe Asp Trp Gln Pro Asn Glu Val Lys Ala Ser Gln
465                 470                 475                 480

Phe Leu Val Gly Lys Ala Val Asp Met Cys Gln Val Leu Asn Pro Lys
                485                 490                 495

Ser Ile Ser Ser Asp Ala Lys Lys Asp Gly Ala His Tyr Asp Ile Thr
            500                 505                 510

Lys Tyr Gln Ser Thr His Thr Cys Gly Gly Ala Val Met Gly Ser Asp
        515                 520                 525

Pro Lys Lys Ser Ala Leu Asn Arg Tyr Leu Gln Ser Trp Asp Val Pro
    530                 535                 540

Asn Val Phe Ala Ile Gly Ala Asn Ala Phe Pro Gln Asn Asn Gly Tyr
545                 550                 555                 560

Asn Pro Thr Gly Leu Val Gly Gly Leu Ala Tyr Trp Ala Ala Thr Ala
                565                 570                 575

Ile Arg Glu Gln Tyr Leu Lys Asn Pro Gly Pro Leu Val Gln Ala
            580                 585                 590

<210> SEQ ID NO 6
<211> LENGTH: 594
<212> TYPE: PRT
<213> ORGANISM: Pantoea citrea

<400> SEQUENCE: 6

Met Ala Ser Val Met Lys Lys Thr Asp Ala Val Ile Val Gly Phe Gly
1               5                   10                  15

Trp Ala Gly Ala Ile Met Ala Lys Glu Leu Thr Glu Ala Gly Leu Asn
            20                  25                  30

Val Val Ala Leu Glu Arg Gly Pro Gln Arg Asp Thr Tyr Pro Asp Gly
```

-continued

```
                35                  40                  45
Ala Tyr Pro Gln Ser Ile Asp Glu Leu Thr Tyr Asn Ile Arg Lys Lys
 50                  55                  60

Leu Phe Gln Asp Leu Ser Lys Ser Thr Val Thr Val Arg His Asn Pro
 65                  70                  75                  80

Ser Gln Thr Ala Val Pro Tyr Arg Gln Leu Asn Ala Phe Leu Pro Gly
                 85                  90                  95

Thr Gly Thr Gly Gly Ala Gly Leu His Trp Ser Gly Val His Phe Arg
                100                 105                 110

Val Asp Pro Ala Glu Leu Arg Leu Arg Ser His Tyr Glu Glu Arg Tyr
            115                 120                 125

Gly Lys Asp Phe Ile Pro Gln Gly Met Thr Ile Gln Asp Phe Gly Val
        130                 135                 140

Ser Tyr Asp Glu Leu Glu Pro Phe Phe Asp Gln Ala Glu Lys Val Phe
145                 150                 155                 160

Gly Thr Ser Gly Thr Ala Trp Thr Val Lys Gly Glu Leu Val Gly Lys
                165                 170                 175

Gly Lys Gly Gly Asn Pro Phe Ala Pro Asp Arg Ser Ser Asp Phe Pro
            180                 185                 190

Leu Lys Ala Gln Lys Arg Thr Tyr Ser Ala Gln Leu Phe Ala Glu Ala
        195                 200                 205

Ala Glu Ser Val Gly Tyr His Pro Tyr Asp Met Pro Ser Ala Asn Thr
    210                 215                 220

Ser Gly Pro Tyr Thr Asn Thr Tyr Gly Ala Gln Met Gly Pro Cys Asn
225                 230                 235                 240

Phe Cys Gly Tyr Cys Ser Gly Tyr Ala Cys Tyr Met Tyr Ser Lys Ala
                245                 250                 255

Ser Pro Asn Val Asn Ile Leu Pro Ala Leu Arg Gln Glu Pro Lys Phe
            260                 265                 270

Glu Leu Arg Asn Asp Ser Tyr Val Leu Arg Val Asn Leu Thr Asp Asp
        275                 280                 285

Lys Lys Arg Ala Thr Gly Val Thr Tyr Val Asp Ala Ser Gly Arg Glu
    290                 295                 300

Phe Glu Gln Pro Ala Asp Leu Val Ile Leu Ser Ala Phe Gln Phe His
305                 310                 315                 320

Asn Val His Leu Met Leu Leu Ser Gly Ile Gly Lys Pro Tyr Asn Pro
                325                 330                 335

Val Thr Asn Glu Gly Val Val Gly Arg Asn Phe Ala Tyr Gln Asn Ile
            340                 345                 350

Ser Thr Leu Lys Ala Leu Phe Asp Lys Asn Ile Thr Thr Asn Pro Phe
        355                 360                 365

Ile Gly Ala Gly Gly Ala Gly Val Gly Val Asp Asp Phe Asn Ala Asp
    370                 375                 380

Asn Phe Asp His Gly Pro His Gly Phe Val Gly Gly Ser Pro Leu Trp
385                 390                 395                 400

Val Asn Gln Ala Gly Val Lys Pro Ile Ser Gly Leu Pro Thr Pro Thr
                405                 410                 415

Gly Thr Pro Ala Trp Gly Ser Glu Trp Lys Ala Ala Val Ala Asp Thr
            420                 425                 430

Tyr Thr His His Val Ser Met Asp Ala His Gly Ala His Gln Ser Tyr
        435                 440                 445

Arg Thr Asn Tyr Leu Asp Leu Asp Pro Asn Tyr Lys Asp Val His Gly
    450                 455                 460
```

```
Gln Pro Leu Leu Arg Met Thr Phe Asp Trp Gln Glu Asn Asp Ile Lys
465                 470                 475                 480

Met Ser Gln Phe Met Val Ser Lys Met His Asn Ile Ala Gln Ala Met
            485                 490                 495

Asn Pro Lys Met Ile Met Gly Gly Pro Lys Thr Ala Gly Thr His Phe
        500                 505                 510

Asp Thr Thr Val Tyr Gln Thr Thr His Met Asn Gly Gly Ala Ile Met
            515                 520                 525

Gly Glu Asp Pro Lys Thr Ser Ala Ile Asn Arg Tyr Leu Gln Ser Trp
530                 535                 540

Asp Val Ser Asn Val Phe Val Pro Gly Ala Ser Ala Phe Pro Gln Gly
545                 550                 555                 560

Leu Gly Tyr Asn Pro Thr Gly Met Val Ala Ala Leu Thr Tyr Trp Ser
                565                 570                 575

Ala Lys Thr Ile Arg Glu Val Tyr Leu Lys Asn Pro Gly Pro Leu Val
            580                 585                 590

Gln Ala

<210> SEQ ID NO 7
<211> LENGTH: 586
<212> TYPE: PRT
<213> ORGANISM: Pantoea citrea

<400> SEQUENCE: 7

Met Thr Lys Lys Leu Pro Ala Thr Asp Val Ile Val Gly Leu Gly
1               5                   10                  15

Trp Ala Gly Ser Ile Leu Ala Lys Glu Leu Cys Asp Gln Gly Leu Asn
            20                  25                  30

Val Ile Gly Leu Glu Arg Gly Pro Trp Arg Asp Thr Ala Lys Asp Phe
        35                  40                  45

Asn Val Ala Thr Ala Pro Asp Glu Leu Arg Tyr Asn Ala Arg Glu Glu
    50                  55                  60

Leu Met Leu Arg Pro Ala Gln Asn Thr Cys Thr Met Arg Asn Asn Pro
65                  70                  75                  80

Ser Glu Thr Ala Leu Pro Met Arg Phe Trp Gly Ser Phe His Pro Gly
                85                  90                  95

Asn Gly Thr Gly Gly Ala Gly Asn His Trp Ala Gly Ile Thr Phe Arg
            100                 105                 110

Tyr Gln Pro Ala Asp Phe Arg Leu Ala Ser His Leu Arg Glu Arg Tyr
        115                 120                 125

Gly Lys Glu Val Asp Pro Ala Leu Thr Leu Gln Asp Trp Gly Ile Thr
    130                 135                 140

Trp Glu Glu Met Glu Pro Phe Tyr Asp Ser Phe Glu Arg Val Ala Gly
145                 150                 155                 160

Ile Ser Gly Lys Ala Gly Asn Ile Lys Gly Ser Ile Ile Glu Gly Gly
                165                 170                 175

Asn Pro Phe Glu Gly Pro Arg Ala Arg Asp Tyr Pro Asn Pro Pro Asn
            180                 185                 190

Ile Gln Thr Ile Ala Gln Thr Phe Phe Ala Lys Thr Ala Thr Glu Met
        195                 200                 205

Gly Tyr Lys Pro Phe Asn Val Pro Ser Ala Leu Ala Ser Gln Gly Tyr
    210                 215                 220

Thr Asn Gln Tyr Gly Val Thr Met Gly Pro Cys Thr Tyr Cys Gly Phe
225                 230                 235                 240

Cys Thr Asn Tyr Gly Cys Ala Asn Tyr Ser Lys Ala Ser Ala Ile Val
```

```
                  245                 250                 255
Asn Val Leu Pro Ala Val Val Ser Met Pro Asn Phe Glu Ala Arg Thr
            260                 265                 270
Asn Cys Glu Val Met Glu Val Leu Lys Asp Ser Ser Gly Lys Lys Ala
        275                 280                 285
Thr Gly Val Val Tyr Ile Asp Ser Asn Gly Glu Arg Tyr Glu Gln Pro
    290                 295                 300
Ala Ser Ile Val Ile Val Ala Ala Phe Thr Phe Glu Asn Val Arg Leu
305                 310                 315                 320
Met Leu Leu Ser Asn Val Gly Val Pro Tyr Asp Pro Val Thr Gly Lys
                325                 330                 335
Gly Thr Thr Gly Arg Asn Tyr Cys Tyr Gln Thr Ala Asn Gly Val Arg
            340                 345                 350
Leu Phe Phe Lys Asp Gln Ile Phe Asn Pro Phe Ile Gly Gly Gly Ala
        355                 360                 365
Ile Gly Met Gly Ile Asp Glu Phe Asn Asn Asp Asn Phe Asp His Ser
    370                 375                 380
Gly Leu Gly Phe Val Gly Gly Ser Thr Arg Val Thr Pro Ile Gly
385                 390                 395                 400
Ala Ala Pro Ile Ala Ser Arg Pro Val Pro Gly Thr Pro Arg Trp
                405                 410                 415
Gly Ser Ala Trp Lys Lys Ala Thr Val Glu His Tyr Leu Thr Asn Met
            420                 425                 430
Ser Ile Gly Cys Glu Ala Ser Ser Tyr Pro Gln Arg Thr Asn Tyr Leu
        435                 440                 445
Ser Leu Asp Pro Asn Tyr Thr Asp Pro His Gly Arg Pro Leu Leu Arg
    450                 455                 460
Ile Thr Phe Asp Phe Pro Asp Asn Asp Met Arg Met Ala Gln Tyr Val
465                 470                 475                 480
Thr Asn Lys Val Gly Glu Ile Ala Leu Arg Met Asn Pro Val Gln Ile
                485                 490                 495
Gln Lys Gln Pro Arg Thr Ala Pro Trp Ala Asn Asn Asp Tyr Gln Ser
            500                 505                 510
Ser His Val Val Gly Phe Val Met Gly Ala Asp Pro Ser Thr Ser
        515                 520                 525
Ala Val Asn Lys Phe Cys Gln Val Trp Asp Ile Pro Asn Leu Phe Val
    530                 535                 540
Val Gly Gly Ser Ala Val Pro Asn Asn Pro Gly Tyr Asn Pro Thr Gly
545                 550                 555                 560
Thr Val Gly Ala Leu Ala Phe Arg Thr Ala His Tyr Ile Arg Thr Gln
                565                 570                 575
Tyr Leu Lys Gln Pro Gly Glu Met Met Val
            580                 585

<210> SEQ ID NO 8
<211> LENGTH: 590
<212> TYPE: PRT
<213> ORGANISM: Pantoea citrea

<400> SEQUENCE: 8

Met Ser Lys Ile Arg Pro Lys Ala Asp Ala Val Ile Val Gly Leu Gly
1               5                   10                  15
Trp Ala Gly Ser Leu Met Ala Asn Glu Leu Thr Gln Ala Gly Leu Asn
            20                  25                  30
Val Val Ala Ile Glu Arg Gly Ser Trp Arg Asp Thr Ser Thr Asp Phe
```

```
                    35                  40                  45
Pro Thr Ser Ile Asp Thr Asp Glu Leu Arg Phe Val Ser Arg Ala
 50                  55                  60
Ile Met Gln Pro Thr Ala Val Glu Thr Met Thr Phe Arg Asn Asn Pro
 65                  70                  75                  80
Leu Gln Gln Ala Leu Pro Leu Arg Glu Phe Asn Thr Tyr Gln Phe Gly
                 85                  90                  95
Met Asn Val Gly Gly Ala Gly Thr His Trp Asn Ala Met Thr Trp Arg
                100                 105                 110
Phe Leu Pro Asn Asp Phe Gln Thr Tyr Thr Asn Thr Val Glu Arg Tyr
            115                 120                 125
Gly Lys Asn Lys Phe Leu Glu Gly Met Gln Val Gln Asp Trp Gly Val
            130                 135                 140
Thr Tyr Asp Asp Leu Glu Pro Phe Tyr Asp Lys Phe Glu Arg Phe Ala
145                 150                 155                 160
Gly Thr Ser Gly Lys Ala Gly Asn Ile Lys Gly Glu Lys Ile Asp Gly
                165                 170                 175
Gly Asn Val Phe Glu Gly Pro Arg Ser Arg Asp Tyr Pro Leu Pro Pro
            180                 185                 190
Leu Lys Arg Thr Gln Leu Ser Met Ile Phe Asp Lys Ala Thr Arg Glu
            195                 200                 205
Met Gly Leu His Pro Phe Ala Val Pro Ala Gly Asn Thr Ser Gly Ala
            210                 215                 220
Tyr Thr Asn Thr Leu Gly Ile Asn Met Ala Pro Cys Thr Tyr Cys Gly
225                 230                 235                 240
Phe Cys Glu Phe Phe Gly Cys Gly Asn Trp Ser Lys Ser Ser Pro Asn
                245                 250                 255
Ala Cys Ile Leu Pro Ala Val Met Gln Arg Ser Asn Phe Ser Val Ile
            260                 265                 270
Thr Glu Ser Glu Val Leu Arg Val Asn Lys Ala Ala Asp Gly Lys Thr
            275                 280                 285
Ala Thr Gly Val Thr Phe Ile Gly Ser Asp Gly Val Glu Trp Glu Gln
            290                 295                 300
Pro Ala Asp Ile Val Ile Ser Ala Tyr Gln Phe Asp Asn Val Arg
305                 310                 315                 320
Leu Met Leu Leu Ser Gly Ile Gly Glu Pro Tyr Asn Tyr Lys Thr Gly
                325                 330                 335
Thr Gly Val Val Gly Arg Asn Tyr Ala Tyr Gln Thr Ile Ser Gly Ala
                340                 345                 350
Gly Val Phe Phe Glu Asn Glu Asn Leu Asn Pro Phe Ile Gly Ala Gly
                355                 360                 365
Ala Leu Ala Gln Ala Val Asp Asp Tyr Asn Ser Asp Asn Phe Asp His
            370                 375                 380
Ser Asn Leu Asp Phe Ile Gly Gly Val Ala Leu Val His Ser Ser
385                 390                 395                 400
Asn Gly Arg Pro Ile Ala Leu Ser Gly Ala Val Pro Pro Gly Thr Pro
                405                 410                 415
Lys Trp Gly Ser Lys Trp Lys Gln Ala Ala Gln Gln Ser Tyr Gln Asn
                420                 425                 430
Tyr Asn Ser Val Tyr Val Met Gly Asn Ser Tyr Pro His Arg Asp Val
            435                 440                 445
Phe Leu Asp Leu Asp Pro Glu Tyr Lys Asp Arg His Gly Gln Pro Leu
450                 455                 460
```

```
Leu Arg Val Thr Phe Asp Trp Ile Glu Asn Asp Lys Arg Ser Gly His
465                 470                 475                 480

Phe Met Ala Asp Arg Ser Val Glu Ile Gly His Ala Met Gly Ala Lys
                485                 490                 495

Thr Val Val Arg Gln Glu Pro Thr Ala Arg Asn Phe Ser Pro Met Asp
            500                 505                 510

Asn Leu Ser Ser His Thr Thr Gly Gly Ala Cys Met Gly Asp Asp Pro
            515                 520                 525

Lys Thr Ser Ala Val Asn Arg Tyr Leu Gln Ser Trp Asp Val His Asn
    530                 535                 540

Val Phe Val Cys Gly Ala Ser Ala Phe Ala Asn Asn Gly Gly Tyr Asn
545                 550                 555                 560

Pro Thr Gly Thr Val Gly Ala Leu Thr Leu Trp Ala Ala Glu Ala Ile
                565                 570                 575

Lys Asn Gln Tyr Leu Lys Ser Pro Gly Pro Leu Val Arg Ile
                580                 585                 590

<210> SEQ ID NO 9
<211> LENGTH: 590
<212> TYPE: PRT
<213> ORGANISM: Pantoea citrea

<400> SEQUENCE: 9

Met Asn Asn Ile Arg Pro Lys Ala Asp Val Val Ile Val Gly Leu Gly
1               5                   10                  15

Trp Cys Gly Ser Leu Ile Ala Glu Glu Leu Thr Arg Ala Gly Met Asn
            20                  25                  30

Val Val Ala Ile Glu Arg Gly Pro Trp Trp Glu Thr Ser Thr Asp Phe
        35                  40                  45

Pro Pro Ser Ile Asp Thr Asp Glu Leu Arg Trp Asp Thr Arg Arg Ser
50                  55                  60

Met Leu Leu Pro Pro Ala Val Glu Thr Thr Thr Phe Arg Asn Asn Thr
65                  70                  75                  80

Ser Gln Gln Ala Leu Pro Ser Arg Asp Trp Asn Leu Asn Glu Leu Gly
                85                  90                  95

Tyr Asn Val Gly Gly Ser Gly Thr His Trp Ala Gly Met Ala Trp Arg
            100                 105                 110

Phe Thr Pro Phe Asp Phe Gln Pro Tyr Ser Gln Thr Val Ala Arg Tyr
        115                 120                 125

Gly Lys Gln Gln Ile Val Pro Gly Leu Ile Leu Gln Asp Trp Gly Val
    130                 135                 140

Ser Tyr Asp Glu Leu Glu Pro Phe Tyr Asp Arg Phe Glu Lys Ile Ala
145                 150                 155                 160

Gly Val Ser Gly Lys Ala Gly Lys Ser Asn Gly Asn Val Val Pro Glu
                165                 170                 175

Gly Asn Pro Phe Glu Gly Asn Arg Ser Ser Glu Tyr Pro Leu Pro Pro
            180                 185                 190

Leu Glu Ser Thr Arg Leu Thr Asp Leu Phe Glu Gln Gly Ala Lys Ser
        195                 200                 205

Leu Gly Leu Asn Pro Phe Met Val Pro Ala Gly Gln Ala Ser Arg Ala
    210                 215                 220

Tyr Val Asn Pro Leu Gly Val Arg Met Gly Pro Cys Thr Tyr Cys Gly
225                 230                 235                 240

Tyr Cys Leu Tyr Tyr Gly Cys Gly Asn Phe Ser Lys Ser Pro Asn
                245                 250                 255
```

```
Ala Cys Val Ile Pro Ala Leu Met Gln Arg Glu Asn Phe Thr Val Leu
            260                 265                 270

Thr Asp Ser Ala Val Val Lys Val Asn Lys Ala Glu Asp Gly Lys Thr
        275                 280                 285

Ala Thr Gly Val Thr Phe Ile Asp Lys Asn Asn Lys Gln Trp Glu Gln
    290                 295                 300

Pro Ala Asp Ile Val Ile Leu Ser Ala Phe Gln Met Gln Asn Val Arg
305                 310                 315                 320

Leu Leu Leu Leu Ser Gln Ile Gly Gln Pro Tyr Asn Pro Gln Thr Lys
                325                 330                 335

Gln Gly Val Val Gly Arg Ala Tyr Ser Phe Gln Thr Val Ser Gly Ala
            340                 345                 350

Ser Leu Phe Phe Lys Asp Glu Tyr Leu Asn Gln Tyr Ile Gly Ala Gly
        355                 360                 365

Ala Leu Ser Gln Gln Val Asp Asp Phe Asn Gly Asp Asn Phe Asp His
    370                 375                 380

Thr Gly Lys Gly Phe Ile Gly Gly Ala Gly Ile Leu Val Val Ala Arg
385                 390                 395                 400

Gly Ala Arg Pro Ile Gly Asn Ala Asp Thr Leu Pro Pro Gly Thr Pro
                405                 410                 415

Arg Trp Gly Lys Glu Trp Lys Gln Ala Tyr Thr His Ala Phe Gln Asn
            420                 425                 430

Ala Thr Phe Ile Phe Gly Gln Gly Thr Ser Tyr Ser His Glu Asp Tyr
        435                 440                 445

Tyr Leu Asp Leu Asp Pro Glu Tyr Lys Asp Lys Tyr Gly Leu Pro Leu
    450                 455                 460

Leu Arg Val Thr Phe Asp Tyr Asn Asp Asn Asp Arg Arg Ser Ala Lys
465                 470                 475                 480

Phe Val Glu Gln Arg Ser Val Glu Ile Gly Lys Ala Met Gly Ala Glu
                485                 490                 495

Arg Val Phe Gly Thr Asn Ser Ala Ser Gly His Tyr Ser Pro Tyr Asn
            500                 505                 510

Phe Ala Ser Asp His Thr Ile Gly Gly Ala Val Met Gly Thr Asp Pro
        515                 520                 525

Arg Thr Ser Val Leu Asn Arg Tyr Gln Gln Ser Trp Asp Val His Asn
    530                 535                 540

Val Phe Val Leu Gly Ala Ser Ser Phe Pro Asn Asn Ala Gly Tyr Asn
545                 550                 555                 560

Pro Thr Gly Thr Ile Gly Ala Leu Ser Leu Trp Thr Ala Lys Ala Ile
                565                 570                 575

Ile Glu Gln Tyr Arg Lys Asn Pro Gly Pro Leu Val Lys Val
            580                 585                 590

<210> SEQ ID NO 10
<211> LENGTH: 590
<212> TYPE: PRT
<213> ORGANISM: Pantoea citrea

<400> SEQUENCE: 10

Met Asn Tyr Thr Arg Pro Lys Ala Asp Ala Val Ile Ile Gly Leu Gly
1               5                   10                  15

Trp Ala Gly Ser Leu Met Ala Glu Glu Leu Thr Arg Ala Gly Leu Asn
            20                  25                  30

Val Val Ala Ile Glu Arg Gly Pro Trp Glu Gln Thr Gln Ser Asn Phe
        35                  40                  45
```

```
Ser Pro Ala Ile Ala Ala Asp Glu Leu Arg Tyr Gly Val Arg Arg Glu
 50                  55                  60

Ile Leu Lys Pro Pro Arg Val Glu Thr Leu Thr Phe Arg Asn Asp Ser
 65                  70                  75                  80

Ser Gln Lys Ala Leu Pro Ala Arg Asp Trp Asn Ala Phe Gln Met Gly
                 85                  90                  95

Tyr Ser Val Gly Gly Ala Gly Lys His Trp Ala Asn Ala Trp Arg
                100                 105                 110

Phe Asn Pro Ser Asp Phe Glu Met Ala Thr Arg His Lys Glu Arg Tyr
            115                 120                 125

Asn Asn Met Pro Leu Ala Asp Gly Leu Ile Leu Gln Asp Trp Gly Val
        130                 135                 140

Ser Tyr Ala Glu Leu Glu Pro Phe Tyr Asp Arg Val Glu Lys Ile Ala
145                 150                 155                 160

Gly Ile Ser Gly Lys Ala Gly Val Leu Asn Gly Ser Thr Gln Glu Gly
                165                 170                 175

Gly Asn Pro Phe Glu Gly Asn Arg Thr Ser Glu Tyr Pro Thr Pro Pro
            180                 185                 190

Leu Ile Arg Ser His Trp Asn Asp Thr Phe His Asn Ile Thr Thr Lys
        195                 200                 205

Met Gly Tyr His Pro Phe Pro Ile Pro Ala Gly Thr Ile Gly Ala Ala
    210                 215                 220

Phe Thr Asn Pro Leu Gly Ile Asn Leu Ala Pro Cys Thr Tyr Cys Gly
225                 230                 235                 240

Tyr Cys Gly Phe Tyr Gly Cys Gly Asn Trp Ser Lys Ser Ser Pro Asn
                245                 250                 255

Ile Cys Val Val Pro Ala Leu Met Asp Arg Thr Asn Phe Thr Leu Leu
            260                 265                 270

Thr Glu Cys Thr Ala Leu Tyr Ile Asn Lys Ala Asp Glu Lys Thr
        275                 280                 285

Val Thr Gly Val Thr Phe Arg Asp Ser Asp Gly Asn Thr Gly Phe Gln
    290                 295                 300

Pro Ala Asp Ile Val Cys Leu Ser Ala Tyr Gln Leu Asp Asn Val Arg
305                 310                 315                 320

Leu Leu Leu Leu Ser Lys Ile Gly Lys Ala Tyr Asp His Ala Thr Gly
                325                 330                 335

Glu Gly Thr Leu Gly Arg Ala Tyr Asn Tyr Gln Thr Met Ser Met Gly
            340                 345                 350

Tyr Leu Tyr Tyr Glu Asn Glu Tyr Met Asn Pro Phe Ile Ser Thr Gly
        355                 360                 365

Ala Leu Ser Thr Gln Ile Asp Asp Phe Asn Gly Asp Asn Phe Asp His
    370                 375                 380

Thr Gly Leu Gly Phe Leu Gly Gly Ala Gly Ile Gln Ala Leu Ser Asp
385                 390                 395                 400

Gln Gly Thr Pro Leu Ser Met Thr Asp Arg Leu Pro Ala Gly Ser Lys
                405                 410                 415

Met Trp Gly Ser Ala Trp Lys Lys Ala Phe Arg His Ser Tyr Gln Asn
            420                 425                 430

Tyr Ala Lys Ile Gln Gly Gln Gly Thr Ser Tyr Ser His Arg Asp Ser
        435                 440                 445

Tyr Leu Ser Leu Asp Pro Asn Tyr Thr Asp Glu Asn Gly Gln Pro Leu
    450                 455                 460

Leu Arg Leu Thr Phe Asp Tyr Asn Gln Asn Asp Arg Leu Met Ala Arg
465                 470                 475                 480
```

Phe Ile Arg Asp Arg Ile Glu Asp Ile Cys Lys Val Ser Gly Ala Ser
                485                 490                 495

Ser Trp Ile Thr Glu Ala Phe Pro Asp Ser His Asn Ser Pro Phe Arg
            500                 505                 510

Ala Tyr Asp Ser Ser His Thr Ile Gly Gly Ala Val Met Gly Leu Asp
        515                 520                 525

Pro Lys Thr Ser Val Leu Asn Arg Tyr Gln Gln His Trp Asp Ala His
    530                 535                 540

Asn Leu Phe Val Leu Gly Ala Ser Ser Tyr Pro Asn Asn Gly Gly Tyr
545                 550                 555                 560

Asn Pro Thr Ile Thr Leu Ser Ala Leu Thr Leu Trp Thr Ala His His
                565                 570                 575

Ile Val Asn Asp Tyr Leu Lys Asn Pro Gly Ser Leu Val Arg
            580                 585                 590

<210> SEQ ID NO 11
<211> LENGTH: 546
<212> TYPE: PRT
<213> ORGANISM: Pantoea citrea

<400> SEQUENCE: 11

Met Ser Gln Asn Asn Val Asp Ala Glu Val Ile Ile Gly Ser Gly
1               5                   10                  15

Val Met Gly Gly Leu Leu Ala Thr Gln Leu Ser Ala Ala Gly Lys Ser
            20                  25                  30

Val Ile Ile Val Glu Ala Gly Pro Arg Val Thr Arg Gln Gln Ile Val
        35                  40                  45

Asp Arg Phe Arg Asn Ser Pro Phe Lys Met Ser Leu Thr Asn Met Lys
    50                  55                  60

Leu Gln Gly Val Gly Ser Pro Tyr Pro Asp Leu Pro His Val Pro Ser
65                  70                  75                  80

Thr Tyr Gly Asn Tyr Leu Gln Gln Val Gly Pro Val Lys Tyr Pro Thr
                85                  90                  95

Lys Tyr Leu Arg Val Val Gly Gly Thr Thr Trp His Phe Gly Ser Ala
            100                 105                 110

Leu Trp Arg Met Ile Pro Asn Asp Phe Lys Leu Lys Thr Leu Tyr Gly
        115                 120                 125

His Gly Arg Asp Trp Pro Phe Gly Tyr Asp Glu Leu Glu Pro Trp Tyr
    130                 135                 140

Cys Glu Ala Glu His Ala Leu Gly Val Ser Gly Val Asp Gly Gln Asp
145                 150                 155                 160

Glu Ser Gly His Gly Gly Lys Pro Trp Pro Arg Ser Lys Pro Phe
                165                 170                 175

Pro Met Pro Gly Leu Pro Thr Ser Tyr Met Phe Asp Arg Leu Ser Glu
            180                 185                 190

Leu Leu Gly Lys Gly Gly Tyr Asn Pro Val Leu Glu Pro Asn Gly Arg
        195                 200                 205

Ala Thr Arg Pro Trp Gly Asn Arg Pro Val Cys Ala Gly Asn Asn
    210                 215                 220

Cys Asn Pro Val Cys Pro Ile Gly Ala Lys Tyr Asp Gly Ser Met His
225                 230                 235                 240

Ile Asp Gln Ala Glu Arg Leu Gly Ala Lys Leu Leu Asp Asn Ser Val
                245                 250                 255

Val Tyr Lys Ile Glu Ala Asp Asp Asn Gly Lys Ile Thr Arg Ile Trp
            260                 265                 270

```
Tyr Lys Lys Pro Asp Gly Ser Glu His Ser Leu Thr Ala Asn Leu Phe
            275                 280                 285

Ile Val Ala Ala Tyr Gly Ile Glu Ser Pro Lys Leu Leu Met Ser
        290                 295                 300

Thr Ser Glu Lys Tyr Pro Asn Gly Ile Ala Asn Ser Ser Asp Gln Val
305                 310                 315                 320

Gly Arg Asn Leu Met Gly His Thr Gly Ile Ser Met Asn Phe Met Met
                325                 330                 335

Ala Glu Asp Val Trp Pro Gly Gln Gly Pro Thr Glu Leu Leu Val Tyr
            340                 345                 350

Leu Asn Asn Arg Asp Gly Glu Phe Arg Lys Thr Phe Pro Ser Tyr Lys
        355                 360                 365

Ile Lys Val Arg Asn Thr Val Pro Thr Ala Asp Tyr Ala Ser Gly Leu
370                 375                 380

Ile Ser Lys Gly Val Leu Gly Ser Glu Leu Asp Glu Gln Leu Arg Lys
385                 390                 395                 400

Leu Ser Ala Arg Ser Leu Asn Phe Ala Ile Asp Phe Glu Thr Val Pro
                405                 410                 415

Leu Pro Glu Asn Arg Val Val Pro Ser Lys Thr Lys Thr Asp Ala Ile
            420                 425                 430

Gly Ile Pro Leu Pro Glu Ile Ser Tyr Ser Val Thr Asp Tyr Trp Gln
        435                 440                 445

Ala Gly Lys Glu Ala Gly Leu Lys Asp Phe Ala Asn Phe Ala Lys Leu
    450                 455                 460

Leu Gly Gly Asp Val Leu Lys Ile Asp Thr Asn Tyr Gln Asp Arg Gln
465                 470                 475                 480

His Ile Met Gly Thr Thr Ile Met Gly Asp Asp Pro Lys Asn Ser Val
                485                 490                 495

Val Asn Ser Asp Cys Arg Thr His Asp His Pro Asn Leu Tyr Ile Ala
            500                 505                 510

Gly Thr Ser Val Met Pro Ser Ala Ser Cys Met Asn Pro Thr Leu Thr
        515                 520                 525

Gly Ala Ala Leu Ser Leu Arg Leu Ala Asn His Leu Leu Lys Asn Val
    530                 535                 540

Leu Val
545

<210> SEQ ID NO 12
<211> LENGTH: 540
<212> TYPE: PRT
<213> ORGANISM: Pantoea citrea

<400> SEQUENCE: 12

Met Ala Asn Thr Thr Leu Asp Phe Asp Tyr Val Ile Val Gly Ser Gly
1               5                   10                  15

Val Thr Gly Ala Leu Ile Ala Trp Gln Leu Ser Arg His Gly Lys Arg
            20                  25                  30

Val Cys Met Ile Glu Ala Gly Asp His Ile Gln Arg Trp Lys Ala Ile
        35                  40                  45

Glu His Tyr Arg Ser Leu Pro Asp Lys Ser Ile Ala Asn Asn Ser Pro
    50                  55                  60

Tyr Pro Asn Leu Glu Trp Ala Pro Asn Pro Ile Gly Gly His Tyr Leu
65                  70                  75                  80

Glu Gln Lys Gly Pro Val Asn Tyr Ala Thr Thr Tyr Ile Arg Met Val
                85                  90                  95
```

```
Gly Gly Thr Thr Trp His Trp Asp Ser Ala Thr Trp Arg Leu Leu Pro
            100                 105                 110
Ser Asp Phe Glu Leu Lys Thr Arg Tyr Gly Val Gly Arg Asp Trp Pro
        115                 120                 125
Ile Gly Tyr Glu Val Leu Glu Pro Trp Tyr Gln Lys Ala Glu Glu Gln
    130                 135                 140
Leu Gly Val Asn Gly Trp Asp Thr Glu Asp Gln Ser Gly Gln Gly Lys
145                 150                 155                 160
Asp His Tyr Pro Pro Arg Ser Gln Pro Tyr Pro Thr Pro Gly His Pro
                165                 170                 175
Phe Ser Trp Gly Gln Gln Val Val Ala Gly Lys Leu Glu Ala Ala Gly
            180                 185                 190
Tyr Ser Ala Ile His Glu Pro Asn Ala Arg Leu Ser Val Ala Thr Ala
        195                 200                 205
Glu Arg Pro Ala Cys Ala Gly Asn Asn Thr Cys Asp Pro Ile Cys Pro
    210                 215                 220
Ile Gly Ala Lys Tyr Thr Ala Asp Phe His Val Gln Lys Ala Leu Asp
225                 230                 235                 240
His Gly Cys Thr Leu Leu Ser Asn Ser Val Val Tyr Arg Val Glu Ala
                245                 250                 255
Gly Asp Asp Gly Lys Ile Thr Ala Val His Phe Arg Arg Pro Asp Lys
            260                 265                 270
Ser Thr Gly Thr Val Ser Gly Lys Val Phe Val Ile Ala Ala Asn Ala
        275                 280                 285
Ile Glu Thr Pro Lys Leu Leu Leu Met Ser Val Ser Glu Arg Tyr Pro
    290                 295                 300
Gln Gly Ile Ala Asn Thr Ser Gly Gln Val Gly Arg Asn Leu Met Asp
305                 310                 315                 320
His Thr Gly Leu Gly Phe Asn Leu Val Thr Glu Asp Glu Val Trp Pro
                325                 330                 335
Gly Thr Gly Pro Asn Ala Leu Leu Val Met Leu Asn Ala Arg Glu Gly
            340                 345                 350
Lys Phe Arg Ala Glu Arg Ala Ser Tyr Lys Thr Lys Phe Arg Asn Thr
        355                 360                 365
Ala Val Asn Phe Ala Val Thr Lys Ser Leu Ile Lys Gln Gly Ile Met
    370                 375                 380
Gly Asn Glu Leu Tyr Arg Gln Ile Lys Tyr Gln Ser Ala Arg Gln Leu
385                 390                 395                 400
Ser Ile Ala Val Asp Leu Glu Thr Leu Pro Asn Pro Gln Asn Arg Ile
                405                 410                 415
Val Pro Ser Lys Asp Arg Thr Asp Ser Leu Gly Ile Pro Val Pro Glu
            420                 425                 430
Ile His Tyr Asp Val Asp Asp Tyr Trp Asn Lys Gly Arg Asp Ala Ala
        435                 440                 445
Ile Ala Asp Val Gln Asn Ile Ala Lys Ile Leu Asn Ala Lys Ile Val
    450                 455                 460
Ala Thr Asp Thr Asn Lys Gln Asn Arg Glu His Ile Leu Gly Thr Met
465                 470                 475                 480
Ile Met Gly Asn Ser Pro Thr Asp Ser Val Val Asp Lys Asn Cys Arg
                485                 490                 495
Thr His Asp His Pro Asn Leu Tyr Ile Ala Gly Thr Ser Val Phe Pro
            500                 505                 510
Ala Val Gly Cys Val Asn Pro Thr Leu Thr Gly Ala Ala Leu Ala Leu
```

```
                  515                 520                 525
Arg Ile Ala Asp Thr Leu Leu Gln Asp Pro Val Thr
        530                 535                 540

<210> SEQ ID NO 13
<211> LENGTH: 534
<212> TYPE: PRT
<213> ORGANISM: Pantoea citrea

<400> SEQUENCE: 13

Met Lys Thr Thr His Ser Ala Thr Val Val Ile Ile Gly Ser Gly Ile
1               5                   10                  15

Ala Gly Ser Gln Ile Ala Gln Lys Leu Gln Lys Ala Gly Ile Asp Thr
            20                  25                  30

Leu Met Leu Glu Ala Gly Ser Arg Ile Glu Arg Trp Lys Ile Val Glu
        35                  40                  45

Asn Tyr Arg Asn Ser Pro Phe Lys Thr Asp Phe Gln Ser Pro Tyr Pro
    50                  55                  60

Pro Thr Arg His Ala Pro His Pro Gln Tyr Ser Pro Glu Asp Asn Gly
65                  70                  75                  80

Tyr Phe Ile Gln Tyr Gly Pro Glu Pro Tyr Lys Ala Gly Tyr Leu Arg
                85                  90                  95

Val Ala Gly Gly Thr Thr Trp His Trp Ser Ala Gln Ala Trp Arg Leu
            100                 105                 110

Leu Pro Asn Asp Met Arg Leu Lys Thr Leu Tyr Gly Val Gly Arg Asp
        115                 120                 125

Trp Pro Ile Ser Tyr Asp Asp Leu Glu Pro Tyr Tyr Tyr Glu Ser Glu
    130                 135                 140

Val Glu Met Gly Val Gly Gly Pro Glu Asp Thr Gly Ser Pro Arg Ser
145                 150                 155                 160

Lys Pro Tyr Pro His Pro Pro Leu Pro Leu Ser Asp Phe Asp Lys Ala
                165                 170                 175

Phe Lys Asn Val Val Asp Lys Asn Gly Tyr His Leu Ile Thr Glu Pro
            180                 185                 190

Ala Ala Arg Asn Thr Glu Pro Phe Asp Gly Arg Pro Ala Cys Cys Gly
        195                 200                 205

Asn Ser Asn Cys Met Pro Ile Cys Pro Ile Glu Ala Gln Tyr Thr Gly
    210                 215                 220

Glu Thr Ala Val Arg Lys Ala Glu Arg Ala Gly Ser Leu Leu Val Pro
225                 230                 235                 240

Asp Ala Val Val Tyr Lys Ile Glu His Asp Ala Lys Gly Asn Ile Thr
                245                 250                 255

Ser Val Leu Tyr Lys Asp Pro Asn Gly Glu Ser Phe Arg Val Thr Gly
            260                 265                 270

Lys Ile Phe Val Leu Ala Ala Asn Ala Ile Glu Thr Pro Lys Leu Met
        275                 280                 285

Leu Ile Ser Arg Ser Asp Lys Tyr Pro Asn Gly Ile Gly Asn Thr Thr
    290                 295                 300

Asp Asn Val Gly Arg His Leu Met Asp His Pro Gly Thr Ser Val Tyr
305                 310                 315                 320

Phe Leu Ser Lys Glu Pro Met Trp Pro Gly Arg Gly Pro Met Arg Leu
                325                 330                 335

Ser Cys Ile Asn Asn Leu Arg Asp Gly Asp Phe Arg Ser Glu His Ser
            340                 345                 350

Ala Met Lys Ile Asn Leu Gly Asn Tyr Ser Pro Thr Leu Ala Val Ser
```

```
                    355                 360                 365
Asn Tyr Leu Leu Ser Lys Gly Val Ser Gly Lys Asp Leu Pro Ala Met
370                 375                 380

Val Arg Asp Tyr Ala Ser Arg Trp Val Ala Val Asn Thr Phe Phe Asp
385                 390                 395                 400

Ile Leu Pro Asp Arg Asp Asn Arg Ile Val Ala Val Asp Ser Gln Lys
                405                 410                 415

Asp Ala Met Gly Ile Pro Lys Pro Gly Val His Tyr His Ile Asn Asp
                420                 425                 430

Tyr Ile Asn Lys Ala Arg Asp Val Ala His Gln His Phe Asp His Ile
            435                 440                 445

Ala Gly Leu Phe Gly Gly Thr Glu Val Arg His Asp Asp Lys Tyr Phe
        450                 455                 460

Asn Asn Asn His Ile Met Gly Thr Leu Ile Met Gly Asn Asp Pro Asn
465                 470                 475                 480

Asp Ser Val Val Asp Ala Asp Leu Arg Thr His Asp His Gln Asn Leu
                485                 490                 495

Phe Val Ala Ser Ser Gly Val Met Ala Ser Ala Gly Thr Val Asn Cys
                500                 505                 510

Thr Leu Thr Leu Ser Ala Leu Ala Met Arg Leu Ala Asp Lys Leu Ile
            515                 520                 525

Ala Glu Cys Gln His Leu
        530

<210> SEQ ID NO 14
<211> LENGTH: 530
<212> TYPE: PRT
<213> ORGANISM: Pantoea citrea

<400> SEQUENCE: 14

Met Ala Thr Glu Phe Asp Ala Asp Val Ile Val Val Gly Ser Gly Ala
1               5                   10                  15

Cys Gly Ser Asn Leu Ala Asn Glu Leu Ala Val Lys Gly Lys Ser Val
                20                  25                  30

Ile Leu Leu Glu Ala Gly Ala Asn Val Pro Arg Trp Lys Ile Leu Glu
            35                  40                  45

Asn Phe Arg Asn Ser Gly Arg His Tyr Asp Arg Asn Asn Ala Tyr Pro
        50                  55                  60

Asn Asn Pro Trp Ser Pro Thr Ser Asn Thr Pro Gly Tyr Ile Glu Asn
65                  70                  75                  80

Val Gly Glu Phe Arg Glu Gln Pro Gly Met Leu Lys Leu Val Gly Gly
                85                  90                  95

Thr Thr Trp His Trp Gly Gly Ala Thr Trp Arg Tyr Ile Pro Asn Asp
                100                 105                 110

Phe Lys Leu Lys Thr Met Tyr Gly Val Gly Arg Asp Trp Pro Ile Ser
            115                 120                 125

Tyr Ser Asp Leu Glu Pro Phe Tyr Thr Arg Ala Glu Tyr Ala Ile Gly
        130                 135                 140

Val Ala Gly Ser Asp Thr Glu Asp Gln Ser Gly Gln Asn Pro Gly Ile
145                 150                 155                 160

Ser Phe Pro Pro Arg Ser Lys Ala Tyr Pro Val Asp Pro Glu Ala Asp
                165                 170                 175

Ile Tyr Ser Asn Ala Lys Leu Lys Ala Ala Leu Leu Pro His Gly His
            180                 185                 190

Ser Val Val His Glu Pro Thr Val Arg Ile His Arg Pro Tyr Asp Gly
```

```
            195                 200                 205
Arg Pro Gly Cys Gln Gly Asn Asn Cys Asp Gln Val Cys Pro Ile
210                 215                 220

Gly Thr Leu Tyr Asn Gly Ser Val His Ala Asp Lys Ala Val Arg Asn
225                 230                 235                 240

Gly Ala Lys Leu Ile Thr Asp Ala Val Val His Lys Ile Thr Lys Gly
            245                 250                 255

Glu Gln Gly Lys Ile Thr Ser Val Ser Tyr Leu Thr Pro Ala Gly Glu
        260                 265                 270

Glu His Thr Leu Thr Ala Lys Tyr Phe Val Leu Ala Ala His Ser Phe
    275                 280                 285

Glu Thr Ser Lys Leu Met Leu Met Asn Asp Ile Gly Asn Ser Ser Asp
290                 295                 300

Met Val Gly Arg Asn Leu Met Asp His Ile Gly Leu Ser Met Asn Phe
305                 310                 315                 320

Leu Ala Asp Glu Pro Met Trp Ala Gly Arg Gly Pro Val Gln Gln Ala
            325                 330                 335

Thr Ile Met Thr Trp Arg Asp Gly Asp Phe Arg Ser Lys Tyr Ser Ala
        340                 345                 350

Asn Lys His Ser Leu Ala Asn Asn Pro Gln Ile Asp Ile Ala Gln
    355                 360                 365

Arg Ala Ile Asn Glu Gly Leu Met Gly Lys Glu Leu Asp Ala Arg Ile
370                 375                 380

Leu Asp Trp Ser Ser Arg Trp Met Ser Ile Tyr Ser Phe Leu Glu Pro
385                 390                 395                 400

Leu Pro Asn Pro Ala Asn Arg Val Gln Pro Asn Pro Ala Trp Lys Asp
            405                 410                 415

Ser Leu Gly Leu Pro Gly Ile Lys Val Thr Phe Asp Val Asp Asp Tyr
        420                 425                 430

Thr Lys Leu Gly Ala Lys His Met Val Glu Gln Tyr Lys Gln Ile Ala
    435                 440                 445

Gly Leu Met Asn Gly Gln Ile Ile Asp Leu Asn Thr Ala Phe Glu Asn
450                 455                 460

His Asp His Leu Met Gly Thr Met Ile Met Gly Asp Asn Pro Lys Asp
465                 470                 475                 480

Ser Val Val Asn His Glu Cys Arg Ser His Asp Pro Asn Leu Phe
            485                 490                 495

Ile Ala Ser Val Gly Val Ile Pro Ala Ala Gly Val Val Asn Pro Thr
        500                 505                 510

Leu Thr Gly Val Ala Leu Ala Ile Arg Ser Ala Asp Ile Ile Ala Lys
    515                 520                 525

Glu Val
530

<210> SEQ ID NO 15
<211> LENGTH: 533
<212> TYPE: PRT
<213> ORGANISM: Pantoea citrea

<400> SEQUENCE: 15

Met Ser Asp Ser Leu Ser Ala Asp Val Val Ile Gly Ala Gly Ile
1               5                   10                  15

Ala Gly Ser Leu Ala Ala Leu Lys Met Ala Lys Ala Gly Ala Ser Val
            20                  25                  30

Leu Ile Leu Glu Ser Gly Pro Glu Ile Lys Arg Asp Glu Ala Val Asn
```

```
                 35                  40                  45
Tyr Phe Arg Asn Ser Pro Phe Lys Gly Asp Phe Thr Glu Pro Tyr Pro
 50                  55                  60

Pro Glu Pro Trp Ala Pro Gln Pro Lys Phe Ile Pro Thr Asp Asn Asn
 65                  70                  75                  80

Tyr Leu Ile Gln Lys Gly Pro Asp Pro Tyr Arg Ala Gln Tyr Leu Arg
                     85                  90                  95

Gly Ile Gly Gly Thr Thr Trp His Trp Ala Gly Gln Ala Phe Arg Leu
                100                 105                 110

Leu Pro Asn Asp Met Lys Ile Asn Thr Leu Tyr Gly Val Gly Arg Asp
                115                 120                 125

Trp Pro Ile Ser Tyr Glu Asp Leu Glu Pro Tyr Tyr Ser Asp Ala Glu
130                 135                 140

Tyr Gln Met Gly Val Ser Gly Asp Asp Leu Asn Ser Pro Arg Ser
145                 150                 155                 160

Arg Pro Tyr Pro Leu Pro Gly Ile Pro Leu Pro Tyr Gly Phe Glu Arg
                165                 170                 175

Leu Lys Gln Arg Leu Ser Pro Leu Gly Tyr Gln Val Gly Ile Gly Pro
                180                 185                 190

Gln Ala Arg Asn Ser Ile Pro Tyr Gln Gly Arg Pro Ala Cys Cys Gly
                195                 200                 205

Asn Asn Asn Cys Met Pro Val Cys Pro Ile Asp Ala Gln Tyr His Gly
210                 215                 220

Gly Ile Ser Ala Arg Lys Ala Val Asp Ala Gly Val Lys Ile Ile Ala
225                 230                 235                 240

Asn Ala Val Val Tyr Arg Ile Glu Ala Asp Asp His Gly Val Ile Gln
                245                 250                 255

Ala Val His Tyr Leu Asp Gln Asn Lys Ala Thr His Arg Val Thr Gly
                260                 265                 270

Lys Gln Phe Val Leu Thr Ala Asn Gly Val Glu Ser Pro Lys Ile Leu
                275                 280                 285

Leu Leu Ser Thr Ser Asp Arg Tyr Pro Asn Gly Ile Ala Asn Ser Ser
290                 295                 300

Gly Met Val Gly Arg Asn Leu Met Asp His Pro Gly Thr Ser Val Glu
305                 310                 315                 320

Phe Tyr Ala Asp Glu Pro Ile Trp Phe Gly Arg Gly Pro Met Arg Pro
                325                 330                 335

Gly Ser Ile Asn Asn Met Arg Asp Gly Ser Trp Arg Ser Glu Arg Ser
                340                 345                 350

Ala Leu Arg Ile Asp Leu Ala Asn Thr Ser Pro Val Arg Tyr Leu Thr
                355                 360                 365

Glu Arg Leu Val Arg Gln Gly Tyr Tyr Gly Lys Ala Leu Asn Asp Lys
                370                 375                 380

Leu Ala Phe Gln Ala Glu Arg Phe Val Gln Leu Lys Cys Leu Leu Glu
385                 390                 395                 400

Met Leu Pro Asp Pro Glu Asn Arg Leu Val Leu Ser Lys Thr Glu Lys
                405                 410                 415

Asp Ala Trp Gly Ile Pro Arg Leu Glu Val Tyr Tyr Lys Phe Pro Glu
                420                 425                 430

Tyr Val His Ala Gly Tyr Asp Gln Ser Met Ser Asp Phe Arg Lys Ile
                435                 440                 445

Val Gln Gln Met Gly Gly Thr Glu Pro Leu Tyr Ser Gln Arg Gly Val
                450                 455                 460
```

```
Tyr Asp Asn Asn Gln His Ile Thr Gly Thr Met Ile Met Gly Ser Asp
465                 470                 475                 480

Pro Lys Asn Ser Val Val Asp Gly Asn Cys Arg Thr His Asp His Pro
                485                 490                 495

Asn Leu Phe Ile Ala Gly Thr Gly Ile Met Pro Ser Ala Ser Thr Val
            500                 505                 510

Asn Ser Thr Leu Thr Gly Thr Ala Leu Ala Leu Arg Met Ala Asp Tyr
        515                 520                 525

Val Leu Lys Ser Leu
        530

<210> SEQ ID NO 16
<211> LENGTH: 543
<212> TYPE: PRT
<213> ORGANISM: Pantoea citrea

<400> SEQUENCE: 16

Met Ser Glu Gln Tyr Ser Ala Asp Val Val Val Gly Gly Gly Ile
1               5                   10                  15

Cys Gly Gly Thr Val Ala Lys Glu Leu Ala Glu Ala Gly Leu Ser Val
                20                  25                  30

Leu Val Leu Asp Ala Gly Pro Arg Trp Glu Arg Gly Glu Val Val Glu
            35                  40                  45

Asn Trp Arg Asn Leu Pro Pro Val Asn Lys Ser Glu Ser Asp Tyr Ala
50                  55                  60

Thr Pro Tyr Pro Ala Glu Pro Trp Ala Val His Pro Gln Leu Tyr Pro
65                  70                  75                  80

Tyr Asn Asn Tyr Pro Glu Val Ser Gly Pro Asp Ala Ser Ala Phe Arg
                85                  90                  95

Gln Gly Met Ile Lys Gly Val Gly Thr Thr Trp His Trp Ala Ala
            100                 105                 110

Ser Cys Trp Arg Phe Leu Pro Ala Asp Met Gln Leu Thr Thr Tyr
            115                 120                 125

Gly Val Gly Arg Asp Trp Val Val Thr Tyr Asp Glu Met Glu Asp Tyr
130                 135                 140

Tyr Tyr Arg Ala Glu Val Leu Ile Gly Val Asn Gly Pro Asn Asp Thr
145                 150                 155                 160

Ser Leu Lys Tyr Val Ala Pro Arg Lys Lys Pro Phe Pro Met Glu Pro
                165                 170                 175

Met Pro Tyr Gly Pro Ala Asp Arg Arg Phe Thr Glu Val Val Ala Thr
            180                 185                 190

Ala Gly Tyr Glu Asn Thr Pro Val Pro Gln Gly Arg Asn Ser Arg Pro
        195                 200                 205

Tyr Asp Gly Arg Pro Gln Cys Cys Gly Asn Asn Cys Met Pro Ile
210                 215                 220

Cys Pro Ile Gly Ala Met Phe Asn Gly Ile His Ser Ile Ile Lys Ala
225                 230                 235                 240

Glu Lys Ala Gly Ala Lys Val Leu Pro Asn Ala Val Val Tyr Lys Phe
                245                 250                 255

Asp Thr Asp Glu Asn Asn Asn Ile Thr Ala Leu Tyr Tyr Asp Pro
            260                 265                 270

Asp Lys Asn Ser His Arg Val Thr Ala Arg Thr Phe Val Leu Ala Gly
        275                 280                 285

Asn Gly Ile Glu Thr Pro Lys Leu Leu Leu Met Ala Ala Asn Asp Arg
290                 295                 300
```

```
Asn Pro Asn Gly Ile Ala Asn Ser Ser Gly Met Val Gly Arg Asn Met
305                 310                 315                 320

Met Asp His Pro Gly Ile Leu Met Ser Phe Gln Ser Ala Glu Pro Ile
            325                 330                 335

Trp Thr Gly Gly Gly Ser Val Gln Met Ser Ser Ile Thr Asn Tyr Arg
        340                 345                 350

Asp Gly Asp Phe Arg Arg Glu His Ser Ala Ile Gln Ile Gly Met Asn
    355                 360                 365

Asn Thr Ser Gln Asn His Lys Ala Gly Val Lys Ala Leu Gln Met Gly
370                 375                 380

Leu Val Gly Lys Lys Leu Asp Glu Glu Ile Arg Arg Arg Ala Ala Cys
385                 390                 395                 400

Gly Met Asp Ile Tyr Val Asn His Asp Ile Leu Ala Asn Pro Asp Asn
                405                 410                 415

Arg Leu Thr Leu Ser Thr Val His Lys Asp Lys Leu Gly Ile Pro Tyr
            420                 425                 430

Pro His Val Thr Tyr Asp Val Gly Asp Tyr Val Arg Lys Ala Ala Val
        435                 440                 445

Ser Ser Arg Glu His Leu Met Thr Ile Ala Lys Leu Phe Gly Ala Thr
450                 455                 460

Glu Ile Glu Met Thr Pro Tyr Phe Asn Pro Asn Asn His Ile Met Gly
465                 470                 475                 480

Gly Thr Ile Gly Gly His Asp Pro Lys Asp Ser Val Val Asp Lys Trp
                485                 490                 495

Met Arg Thr His Asp His Gln Asn Leu Tyr Ile Ala Ser Gly Gly Val
            500                 505                 510

Met Ala Ala Ala Gly Thr Val Asn Ser Thr Leu Ser Met Val Ala Leu
        515                 520                 525

Ser Leu Arg Ala Thr Asp Ser Ile Lys Arg Asp Leu Gln His Gly
530                 535                 540

<210> SEQ ID NO 17
<211> LENGTH: 541
<212> TYPE: PRT
<213> ORGANISM: Pantoea citrea

<400> SEQUENCE: 17

Met Asn Ala Asp Val Ile Val Gly Thr Gly Val Val Gly Cys Leu
1               5                   10                  15

Ile Ala Glu Gln Leu Leu Asp Ser Gly His Ser Val Val Met Leu Glu
            20                  25                  30

Ala Gly Pro Arg Val Glu Arg Trp Gln Ile Val Glu Asn Tyr Arg Asn
        35                  40                  45

Leu Pro Pro Val Ser Arg Leu His Phe Asn Ala Pro Tyr Pro Pro Glu
50                  55                  60

Pro Trp Ala Pro His Leu Met Ser Ala Thr Pro Glu Gln Ala Ala Glu
65                  70                  75                  80

Tyr Leu Gln Leu Glu Gly Pro Asn Ala Arg Ala Tyr Gln Gln Gly Tyr
                85                  90                  95

Val Arg Tyr Ala Gly Gly Ala Thr Trp His Trp Ala Gly Ile Cys Trp
            100                 105                 110

Arg Leu Thr Pro Glu Asp Met Gln Leu Lys Thr Leu Tyr Gly Val Gly
        115                 120                 125

Arg Asp Trp Ala Phe Asp Tyr Ala Thr Leu Glu Pro Tyr Tyr Thr Arg
    130                 135                 140
```

```
Ala Glu Tyr Ala Leu Gly Val Cys Gly Pro Ser Glu Pro Glu Leu Gln
145                 150                 155                 160

Trp Pro Pro Val Arg Ser Lys Pro Tyr Pro Met Gly Arg Leu Pro Phe
            165                 170                 175

Gly Pro Gly Glu Gln Arg Phe Thr Asp Ala Ala Ser Ile Gly Leu
        180                 185                 190

Thr Asn Leu Pro Ser Ala Gln Ala Arg Asn Ser Gly Ile Ala Tyr Gly
    195                 200                 205

Asp Arg Pro Ala Cys Cys Gly Asn Asn Cys Ile Pro Val Cys Pro
    210                 215                 220

Ile Gly Ala Lys Tyr Asp Ala Ala Thr Ser Leu Thr Arg Ile Glu Ser
225                 230                 235                 240

Lys Gly Gly Lys Ile Gln Pro Asn Ala Val Val Tyr Lys Ile Glu Thr
                245                 250                 255

Gly Ala Asp Asn Lys Val Gln Ala Val His Tyr Phe Asp Asn Lys
                260                 265                 270

Gln Thr His Arg Val Thr Gly Ser Val Phe Val Ile Ala Cys Asn Gly
            275                 280                 285

Ile Glu Thr Pro Lys Leu Leu Leu Met Ser Ala Asp Ser Arg Asn Pro
290                 295                 300

His Gly Val Ala Asn Ser Ser Asp Gln Val Gly Arg Asn Met Met Asp
305                 310                 315                 320

Gln Pro Lys Leu Val Val Glu Leu Glu Leu Ala Glu Pro Ala Trp Thr
                325                 330                 335

Gly Val Gly Pro Val Gln Gly Ser Ser Ile Met Glu Thr Ser Gln Gly
            340                 345                 350

Ser Phe Arg Ser Glu Tyr Cys Gly Ala Leu Phe Arg Phe Asn Asn Met
            355                 360                 365

Ala Arg Ser Arg Ile Gly Ala Met Ala Ala Leu Glu Lys Gly Leu Val
            370                 375                 380

Gly Lys Ala Leu Asp Thr Glu Ile Arg Arg Leu Ser Ala Cys Thr Thr
385                 390                 395                 400

Glu Ile Ala Ile Glu His Glu Leu Met Pro Asp Ala Asn Asn Arg Leu
                405                 410                 415

Thr Leu Ser Ala Lys Lys Asp Trp Leu Gly Leu Pro Lys Pro Asn Ile
            420                 425                 430

Tyr Tyr Asp Val Gly Asp Tyr Val Arg Gln Gly Ser Gln Arg His Ser
        435                 440                 445

Leu Pro Ile Ala Arg Gln Leu Ala Lys Ala Met Gly Ala Thr Lys Val
    450                 455                 460

Asp Ile Ser Thr Glu Tyr Thr Asn Ser Asp His Ile Met Gly Gly Cys
465                 470                 475                 480

Ile Met Gly Thr Asp Pro Ala Val Ser Val Asp Val Asp Cys Arg
                485                 490                 495

Ala His Asp His Glu Asn Leu Phe Leu Pro Gly Gly Ala Met Thr
        500                 505                 510

Thr Gly Gly Cys Gly Asn Ser Thr Leu Thr Met Ser Ala Leu Ala Leu
            515                 520                 525

Lys Ala Ala Asp Ala Ile His Ala Gln Leu Gly Lys Ala
530                 535                 540

<210> SEQ ID NO 18
<211> LENGTH: 534
<212> TYPE: PRT
<213> ORGANISM: Pantoea citrea
```

<400> SEQUENCE: 18

```
Met Ser Glu Thr Ile Ser Thr Asp Ile Val Ile Gly Ser Gly Val
1               5                   10                  15

Val Gly Ser Leu Thr Ala Arg Lys Leu Ala Leu Ala Gly Arg Lys Val
                20                  25                  30

Leu Met Leu Glu Ala Gly Pro Arg Ile Gln Arg Asp Gln Ile Val Ser
                35                  40                  45

Asn Phe Arg His Ser Ala Arg Lys Asp Asp Phe Ile Ala Pro Tyr Pro
50                  55                  60

Asn Ser Glu Ile Ala Pro Phe Pro Asp Tyr Lys Pro Glu Asp Asn Gly
65                  70                  75                  80

Tyr Leu Asp Gln Thr Gly Pro Lys Asp Tyr Lys Pro Glu Tyr Leu Arg
                    85                  90                  95

Val Val Gly Gly Thr Ser Trp His Trp Ala Ala Gln Ala Trp Arg Leu
                100                 105                 110

Val Pro Asn Asp Phe Arg Leu Lys Ser Gln Tyr Gly Val Gly Arg Asp
                115                 120                 125

Trp Pro Ile Ser Tyr Glu Asp Leu Glu Pro Tyr Tyr Tyr Glu Ala Glu
130                 135                 140

Ile Leu Trp Gly Val Ser Gly Pro Ala Glu Met Ala Lys Tyr Ser Pro
145                 150                 155                 160

Arg Lys His Pro Tyr Pro Met Glu Gly Val Lys Met Ser Tyr Leu Glu
                    165                 170                 175

Gln Arg Val Thr Ala Arg Leu Ala Pro Lys Tyr Glu Val Leu Thr Asn
                180                 185                 190

Thr Thr Gly Arg Asn Ser Val Pro Tyr Asp Gly Arg Pro Gln Cys Cys
                195                 200                 205

Gly Asn Asn Asn Cys Met Pro Ile Cys Pro Ile Asp Ala Gln Tyr His
            210                 215                 220

Gly Gly Ile Ala Ala Ala Ala Glu Ile Ala Gly Val Lys Leu Ile
225                 230                 235                 240

Pro Gln Ala Val Val Tyr Lys Leu Glu His Asn Ser His Gly Lys Ile
                245                 250                 255

Thr Ala Leu His Tyr Tyr Asp Trp Asn Lys Gln Ser His Arg Val Glu
                260                 265                 270

Ala Glu Ile Phe Val Met Ala Ala Asn Ala Val Glu Thr Pro Arg Ile
                275                 280                 285

Leu Met Leu Ser Ala Asp Asp Lys Asn Pro Asn Gly Leu Cys Asn Asn
290                 295                 300

Tyr Asp Gln Leu Gly Arg Asn Leu Met Asp His Pro Ser Asn Ser Ala
305                 310                 315                 320

Thr Phe Tyr Val Asp Glu Pro Leu Trp Pro Gly Arg Gly Pro Met Ser
                325                 330                 335

Pro Ser Ser Ile Gln Gln Leu Arg Asp Gly Ala Phe Arg Ser Glu Ser
                340                 345                 350

Ala Ala Phe Arg Ile Asp Ile Ser Asn Ser Ser Arg Val Ala Gly Val
                355                 360                 365

Thr Ala Gly Ala Ile Lys Glu Gly Leu Thr Gly Ala Asp Leu Asp Ser
370                 375                 380

Ala Ile Leu Tyr Arg Ala Ser His Glu Leu Ser Ile Lys Asn Val Leu
385                 390                 395                 400

Glu Gln Leu Pro Asp Pro Lys Asn Arg Thr Met Leu Ser Thr Arg Lys
                405                 410                 415
```

-continued

Lys Asp Ala Leu Gly Leu Pro Val Pro Ala Phe Ser Tyr Ser Phe Asp
            420                 425                 430

Glu Tyr Ile Glu Lys Gly Met Gln His Ser Leu Glu Val Tyr Ala Asp
            435                 440                 445

Ile Ala Arg Met Leu Gly Ala Thr Asn Val Arg Tyr Ser Thr Pro Gly
            450                 455                 460

Val Tyr Ser Asn Asn Gln His Ile Thr Gly Thr Leu Ala Met Gly Thr
465                 470                 475                 480

Asp Glu Lys Thr Ser Val Thr Asp His Val Gly Lys Ala Trp Glu Tyr
                485                 490                 495

Asp Asn Leu Tyr Met Val Ser Thr Gly Val Met Pro Thr Val Ala Thr
                500                 505                 510

Ala Asn Ser Thr Leu Thr Ala Cys Ala Leu Gly Leu Arg Thr Ala Asp
                515                 520                 525

Ala Ile Leu Gly Lys Ile
                530

<210> SEQ ID NO 19
<211> LENGTH: 553
<212> TYPE: PRT
<213> ORGANISM: Pantoea citrea

<400> SEQUENCE: 19

Met Met Met Lys Lys Pro Glu Phe Thr Pro Gly Gly Asp Ala Ser Ala
1               5                   10                  15

Asp Ile Val Ile Val Gly Ser Gly Ile Val Gly Leu Ile Ala Asp
            20                  25                  30

Arg Leu Val Ser Gln Gly Tyr Ser Val Leu Ile Leu Glu Ala Gly Leu
            35                  40                  45

Arg Ile Ser Arg Ala Gln Ala Val Glu Asn Trp Arg Asn Met Pro Phe
        50                  55                  60

Ala Asn Arg Ala Gly Ser Asp Phe Gln Gly Leu Tyr Pro Gln Ser Pro
65                  70                  75                  80

Leu Ala Pro Ala Pro Leu Tyr Phe Pro Pro Asn Asn Tyr Val Asn Val
                85                  90                  95

Thr Gly Pro Ser Ala Gly Ser Phe Gln Gln Gly Tyr Leu Arg Thr Val
                100                 105                 110

Gly Gly Thr Thr Trp His Trp Ala Ala Ser Cys Trp Arg His His Pro
            115                 120                 125

Ser Asp Phe Val Met Lys Ser Lys Tyr Gly Val Gly Arg Asp Trp Pro
        130                 135                 140

Ile Ser Tyr Asp Glu Met Glu Pro Trp Tyr Cys Glu Ala Glu Tyr Glu
145                 150                 155                 160

Ile Gly Val Ala Gly Pro Ser Asp Pro Ser Met Gln Ser Pro Ser Glu
                165                 170                 175

Arg Ser Arg Pro Tyr Pro Met Asp Met Val Pro Phe Ala His Gly Asp
                180                 185                 190

Thr Tyr Phe Ala Ser Val Val Asn Pro His Gly Tyr Asn Leu Val Pro
            195                 200                 205

Ile Pro Gln Gly Arg Ser Thr Arg Pro Trp Glu Gly Arg Pro Val Cys
        210                 215                 220

Cys Gly Asn Asn Asn Cys Gln Pro Ile Cys Pro Ile Gly Ala Met Tyr
225                 230                 235                 240

Asn Gly Ile His His Ile Glu Arg Ala Glu Ser Lys Gly Ala Val Val
                245                 250                 255

```
Leu Ala Glu Ser Val Val Tyr Lys Ile Asp Thr Asp Asn Asn Arg
            260                 265                 270

Val Thr Ala Val His Trp Leu Asp Asn Gln Gly Ala Ser His Lys Ala
        275                 280                 285

Thr Gly Lys Ala Phe Ala Leu Ala Cys Asn Gly Ile Glu Thr Pro Arg
        290                 295                 300

Leu Leu Leu Gln Ala Ala Asn Lys Ala Asn Pro Thr Gly Ile Ala Asn
305                 310                 315                 320

Ser Ser Asp Met Val Gly Arg Asn Met Met Asp His Ser Gly Phe His
                325                 330                 335

Cys Ser Phe Leu Thr Glu Glu Pro Val Trp Leu Gly Arg Gly Pro Ala
                340                 345                 350

Gln Ser Ser Cys Met Val Gly Pro Arg Asp Gly Ala Phe Arg Ser Glu
            355                 360                 365

Tyr Ser Ala Asn Lys Met Ile Leu Asn Asn Ile Ser Arg Val Val Pro
        370                 375                 380

Ala Thr Lys Gln Ala Leu Ala Lys Gly Leu Val Gly Lys Ala Leu Asp
385                 390                 395                 400

Glu Glu Ile Arg Tyr Arg Ser Ile His Gly Val Asp Leu Ser Ile Ser
                405                 410                 415

Leu Glu Pro Leu Pro Asp Pro Glu Asn Arg Leu Thr Leu Ser Lys Thr
            420                 425                 430

Arg Lys Asp Pro His Gly Leu Ala Cys Pro Asp Ile His Tyr Asp Val
        435                 440                 445

Gly Asp Tyr Val Arg Lys Gly Ala Thr Ala Ala His Glu Gln Leu Gln
        450                 455                 460

His Ile Gly Ser Leu Phe Asn Gly Lys Glu Phe Asn Ile Thr Thr Ala
465                 470                 475                 480

Leu Asn Ala Asn Asn His Ile Met Gly Gly Thr Ile Met Gly Lys Ser
                485                 490                 495

Ala Lys Asp Ala Val Val Asp Gly Asn Cys Arg Thr Phe Asp His Glu
            500                 505                 510

Asn Leu Trp Leu Pro Gly Gly Gly Ala Ile Pro Ser Ala Ser Val Val
        515                 520                 525

Asn Ser Thr Leu Ser Met Ala Ala Leu Gly Leu Lys Ala Ala His Asp
530                 535                 540

Ile Ser Leu Arg Met Lys Glu Phe Ala
545                 550

<210> SEQ ID NO 20
<211> LENGTH: 425
<212> TYPE: PRT
<213> ORGANISM: Pantoea citrea

<400> SEQUENCE: 20

Met Lys Lys Met Thr Phe Lys Arg Leu Leu Leu Ala Asn Thr Val Val
1               5                   10                  15

Leu Ala Cys Gly Leu Ala Gly Ala Val Gln Ala Asp Ala Pro Asn
                20                  25                  30

Gln Asp Gln Leu Val Lys Gln Gly Glu Tyr Leu Ala Arg Leu Gly Asp
            35                  40                  45

Cys Met Ala Cys His Thr Thr Ser Gly Arg Pro Asp Tyr Ser Gly Gly
        50                  55                  60

Leu Ala Ile Lys Ser Asp Leu Gly Thr Ile Tyr Ser Thr Asn Ile Thr
65                  70                  75                  80
```

```
Pro Asp Lys Gln Tyr Gly Ile Gly Asn Tyr Thr Glu Gln Gln Phe Ala
                85                  90                  95

Asp Ala Val Arg Lys Gly Val Arg Pro Asp Gly Ser Phe Leu Tyr Pro
            100                 105                 110

Ala Met Pro Tyr Pro Asp Tyr Ala Lys Thr Ser Asp Ala Asp Ile His
        115                 120                 125

Ala Leu Tyr Ser Tyr Phe Met His Gly Val Thr Ala Ser Asn Ser Gln
    130                 135                 140

Pro Pro Gln Thr Asp Leu Ser Phe Pro Phe Ser Gln Arg Trp Gly Met
145                 150                 155                 160

Arg Phe Trp Asn Met Val Phe Thr Ser Asp Lys Pro Phe Gln Pro Ile
                165                 170                 175

Gly Gly Ala Ser Glu Gln Val Asn Arg Gly Ala Tyr Ile Val Glu Ser
            180                 185                 190

Leu Gly His Cys Ser Ser Cys His Thr Pro Arg Gly Val Ala Met Glu
        195                 200                 205

Glu Lys Ala Leu Asp Ser Ser Asp Ser Asn Phe Leu Ser Gly Gly Asn
    210                 215                 220

Leu Asn Gly Trp Asp Val Pro Ser Leu Arg Gly Ile Ala Arg Trp Ser
225                 230                 235                 240

Pro Asp Glu Ile Val Asp Tyr Leu Gln Ser Gly Arg Asn Asp Lys Ala
                245                 250                 255

Gly Val Ala Gly Glu Met Thr Ser Val Val Lys Asn Ser Thr Ser His
            260                 265                 270

Met Thr Asp Ala Asp Leu Gln Ala Ile Ala Ala Tyr Leu Lys Phe Leu
        275                 280                 285

Gly Gly Asn Pro Pro Leu Gln Ala Tyr Asp Gln Gln Lys Asn Gln Ala
    290                 295                 300

Thr Thr Ala Lys Leu Thr Ala Ala Val Asp Leu Thr Glu Gly Gln Thr
305                 310                 315                 320

Leu Tyr Leu Asn Asn Cys Gly Ala Cys His Phe Val Asn Gly Leu Asp
                325                 330                 335

Ala Ala Arg Ala Phe Pro Gln Leu Asp Gln Ala Ser Val Val Asn Ala
            340                 345                 350

Lys Asp Pro Gln Gly Leu Ile His Ile Leu Gln Gly Ala Gln Leu
        355                 360                 365

Pro Ala Thr Glu Lys Ser Pro Ser Met Leu Lys Met Pro Gly Phe Gly
    370                 375                 380

His Arg Leu Ser Asp Asp Gln Val Ala Lys Leu Ala Thr Phe Val Arg
385                 390                 395                 400

Gln Gly Trp Ser Asn Asp Ala Ser Ala Val Thr Ala Asp Gln Val Lys
                405                 410                 415

Lys Val Arg Glu Gly Leu Glu Gln His
            420                 425

<210> SEQ ID NO 21
<211> LENGTH: 436
<212> TYPE: PRT
<213> ORGANISM: Pantoea citrea

<400> SEQUENCE: 21

Met Lys Thr Ile Phe Val Lys Leu Leu Pro Leu Ala Ile Met Ser Val
1               5                   10                  15

Ile Gly Val Ile Gly Leu Lys Gln Ala Tyr Ala Asp Ser Asn Asp Ser
            20                  25                  30
```

```
Ala Asp Leu Ile Lys Gln Gly Ala Tyr Leu Ala Arg Ala Gly Asp Cys
         35                  40                  45

Thr Ala Cys His Thr Glu Ala Gly Lys Pro Phe Ala Gly Gly Leu
 50                  55                  60

Ala Ile Arg Ser Pro Met Gly Val Ile Tyr Ser Thr Asn Ile Thr Pro
 65                  70                  75                  80

Asp Lys Asn Ala Gly Ile Gly Ser Tyr Thr Glu Gln Gln Phe Ala Glu
                 85                  90                  95

Ala Val Arg Lys Gly Val Arg Arg Asp Gly Ser Asn Leu Tyr Pro Ala
                100                 105                 110

Met Pro Tyr Pro Asp Tyr Ser Gly Ile Thr Asp Lys Asp Ile His Ala
            115                 120                 125

Leu Tyr Val Tyr Phe Met His Gly Val Ala Pro Val Ser Val Lys Ala
        130                 135                 140

Pro Gln Thr Ser Leu Thr Phe Pro Phe Ser Leu Arg Trp Gly Met Lys
145                 150                 155                 160

Phe Trp Asn Ile Ala Phe Ala Ser Gly Asn Ser Tyr Pro Pro Ala Pro
                165                 170                 175

Thr Thr Gln Ser Asp Ser Ala Asp Ala Gln Ala Leu Ser Arg Gly Arg
            180                 185                 190

Tyr Leu Val Asp Thr Leu Gly His Cys Ser Ser Cys His Thr Pro Arg
        195                 200                 205

Gly Ile Gly Met Gln Glu Lys Ala Leu Asn Asp Ser Asp Ser Arg Phe
    210                 215                 220

Leu Ser Ser Gly Met Leu Asn Asp Trp Thr Val Pro Ser Leu Arg Asn
225                 230                 235                 240

Pro Asp Gly Trp Ser Val Asn Asp Ile Ala Glu Tyr Leu Ser Thr Gly
                245                 250                 255

Arg Asn Asp Phe Ala Ser Val Gly Gly Glu Met Thr Gly Val Val Gln
            260                 265                 270

His Ser Met Gln His Met Asn Gln Ala Asp Leu His Ala Ile Ala Leu
        275                 280                 285

Tyr Leu Lys Ser Leu Pro Ala Ser Thr Lys Gln Gln His Asn Val Lys
    290                 295                 300

Pro Asp Leu Gln Asn Asp Thr Gln Lys Thr Val Asp Thr Leu Thr Leu
305                 310                 315                 320

Gly Lys Asn Leu Asn Ser Gly Gln Met Leu Tyr Leu Asn Asn Cys Glu
                325                 330                 335

Ala Cys His Leu Thr Asp Gly Gly Ala Lys Lys Ile Phe Pro Arg
            340                 345                 350

Leu Asn Gly Ala Ser Ile Val Leu Ala Asp Asn Pro Thr Gly Leu Ile
        355                 360                 365

Ser Val Met Leu Lys Gly Ala Gln Thr Pro Ser Thr Ala Asn Ala Pro
    370                 375                 380

Ser Val Gln Phe Met Pro Gly Phe Glu Gln Arg Leu Asn Asp Gln Gln
385                 390                 395                 400

Ile Ala Glu Leu Ala Ser Phe Val Arg Ser Gly Trp Gly Asn Asn Ala
                405                 410                 415

Pro Pro Val Ser Ala Ala Asp Val Ala Lys Val Arg Ala Ser Leu Asn
            420                 425                 430

Thr Ser Gln Lys
        435
```

```
<210> SEQ ID NO 22
<211> LENGTH: 440
<212> TYPE: PRT
<213> ORGANISM: Pantoea citrea

<400> SEQUENCE: 22

Met Lys Lys Ile Thr Leu Leu Tyr Ser Ala Val Leu Ala Gly Leu Leu
1               5                   10                  15

Gly Cys Thr Val Ala Gln Ala Asp Asp Ser Gly Gly Gln Leu Val Ala
            20                  25                  30

Arg Gly Glu Tyr Leu Ala Thr Ala Gly Asp Cys Val Ala Cys His Thr
        35                  40                  45

Ala Ser Gly Pro Ala Phe Thr Gly Gly Leu Lys Met Thr Thr Pro Val
    50                  55                  60

Gly Ala Ile Tyr Ser Thr Asn Ile Thr Pro Asp Lys Gln Thr Gly Ile
65                  70                  75                  80

Gly Asp Tyr Thr Tyr Asp Asp Phe Ala Arg Ala Leu Arg Gln Gly Ile
                85                  90                  95

Ala Arg Asp Gly Arg His Leu Tyr Pro Ala Met Pro Tyr Thr Glu Tyr
            100                 105                 110

Ala Lys Val Asn Asp Asp Met His Ala Leu Tyr Ala Tyr Phe Met
        115                 120                 125

His Gly Val Thr Ala Val His Gln Pro Asn Lys Pro Ser Asp Ile Pro
130                 135                 140

Trp Pro Leu Asn Met Arg Trp Pro Leu Ala Val Trp Asn Lys Leu Phe
145                 150                 155                 160

Leu Asp Asn Thr Pro Phe Lys Asn Asp Pro Ala Gln Ser Ala Glu Trp
                165                 170                 175

Asn Arg Gly Ala Tyr Leu Val Gln Gly Leu Glu His Cys Gly Ala Cys
            180                 185                 190

His Thr Pro Arg Gly Ile Ala Phe Gln Glu Lys Ala Ser Asp Glu Lys
        195                 200                 205

Gly Ala Asp Phe Leu Thr Gly Gly Thr Leu Glu Gly Trp His Ala Pro
    210                 215                 220

Asp Leu Thr Gly Asn Val Lys Ser Gly Leu Gly Arg Trp Ser Thr Gly
225                 230                 235                 240

Asp Leu Gln Thr Phe Leu Lys Thr Gly Arg Asn Asp Gln Ser Ala Ala
                245                 250                 255

Phe Gly Ser Met Ser Glu Ala Ile Gly His Ser Thr Gln His Leu Thr
            260                 265                 270

Asp Ala Asp Leu His Ala Met Ala Val Tyr Ile Lys Ser Leu Lys Ser
        275                 280                 285

Ser Asp Pro Glu Ala Gln Pro Pro Ala Thr Thr Asp Ser Thr Thr Ala
    290                 295                 300

Ala Leu Ile Arg Gly Asp Leu Ser Gln Thr Gly Ala Glu Glu Tyr Met
305                 310                 315                 320

Asp Asn Cys Ala Ala Cys His Arg Leu Asp Gly Lys Gly Tyr Ala Lys
                325                 330                 335

Thr Phe Pro Thr Leu Ala Gly Asn Pro Val Leu Leu Ser Asp Asp Pro
            340                 345                 350

Ser Ser Leu Ile Ser Ile Val Leu Thr Gly Gly Lys Met Pro Val Thr
        355                 360                 365

Gln Gln Ser Val Thr Gly Leu Thr Met Pro Asp Phe Gly Trp Arg Leu
    370                 375                 380

Ser Asp Gln Gln Val Ala Asp Val Val Ser Phe Ile Arg Ser Ser Trp
```

```
              385                 390                 395                 400
Gly Asn Asn Ala Gly Lys Val Glu Ala Lys Gln Val Ala Asp Ile Arg
                405                 410                 415
Lys Leu Met Pro Val Pro Asn Gln Ala Asp Asn Pro Gln Val Lys Ala
                420                 425                 430
Glu Lys Pro Asp Pro Ala Lys Lys
                435                 440

<210> SEQ ID NO 23
<211> LENGTH: 449
<212> TYPE: PRT
<213> ORGANISM: Pantoea citrea

<400> SEQUENCE: 23

Met Lys Ala Ile Lys Gly Ile Ile Val Val Ile Leu Val Leu Val Ile
 1               5                  10                  15

Ile Leu Leu Ala Tyr Ala Leu Trp Pro Thr Lys Thr Ala Ser Leu Ser
                20                  25                  30

Pro Leu Pro Ala Asp Asn Ser Pro Gln Leu Ala Ser Leu Val Ser Gln
                35                  40                  45

Gly Gln Tyr Leu Ala Thr Ala Gly Asp Cys Ala Ala Cys His Thr Gln
                50                  55                  60

Pro Gly Gly Lys Pro Leu Ala Gly Gly Leu Pro Ile Arg Ser Pro Ile
 65              70                  75                  80

Gly Val Ile Tyr Thr Thr Asn Ile Thr Pro Asp Lys Gln Thr Gly Ile
                85                  90                  95

Gly Asn Tyr Ser Leu Asp Asp Phe Glu Arg Ala Val Arg His Gly Ile
                100                 105                 110

Leu Pro Asn Gly Asp Thr Leu Tyr Pro Ala Met Pro Tyr Pro Ser Tyr
                115                 120                 125

Ala Lys Ile Ser Asp Asp Val Arg Ala Leu Tyr Ala Trp Phe Met
                130                 135                 140

His Gly Val Gln Pro Val Ser Gln Gln Asn Arg Ala Ser Asp Ile Pro
145                 150                 155                 160

Trp Pro Leu Ser Met Arg Leu Pro Leu Ala Val Trp Arg Lys Met Phe
                165                 170                 175

Ala Pro Asp Pro Ala Asn Thr Gly Phe Thr Ala Asp Lys Tyr Gln Ser
                180                 185                 190

Ala Ser Leu Ala Arg Gly Ala Tyr Leu Val Gln Gly Leu Gly His Cys
                195                 200                 205

Gly Thr Cys His Thr Pro Arg Ala Gly Thr Leu Gln Glu Lys Ala Leu
                210                 215                 220

Asp Asp Ser Gly Gln Gln Tyr Leu Ala Gly Gln Val Ile Asp Gly
225                 230                 235                 240

Trp Leu Ala Val Asn Leu Arg Gly Asp Lys Ala Asp Gly Leu Gly Asn
                245                 250                 255

Trp Thr Glu Gln Asp Ile Ile Asp Thr Leu Arg Thr Gly His Asn Val
                260                 265                 270

Ser His Thr Val Val Gly Gln Pro Met Ala Glu Val Val Ala Lys Ser
                275                 280                 285

Thr Ser His Met Ser Asp Ala Asp Leu Ala Ala Ile Ala Ala Tyr Ile
                290                 295                 300

Lys Ser Leu Pro Ala Gly Gln Gly Ser Lys Ala Ser Tyr Thr Glu Ser
305                 310                 315                 320

Ser Gln Thr Ala Asp Met Leu Ala Arg Gly Glu Asn Pro Thr Pro Gly
```

```
                    325                 330                 335
Ala Gln Leu Tyr Val Asp Asn Cys Ser Ala Cys His Gln Thr Ser Gly
                340                 345                 350

Lys Gly Val Gln His Ile Phe Pro Ala Met Ala Asp Asn Pro Thr Ile
            355                 360                 365

Leu Ala Asp Asn Pro Val Ser Val Ile His Leu Ile Leu Asp Gly Ser
        370                 375                 380

Arg Leu Pro Ala Thr Pro Gln Ser Pro Ser Ala Leu Ala Met Pro Gly
385                 390                 395                 400

Phe Gly Trp Arg Leu Ser Asp Lys Gln Val Ala Asp Leu Ser Asn Phe
                405                 410                 415

Ile Arg Asn Ser Trp Gly Asn Lys Ala Thr Glu Val Thr Glu Gln Gln
                420                 425                 430

Val Lys Gln Val Arg Ala Asp Tyr Pro Pro Lys Gly Glu Asn Lys Asp
            435                 440                 445

Pro

<210> SEQ ID NO 24
<211> LENGTH: 440
<212> TYPE: PRT
<213> ORGANISM: Pantoea citrea

<400> SEQUENCE: 24

Met Lys Lys Ser Ile Leu Ala Leu Val Phe Gly Ser Leu Ala Phe Ser
1               5                   10                  15

Ala Met Ala Glu Asp Asn Ser Gly Gln Asp Leu Val Lys Arg Gly Glu
                20                  25                  30

Tyr Leu Ala Arg Ala Gly Asp Cys Val Ala Cys His Thr Ser Glu Gly
            35                  40                  45

Gly Gln Pro Phe Ala Gly Gly Leu Pro Met Ala Thr Pro Ile Gly Lys
        50                  55                  60

Ile Tyr Ser Thr Asn Ile Thr Pro Asp Lys Thr Tyr Gly Ile Gly Asp
65                  70                  75                  80

Tyr Thr Tyr Asp Asp Phe Gln Lys Ala Val Arg His Gly Val Ala Lys
                85                  90                  95

Asn Gly Glu Thr Leu Tyr Pro Ala Met Pro Tyr Pro Ser Tyr Ala Val
            100                 105                 110

Val Ser Asp Asp Asp Met His Ala Leu Tyr Ala Tyr Phe Met Gln Gly
        115                 120                 125

Val Lys Pro Val Ser Gln Pro Asn His Ala Thr Asp Ile Pro Trp Pro
130                 135                 140

Leu Ser Met Arg Trp Pro Leu Ala Ile Trp Arg Gly Met Phe Ala Pro
145                 150                 155                 160

Ala Val Lys Pro Ala Thr Ala Gln Pro Gly Glu Asp Pro Val Leu Ala
                165                 170                 175

Arg Gly Arg Tyr Leu Val Glu Gly Leu Gly His Cys Gly Ala Cys His
            180                 185                 190

Thr Pro Arg Ser Ile Thr Met Gln Glu Lys Ala Leu Asn Asn Ser Glu
        195                 200                 205

Gly Thr Asp Tyr Leu Ser Gly Ser Ala Pro Ile Asp Gly Trp Thr
210                 215                 220

Ala Ile Asn Leu Arg Gly Asp Arg Asp Gly Leu Gly Arg Trp Ser
225                 230                 235                 240

Thr Ser Asp Ile Ala Gln Phe Leu Arg Tyr Gly Arg Asn Asp Arg Thr
                245                 250                 255
```

```
Ala Val Phe Gly Gly Met Thr Asp Val Val Gln His Ser Leu Gln Tyr
            260                 265                 270

Leu Ser Asp Asp Ile Asn Ala Ile Ala Arg Tyr Leu Lys Ser Leu
        275                 280                 285

Ser Pro Arg Asp Ser His Gln Pro Val Phe Lys Ala Asp Ser Val
290                 295                 300

Ser Gln Ala Leu Trp Lys Gly Asn Asp Gln Arg Thr Gly Ala Ala Glu
305                 310                 315                 320

Tyr Val Asp Ser Cys Ala Ala Cys His Lys Thr Asp Gly Ser Gly Tyr
                325                 330                 335

Thr Arg Phe Phe Pro Ala Leu Lys Gly Asn Pro Val Leu Ala Glu
            340                 345                 350

Asp Pro Thr Ser Leu Ile His Ile Val Leu Thr Gly Asp Thr Leu Pro
            355                 360                 365

Gly Val Gln Gly Ala Pro Ser Ala Ile Thr Met Pro Ala Phe Gly Trp
    370                 375                 380

Arg Leu Asn Asp Gln Gln Val Ala Asn Val Val Asn Phe Ile Arg Ser
385                 390                 395                 400

Ser Trp Gly Asn Thr Ser Thr Ala Ala Val Ser Ala Asp Gln Val Ala
                405                 410                 415

Lys Leu Arg Lys Ser Ala Asp Val Gln Gly Lys Met Gly Asp Ala Ser
                420                 425                 430

Val Glu Lys Leu Pro Lys Gln Pro
            435                 440

<210> SEQ ID NO 25
<211> LENGTH: 441
<212> TYPE: PRT
<213> ORGANISM: Pantoea citrea

<400> SEQUENCE: 25

Met Ala Lys Lys Thr Arg Arg Val Ile Ser Val Val Ala Ala Val Val
1               5                   10                  15

Ile Ala Gly Ala Leu Gly Tyr Thr Ala Tyr Glu Gln Tyr Gly Ile His
            20                  25                  30

Lys Asn Tyr Pro Gln Thr Val Ser Leu Glu Thr Gly Pro Ala Leu Gln
        35                  40                  45

Asp Gln Ile Lys Arg Gly Glu Tyr Ile Ala Arg Leu Ser Asp Cys Thr
    50                  55                  60

Ala Cys His Thr Ala Glu Gly Gly Gln Pro Phe Ala Gly Gly Tyr Ala
65                  70                  75                  80

Leu Gln Thr Pro Phe Gly Lys Ile Leu Ser Ser Asn Ile Thr Ser Asp
                85                  90                  95

Arg Glu Thr Gly Ile Gly Gly Trp Thr Gln Glu Gln Phe Asp Lys Ala
            100                 105                 110

Val Arg His Gly Val Gly Ser His Gly Tyr Leu Tyr Ala Ala Met Pro
        115                 120                 125

Tyr Pro Ala Tyr Ser Arg Leu Thr Asp Ala Asp Leu Thr Asp Leu Trp
    130                 135                 140

Ala Tyr Ile Arg Asn Leu Pro Ala Val Asn His Lys Val Val Glu Asn
145                 150                 155                 160

Gln Leu Pro Phe Pro Phe Asn Gln Arg Trp Thr Leu Ala Gly Trp Asn
                165                 170                 175

Met Leu Phe Phe Lys Asp Ala Ala Phe Thr Pro Asn Pro Gln Ala Ser
            180                 185                 190
```

Glu Gln Val Asn Arg Gly Gln Tyr Leu Val Asp Gly Pro Gly His Cys
            195                 200                 205

Ala Ser Cys His Thr Ala Lys Asn Met Leu Gly Gly Asp Ser Ser Ala
    210                 215                 220

Tyr Leu Gln Gly Ala Leu Gln Gly Trp Tyr Ala Pro Asp Leu Thr
225                 230                 235                 240

Pro Asp Pro His Ser Gly Leu Gly Asn Trp Ser Asn Ala Asp Ile Val
                245                 250                 255

Ser Tyr Leu Arg Ser Gly Ser Asn Arg Ile Thr Ala Ser Ser Gly Pro
            260                 265                 270

Met Thr Glu Ala Val Glu Asn Ser Thr Gln Tyr Met Asn Asp Asn Asp
        275                 280                 285

Leu Asn Ala Ile Ala Ala Tyr Leu Lys Ser Ile Pro Ala Ser His Pro
    290                 295                 300

Gln Val Pro Thr Ala Leu Thr Ala Asp Asp Gln Gln Met Val Ser Gly
305                 310                 315                 320

Lys Lys Val Phe Glu Ser Gln Cys Ser Ala Cys His Val Ser Asp Gly
                325                 330                 335

Ala Gly Ile Arg Asn Met Ile Pro Ala Leu Ala Gly Asn Pro Gln Val
            340                 345                 350

Asn Ser Ala Asp Pro Ser Ser Leu Leu Asn Val Val Leu Asn Gly Ser
        355                 360                 365

Glu Gly Pro Phe Thr His Ala Asn Pro Thr Ala Gly Met Pro Ser
370                 375                 380

Phe Gly Trp Lys Leu Ser Asp Ala Asn Ile Ala Glu Ala Leu Thr Tyr
385                 390                 395                 400

Ile Arg Asn Ser Trp Gly Asn Ala Ala Pro Ala Val Thr Ala Asp Gln
            405                 410                 415

Val Ser Ala Ala Arg Lys Ala Thr Gly Ala Lys Ser Trp Leu Gly Asp
        420                 425                 430

Ser Ile Ala Ser Gln Asp Ser Gly Lys
            435                 440

<210> SEQ ID NO 26
<211> LENGTH: 441
<212> TYPE: PRT
<213> ORGANISM: Pantoea citrea

<400> SEQUENCE: 26

Met Lys Lys Thr Thr Ile Ala Ile Ala Val Ala Gly Ile Val Val Val
1               5                   10                  15

Gly Ala Leu Ala Ala Leu Trp Met Asn Gly Ser Thr Arg Ala Asp Asp
            20                  25                  30

Val Ala Gly Asp Gln Val Gln Thr Ser Gln Pro Val Ser Ala Glu Asp
        35                  40                  45

Ser Ala Ala Val Lys Arg Gly Glu Tyr Ile Ala Val Ala Gly Asp Cys
    50                  55                  60

Val Ala Cys His Thr Ala Pro Gly Ser Lys Thr Pro Phe Ser Gly Gly
65                  70                  75                  80

Tyr Gly Ile Asp Thr Pro Phe Gly Thr Ile Tyr Ala Ser Asn Ile Thr
                85                  90                  95

Pro Asp Asn Gln Thr Gly Ile Gly Gln Trp Thr Glu Arg Asp Phe Tyr
            100                 105                 110

Arg Ala Val Arg His Gly Ile Gly Arg Gln Gly Glu Asn Leu Tyr Pro
        115                 120                 125

Ala Met Pro Tyr Asn Ala Tyr Val Lys Val Ser Asp Gln Asp Met His
        130                 135                 140

Asp Leu Trp Met Tyr Met Arg Thr Val Lys Pro Val Asn Gln Gln Pro
145                 150                 155                 160

Pro Glu Thr His Leu Pro Phe Pro Tyr Asn Ile Arg Leu Ala Met Arg
                165                 170                 175

Gly Trp Asn Leu Leu Phe Phe Lys Asn Ser Gly Phe Asp Ala Asn Ser
            180                 185                 190

Ser Gln Ser Ala Glu Trp Asn Arg Gly Ala Tyr Leu Val Gln Gly Leu
        195                 200                 205

Glu His Cys Ala Ala Cys His Thr Pro Lys Asn Met Leu Gly Gly Asp
    210                 215                 220

Thr Ser Ala Tyr Leu Gln Gly Ser Ser Leu Gly Gln Trp His Ala Pro
225                 230                 235                 240

Glu Ile Thr Gly Asn Thr Tyr Thr Gly Ile Gly Gln Trp Ser Glu Gln
                245                 250                 255

Gln Val Val Asp Tyr Leu Lys Ser Gly Ser Asn Gln Val Ala Val Ala
            260                 265                 270

Ser Gly Pro Met Ala Glu Ala Val Thr Asn Ser Thr Gln His Leu Thr
        275                 280                 285

Asp Ala Asp Leu Arg Ala Ile Ala Val Tyr Leu Lys Ser Gln Pro Gly
    290                 295                 300

Ser Ala Asn Gln Lys Pro Ala Ala Leu Ala Thr Ser Pro Leu Met
305                 310                 315                 320

Gln Gln Gly Ala Asn Val Tyr Gln Ala Asn Cys Ser Ala Cys His Asn
                325                 330                 335

Ser Asp Gly Arg Gly Ile Pro Gln Leu Ala Ala Gly Leu Arg Asp Asn
            340                 345                 350

Pro Gly Ile Met Ala Ala Asp Ser Ser Ser Val Ile Thr Thr Ile Leu
        355                 360                 365

Glu Gly Gly Arg Gly Ala Val Thr Leu Asn Asn Pro Thr Ser Gly Ala
    370                 375                 380

Met Pro Ser Phe Ala Trp Lys Leu Ser Asp Gln Gln Ile Ala Ala Val
385                 390                 395                 400

Ser Ser Tyr Ile Arg Asn Ser Trp Gln Asn Ala Ala Pro Ala Val Thr
                405                 410                 415

Ser Gln Gln Val Ala Ala Met Arg Lys Gln Leu Lys Leu Thr Pro Gln
            420                 425                 430

Leu Pro Asp Asn Gly Glu Pro Ala His
        435                 440

<210> SEQ ID NO 27
<211> LENGTH: 436
<212> TYPE: PRT
<213> ORGANISM: Pantoea citrea

<400> SEQUENCE: 27

Met Thr Ile Lys Lys Tyr Ile Ala Ser Val Gly Val Ala Val Val
1               5                   10                  15

Ala Gly Leu Gly Phe Thr Gly Trp Lys Cys Trp His Asn Ala His Gln
            20                  25                  30

Asp His Ser Phe Val Ala Pro Ala Ser Ala Gly Asp Thr Gly Ser Thr
        35                  40                  45

Ala Ile Ala Arg Gly Lys Tyr Leu Ala Thr Ala Gly Asp Cys Val Ala
    50                  55                  60

```
            Cys His Thr Ala Pro Gly Gly Lys Pro Tyr Ala Gly Leu Gly Leu
            65                  70                  75                  80

Asn Thr Pro Phe Gly Thr Ile Tyr Ala Thr Asn Ile Thr Pro Asp Lys
                            85                  90                  95

Glu Thr Gly Ile Gly Gly Trp Thr Asp Gln Gln Phe Met Asn Ala Val
                        100                 105                 110

Arg Asn Gly Lys Gly Ala Asn Gly Glu Asn Leu Tyr Pro Ala Met Pro
                    115                 120                 125

Tyr Asn Val Tyr Ala Gln Val Ser Asp Gln Asp Leu Lys Asp Ile Lys
                130                 135                 140

Ala Tyr Leu Asp Ser Val Pro Ala Val His Tyr Thr Gly Pro Lys Thr
            145                 150                 155                 160

Asp Leu Pro Phe Pro Tyr Asn Ile Arg Leu Met Met Met Gly Trp Asn
                            165                 170                 175

Leu Leu Phe Leu Asn Thr Ala Ala Phe Lys Ala Asp Pro Ala Gln Ser
                        180                 185                 190

Ala Gln Trp Asn Arg Gly Ala Tyr Leu Val Glu Gly Leu Gly His Cys
                    195                 200                 205

Thr Ser Cys His Thr Pro Lys Asn Met Leu Gly Ala Asp Lys Met Gly
                210                 215                 220

Val His Leu Gln Gly Gly Glu Leu Glu Gly Trp Leu Ala Pro Glu Ile
            225                 230                 235                 240

Thr Gly Asn Thr Arg Gln Gly Ile Gly Gly Trp Ser Asp Asp Glu Leu
                            245                 250                 255

Val His Tyr Leu Lys Thr Gly Ala Asn Asp Lys Thr Val Ala Ala Gly
                        260                 265                 270

Pro Met Ala Glu Ala Val His Asn Ser Leu Gln His Leu Asn Asp Gln
                    275                 280                 285

Asp Leu Thr Ala Met Ala Thr Tyr Leu Lys Ser Leu Pro Gly Ser Glu
                290                 295                 300

Asp Lys Ser Val Ala Leu Ser Gly Met Asp Asp Val Met Ala Arg Gly
            305                 310                 315                 320

Gln Ser Ile Tyr Gln Ala Asn Cys Ser Ala Cys His Gln Ser Asp Gly
                            325                 330                 335

Ala Gly Val Arg Asp Met Val Pro Ala Leu Arg Gly Asn Asn Gly Leu
                        340                 345                 350

Gln Ala Phe Glu Pro Thr Asn Val Leu His Val Leu Met Ile Gly Ala
                    355                 360                 365

Gln Gly Ala Ala Thr Ala Ser Asn Pro Thr Ser Ala Ala Met Pro Glu
                370                 375                 380

Phe Gly Trp Lys Leu Thr Asp Gln Gln Met Ala Asp Val Ser Thr Tyr
            385                 390                 395                 400

Val Arg Asn Ser Trp Gly Asn Lys Ala Pro Ala Val Thr Ala Ser Gln
                            405                 410                 415

Ala Ala Ala Ala Arg Lys Leu Leu Ser Gly Ser Pro Ala Leu His Asn
                        420                 425                 430

Pro Ala Ala Asn
                    435

<210> SEQ ID NO 28
<211> LENGTH: 408
<212> TYPE: PRT
<213> ORGANISM: Pantoea citrea

<400> SEQUENCE: 28
```

```
Met Met Lys Lys Leu Met Leu Thr Ala Gly Ser Leu Leu Leu Thr
1               5                   10                  15

Ala Gly Tyr Ala His Ala Asp Ser Gly Gly Asp Ser Trp Asp Leu Val
            20                  25                  30

Ser Lys Gly Arg Tyr Ile Ala Gln Leu Gly Asp Cys Thr Ala Cys His
            35                  40                  45

Thr Glu Pro Gly His Pro Leu Phe Ser Gly Val Ala Ile Glu Thr
    50                  55                  60

Pro Phe Gly Lys Leu Val Gly Ala Asn Ile Thr Pro Asp Pro Glu Thr
65                  70                  75                  80

Gly Ile Gly Lys Trp Thr Phe Glu Asp Phe Gln Asn Ala Met Arg Lys
                85                  90                  95

Gly His Ser Arg Asp Gly Gln Leu Leu Tyr Gly Ala Met Pro Phe Thr
            100                 105                 110

Ala Tyr Thr Lys Val Thr Thr Asp Asp Asn Arg Ala Leu Trp Ser Tyr
            115                 120                 125

Leu Gln Thr Val Gln Pro Val Asn Arg Val Val Asn Thr Asn Gln Leu
    130                 135                 140

Pro Phe Pro Phe Asn Ile Arg Thr Ser Leu His Val Trp Asp Met Leu
145                 150                 155                 160

Asn Phe Thr Glu Gly Glu Tyr Lys Pro Asp Pro Lys Gln Ser Ala Glu
                165                 170                 175

Trp Asn Arg Gly Ala Tyr Leu Val Gln Gly Leu Gly His Cys Ser Thr
            180                 185                 190

Cys His Thr Pro Lys Asn Met Leu Gly Gly Asp Lys Asp Ser Lys Phe
    195                 200                 205

Leu Gln Gly Gly Ser Leu Gly Val Trp Phe Ala Pro Asp Ile Thr Ala
    210                 215                 220

Asn Thr His Ser Gly Ile Gly Gln Trp Thr Gln Gln Glu Ile Val Glu
225                 230                 235                 240

Tyr Leu Lys Thr Gly Ala Asn Lys Tyr Asp Ile Ala Ser Gly Pro Met
                245                 250                 255

Ala Glu Ala Val Glu His Ser Thr Gln Tyr Trp Lys Asp Glu Asp Leu
            260                 265                 270

Asn Ala Ala Ala Val Tyr Leu Lys Ser Leu Lys Asn Asp Ser Ser Gln
        275                 280                 285

Pro Gln Pro Leu Ala Ala Asp Asn Gly Gln Met Val Asn Gly Lys Ala
    290                 295                 300

Ile Tyr Ala Asp Arg Cys Ser Ala Cys His Val Ser Gln Gly Gln Gly
305                 310                 315                 320

Val Ser His Leu Phe Pro Gln Leu Ala Asn Ala Pro Leu Val Asn Ala
                325                 330                 335

Val Asp Pro Ala Ser Leu Ile His Val Val Leu Ala Gly Ser Arg Ala
            340                 345                 350

Gly Gly Thr Ala Ala Ala Pro Thr Ala Pro Ala Met Pro Ala Phe Gly
        355                 360                 365

Trp Asn Met Thr Asp Gln Asn Val Ala Asp Val Leu Thr Tyr Ile Arg
    370                 375                 380

Asn Ser Trp Gly Asn Ala Ala Pro Ser Val Thr Ala Ser Asp Val Lys
385                 390                 395                 400

Asn Met Arg Ser Thr Leu Glu Lys
                405
```

-continued

```
<210> SEQ ID NO 29
<211> LENGTH: 432
<212> TYPE: PRT
<213> ORGANISM: Pantoea citrea

<400> SEQUENCE: 29

Met Gln Lys Leu Arg Val Phe Thr Pro Leu Ala Ile Met Leu Ala Gly
1               5                   10                  15

Phe Cys Gly Ser Val Tyr Ala Asp Asn Ser Pro Ala Ser Ser Asp Ser
            20                  25                  30

Thr Ser Leu Ser Arg Gly Glu Tyr Leu Ala Arg Ala Gly Asp Cys Val
        35                  40                  45

Ala Cys His Thr Ala Glu Gly Gly Lys Pro Phe Ala Gly Gly Leu Lys
    50                  55                  60

Met Thr Thr Pro Val Gly Ala Ile Tyr Ser Thr Asn Ile Thr Pro Asp
65                  70                  75                  80

Lys Asp Thr Gly Ile Gly Asn Tyr Ser Tyr Asp Asp Phe Val Lys Ala
                85                  90                  95

Val Arg Gln Gly Val Ser Lys Ser Gly Ser Thr Leu Tyr Pro Ala Met
            100                 105                 110

Pro Tyr Ala Ser Phe Thr Arg Ile Ser Asp Gln Asp Met His Asp Leu
        115                 120                 125

Tyr Asn Tyr Phe Met Gln Gln Val Lys Pro Val Ser Gln Gln Asn Lys
    130                 135                 140

Ala Ser Asp Ile Pro Trp Pro Leu Ser Met Arg Trp Pro Leu Ala Phe
145                 150                 155                 160

Trp Arg Trp Thr Phe Thr Asp Asp Lys Arg Phe Gln Pro Val Glu Gly
                165                 170                 175

Lys Ser Ala Glu Trp Gln Arg Gly Ala Tyr Leu Val Glu Gly Leu Glu
            180                 185                 190

His Cys Gly Ala Cys His Thr Pro Arg Gly Ile Ala Phe Gln Glu Lys
        195                 200                 205

Ala Leu Asp Gln Ser Asp Pro Val Tyr Leu Thr Gly Asn Thr Leu Glu
    210                 215                 220

Gly Trp Tyr Ala Pro Asp Leu Thr Gly Thr Gln Ser Asp Gly Leu Gly
225                 230                 235                 240

Arg Trp Ser Gln Gln Asp Ile Val Ser Phe Leu Lys Asn Gly Val Thr
                245                 250                 255

Ala Gln Ser Ser Ala Phe Gly Ser Met Ser Glu Val Val His Asp Ser
            260                 265                 270

Thr Ser Tyr Leu Thr Asp Ser Asp Leu Gln Ala Ile Ala Val Tyr Leu
        275                 280                 285

Lys Ser Leu Pro Ala Ala His Gln Thr Gln Ala Pro Ala Ser Asn Asn
    290                 295                 300

Ala Thr Ala Gln Ala Leu Phe Lys Gly Asp Val Ser Ala Thr Gly Ala
305                 310                 315                 320

Gln Val Tyr Leu Asp Asn Cys Ser Ala Cys His Arg Ser Asp Gly Lys
                325                 330                 335

Gly Tyr Asp Lys Thr Phe Pro Ser Leu Ala Gly Asn Ser Ala Val Leu
            340                 345                 350

Asn Ser Asp Pro Ser Ser Val Ile His Ile Ile Leu Gln Gly Gly Gln
        355                 360                 365

Arg Ala Val Thr Pro Asp Met Pro Thr Gly Leu Thr Met Pro Asp Phe
    370                 375                 380

Gly Trp Arg Leu Ser Asp Gln Gln Val Ala Asp Val Ala Thr Phe Ile
```

```
            385                 390                 395                 400
Arg Gln Gly Trp Gly Asn Asn Ala Ala Val Thr Ala Ser Gln Val
                    405                 410                 415

Ala Asp Ile Arg Lys Leu Ile Pro Lys Pro Ala Ser Gln Ala Ala Lys
                420                 425                 430

<210> SEQ ID NO 30
<211> LENGTH: 468
<212> TYPE: PRT
<213> ORGANISM: Pantoea citrea

<400> SEQUENCE: 30

Met Ser Arg Ser Val Lys Val Arg Pro Thr Ser Leu Ala Leu Ile Ile
1               5                   10                  15

Gly Leu Ser Val Phe Ser Gly Lys Ala Val Gln Ala Ala Asp Thr Pro
            20                  25                  30

Ser Ala Ser Thr Ile Ile Glu Gln Gly Lys Tyr Leu Ser Val Ala Ala
        35                  40                  45

Asp Cys Gly Ala Cys His Asn Ser Pro Thr Ser Gly Ala Ala Met Ala
    50                  55                  60

Gly Gly Tyr Ala Ile Ala Ser Pro Met Gly Asn Ile Ile Ala Ser Asn
65                  70                  75                  80

Ile Thr Pro Ser Val Thr Ala Gly Ile Gly Asn Tyr Thr Glu Gln Gln
                85                  90                  95

Phe Ala Arg Ala Val Arg Glu Gly Val Asn Ala Gln Gly Asp His Leu
            100                 105                 110

Tyr Pro Ala Met Pro Tyr Thr Ser Tyr Ser Lys Met Thr Asp Ser Asp
        115                 120                 125

Ile His Ala Leu Tyr Gln Tyr Phe Met His Gly Val Gln Pro Val Asp
    130                 135                 140

Thr Pro Ala Pro Ala Thr Lys Leu Pro Phe Pro Phe Ser Ile Arg Ser
145                 150                 155                 160

Ser Met Ala Leu Trp Asn Met Leu Phe Ala Ser Gln Gln Arg Phe Thr
                165                 170                 175

Pro Asp Ser Gln Lys Ser Ala Gln Leu Asn Arg Gly Asp Tyr Leu Val
            180                 185                 190

Asn Val Leu Glu His Cys Asp Ala Cys His Thr Pro Arg Asn Phe Leu
        195                 200                 205

Met Gly Gln Lys Asn Asp Leu Ala Leu Ser Gly Gly Gln Val Gly Ser
    210                 215                 220

Trp Tyr Ala Pro Asn Ile Thr Ser Asp Lys Thr Ala Gly Ile Gly Ser
225                 230                 235                 240

Trp Ser Asp Asp Gln Leu Phe Gln Tyr Leu Lys Thr Gly His Val Ala
                245                 250                 255

Gly Lys Ala Gln Ala Ala Gly Pro Met Ala Glu Ala Ile Glu Asn Ser
            260                 265                 270

Leu Gln His Leu Ser Asp Asp Leu His Ala Ile Val Ala Trp Leu
        275                 280                 285

Lys Gln Val Pro Ala Ser Gly Ala Thr Ala Thr Glu Ser Arg Phe Thr
    290                 295                 300

Gln Gly Ala Pro Ser Asp Ser Glu Ala Ala Met Arg Ala Thr Asp His
305                 310                 315                 320

Pro Asp Ala Gly Trp Val Val Phe Ser Asn Ser Cys Ala Asn Cys His
                325                 330                 335

Gln Ala Asn Gly Glu Gly Ser Gln Phe Tyr Pro Ser Leu Phe His Asn
```

-continued

```
                    340                 345                 350
Ser Ala Thr Gly Ala Ala Gln Pro Asp Asn Leu Ile Ala Thr Ile Leu
                355                 360                 365

Phe Gly Val Arg Arg His Ala Asp Gly Gln Tyr Val Ala Met Pro Ala
            370                 375                 380

Phe Gly Pro Ala Ala Ser Phe Val Asp Arg Leu Asn Asp Gln Gln Val
385                 390                 395                 400

Ala Asp Val Ala Asn Tyr Val Leu Lys Asn Tyr Gly Asn Ala Ser Leu
                405                 410                 415

Thr Val Thr Ala Asp Gln Val Lys Thr Val Arg Glu Gly Gly Pro Val
            420                 425                 430

Pro Ala Ile Ala Tyr Leu Ser Asn Pro Ala Val Leu Ala Ile Gly Ala
            435                 440                 445

Leu Ile Val Leu Val Ile Leu Gly Leu Ile Val Thr Ala Val Arg Arg
        450                 455                 460

Arg Gly Lys Lys
465

<210> SEQ ID NO 31
<211> LENGTH: 495
<212> TYPE: PRT
<213> ORGANISM: Pantoea citrea

<400> SEQUENCE: 31

Met Lys Gln Gln His Lys Leu Asn Ala His Lys Ala Ala Gly Phe Arg
1               5                   10                  15

Arg Lys Leu Leu Ser Leu Cys Leu Gly Leu Ser Ala Leu Ser Ala Val
            20                  25                  30

Pro Val Met Ala Ala Glu Gln Val Pro Val Ser Gln Pro Ser Val Asp
        35                  40                  45

Asn Ser Ala Asp Ala Leu Leu Lys Gln Gly His Tyr Leu Ala Ile Ala
    50                  55                  60

Ala Asp Cys Ala Ala Cys His Thr Asp Pro Gln Thr Lys Lys Thr Phe
65                  70                  75                  80

Ala Gly Gly Tyr Ala Ile His Ser Pro Met Gly Val Ile Tyr Ser Thr
                85                  90                  95

Asn Ile Thr Pro Ser Arg Gln Tyr Gly Ile Gly Ser Tyr Ser Glu Ala
            100                 105                 110

Gln Phe Glu Gln Ala Val Arg His Gly Ile Arg Gly Asp Gly Ser His
        115                 120                 125

Leu Tyr Pro Ala Met Pro Tyr Thr Ser Tyr Ser Gly Leu Thr Asp Gln
    130                 135                 140

Asp Ile His Ala Leu Tyr Tyr Tyr Phe Thr His Gly Val Gln Pro Val
145                 150                 155                 160

Glu Gln Ala Asn Arg Pro Thr Glu Leu Ser Phe Pro Phe Asn Ile Arg
                165                 170                 175

Glu Ala Met Trp Gly Trp Asn Leu Leu Phe Leu Lys Gln Lys Pro Phe
            180                 185                 190

Arg Asp Asp Pro Ser Gln Ser Pro Gln Trp Asn Arg Gly Lys Tyr Leu
        195                 200                 205

Val Ala Asn Leu Glu His Cys Gly Glu Cys His Thr Pro Arg Asn Thr
    210                 215                 220

Leu Met Gly Ser Glu Thr Gly Ser Ala Gln Tyr Ser Gly Ala Ala Leu
225                 230                 235                 240

Gly Ser Trp Phe Ala Pro Asn Leu Thr Ser Asp Gln Gln Ser Gly Leu
```

```
                        245                 250                 255
Gly Ser Trp Gln Arg Asp Gln Leu Ile Thr Tyr Leu Lys Thr Gly His
            260                 265                 270

Val Ala Gly Lys Ala Gln Ala Ala Gly Pro Met Ala Glu Ala Val Thr
        275                 280                 285

Asn Ser Leu Gln Tyr Leu Ser Asp Asp Ile Gly Ala Ile Val Thr
    290                 295                 300

Tyr Leu Gln Ser Leu Pro Pro Val Ser Glu Pro Asp Gln Ala Lys Ala
305                 310                 315                 320

Thr Gly Asp Phe Gly Ser Ser Ala Gly Asn Ser Ser Asp Ser Glu Val
                325                 330                 335

Arg Gly Thr Gln Pro Met Gly Ser Val Leu Pro Asp Asp Ile Thr Gly
            340                 345                 350

Lys Ala Leu Tyr Asp Thr Thr Cys Ala Ser Cys His Gln Ser Ser Gly
        355                 360                 365

Ala Gly Thr Thr Asp Asn Phe Tyr Pro Ser Leu Phe His Asn Thr Ala
    370                 375                 380

Thr Gly Gly Asn Thr Pro Asn Asn Leu Val Ser Ala Ile Leu Phe Gly
385                 390                 395                 400

Val Gln Arg Glu Val Asn Gly Lys Gln Val Leu Met Pro Ala Phe Gly
                405                 410                 415

Pro Gly Ser Asp Val Gln Ser Leu Asn Asp Glu Gln Val Ala Lys Leu
            420                 425                 430

Ser Asn Tyr Ile Phe Lys Gln Phe Gly Asn Pro Gln Leu Ser Val Thr
        435                 440                 445

Ala Asp Gln Val Lys Thr Leu Arg Glu Gly Gly Pro Gln Pro Phe Leu
    450                 455                 460

Ala Lys Tyr Ala Ala Ser Gly Ser Ala Val Gly Val Ile Leu Leu
465                 470                 475                 480

Leu Ile Ile Val Leu Ile Ile Val Arg Ile Ser Arg Lys Arg Arg
                485                 490                 495

<210> SEQ ID NO 32
<211> LENGTH: 471
<212> TYPE: PRT
<213> ORGANISM: Pantoea citrea

<400> SEQUENCE: 32

Met Lys Cys Ala Tyr Leu Ser Leu Leu Ile Ser Thr Leu Leu Tyr Ala
1               5                   10                  15

Gly Phe Ser Pro Ala Thr Gln Ala Glu Thr Pro Ala Thr Ala Glu Thr
            20                  25                  30

Leu Leu Ala Gln Gly Lys Tyr Leu Ser Val Ala Ala Asp Cys Ser Ala
        35                  40                  45

Cys His Asp Ser Pro Asp His His Val Met Ala Gly Gly Asn Ser Ile
    50                  55                  60

Asn Ser Pro Leu Gly Lys Ile Val Ala Ser Asn Ile Thr Pro Ser Val
65                  70                  75                  80

His Tyr Gly Ile Gly Ser Tyr Thr Glu Gln Gln Phe Ser Asp Ala Val
                85                  90                  95

Arg Lys Gly Ile Asn Ala Gln Gly Glu Asn Leu Tyr Pro Ala Met Pro
            100                 105                 110

Tyr Thr Ser Tyr Ser Gln Leu Thr Asp Ser Asp Ile His Ala Leu Tyr
        115                 120                 125

Tyr Tyr Phe Met His Gly Val Thr Ala Val Asp Arg Ala Ala Gly Ala
```

```
                130             135             140
Thr Gln Leu Pro Phe Pro Phe Asn Leu Arg Ile Ser Met Lys Leu Trp
145                 150                 155                 160

Asn Ala Leu Tyr Ala Asp Asn Lys Pro Phe Arg Pro Ser Ser Ser Gln
                165                 170                 175

Thr Asp Gln Val Asn Arg Gly Asn Tyr Leu Ile Tyr Gly Leu Ala His
            180                 185                 190

Cys Asp Thr Cys His Thr Pro Arg Asn Ala Leu Met Ala Glu Lys Ser
                195                 200                 205

Asp Gln Ser Leu Ser Gly Gly Ser Leu Gly Gln Trp Tyr Ala Pro Asn
210                 215                 220

Ile Thr Ser Asp Lys Ser Ser Gly Ile Gly Asn Trp Ser Asp Gln Gln
225                 230                 235                 240

Leu Tyr Gln Tyr Leu Lys Thr Gly His Ala Val Gly Lys Ala Gln Ala
                245                 250                 255

Ala Gly Pro Met Ala Glu Ala Ile Glu His Ser Leu Gln Tyr Leu Ser
                260                 265                 270

Asp Asp Asp Leu His Ala Ile Val Ala Ser Leu Arg Leu Thr Arg Pro
            275                 280                 285

Val Asn Thr Ala Ser Ala Asp Arg Gly Met Gln Gly Lys Ala Ile Ser
290                 295                 300

Asp Glu Asn Ser Ile Arg Gly Thr Lys Val Ala Ser Gly Glu Pro Val
305                 310                 315                 320

Ser Gly Pro Met Ser Gly Ala Ile Leu Tyr Ser Gly Asn Cys Ala Ala
                325                 330                 335

Cys His Thr Pro Ser Gly Ala Gly Ser Tyr Ser Gln Asn Tyr Pro Ser
                340                 345                 350

Leu Val His Asn Thr Thr Val Gly Ser Thr Asp Pro Thr Asn Leu Ile
            355                 360                 365

Ala Thr Leu Leu Phe Gly Val His Arg Thr Val Asp Gln Gln Ser Ile
            370                 375                 380

Thr Met Pro Ala Phe Gly Pro Gln Gly Tyr Thr Asp Arg Leu Ser Phe
385                 390                 395                 400

Ala Glu Ile Ala Thr Leu Ala Thr Tyr Val Arg Gln Thr Tyr Gly Ala
                405                 410                 415

Gly Gly Glu Ala Val Ser Glu Gln Val Gln Val Tyr Gln Gly
                420                 425                 430

Gly Pro Lys Pro Leu Ile Gly Trp Leu Ala Asp Gly Arg Ile Gln Ala
            435                 440                 445

Leu Ile Val Val Val Leu Leu Leu Ala Gly Leu Ile Ile Thr Val
450                 455                 460

Val Arg Lys Gly Arg Lys Ala
465                 470

<210> SEQ ID NO 33
<211> LENGTH: 474
<212> TYPE: PRT
<213> ORGANISM: Pantoea citrea

<400> SEQUENCE: 33

Met Lys Lys His Ala Ile Lys Phe Ser Leu Ser Leu Met Phe Ala Gly
1               5                   10                  15

Ser Met Leu Trp Ala Gly Ser Ala Ala Ala Thr Gly Asp Ala Ala
                20                  25                  30

Ala Ala Ile Ser Arg Gly Glu Tyr Leu Ala Thr Ala Ser Asp Cys Ala
```

```
                 35                  40                  45
Ala Cys His Thr Asp Lys Gly Leu Pro Phe Ala Gly Gly Leu Lys
 50                  55                  60
Ile Glu Ser Pro Val Gly Thr Ile Ile Ala Ser Asn Ile Thr Pro Ser
 65                  70                  75                  80
Leu Thr Ala Gly Ile Gly His Tyr Thr Glu Gln Gln Phe Ala Asp Ala
                 85                  90                  95
Val Arg Lys Gly Ile Arg Ala Asp Gly Ala Asn Leu Tyr Pro Ala Met
                100                 105                 110
Pro Tyr Thr Ala Tyr Ser Val Met Thr Asp Gln Asp Ile His Asp Leu
                115                 120                 125
Tyr Gln Tyr Phe Met Gln Gly Val Lys Pro Val Asp His Pro Ala Ala
                130                 135                 140
Glu Thr Glu Leu Pro Phe Pro Met Asn Ile Arg Met Met Met Lys Ala
145                 150                 155                 160
Trp Asn Leu Leu Phe Leu Asn Asp Lys Pro Phe Ser Pro Asp Ala Ser
                165                 170                 175
Gln Ser Ala Ala Trp Asn Arg Gly Lys Tyr Leu Val Thr Gly Ala Ala
                180                 185                 190
His Cys Ser Thr Cys His Thr Pro Arg Gly Pro Leu Met Glu Glu Glu
                195                 200                 205
Ser Ser Gln Phe Leu Ser Gly Gly Gln Val Gly Ala Trp Tyr Ala Pro
                210                 215                 220
Asn Ile Thr Ser Asp Pro Gln Ser Gly Ile Gly Arg Trp Ser Gln Ala
225                 230                 235                 240
Asp Ile Val Gln Tyr Leu Arg Thr Gly Asn Leu Pro Gly Lys Ala Gln
                245                 250                 255
Ala Ala Gly Ser Met Gly Glu Ala Val Glu His Ser Phe Gln His Leu
                260                 265                 270
Thr Asp Asp Leu Asn Ala Ile Ala Thr Tyr Ile Arg Thr Val Lys
                275                 280                 285
Pro Val Ala Thr Pro Glu Asn Ala Gly Ser Arg Phe Met Gln Gly Asp
                290                 295                 300
Ser His Asp Ala Thr Gly Lys Ile Arg Gly Leu Ser Gln Gln Val
305                 310                 315                 320
Thr Asp Ala Lys Gln Gln Gly Leu Ala Leu Phe Gln Gly Asn Cys Ala
                325                 330                 335
Ser Cys His Glu Ala Gly Gly Gly Ser Arg Asp Ser Tyr Tyr Pro
                340                 345                 350
Ser Leu Phe His Asn Ser Val Thr Gly Ala Glu Asn Ser Asn Leu
                355                 360                 365
Ile Ala Thr Ile Leu Asn Gly Val Asn Arg Thr Thr Arg Asp Gly Gln
                370                 375                 380
Val Phe Met Pro Gly Phe Gly His His Pro Asn Asp Ile Asn Asn Leu
385                 390                 395                 400
Thr Asp Glu Gln Ile Ala Ser Leu Ala Asn Tyr Val Leu Thr Thr Tyr
                405                 410                 415
Gly Lys Pro Ser Lys Pro Val Thr Ala Ala Met Val Ala Thr Val Arg
                420                 425                 430
Gln Gly Gly Pro Gly Ser Ser Leu Val Leu Ala Arg Phe Gly Ile
                435                 440                 445
Ala Ala Gly Val Val Val Val Leu Ile Leu Leu Gly Phe Trp Val Val
                450                 455                 460
```

```
Arg Arg Lys Lys Asn Val Arg Asp Pro Ser
465                 470
```

<210> SEQ ID NO 34
<211> LENGTH: 451
<212> TYPE: PRT
<213> ORGANISM: Pantoea citrea

<400> SEQUENCE: 34

```
Met Lys Lys Leu Leu Ser Leu Cys Ile Ala Gly Ala Leu Ala Gly Ile
1               5                   10                  15

Met Leu Asn Ser Ala Ala Met Ala Glu Asp Ser Asn Ala Gln Ser Leu
            20                  25                  30

Ile Ala Lys Gly Gln Tyr Leu Ser Val Ala Gly Asp Cys Ala Ala Cys
        35                  40                  45

His Thr Thr Ser Gly Gly Lys Pro Phe Ala Gly Leu Ala Ile Ala
    50                  55                  60

Thr Pro Ile Gly Lys Ile Phe Ser Thr Asn Ile Thr Pro Ser Lys Thr
65                  70                  75                  80

Ser Gly Ile Gly Asp Tyr Ser Leu Gln Glu Phe Glu Lys Ala Val Arg
                85                  90                  95

Gln Gly Val Arg Lys Asp Gly Ala Asn Leu Tyr Pro Ala Met Pro Tyr
            100                 105                 110

Thr Ser Tyr Ala Lys Ile Ser Asp Glu Asp Met Gln Ala Leu Tyr Ala
        115                 120                 125

Tyr Phe Met His Gly Val Ala Pro Val Asp Glu Lys Gly Pro Gln Thr
    130                 135                 140

Ala Leu Pro Phe Pro Phe Asn Ile Arg Leu Ser Met Ala Gly Trp Asn
145                 150                 155                 160

Leu Ile Phe Ala Gly Asp Lys Pro Phe Thr Pro Asp Ser Asn Gln Ser
                165                 170                 175

Ala Glu Trp Asn Arg Gly Ala Tyr Leu Val Gln Gly Leu Ala His Cys
            180                 185                 190

Ser Thr Cys His Thr Pro Arg Asn Ala Leu Met Ala Glu Glu Ser Gly
        195                 200                 205

Gln Ala Leu Ala Gly Ala Ser Leu Gly Thr Trp Phe Ala Pro Asn Ile
    210                 215                 220

Thr Pro Asp Ala His Ala Gly Ile Gly Lys Trp Ser Ala Ser Asp Leu
225                 230                 235                 240

Ala Thr Tyr Leu Ser Thr Gly Arg Ser Pro Asn Gly Ser Gln Ala Gly
                245                 250                 255

Gly Pro Met Leu Glu Ala Ile Asp Lys Ser Phe Ser Lys Leu Ser Gln
            260                 265                 270

Ser Asp Ile Asn Ala Ile Val Thr Tyr Val Arg Ser Val Lys Pro Gln
    275                 280                 285

Ser Ala Asn Ala Ala Pro Gly Gln Val Pro Ala Ser Ala Pro Val Val
    290                 295                 300

Ser Asp Phe Ala Leu Met Asn Gly Thr Ala Ser Asp Gly Ala Lys Leu
305                 310                 315                 320

Tyr Glu Ala His Cys Ser Thr Cys His Gln Ala Ser Gly Gln Gly Ser
                325                 330                 335

Asn Gly Leu Pro Ala Leu Tyr Gly Asn Ala Ala Leu His Arg Pro Val
            340                 345                 350

Ala Asp Asn Ala Val Met Ala Ile Leu Asp Gly Leu Thr Pro Thr Gln
    355                 360                 365
```

```
Gly Gln Ala Met Pro Ser Phe Lys Thr Ala Met Asn Asp Gln Gln Ile
    370                 375                 380

Ala Thr Leu Thr Asn Tyr Leu Phe Lys Thr Phe Gly Asp Ala Gly Val
385                 390                 395                 400

Gln Thr Thr Ala Asp Arg Val Lys Val Leu Arg Glu Gly Gly Ala Pro
                405                 410                 415

Ser Pro Leu Leu Ala Ile Ala Lys Gly Gly Met Ile Ala Ala Val Ile
            420                 425                 430

Val Val Leu Leu Leu Ile Val Gly Val Met Val Lys Ser Arg Arg
                435                 440                 445

Lys Arg Arg
    450

<210> SEQ ID NO 35
<211> LENGTH: 476
<212> TYPE: PRT
<213> ORGANISM: Pantoea citrea

<400> SEQUENCE: 35

Met Lys Lys Tyr Ser Ala Leu Leu Thr Leu Ser Ala Ala Phe Leu Phe
1               5                   10                  15

Ser Pro Leu Ala Leu Ala Ala Thr Ser Ser Asn Ser Asp Leu Val Ser
            20                  25                  30

Arg Gly Glu Tyr Leu Ala Arg Ala Gly Asp Cys Thr Ala Cys His Thr
        35                  40                  45

Ala Ala Gly Gly Ala Glu Tyr Ala Gly Gly Tyr Lys Phe Asn Met Pro
    50                  55                  60

Met Gly Thr Ile Val Ala Pro Asn Ile Thr Ser Ser Val Gln Tyr Gly
65                  70                  75                  80

Ile Gly Asn Trp Ser Glu Ala Asp Phe Ala Lys Ala Val Arg Gln Gly
                85                  90                  95

Val Arg Pro Asp Gly Ser His Leu Tyr Pro Ala Met Pro Tyr Thr Ser
            100                 105                 110

Tyr Ala Thr Val Thr Asp Glu Asp Met Gln Ala Leu Tyr Ala Phe Phe
        115                 120                 125

Lys Thr Val Pro Ala Val Asp Lys Ala Pro Ala Asp Lys Asn Asp Leu
    130                 135                 140

Lys Phe Pro Phe Asn Leu Pro Gly Leu Met Gly Ile Trp Asn Ala Leu
145                 150                 155                 160

Phe Ala Ser Asp Ala Pro Phe Lys Ala Asp Pro Ala Leu Thr Ala Glu
                165                 170                 175

Gln Asn Arg Gly Lys Tyr Leu Ala Glu Gly Leu Ala His Cys Ser Thr
            180                 185                 190

Cys His Ser Pro Arg Asn Gln Met Met Ala Glu Asp Thr His Gln Leu
        195                 200                 205

Leu Ala Gly Asn His Val Asp Gly Trp Leu Ala Pro Asn Ile Thr Ser
    210                 215                 220

Asp Ala Val Ser Gly Ile Gly Gly Trp Ser Gln Gln Glu Leu Thr Glu
225                 230                 235                 240

Tyr Leu Lys Thr Gly His Val Glu Gly Lys Ala Gln Ala Gly Gly Pro
                245                 250                 255

Met Ala Asp Ala Ile Glu His Ser Phe Ser His Leu Ser Asp Ser Asp
            260                 265                 270

Leu Ala Ser Ile Ala Thr Trp Leu Lys Thr Val Pro Ala Ile Arg Thr
        275                 280                 285
```

```
Pro Gly Gln Thr Gln Pro Ser Trp Ala Ala Pro Ala Ser Lys Val
    290                 295                 300

Asp Trp Thr Ser Tyr Gln Thr Gly Gly Gly Lys Asn Asn Ser Pro Ala
305                 310                 315                 320

Tyr Arg Asp Ser Thr Thr Asp Gly Ala Val Leu Phe Asp Ser Ser
                325                 330                 335

Cys Ala Ala Cys His Gln Ser Ser Gly Gln Gly Ser Asp Asp His Tyr
                340                 345                 350

Phe Pro Ser Leu Thr His Asn Ser Ala Val Gly Ala Ala Asp Pro Ser
                355                 360                 365

Asn Leu Val Met Ala Ile Val Asp Gly Ile His Arg Lys Thr Pro Glu
    370                 375                 380

Gly Glu Ala Val Met Pro Ala Phe Ser Ser Glu Thr Gln Ala Ile His
385                 390                 395                 400

Ser Trp Leu Asn Asn Asp Gln Ile Ala Ala Val Thr Asn Tyr Val Thr
                405                 410                 415

Glu Lys Phe Gly His Gly Asn Ala Gly Leu Thr Gly Ala Asp Val Glu
                420                 425                 430

Lys Ile Arg Asn Gly Asn Ser Asn Val Pro Phe Leu Ile Lys Asn Ala
                435                 440                 445

Gly Gly Leu Thr Ile Gly Gly Ile Val Ile Val Ile Ile Ile Ile
    450                 455                 460

Ala Leu Leu Ala Ala Arg Ser Arg Lys Lys Arg Arg
465                 470                 475

<210> SEQ ID NO 36
<211> LENGTH: 437
<212> TYPE: PRT
<213> ORGANISM: Pantoea citrea

<400> SEQUENCE: 36

Met Lys Ala Val Ile Ile Arg Ser Ala Ile Ala Leu Ala Leu Met His
1               5                   10                  15

Gly Ser Leu Ala Leu Ala Ala Asp Asp Asn Ala Asp Leu Ile Lys Arg
            20                  25                  30

Gly Glu Tyr Leu Ala Thr Ala Ser Asp Cys Thr Ala Cys His Thr Ala
        35                  40                  45

Pro Gly Gly Pro Ala Tyr Gly Gly Tyr Pro Val Ala Thr Pro Phe
    50                  55                  60

Gly Lys Ile Trp Gly Ser Asn Ile Ser Ser Asp Lys Gln Phe Gly Ile
65              70                  75                  80

Gly Ser Trp Thr Asp Asp Gln Phe Val Ala Val Arg Gln Gly Val
                85                  90                  95

Gly Lys Asn Gly Glu Gln Leu Tyr Pro Ala Met Pro Tyr Asp Ala Phe
            100                 105                 110

Thr Lys Met Lys Arg Asp Asp Val Leu Ala Ile Lys Ala Tyr Leu Met
        115                 120                 125

Ser Leu Pro Ala Val His Lys Ala Ala Pro Glu Thr Ser Leu Pro Phe
    130                 135                 140

Pro Phe Asn Gln Arg Trp Gly Met Arg Phe Trp Lys Met Phe Asn Leu
145                 150                 155                 160

Thr Glu Gly Glu Leu Lys Asn Asp Pro Gln Gln Ser Pro Gln Trp Asn
                165                 170                 175

Asn Gly Arg Tyr Leu Val Glu Ala Leu Ala His Cys Thr Thr Cys His
            180                 185                 190
```

```
Thr Pro Arg Asn Leu Thr Met Gly Met Asp Thr Ser Lys Pro Leu Ser
    195                 200                 205

Gly Gly Asp Leu Gly Asp Trp Ile Ala Phe Asn Ile Thr Pro Gly Lys
210                 215                 220

Ser Gly Ile Gly Asp Trp Ser Ser Gln Asp Ile Val Thr Tyr Leu Lys
225                 230                 235                 240

Thr Gly Tyr Leu Ala Gly Lys Ala Ser Ala Ser Gly Pro Met Ala Glu
                245                 250                 255

Ala Ile Glu His Ser Leu Gln Tyr Leu Pro Asp Ser Asp Leu Gln Asp
            260                 265                 270

Ile Ala Thr Tyr Leu Lys Ser Val Lys Pro Val Asp Asp Glu Lys Gln
        275                 280                 285

Ser Val Pro Arg Asp Ser Gln Gly Gln Pro Ser Asp Ala Ile Ile Arg
    290                 295                 300

Leu Arg Gly Ala Asp Ala Ala Thr Leu Gln Ser Gln Pro Gly Ala Val
305                 310                 315                 320

Val Phe Glu Gly Asn Cys Ser Thr Cys His Gly Ala Glu Gly Ala Gly
                325                 330                 335

Ser Gly Gln Gly Phe His Ala Tyr Pro Ser Leu Phe His His Ser Ser
            340                 345                 350

Thr Gly Ala Ile Asp Pro Lys Asn Val Val Ser Val Ile Leu Asn Gly
        355                 360                 365

Val Asn Arg His Met Gln Gln Gly Asp Ile Phe Met Pro Ser Phe Ala
    370                 375                 380

Pro Gln Leu Asn Asp Gln Gln Val Ala Asp Val Ala Asn Phe Val Met
385                 390                 395                 400

Gln Lys Phe Gly Asn Pro Ala Ala Glu Lys Val Asp Thr Ser Gln Val
                405                 410                 415

Ser Lys Ala Arg Lys Asn Ala Ser Leu Pro Leu Pro Pro Thr Phe Ala
            420                 425                 430

Asp Gly Ala Asn Pro
        435

<210> SEQ ID NO 37
<211> LENGTH: 486
<212> TYPE: PRT
<213> ORGANISM: Pantoea citrea

<400> SEQUENCE: 37

Met Ile Arg Ser Ser Phe Lys Arg Ser Arg Asn Phe Leu Pro Leu Ala
1               5                   10                  15

Gly Leu Leu Phe Cys Ala Ala Gly Tyr Ala Gln Thr Gly Ser Ala Gln
            20                  25                  30

Pro Asp Pro Val Ala Thr Gln Pro Thr Pro Thr Gln Pro Ala Ala Ala
        35                  40                  45

Ala Gly Thr Gln Gly Thr Thr Leu Ile Gln Gln Gly Glu Tyr Leu Ala
    50                  55                  60

Lys Ala Ala Asp Cys Glu Val Cys His Thr Ala Thr Gly Gly Gln Thr
65                  70                  75                  80

Phe Ala Gly Gly Leu Gly Phe Lys Thr Pro Phe Gly Thr Ile Phe Ser
                85                  90                  95

Ser Asn Ile Thr Pro Asp Lys Thr His Gly Ile Gly Gln Trp Ser Glu
            100                 105                 110

Lys Gln Phe Ser Asp Ala Leu Arg Tyr Gly Ile Arg Ala Asp Gly Lys
        115                 120                 125
```

```
Asn Leu Tyr Pro Ala Met Pro Tyr Thr Ser Tyr Ser Lys Leu Thr Asp
        130                 135                 140
Ala Asp Ile His Ala Met Tyr Ala Phe Phe Met Ser Leu Lys Pro Val
145                 150                 155                 160
Ala Thr Asp Pro Pro Glu Asn Lys Met Gly Phe Pro Tyr Asn Gln Arg
                165                 170                 175
Ile Ala Leu Lys Gly Trp Asn Leu Ile Asn Phe His Tyr Gln Pro Phe
            180                 185                 190
Lys Gln Asp Pro Asp Gln Ser Ala Glu Trp Asn Arg Gly His Tyr Leu
        195                 200                 205
Ala Thr Ala Leu Gly His Cys Glu Glu Cys His Thr Pro Arg Asn Leu
    210                 215                 220
Ala Met Gly Leu Ser Asp Lys Ser Tyr Ala Gly Ala Met Val Asp Gly
225                 230                 235                 240
Trp Glu Ala Phe Asn Ile Ser Ser Asp Asn Thr Ser Gly Ile Gly Arg
                245                 250                 255
Trp Ser His Ala Asp Leu Met Gln Tyr Leu Lys Thr Gly Ser Val Pro
            260                 265                 270
Gly Val Ala Thr Thr Gly Gly Met Ala Asp Val Ile Ser His Ser
        275                 280                 285
Leu Arg Phe Leu Ser Asn Asp Asp Leu Ser Ala Leu Ala Thr Tyr Ile
    290                 295                 300
Lys Ser Val Pro Pro Gln Lys Thr Ala Ser Gln Asn Arg Ser Gly Tyr
305                 310                 315                 320
Gly Asp Asn Val Gln Ser Asp Ile Thr Gln Ala Val Arg Gly Met Pro
                325                 330                 335
Ile Asp Asp Ser Ala Pro Ser Gly Ala Val Leu Phe Asn Gly Asn Cys
            340                 345                 350
Ala Ser Cys His Gly Thr Lys Gly Gln Gly Ile Gly Glu Asn Arg Tyr
        355                 360                 365
Tyr Pro Ser Leu Ser Asn Asn Ser Val Val Gly Ala Asp Lys Ala Asn
    370                 375                 380
Asn Leu Val Gln Val Ile Leu Tyr Gly Ile Asp Arg Thr Asn Gly Lys
385                 390                 395                 400
Gly Glu His Ile Val Met Pro Gly Phe Gly Asp Glu Leu Thr Asp Ser
                405                 410                 415
Gln Ile Ala Thr Leu Thr Asn Tyr Leu Arg Thr Asn Phe Gly Thr Asn
            420                 425                 430
Pro Ala Pro Val Asp Ala Ala Gln Val Lys Ala Leu Arg Glu Asn Asn
        435                 440                 445
Val Met Val Ile Pro Gly Tyr Leu Leu Ile Leu Gly Gly Val Ile Gly
    450                 455                 460
Val Ile Ile Leu Val Ala Ile Ile Met Tyr Phe Arg Arg Arg Lys Ala
465                 470                 475                 480
Ala Arg Asn His Ala Gly
                485

<210> SEQ ID NO 38
<211> LENGTH: 475
<212> TYPE: PRT
<213> ORGANISM: Pantoea citrea

<400> SEQUENCE: 38

Met Lys Arg Phe Ser Arg Val Lys Leu Thr Leu Leu Gly Leu Leu Cys
1               5                   10                  15
```

-continued

```
Gly Gly Leu Thr Ser Leu Ala Ala Asn Ala Ala Asp Ile Asp Gln Ala
            20                  25                  30
Leu Leu Gln Gln Gly Glu Gln Val Ala Thr Ala Ser Asp Cys Gln Ala
        35                  40                  45
Cys His Thr Ala Pro Gly Ser Lys Thr Ala Phe Ser Gly Gly Tyr Ala
50                  55                  60
Ile Ala Ser Pro Met Gly Ala Ile Tyr Ser Thr Asn Ile Thr Pro Asp
65                  70                  75                  80
Pro Ala Thr Gly Ile Gly Lys Tyr Thr Glu Gln Gln Phe Ile Glu Ala
                85                  90                  95
Val Arg His Gly Val Arg Ala Asp Gly Ala Gln Leu Tyr Pro Ala Met
            100                 105                 110
Pro Tyr Thr Ser Tyr Arg Met Met Thr Asp Ser Asp Ile His Ala Leu
        115                 120                 125
Tyr Tyr Tyr Phe Met His Gly Val Lys Pro Val Asp Gln Gln Asn Thr
    130                 135                 140
Glu Thr Gln Leu Ser Phe Pro Phe Asn Met Arg Phe Ser Met Lys Phe
145                 150                 155                 160
Trp Asn Leu Leu Tyr Ala Asp Thr Lys Thr Phe Gln Gln Asp Pro Gln
                165                 170                 175
Lys Ser Ala Glu Trp Asn Arg Gly Asn Tyr Leu Val Asn Gly Leu Ala
            180                 185                 190
His Cys Asp Thr Cys His Thr Pro Arg Gly Phe Met Met Asn Glu Gln
        195                 200                 205
Thr Asp Gln Pro Leu Ala Gly Ala Pro Leu Gly Ser Trp Tyr Ala Pro
    210                 215                 220
Asn Ile Thr Ser Asp Lys Val Ser Gly Ile Gly Gly Trp Ser Asn Asp
225                 230                 235                 240
Glu Ile Val Gln Tyr Leu Lys Thr Gly Arg Ala Ala Gly Lys Asn Gln
                245                 250                 255
Ala Ala Gly Gly Met Ala Glu Ala Val Glu His Ser Leu Gln Tyr Leu
            260                 265                 270
Pro Asp Ser Asp Leu Gln Ala Ile Ala Thr Tyr Leu Lys Gln Thr Thr
        275                 280                 285
Pro Ile Arg Thr Pro Gly Glu Thr Gln Ala Ala Tyr Ser Tyr Gly Ser
    290                 295                 300
Ser Ser Thr Asn Val Asp Asp Gln Val Arg Gly Met Ala Pro Asn Asn
305                 310                 315                 320
Ala Arg Asp Ser Leu Thr Ser Gly Ala Ala Leu Phe Ser Gly Ser Cys
                325                 330                 335
Ala Ser Cys His Gln Pro Asp Gly Ala Gly Ser Lys Asn Gln Thr Tyr
            340                 345                 350
Pro Ser Leu Phe Asn Asn Thr Ala Thr Gly Met Ile His Pro Gln Asn
        355                 360                 365
Leu Ile Ala Thr Ile Leu Phe Gly Val Gln Arg Asn Thr Lys Asp His
    370                 375                 380
Gln Val Leu Met Pro Gly Phe Gly Ala Ser Thr Ser Tyr Val Asp Ser
385                 390                 395                 400
Leu Thr Asp Gln Gln Ile Ala Asp Ile Ser Asn Tyr Val Leu His Asn
                405                 410                 415
Tyr Gly Asn Pro Ala Val Thr Val Lys Ala Gly Asp Val Ala Trp Val
            420                 425                 430
Arg Lys Gly Gly His Pro Pro Ala Leu Val Ala Leu Gln Pro Tyr Met
        435                 440                 445
```

```
Ile Pro Ala Ile Ala Val Gly Val Ile Ile Ile Leu Leu Leu Val
    450                 455                 460

Ala Phe Arg Leu Arg Arg Ser Arg Arg Lys Ser
465                 470                 475

<210> SEQ ID NO 39
<211> LENGTH: 245
<212> TYPE: PRT
<213> ORGANISM: Pantoea citrea

<400> SEQUENCE: 39

Met Ser Glu Gln Asn Lys Gly Gln Ser Arg Arg Asp Phe Leu Leu Lys
1               5                   10                  15

Thr Ile Thr Leu Ala Pro Ala Met Ala Val Gly Ser Thr Ala Ile Gly
                20                  25                  30

Ser Leu Ala Leu Ser Pro Ala Val Gln Ala Ala Asp Thr Gln Thr Ser
            35                  40                  45

Gly Pro Gln Lys Ala Arg Asp Tyr Gln Pro Asn Trp Phe Thr Lys Glu
        50                  55                  60

Glu Phe Ala Phe Ile Thr Ala Ala Val Ala Lys Leu Ile Pro Ala Asp
65                  70                  75                  80

Ser Arg Gly Pro Gly Ala Leu Glu Ala Gly Val Pro Glu Tyr Ile Asp
                85                  90                  95

Arg Gln Met Asp Thr Pro Tyr Ala Thr Gly Ser Asn Trp Tyr Met Gln
                100                 105                 110

Gly Pro Phe Ala Pro Asp Thr Pro Lys Glu Leu Gly Tyr Gln Leu Pro
            115                 120                 125

Leu Val Pro Arg Gln Ile Tyr Arg Leu Gly Leu Ala Asp Ala Asp Asn
130                 135                 140

Phe Cys Lys Gln Gln Tyr Gly His Val Phe Ala Glu Leu Ser Asp Asp
145                 150                 155                 160

Gln Gln Val Thr Ala Leu Lys Ala Phe Glu Ser Gly Gln Ala Lys Phe
                165                 170                 175

Thr Gln Leu Pro Ala Thr Leu Phe Phe Ser Tyr Leu Leu Gln Asn Thr
            180                 185                 190

Arg Glu Gly Phe Phe Ser Asp Pro Ile His Gly Gly Asn Gln Gly Met
        195                 200                 205

Ala Gly Trp Lys Leu Ile Gly Phe Pro Gly Ala Arg Ala Asp Phe Met
    210                 215                 220

Asp Trp Val Glu Arg Gly Glu His Tyr Pro Phe Pro Pro Val Ser Ile
225                 230                 235                 240

Arg Gly Glu Arg Ala
                245

<210> SEQ ID NO 40
<211> LENGTH: 242
<212> TYPE: PRT
<213> ORGANISM: Pantoea citrea

<400> SEQUENCE: 40

Met Lys Asn Thr Pro Arg Ser Lys Asp Ser Thr Gly Arg Arg Leu Phe
1               5                   10                  15

Leu Gln Arg Ser Leu Ser Leu Ile Pro Leu Val Ala Ala Thr Gly Thr
                20                  25                  30

Pro Phe Ala Thr Ser Gln Ala Ala Glu Lys Lys Thr Pro Ala Val Thr
            35                  40                  45
```

```
Gln Asp Tyr Val Pro Gln Phe Phe Asp Pro Gln Gln Trp Ala Phe Ile
 50                  55                  60

Asn Ala Ala Val Asp Arg Leu Ile Pro Glu Asp Gln Asn Gly Ala Gly
 65                  70                  75                  80

Ala Val Ser Glu Gly Val Pro Val Tyr Ile Asp Arg Gln Met Glu Leu
                 85                  90                  95

Pro Tyr Gly Tyr Gly His Leu Trp Tyr Met Gln Pro Pro Phe Ala Ser
                100                 105                 110

His Ser Asp Pro Thr Leu Gly Tyr Gln Ser Pro Leu Val Pro Arg Glu
                115                 120                 125

Leu Tyr Arg Gln Gly Ile Ala Leu Thr Glu His Tyr Cys Gln Gln Thr
130                 135                 140

Phe His Lys Ser Phe Ala Gln Leu Thr Thr Asp Gln Gln Asp Gln Val
145                 150                 155                 160

Leu Gln Leu Leu Glu Lys Asn Thr Leu Thr Asp Asn Asn Leu Ser Gly
                165                 170                 175

Ser Leu Phe Phe Glu Gln Leu Leu Asp Asn Thr Lys Glu Gly Tyr Leu
                180                 185                 190

Ala Asp Pro Val His Gly Gly Asn Gln Thr Leu Ala Ser Trp Lys Leu
                195                 200                 205

Ile Gly Tyr Pro Gly Ala Arg Ala Asp Tyr Thr Asp Thr Val Ala Gln
210                 215                 220

Pro Asn Val Pro Tyr Pro Leu Gly Pro Val Ser Ile Ser Gly Lys Arg
225                 230                 235                 240

Ser Val

<210> SEQ ID NO 41
<211> LENGTH: 244
<212> TYPE: PRT
<213> ORGANISM: Pantoea citrea

<400> SEQUENCE: 41

Met Ser Asp Lys Pro Ser His Ser Arg Arg Asp Phe Leu Leu Lys Ser
 1               5                  10                  15

Leu Thr Leu Ile Pro Ala Val Ser Val Gly Gly Ala Ile Thr Ser Gly
                 20                  25                  30

Ile Ala Gly Pro Gly Asn Ala Gln Ala Ala Glu Thr Ser Ala Thr Ala
                 35                  40                  45

Ala Thr Ala Gln Thr Pro Tyr Ser Pro Val Phe Phe Lys Pro Asp Glu
 50                  55                  60

Trp Ala Phe Val Lys Ala Ala Cys Ala Arg Leu Ile Pro Ala Asp Asp
 65                  70                  75                  80

Met Gly Ser Gly Ala Leu Glu Ala Gly Val Pro Glu Phe Leu Asp Arg
                 85                  90                  95

His Leu Gln Thr Pro Tyr Ala Asn Gly Ser Val Trp Tyr Thr Gln Gly
                100                 105                 110

Pro Phe Val Glu Ala Gly Pro Glu Phe Gly Tyr Gln Gly Arg Lys Thr
                115                 120                 125

Leu Ser Glu Ile Ile Arg Ser Gly Ile Arg Gly Val Ile Gly Trp Thr
130                 135                 140

Gln Ser Asn Lys Gln Gln Thr Phe Asp Ala Leu Thr His Ala Glu Gln
145                 150                 155                 160

Glu Glu Ile Leu Val Ala Leu Glu Lys Gly Lys Ile His Leu Glu Glu
                165                 170                 175

Met Asp Ala Lys Thr Phe Phe Asp Tyr Phe Leu Gly Glu Val Arg Asn
```

```
                    180                 185                 190
Gly Phe Phe Ala Asp Pro Ser Tyr Gly Gly Asn Lys Gly Met Val Gly
                195                 200                 205

Trp Lys Leu Ile Gly Phe Pro Gly Met Arg Ala Asp Tyr Ile Asp Phe
    210                 215                 220

Ile Thr Val Arg Asp Lys Pro Tyr Pro Leu Gly Pro Val Asp Leu Ala
225                 230                 235                 240

Gly Asn Arg Gly

<210> SEQ ID NO 42
<211> LENGTH: 239
<212> TYPE: PRT
<213> ORGANISM: Pantoea citrea

<400> SEQUENCE: 42

Met Lys Glu Asn Ser Gln Pro Ala Ala Ser Arg Arg Lys Phe Leu
1               5                   10                  15

Gln Thr Ala Leu Ala Ile Ile Pro Ser Thr Ala Leu Ala Thr Ser Val
                20                  25                  30

Val Pro Ala Ala Leu Ala Ala Glu Gln Thr Lys Asn Pro Thr Arg Asp
            35                  40                  45

Tyr Val Pro Val Phe Phe Lys Asp Asp Glu Trp Arg Phe Ile Ile Ala
    50                  55                  60

Ala Thr Asp Val Leu Ile Pro Gly Asp Glu Tyr Gly Pro Gly Ala Val
65                  70                  75                  80

Ser Glu Gly Val Pro Val Phe Ile Asp Arg Gln Met Glu Met Pro Tyr
                85                  90                  95

Gly Tyr Gly Gln Leu Trp Tyr Met Lys Pro Pro Phe Gln Glu Gly Ser
                100                 105                 110

Pro Leu Leu Gly Tyr Gln Lys Asn Leu Thr Pro Arg Asp Ile Tyr Arg
            115                 120                 125

Arg Gly Ile Ala Ala Leu Asn Lys Ala Cys Gln Thr Thr Tyr Gln His
        130                 135                 140

Pro Phe Ala Ser Leu Ala Thr Ala Asp Lys Val Gln Val Met Glu Asp
145                 150                 155                 160

Leu Glu Ser Gly Lys Leu Val Thr Glu Asp Val Asp Gly Lys Leu Phe
                165                 170                 175

Phe Ala Gln Leu Leu Glu Asn Thr Lys Glu Gly Tyr Leu Ala Asp Pro
            180                 185                 190

Ile His Gly Gly Asn Gln Thr Met Ala Ser Trp Lys Met Ile Gly Phe
        195                 200                 205

Pro Gly Ala Arg Ala Asp Tyr Val Gln Val Met Asp Asn Pro Gly Lys
    210                 215                 220

Pro Tyr Leu Pro Gly Pro Val Ser Ile Ser Gly Lys Tyr Gly Ala
225                 230                 235

<210> SEQ ID NO 43
<211> LENGTH: 243
<212> TYPE: PRT
<213> ORGANISM: Pantoea citrea

<400> SEQUENCE: 43

Met Lys Gln Ser Gly Ile Gly Arg Arg Pro Phe Ile Ile Gly Ser Leu
1               5                   10                  15

Ile Gly Ile Ala Ser Leu Gly Met Lys Cys Gly Val Ser Val Phe
                20                  25                  30
```

```
Ala Ala Val Thr Ser Pro Leu Asp Glu Leu Asn Ser Tyr Gln Pro Val
         35                  40                  45

Phe Phe Lys Pro Glu Glu Trp Gln Phe Ile Met Ala Ala Cys Asp Arg
 50                  55                  60

Leu Ile Pro Gln Asp Glu Gly Pro Gly Ala Leu Glu Thr His Val
 65                  70                  75                  80

Pro Val Phe Ile Asp Lys Gln Met Leu Thr Pro Tyr Gly Lys Gly Glu
                 85                  90                  95

Asp Trp Tyr Met Glu Gly Pro Phe Asn Ala His Ala Ser Thr Leu Phe
                100                 105                 110

Gly Tyr Gln Leu Pro Phe Pro Leu Gln Val Met Tyr Gln Arg Gly Ile
                115                 120                 125

Lys Ala Thr Asn Ser Tyr Thr Arg Leu His Phe Asn Gln Asp Phe Ala
130                 135                 140

Ala Leu Thr Ala Ala Gln Gln Asp Ala Val Leu Ser Ala Leu Glu Glu
145                 150                 155                 160

Asn Lys Ile Thr Phe Ser Glu Phe Ser Glu Pro Asp Leu Ser Ala Ser
                165                 170                 175

Tyr Phe Phe Thr Arg Leu Leu Glu Asn Thr Lys Glu Gly Tyr Leu Ser
                180                 185                 190

Asp Pro Lys Tyr Gly Gly Asn Lys Gly Met Ala Ala Trp Val Met Ile
                195                 200                 205

Asn Phe Pro Gly Ala Arg Ala Ser Phe Pro Thr Trp Ile Lys Ile His
210                 215                 220

Asn Val Lys Tyr Pro Leu Gly Pro Val Ala Leu Asn Gly Asp Val Ala
225                 230                 235                 240

Gln Ser Ser

<210> SEQ ID NO 44
<211> LENGTH: 249
<212> TYPE: PRT
<213> ORGANISM: Pantoea citrea

<400> SEQUENCE: 44

Met Ser Asp Pro Ser Ser Lys Gly Ile Ser Arg Arg Arg Leu Leu Ser
 1               5                  10                  15

Gly Ser Ala Gly Leu Thr Val Ala Ala Val Ser Ser Ala Asn Ala
                20                  25                  30

Thr Thr Ile Thr Gly Ile Pro Arg Trp Met Leu Phe Asp His Asn Ser
                35                  40                  45

Pro Ile Thr Pro Thr Ser Pro Gly Leu Lys Phe Leu Thr Gln Glu Glu
 50                  55                  60

Ala Thr Glu Val Asp Ala Ile Val Ser Gln Leu Ile Pro Ala Asp Glu
 65                  70                  75                  80

Leu Ser Val Ser Gly Lys Asp Ala Gly Cys Thr Val Phe Ile Asp Arg
                 85                  90                  95

Gln Leu Ala Gly Ser Tyr Gly Asp Ala Ser Arg Asn Tyr Met Arg Gly
                100                 105                 110

Pro Phe Arg Glu Gly Thr Pro Ala Gln Gly Asp Gln Ser Pro Leu Val
                115                 120                 125

Pro Arg Glu Arg Tyr Arg Leu Gly Leu Ala Gly Leu Ser Asp Tyr Cys
                130                 135                 140

Gln Gln Lys Tyr Gln Lys Leu Phe Ser Gln Leu Asp Ser Ala Thr Arg
145                 150                 155                 160

Asp Glu Val Leu Thr Gly Leu Glu Gln Gly Lys Ile Asn Leu Thr Gly
```

```
                    165                 170                 175
Ile Ser Gly Lys Met Phe Phe Asp Gln Val Leu Thr Asn Thr Met Glu
                180                 185                 190

Gly Phe Phe Ser Asp Pro Val Tyr Gly Gly Asn Arg Asn Met Val Ser
            195                 200                 205

Trp Lys Met Ile Gly Phe Pro Gly Ala Arg Tyr Asp Tyr Arg Asp Tyr
        210                 215                 220

Leu Thr Lys Thr Asp Gln Lys Leu Asp Leu Val Pro Ile Ser Ile Met
225                 230                 235                 240

Gly Ser Thr Ala Trp Asn Ala Lys Val
                245

<210> SEQ ID NO 45
<211> LENGTH: 238
<212> TYPE: PRT
<213> ORGANISM: Pantoea citrea

<400> SEQUENCE: 45

Met Lys Arg Arg Glu Phe Leu Ser Ser Met Ala Ala Phe Gly Ala Ala
1               5                   10                  15

Ser Ala Ile Pro Leu Thr Asn Ala Ala Glu Ile Ser Gly Gly Gln Pro
            20                  25                  30

Trp Pro Pro Gly Gln Val Ser Leu Pro Pro Gly Leu Pro Arg Lys Gly
        35                  40                  45

Gly Leu Gln Phe Phe Thr Arg His Gln Leu Glu Thr Val Gly Ala Ile
    50                  55                  60

Ala Glu Arg Phe Ile Pro Ala Asp Glu Leu Ser Ile Ser Gly Lys Glu
65                  70                  75                  80

Ala Gly Cys Ala Ile Phe Ile Asp Arg Gln Leu Ala Gly Asp Phe Gly
                85                  90                  95

Gln Ala Val Thr Val Tyr Arg Leu Gly Arg Phe Val Lys Gly Thr Pro
            100                 105                 110

Glu Gln Gly Pro Gln Ser Pro Leu Thr Pro Ala Asp Gln Tyr Arg Leu
        115                 120                 125

Gly Leu Asn Ala Leu Asp Ser Tyr Cys Gln Gln Phe His His Asn
    130                 135                 140

Phe Thr Glu Leu Thr Gly Asp Gln Gln Asp Gln Val Leu Gln Gly Met
145                 150                 155                 160

Glu Thr Gly Lys Ile Ser Leu Ala Glu Asn Phe Asp Ser Lys Val Phe
                165                 170                 175

Phe Glu Leu Leu Leu Gln Asn Val Arg Glu Gly Phe Leu Ser Asp Pro
            180                 185                 190

Leu Tyr Gly Gly Asn Lys Asp Met Ala Ser Trp Lys Met Ile Gly Phe
        195                 200                 205

Pro Gly Ala Arg Tyr Asp Phe Arg Asp Val Ile Ala Lys Lys Gly Gln
    210                 215                 220

Lys Leu Asn Ile Ile Pro Thr Ser Leu Ile Asp Asn Asn Leu
225                 230                 235

<210> SEQ ID NO 46
<211> LENGTH: 242
<212> TYPE: PRT
<213> ORGANISM: Pantoea citrea

<400> SEQUENCE: 46

Met Leu Leu Gln Lys Asn Thr Thr Arg Arg Lys Phe Leu Leu Gly Ser
1               5                   10                  15
```

```
Leu Met Ala Leu Pro Leu Thr Glu Leu Val Leu Lys Gly Leu Thr Ala
             20                  25                  30

Ala Gln Ala Ala Asp Met Ala Ala Pro Glu Leu Thr Ser Tyr Lys Pro
         35                  40                  45

Ala Phe Phe Thr Ala Asp Glu Trp Gln Phe Ile Leu Ala Ala Thr Asp
     50                  55                  60

Arg Ile Ile Pro Ala Gly Gly Pro Gly Lys Ala Pro Gly Ala Leu Glu
 65                  70                  75                  80

Thr Asn Val Pro Ile Phe Ile Asp Gln Gln Leu His Asp Glu His Phe
                 85                  90                  95

Gly Lys Glu Ile Tyr Met Glu Gly Pro Phe Asn Pro His Ala Pro Ala
             100                 105                 110

Thr Met Gly Tyr Gln Val Pro Leu Tyr Pro Gln Gln Ile Tyr Gln Thr
         115                 120                 125

Gly Ile Arg Leu Thr Asn Gln Trp Ser Gln Gln Asn Leu Gln Lys Pro
130                 135                 140

Phe His Gln Leu Ser Glu Ala Asp Lys Asp Lys Val Leu Thr Gly Leu
145                 150                 155                 160

Gln Lys Asn Thr Leu Asp Phe Ala Ala Leu Gly Glu Asn Thr Leu Lys
                 165                 170                 175

Gly Ser Leu Phe Phe Ser Gln Leu Leu Gly Glu Thr Lys His Gly Tyr
             180                 185                 190

Leu Ala Asp Pro Met Tyr Gly Gly Asn Lys Gly Met Lys Ala Trp Ile
         195                 200                 205

Ala Ile Gly Phe Pro Gly Ala Arg Ala Ser Tyr Leu Glu Trp Val Lys
     210                 215                 220

Gln His Asn Val Lys Tyr Pro Leu Gly Pro Val Ser Leu Leu Gly Glu
225                 230                 235                 240

Thr Ala

<210> SEQ ID NO 47
<211> LENGTH: 245
<212> TYPE: PRT
<213> ORGANISM: Pantoea citrea

<400> SEQUENCE: 47

Met Gln Arg Arg Lys Phe Ile Lys Thr Gly Leu Ile Leu Ala Gly Thr
 1               5                  10                  15

Gly Thr Ala Ala Ser Val Phe Lys Pro Ala Gly Ala Ala Ala Arg Asp
             20                  25                  30

Asn Ile Leu Asn Gly Gly Lys Leu Trp Lys Ala Lys Glu Thr Pro Pro
         35                  40                  45

Pro Thr Pro Ala Asp Pro Thr Lys Arg Leu Tyr Leu Thr Glu Gln Glu
     50                  55                  60

Tyr Ala Gln Ile Thr Ala Ile Phe Asn Arg Leu Ile Pro Ala Asp Glu
 65                  70                  75                  80

Leu Thr Val Ser Ala Ser Asp Ala Gly Cys Val Val Phe Ile Asp Asn
                 85                  90                  95

Gln Leu Ala Gly Asn Tyr Gly Lys Ala Ser Trp Arg Tyr Asn Val Gly
             100                 105                 110

Pro Phe Glu Asn Gly Thr Pro Ser Gln Gly Asn Gln Pro Tyr Thr
         115                 120                 125

Pro Ala Gln Ile Tyr Arg Ile Gly Leu Ala Glu Ile Glu Lys Asp Cys
130                 135                 140
```

-continued

Gln Ser Lys Phe Ser Lys Ser Phe Ser Glu Leu Thr Asn Asp Gln Gln
145                 150                 155                 160

Asp Lys Tyr Leu Glu Gln Met Glu Ala Asp Gln Ile Lys Tyr Pro Thr
            165                 170                 175

Leu Ser Ser Lys Asp Val Phe Ser Gln Phe Leu Ser Asn Val Gln Glu
        180                 185                 190

Gly Phe Leu Ala Asp Pro Ile Tyr Gly Gly Asn Arg Asn Met Ile Gly
    195                 200                 205

Trp Lys Met Ile Gly Phe Pro Gly Ala Arg Tyr Asp Tyr Arg Asp Tyr
210                 215                 220

Ala Pro Leu Lys Gly Thr Lys Leu Asn Ile Glu Pro Val Ser Ile Ile
225                 230                 235                 240

Gln Leu Leu Lys Ala
            245

<210> SEQ ID NO 48
<211> LENGTH: 239
<212> TYPE: PRT
<213> ORGANISM: Pantoea citrea

<400> SEQUENCE: 48

Met Lys Arg Arg Arg Phe Leu Ala Ser Leu Gly Val Leu Leu Ile Ser
1               5                   10                  15

Thr Ala Leu Lys Val Lys Ala Lys Ile Ile Ser Gly Gly Met Pro Trp
            20                  25                  30

Val Val His Ala Val Lys Pro Pro Gln Pro Val Val Ala Gly Glu Trp
        35                  40                  45

Gln Phe Phe Thr Pro Glu Glu Val Ala Ile Ile Glu Ala Ile Ala Asp
    50                  55                  60

Arg Ile Ile Pro Gln Asp Glu Leu Ser Ile Gly Lys Glu Ala Gly
65                  70                  75                  80

Cys Ala Leu Phe Leu Asp Arg Gln Leu Ala Gly Asp Tyr Gly Lys Ala
                85                  90                  95

Val Ser Ile Tyr Arg Leu Gly Pro Phe Ile Gln Asn Gly Leu Pro Glu
            100                 105                 110

Ala Gly Pro Gln Tyr Lys Asp Val Pro Ala Glu Arg Tyr Arg Leu Gly
        115                 120                 125

Leu Ala Ser Val Asn Glu Ile Ser Gln Ala Lys Tyr Asn Gly Lys Lys
    130                 135                 140

Phe Asn Glu Ile Ser Glu Glu Gln Asp Asp Leu Leu Gly Lys Ile
145                 150                 155                 160

Glu Ser Gly Val Leu Pro Leu Thr Gly Val Asp Gly Lys Leu Phe Phe
                165                 170                 175

Asp Gln Leu Val Ile Asn Met Arg Glu Gly Phe Phe Ala Asp Pro Leu
            180                 185                 190

Tyr Gly Gly Asn Lys Asp Met Ala Gly Trp Lys Met Leu Gly Phe Pro
        195                 200                 205

Gly Ala Gln Tyr Asp Phe Arg Asp Val Ile Asp Lys Arg Gly Glu Glu
    210                 215                 220

Leu Asn Ile Lys Pro Val Ser Met Val Thr Asn Asn Asp Gln Ser
225                 230                 235

<210> SEQ ID NO 49
<211> LENGTH: 177
<212> TYPE: PRT
<213> ORGANISM: Pantoea citrea -continued

```
<400> SEQUENCE: 49

Met Thr Ala Asn Asn Arg His Pro Ser Gly Val Ser Arg Arg Leu
1               5                   10                  15

Leu Gln Gly Met Gly Ile Leu Ser Val Ala Gly Leu Cys Gly Ser Leu
                20                  25                  30

Phe Pro Ser Phe Arg Ala Ala Ala Glu Leu Gln Asp Ser Gly Phe
        35                  40                  45

Ile Pro Leu Ser Glu Phe Leu Val Asn Arg Arg Val Asn Pro Ile Leu
    50                  55                  60

Ala Gln Arg Tyr Tyr Asp Ala Leu His Arg His Asp Glu Lys Phe Asp
65                  70                  75                  80

Gln Lys Leu Ala Leu Leu Lys Gln Asp Ile Gln Pro Gly Lys Tyr Gln
                85                  90                  95

Asn Ile Asp Asp Phe Leu Gln Lys Asn Ala Val Gly Thr Asp Leu Arg
            100                 105                 110

Gln Ala Ala Gly Gln Val Ile Ser Ala Trp Tyr Thr Gly Val Val Gly
        115                 120                 125

Asn Asp Glu Lys Leu Glu Leu Ile Ala Tyr Ala Asp Ala Met Met Tyr
130                 135                 140

Val Pro Thr Ser Gly Val Leu Val Pro Thr Tyr Gly Ser Gly Pro
145                 150                 155                 160

Ile Ser Trp Ala Ala Val Asp Asn Lys Pro Ala His Gln Gly Pro Ala
                165                 170                 175

Val

<210> SEQ ID NO 50
<211> LENGTH: 182
<212> TYPE: PRT
<213> ORGANISM: Pantoea citrea

<400> SEQUENCE: 50

Met Lys Leu Thr Asp Thr Ile Ser Thr Asp Arg Arg Lys Leu Ile Lys
1               5                   10                  15

Ser Leu Ser Leu Leu Thr Val Phe Ser Val Ser Gly Leu Arg Leu Val
                20                  25                  30

Thr Cys Pro Ala Phe Ala Gly Gly Leu Pro Ala Ser Ala Asp Phe His
            35                  40                  45

Glu Phe Ser Thr Phe Val Ile Gly Arg Pro Val Asp Pro Val Leu Ser
    50                  55                  60

Gly Arg Tyr Phe Ala Ala Leu Gln Ala Ala Asp Gly His Phe Ile Gln
65                  70                  75                  80

Gln Leu Asn Gln Ala Met Val Ala Ser Val Pro Phe Arg Ser Gln Gly
                85                  90                  95

Ile Asp Thr Met Leu Ala Ser Leu Pro His Asp Ser Asp Ile Phe Asn
            100                 105                 110

Thr Leu Lys Lys Ile Thr Ser Ala Trp Tyr Leu Gly Ile Val Gly Glu
        115                 120                 125

Gly Ala Gly Ala Thr Leu Ile Ala Phe His Asp Ala Leu Met Phe Gln
130                 135                 140

Pro Thr Arg Glu Tyr Val Phe Val Pro Gly Tyr Gly Gly Pro Asp
145                 150                 155                 160

Ser Trp Val Ser Leu Lys His Pro Asp Leu Leu Ser Glu Asp Thr Glu
                165                 170                 175

Gln Glu Gln Lys Asn Gly
            180
```

<210> SEQ ID NO 51
<211> LENGTH: 182
<212> TYPE: PRT
<213> ORGANISM: Pantoea citrea

<400> SEQUENCE: 51

Met Lys Asn Glu Ile Ile Arg Asp Asp Ser Pro Ala Glu Tyr Asn Leu
1               5                   10                  15

Ser Arg Arg Lys Val Leu Leu Gly Gly Leu Ile Leu Leu Gly Ser Ser
                20                  25                  30

Tyr Leu Gly Pro Ser Leu Pro Ala Trp Ala Asp Thr Leu Asn Asp Gln
            35                  40                  45

Ala Thr Ile Asp Gln Phe Met Gln Leu Ser Gln Leu Leu Val Asn His
        50                  55                  60

Gln Leu Asp Pro Val Thr Gly Gln Arg Leu Ala Ala Ala Met Ile Ser
65                  70                  75                  80

Gly Asn Met Ile Thr Arg Gln Gln Ile Thr Ser Leu Leu Ala Val Ala
                85                  90                  95

Gln Ala Arg Gln Ala Lys Val Val Glu Asp Phe Phe Ser Asp Ile Pro
            100                 105                 110

Gln Gly Glu Leu Lys Asn Ala Ala Leu Ser Ile Ile Ser Ala Trp Tyr
        115                 120                 125

Lys Gly Val Leu Ile Asp Ala Pro Gly Ala Glu Val Phe Ala Tyr Glu
130                 135                 140

Lys Ala Leu Met Tyr Gln Pro Thr Ile Asp Val Met Thr Ile Pro Thr
145                 150                 155                 160

Tyr Ala Ile Thr Gly Pro Asn Gly Trp Ser Ser His Ala Ala Pro Leu
                165                 170                 175

Ala Asp Met Pro Asp Phe
            180

<210> SEQ ID NO 52
<211> LENGTH: 167
<212> TYPE: PRT
<213> ORGANISM: Pantoea citrea

<400> SEQUENCE: 52

Met Ile Asp Met Leu Asn Met Ile Ser Arg Arg Ile Leu Gln Gly
1               5                   10                  15

Met Gly Ala Leu Ala Ala Thr Thr Leu Leu Pro Ser Gly Ile Leu Pro
                20                  25                  30

Ala Phe Ala Asp Thr Pro Ala Asn Ser Asp Phe Asn Asp Ile Ser Arg
            35                  40                  45

Leu Leu Thr Gly Arg Asn Thr Leu Ser Ala Glu Phe Ser Ser Ala Leu
        50                  55                  60

Phe Ser Ala Phe Thr Lys Ile Asp Ser Arg Phe Pro Gln Gln Leu Ala
65                  70                  75                  80

Arg Leu Lys Gln Trp Ile Thr Ala Asn Ser Val Pro Ala Ala Asp Leu
                85                  90                  95

Gln Lys Arg Leu Thr Ala Asp Ser Val Ala Asp Leu Ala Gly Leu
            100                 105                 110

Pro Ala Leu Ile Leu Thr Gly Trp Tyr Leu Gly Ile Ala Gly Ser Gly
        115                 120                 125

Asp Lys Ala Val Cys Val Thr Tyr Val Asp Ala Leu Ala Asn Gln Glu
130                 135                 140

```
Val Ala Ser Val Leu Asn Pro Pro Thr Tyr Ala Tyr Gly Ala Tyr Gly
145                 150                 155                 160

Ser Trp Ala Thr Lys Pro Phe
                165

<210> SEQ ID NO 53
<211> LENGTH: 195
<212> TYPE: PRT
<213> ORGANISM: Pantoea citrea

<400> SEQUENCE: 53

Met Asn Asn His Asn Ala Pro Glu Thr Gln Pro Glu Leu Ser Glu Glu
1               5                   10                  15

Gly Leu Arg Arg Arg Lys Leu Phe Gly Gln Thr Gly Gly Leu Val Ala
            20                  25                  30

Ser Phe Ala Ile Gly Ser Ala Ile Ala Gly Ser Thr Leu Ser Asn Gly
        35                  40                  45

Ala Asn Ala Ala Thr Thr Ser Ala Gly Pro Asp Thr Gln Thr Leu Asn
    50                  55                  60

Gln Phe Met Lys Thr Ser Arg Leu Leu Thr Gly His Gln Asn Leu Asp
65                  70                  75                  80

Leu Thr Leu Gly Gln Arg Leu Tyr Val Ala Phe Ser Glu Lys Asp Pro
                85                  90                  95

Gln Phe Ile Thr Gln Leu Ser Ala Leu Asn Gln Trp Ile Ala Asp Lys
            100                 105                 110

Gln Pro Ala Asp Val Glu Ala Leu Asp Ser Gln Leu Ser Gly Gln Pro
        115                 120                 125

Leu His Ala Leu Met Met Ser Val Ile Lys Gly Trp Tyr Leu Gly Val
    130                 135                 140

Ile Asp Asp Ser His His Ala Lys Val Tyr Ala Tyr Gln Asn Ala Leu
145                 150                 155                 160

Met Tyr Gln Val Pro Arg Asp Gly Met Val Ile Pro Thr Tyr Ala His
                165                 170                 175

Asn Gly Pro Asp Tyr Trp Thr Ala Asp Pro Pro Val Asp Arg Leu
            180                 185                 190

Leu Asn Phe
        195

<210> SEQ ID NO 54
<211> LENGTH: 180
<212> TYPE: PRT
<213> ORGANISM: Pantoea citrea

<400> SEQUENCE: 54

Met Asn Lys Ala Thr Pro Val Ser Pro Gly Glu Arg Arg Phe Ile
1               5                   10                  15

Lys Leu Leu Ala Ala Ser Thr Val Ala Gly Thr Val Ser Ser Leu Leu
            20                  25                  30

Pro Gly Gln Ile Ala Trp Ala Ile Asp Ala Gly Gln Pro Ala Val Ala
        35                  40                  45

Gly Phe Pro Ala Phe Met Thr Val Ser Glu Ile Ile Cys Gly Tyr Pro
    50                  55                  60

Thr Leu Asp Asn Ala Leu Gly Lys Arg Ile Phe Ser Leu Ile Ser Ala
65                  70                  75                  80

Glu His Gly Asp Ala Ser Gln Ser Ile Ala Glu Leu Gln Lys Gln Leu
                85                  90                  95

Asn Ala Asp Met Ser Ser Ala Glu Met Gln Ala Ala Leu Lys Thr Leu
```

```
                  100                 105                 110
Asp Thr Pro Ala Gln Gln Leu Phe Ser Glu Ile Leu Arg Gly Trp Gln
            115                 120                 125

Ile Gly Ile Val Gly Ser Gly Lys Gln Ser Gln Val Val Ala Tyr Glu
        130                 135                 140

Tyr Ala Leu Met Tyr Ala Pro Ile Ser Asp Val Val Leu Pro Thr
145                 150                 155                 160

Phe Ala Arg Gly Glu Pro His Tyr Trp Ala Tyr Pro Pro Val Ile Lys
                165                 170                 175

Thr Gly Lys Leu
            180

<210> SEQ ID NO 55
<211> LENGTH: 184
<212> TYPE: PRT
<213> ORGANISM: Pantoea citrea

<400> SEQUENCE: 55

Met Lys Phe Val Ile Asp Gln Glu Ser Asp Thr Gly Glu Ile Ser Ala
1               5                   10                  15

Ser Arg Arg Ser Phe Leu Ile Lys Ile Thr Ala Leu Leu Ala Ser Phe
            20                  25                  30

Thr Leu Ile Pro Ala His Ala Val Ile Thr Thr Pro Ala Asp Val Gly
        35                  40                  45

Ala Ser Val Ile Ser Gln Leu Gln Thr Thr Ala Gln Phe Leu Thr Glu
    50                  55                  60

Ser Gln Gln Asp Pro Gln Leu Ile Ile Arg Ala Ala Asn Ala Leu Leu
65                  70                  75                  80

Lys Val Asn Ser Asn Phe Ala Gly Asp Leu Gln Leu Ser Ser Leu
                85                  90                  95

Ile Ala Asp Asn His Ile Ala Asn Leu Lys Asp Leu Lys Thr Ser Asn
            100                 105                 110

Leu Phe Glu Gly Lys Pro Gln Gln Thr Ala Lys Asp Ile Leu Ser Ala
        115                 120                 125

Leu Tyr Leu Gly Tyr Ala Gly Thr Pro Val Met Leu Ser Ser Glu Asp
    130                 135                 140

Asn Val Val Phe Val Ala Tyr Ala Gln Ala Arg Thr Tyr Gln Leu Thr
145                 150                 155                 160

Lys Asp Phe Thr Pro Val Pro Ser Tyr Ser Arg Trp Lys Ser Gly Tyr
                165                 170                 175

Trp Ala His Leu Pro Ala Gly Val
            180

<210> SEQ ID NO 56
<211> LENGTH: 174
<212> TYPE: PRT
<213> ORGANISM: Pantoea citrea

<400> SEQUENCE: 56

Met Asn Leu Thr Arg Arg Leu Leu Thr Gly Ser Ala Gly Leu Ile
1               5                   10                  15

Val Ala Gly Val Leu Ser Gln Thr Leu Ser Gly Arg Tyr Ala Leu Ala
            20                  25                  30

Ser Pro Pro Leu Ala Ser Ala Val Ala Pro Ser Ala Gly Phe Asn Thr
        35                  40                  45

Leu Ser Val Leu Ile Thr Gly Gln Asp Lys Pro Asp Ala Leu Leu Ala
    50                  55                  60
```

```
Gln Arg Leu Tyr Ser Trp Leu Ala Ala His Thr Ser Gly Leu Asp Ser
 65                  70                  75                  80

Gln Leu Glu Thr Leu Ser Ser Leu Leu Gln Gln His Ser Asp Ala Asn
                 85                  90                  95

Gly Ser Thr Leu Leu Ser Leu Met Lys Ser Gln Pro Glu Asn Ile Asn
            100                 105                 110

Thr Leu Tyr Gln Ser Leu Val Ser Gly Trp Tyr Leu Gly Val Val Gly
        115                 120                 125

Pro Leu Pro Arg Pro Asp Cys Ile Ala Phe Glu Asn Ile Val Ser Tyr
    130                 135                 140

Gln Leu Leu Lys Gln Ser Val Leu Pro Pro Ser Tyr Ala Pro Gly Gln
145                 150                 155                 160

Pro Gly Phe Trp Val Gln Pro Ala Gly Arg Val His Val
                165                 170
```

<210> SEQ ID NO 57
<211> LENGTH: 189
<212> TYPE: PRT
<213> ORGANISM: Pantoea citrea

<400> SEQUENCE: 57

```
Met Lys Gln Ile Phe Glu Gln Ser His Thr Asp Leu Pro Glu Asn Gly
  1               5                  10                  15

Thr Gly Ser Ser Arg Arg Gly Phe Ile Lys Ser Ala Leu Val Leu Thr
             20                  25                  30

Ala Ser Gly Leu Val Ala Ser Leu Pro Leu Arg Ser Phe Ala Ser Ser
         35                  40                  45

Val Val His Gly Gly Asp Thr Thr Gln Asp Phe Ile Ser Val Ser Gln
     50                  55                  60

Ala Ile Thr Glu His Lys His Ile Asn Pro Gln Leu Ala Ala His Phe
 65                  70                  75                  80

Leu Ser Ala Phe Ile Lys Arg Asp Asn Gln Phe Ser Ser Lys Ile Thr
                 85                  90                  95

Arg Leu Ala Gln Leu Tyr Gln Thr Gly Asp Thr Ala Ile Val Phe Lys
            100                 105                 110

Asn Lys Ala Val Ala Ala Gly Leu Gly Asp Phe Leu Gln Gln Ile Leu
        115                 120                 125

Thr Ala Trp Tyr Thr Gly Thr Ile Gly Asp Asp Tyr Lys Gly Thr Leu
    130                 135                 140

Val Ala Tyr Lys Glu Ala Leu Met Tyr Asp Thr Val Ser Asp Gly Leu
145                 150                 155                 160

Val Val Pro Thr Tyr Cys Gly Asn Gly Pro Leu Trp Trp Thr Val Pro
                165                 170                 175

Val Pro Asp Pro Leu Asp Pro Glu Leu Ile Asn Asn Leu
            180                 185
```

<210> SEQ ID NO 58
<211> LENGTH: 152
<212> TYPE: PRT
<213> ORGANISM: Pantoea citrea

<400> SEQUENCE: 58

```
Met Lys Thr Lys Thr Leu Leu Ala Ala Ala Leu Leu Leu Thr Thr Gly
  1               5                  10                  15

Tyr Ala Ala Thr Ala Gly Ala Ala Thr Leu Thr Asn Ser Gln Ala Asn
             20                  25                  30
```

His Val Ile Glu Asn Ala Glu Ser Thr Ile Lys Ala Gln Asn Ser Thr
             35                  40                  45

Gly Cys Ala Val Val Val Asp Asn Asp Gly Met Leu Leu Ser Phe Gln
 50                  55                  60

Arg Leu Asp Gly Ala Thr Pro Gly Cys Ile Asp Ala Ala Ile Gly Lys
 65                  70                  75                  80

Ala Arg Thr Ser Ala Leu Tyr His Ala Pro Ser Val Lys Phe Met Gln
                 85                  90                  95

Arg Leu Gln Ser Gly Glu Thr Thr Val Leu Ala Ile Pro His Ala Val
                100                 105                 110

Pro Leu Gly Gly Gly Tyr Pro Leu Thr Leu Gln Gly Glu Val Val Gly
            115                 120                 125

Ala Val Gly Val Ser Thr Pro Lys Gln Asp Leu Asp Asn Gln Ala Ser
130                 135                 140

Glu Thr Ala Ala Lys Ser Leu Lys
145                 150

<210> SEQ ID NO 59
<211> LENGTH: 1767
<212> TYPE: DNA
<213> ORGANISM: Pantoea citrea

<400> SEQUENCE: 59
atggctcaga taactaagaa agaagtcgac gtcgtggttt gcggattcgg ctgggccggt      60
tcactgatga gtattgaact ggccatggca ggactgacag tgcgtgcact ggaaaaaggt     120
cctgaacgtg attatgaagc gtttgcctat cctaaaccgg cagacgaata tgcctatgcg     180
gttcgtaaca aggtgatgac cacccccgca gattctgcgg tgaccgtgcg ttacaccatg     240
caggacaccg cactgccaac ccgtaagtgg ggcgcctttg tgcctggcgg cggtgtgggt     300
ggtgccggta tgcactggac cggtgtgtta ctgcgtccga ccccgaccga tattaaactc     360
aaaacctatg ccgatgaggc ctacaaaccg ggtgtattac aggaagatat gcgggtgcgt     420
gatttcccgt ttacctggaa tgagattgag ccatggtttg aaaaatttga gcatatctgc     480
ggattatccg gtaacaccgg taacctgcgc ggccagataa tggaaggcgg agatccgttt     540
gaagggcccc gtgccaatcc gatgccattg ccggcactgg aaaatacgct caataacgtg     600
atgtttggcg ataccgtgaa aaaaatgggt tatcacccgt tcaccattcc gtcggctgcc     660
gcttcccgtg tctggaccaa cccttacgga acactattg ctccgtgtaa ctattgcggt     720
tactgctcta aatatccgtg cctcaactac tccaaagcct caccccagac cgcagtgctg     780
gattcactga gcagatggaa taacttctct tatgaagtaa acgcggaagt gttgagagtg     840
gtgctgcatg atgataagaa aaccgccaaa ggggttatct atatcgatga gcagggtaac     900
gaatgctttc agccggcaaa aattgtcatc ctcagcagct tccagttcta taacgtgcgt     960
ctgatgctgc tgtccggtat tggccagcct tacaacccgg tcaccgaaga aggggtagtc    1020
ggacgtaact atgcgttcct gagtaatggt tctgcgactc tgttttcaa agataaaaac    1080 tttaacccgt tgtcagctc cggaccgacc ggtatgcagt tcaacgatat ctctccgggc    1140
aacttcgacg gtccgggact tggcattatc ggcggagcaa aaattcagag tgcccagtcg    1200
accggaaccc caatcagcac cgcgctgccg ccgggtactc cctcctgggg agcgggctgg    1260
aaagaggggc tggaaaactg gtacggccat tcaatgaagg tggggatcac cacttcctgt    1320
atgtcgtacc gtgacgttta cctggatctg accccgacct ataaagatcg ccacggtcag    1380
ccattattgc gcatgacctt taactggaag cacaacgaac tgcagttaca gcagtacctg    1440

| | |
|---|---|
| aaaggcattg tcggcaatat cgtcaaagag atgaaccctg acagtttcag catgagtttc | 1500 |
| ctgccgatgg gcgctgactt tgatctgacc aagtatgtct ctacccataa cgtgggcggg | 1560 |
| gctattatgg gcgatgatcc gaaaacatcg gccctgaacc gttacctgca aagctgggat | 1620 |
| gttcataacg tatttgtgcc gggaggtaat gcgttcccgc agaacttcca gtccaacccg | 1680 |
| accaacacta tcggtgcaat tacgctgatg gcagctaatg ccattaaaga acagtatctg | 1740 |
| aaaaatccgg gcccaatggt acaggtg | 1767 |

<210> SEQ ID NO 60
<211> LENGTH: 1767
<212> TYPE: DNA
<213> ORGANISM: Pantoea citrea

<400> SEQUENCE: 60

| | |
|---|---|
| atgaaaatta ccaatgaacc tgttgatgtg gtcatcgtcg gtctgggttg gaccggtgct | 60 |
| attcaggta ttgagttagc caggacagga ttaaagatac gagcacttga gcgtggggcc | 120 |
| gatcgtacca gcgccgaatt tgcatacccg gttccggcag atgaactggc ttacaccaag | 180 |
| cgccacaaaa taatgcaaag cccggcggtt gccgcattca ccacgacaa taatctgaat | 240 |
| gaagttgcgt tgccaatgcg agaactgggt tcttttaggc ttggagatgg tgtcggaggc | 300 |
| gcagatttac actggacagc catgattacc cggccaactc cggttgacct gaaactggca | 360 |
| acctatgccc gagaaaaatt tgaaaaatct cagctggata agaactgag gatttatgac | 420 |
| tttccggtaa gttggtctga gattgaacct catatggact ttttgatca ggtttgcgga | 480 |
| tcatcaggtc aggcaggcaa tgtccgcggc caaatcctgc caggggtga ccctttgaa | 540 |
| ggtcctcgct ccagtccatt tccaaatcca ccactgatcg atacactgaa tagcagtatg | 600 |
| tttcgccagg cggccactga aatgggatat catccctatt caatcccttc cgctgccgtt | 660 |
| tctcaggcat tcactaaccc ctatggccag cagattgctc cttgtaacta ctgtggttac | 720 |
| tgtcagtttt attcctgcct taattactca aaggcctcac ctcagacggc aattctggat | 780 |
| cgcctgaagc agtatgataa ttttgactac aaaaactcatg ccaacgttat ccgtgtagaa | 840 |
| aaacatgcag atggcaaaac tgcaacaggg gtaacctata tcgatgaaaa cgataatgaa | 900 |
| gttttcagc cagcaaaaat cgtcattctg gccagttttg ggctgaacaa cgtacgtttg | 960 |
| ctgctaaatt ctaaaattgg tcagccgtac aatccagtga ccgaagaagg ggtggttgga | 1020 |
| cgtaactata cccaccagta tggtggtggt atcacgcttt actttaatca acttgaattt | 1080 |
| aatccatttg caactgcagg accgaccgga gtcgttatta ccgattttgg taccggaaac | 1140 |
| atcaatactg cagaccttgg ttttatcggt ggtgccaaaa tctatagttc gcagccgacg | 1200 |
| ggaaccccga tgggcgcgcc ggtgattgat tccgccgcta agtggggaag tcgctggaag | 1260 |
| aaaggcctga acaaagcta cggacattca atggccatta agctggaagg ctccaatatg | 1320 |
| gccactcaga ccaattatct tgatctggat cctaactata aagataaatt cggtatgcct | 1380 |
| ttgctacgcg tcacttatga ctatgtgcaa aatgatttac gcatgctgca atttatgcgc | 1440 |
| gagaaaatgg ttggtatcgc tgaacatcta aaaccagacc attattccgt tggaatgcta | 1500 |
| aaaatggata gccattttgc cagttctccg gcttatgcta atacccataa tgcaggtggt | 1560 |
| gcaatcatgg gagataaccc gaaaacctca gtcgtaaatc gctatttgca aagctgggat | 1620 |
| gtgcataacg tatttgtcat gggtgcctgt gtgtttccac aaaatgtcta tgctaatccg | 1680 |
| acagcattgg ttgcagggct gacttactgg tcagctaagg ccattcgtga aacgtatcta | 1740 |
| aataaccccg gtccgctggt tcaggca | 1767 |

```
<210> SEQ ID NO 61
<211> LENGTH: 1776
<212> TYPE: DNA
<213> ORGANISM: Pantoea citrea

<400> SEQUENCE: 61
atggcaacaa ctaaaaaacc ggcagccgac atcgtcattg ttggctttgg ctggacaggt      60
tctctgatgg cccgtgaatt agcagattcc ggattaaaga tcgtcgcgct ggaacgaggt     120
gaacaacgag atacttatcc ggattttgct tatccacgta taaccgatga actcacctat     180
ggcattcgtc tgaaattatt tcagaacgca gcacgggaaa ccgtcaccgt ccgtcatact     240
tcgtcccaga cagcactgcc ttatcggcgt tttgggtcct ttctgccagg taatggtgtg     300
ggtggcgcag gtgtccactg gaatggcatg ttgtggcgtc cactggccgc cgatttaaaa     360
atgcactcaa ctctggttga aaatatggcg cgaattttta ttccgcagga tatgaccgtc     420
caggactatc ctttcactta tgaagagatg aaccttttt  tcgacaaatt cgaaaaaata     480
tgtggtgctt ccggacaagc tggcaatctg aatggtgaaa ttcagtcagg cggaaacccg     540
tttgaacagc ccagacaaaa cccctacccg accaaaccac tgcaacgctt gtatgccggt     600
gatgtgttcg ccaaagcggc agaaaaaatg ggttatcacc cattcccttg ccctgctgct     660
aactgtaccg aagcctggac caacccttat aaagtgcaac tgggagtatg taactattgt     720
ggtttctgtg aacgctttgg ttgtttcaat tattccaaag gctctccaca aagttgcgta     780
attccgtcac tcaaggccta tgataatttc gaactgcgaa cgaacgccca ggtgattcgg     840
gtcaataccg ataatacggg taaacaagct accggagtga cctatattga tggcagcggt     900
aatgaagtgg aacaacctgc atccctggtg attcttagtg cttttccagct gcataatgtc     960 cggttgttat tactctctaa aatcggtaag ccctatgatc cgcaaaccgg cgaaggtgtt    1020
gtcgggcgaa attatgctta ccagatgaca ggaggttcaa aactgttttt tggacctgat    1080
caggatttta aaccgttcgc ggctacaggt accacagcaa cctttatcga caactttaat    1140
gccgaaaact tcgaccattc atcgcttgga tttgtcggcg gctcaacaat ttctgcagca    1200
ttcagtggtg gccgtcctat tcaacagaca ctgctaccct ctgacgctcc ccgttgggga    1260
agtggctgga aaaccgcaat aaaaacccac tatgcacata ccatgtctat tggtgcttca    1320
ggttcggtaa tgcccaccg gcaatgttat ctcgatctgg acccgactta tcatgatgtt    1380
aacggacaac cattactgag aatgacgttc gactggcaac taatgaact  gaaaatgact    1440 gagtttattg gcgaaaaagt tgaagagatc atcaaggtca ttaatccgcc acactatgaa    1500
atgggcttta tgaacatgaa cagtcactat gatgttcgcc cttatcagtc aacacatact    1560
accggcggtg cagtcatggg cgactccccc cgcaccagcg tcgtcaacaa ataccctgcaa   1620 agctgggatg ttcctaacct gtttgtcctt ggagcctgct gtttcccgca aaacctggcc    1680
tacaacccga caggtattgt ctgtgctaca gcattgttct cggcacatgc gattaaaacc    1740
cgctatctgg ctgcacctgg cccgctggtt acaata                              1776

<210> SEQ ID NO 62
<211> LENGTH: 1773
<212> TYPE: DNA
<213> ORGANISM: Pantoea citrea

<400> SEQUENCE: 62
atgacaatta aaaagatcc ggtagatgta gttattgttg gttttggctg gacaggctct       60
gtgatggcaa tggaactggc cgaaaccggc ctgaaaattg ttgcactgga acgtggtgaa     120
```

```
cagcgggata cctatcctga ttttgcctat ccacgaattg tggatgagct gacttacggt      180
gtccggttaa aactattcca gaacctgtct aacgaaacgg tgacggtgcg tcatgcaccg      240
ggcgatctgg ctctgcctta tcggaaaatg gggtctttcc tgccaggtga cggggtaggc      300
ggcgcaggtg ttcactggaa tggcctgctg tggcgccctc tggaaaccga tctgcgactg      360
aaatcaacga tcaccgaaaa gtacggagcc gcgtttattc cacaggacat gacgttacag      420
gattatccgt ttacctatgc tgaaatggag ccgttcttta cccgttttga aaaaatctgt      480
ggtgcttccg gccaggccgg caatattaac ggtgaaattc agcaggggg taacccgttt       540 gaagccccgc gcagtggtgc ctatccgacc agcgccctga aaagccagta ttccggagaa      600
ctgtttggca agtcgccaa agagcatggt tatagtccgt tcccggggcc tgcggcaatc       660
tgtaccgaat cgtatcagaa tccgtacggg gtccagttag gggtgtgtaa ctactgcggt      720
ttctgtgagc gttttggttg tttcaactac tcgaaagctt ctccgcaaac ctgtgttatc      780
cctgcgttgc gccagcatac taattttgaa ttgcgcactc attctcatgt aattcgtgtt      840
aacaaagaca gcacagggaa aaagcgacc ggagttacct atattgatgc caatggccag       900
gaagtggagc aaccggcggc cctggtggtc tcggagcgt tccagctgca caatgttcgt       960
ctgctgttgc tgtcagggat aggtcagccg tatgaccctc gtaccggcga aggtgtggtc      1020
ggccgaaatt atgcctacca ggtcaatggt ggtgtgaaat tgtttttatga caaagaccag    1080 tattttaata attttgccgc gaccgggtgc tcaggaacct atatcgataa ctttaacggt      1140
gagaatttcg accactcctc actcgggttt attggtggag cactatttc cgcacatgcc       1200 accggcggcc gtcctattca gcagacagaa ctgccttccg gcagccctaa atggggtacc      1260
ggctggaaaa aagcgatgaa agataattat ctgcacagta tgagtgttgg ttcagcttcc     1320
tcagtgatgc cttataagca gtgttatctg gatctggatc ctacctatac cgacggctac      1380
ggtttgcctt tgctgagaat gacgtttgac tggcaggaga atgatctgcg tgtgacacag      1440
tttgttgccg gtaaaaccga ggaactggtc aaagcgctaa aacctcgcag ttatgatatg      1500
ggattcaaga agctcaatac tcactatgat gtccgtcctt atcagtccac gcataccacc      1560
ggcggtgcgg tgatggggga taaccctcgt accagtgtag tgaataaata tctgcaaagc      1620
tgggatgtgc caaatgtgtt tgtccttggt gcctgctgct ccccgcagaa tattgcctac     1680
aaccccaccg gcatcgtagg ggcaaccaca ctgtttgccg cgcatgcgat taaaactcag      1740
tatctccgta acccgggacc actggtacag gcc                                    1773

<210> SEQ ID NO 63
<211> LENGTH: 1773
<212> TYPE: DNA
<213> ORGANISM: Pantoea citrea

<400> SEQUENCE: 63
atggctattg taaaaaataa gaccgatgta gtgatcgtgg ggatggggttg gaccggtgcc       60 attatggcga aagagatgac agatgccggg ctttcggtag tcgctctcga acgcggagct      120
gatcgggata cggaaccaga ttttgcttat cctggagtcg tagacgaatt acagggttcg      180
gtgcaccgcc gctatctgca aagcctgcac caggaaacgg ttactgtgcg tcataacacg      240
ggttctgtgg cggttcctta ccgtcagatg ggctcattta gcctggcac cggagtggga       300 ggcgccggca gccactggtc aggatgccat tttcgtccgc tgcctgaaga tttacgcctg      360
cgtagtaacc tggaggaacg ttacggcaaa tcttttattc cgtcagatat gactatcgac      420
gattttccgg tcagctacga tgaactggaa ccgcatctcg atatgtttga aaaggtttgt      480
```

-continued

| | | |
|---|---|---|
| ggtacctcag gcaaggccgg agtgatccgt ggagttgttc aggcgggagg aaatccgttc | 540 | |
| gaaggctcgc gtagcggaga gtatccactg ggccctaacc ccaactatct gggtgccgag | 600 | |
| tggttttata aagccgccag ggaaaagggc tatcacccct atcctatccc ggcctccaat | 660 | |
| gccgccggcc cttacattaa cccttatggc tgtcagatgg gcccctgtaa tgcctgtggt | 720 | |
| ttttgcagtg attacggttg tcttaattat tcaaaagcga gtccgaacat ctgtattatg | 780 | |
| ccggttttgc gtcagcgtaa aaattttgaa ttacgcaccc atgctcaggt tctgaaagta | 840 | |
| aatctgagca gcgacggcaa aaaagctacc ggagtaacct atctggacag taatggtcag | 900 | |
| gaaaccgaac aaccgctga cctggtgctg ttatgcgcct ctcactcta aacgtccat | 960 | |
| ctgatgctgc tgtcacaaat tggcaagcct tacgaccctg tcagtaatga aggaaccgta | 1020 | |
| ggccgcaact actcctacca gaaccttaac cgcgtgatga tgttctatga tcaaagcgta | 1080 | |
| caggccaacg gctttattgg aatcggtggt tccggaacca caatgatga tctgaacggc | 1140 | |
| aatcagctgg acaatgcgca ggccgggttt gtcggcggcg aatcatctg ggcaaggcag | 1200 | |
| ccaggcaatg gtccggtgcg cggcgttgct gtgccaaaag gtaccccggg ttggggatcg | 1260 | |
| gcctggaaaa aagcagtttc agaaagcttc cgtcattcgt tctattacga agtccaggga | 1320 | |
| gcctgcatgt cttatcagca aaactatctg agcctggacc ctacctggaa agatgctttt | 1380 | |
| ggccgtcctc tgttacggat gacttttgac tggcagccta acgaagttaa ggcttcacag | 1440 | |
| tttctggtcg ggaaagcggt ggatatgtgt caggtactca atccgaaatc tatctccagc | 1500 | |
| gatgccaaaa aagacggcgc tcattacgat atcaccaaat atcagagtac ccacacctgt | 1560 | |
| ggcggtgcgg taatgggcag cgacccgaaa aaatcggcac tgaaccgtta tctgcaatcc | 1620 | |
| tgggatgtgc caaacgtgtt tgctatcggg gcgaatgcct ttccacagaa taatggatac | 1680 | |
| aaccctaccg gtctggtggg cgggctggcc tactgggctg ccaccgctat tcgtgaacaa | 1740 | |
| tacctgaaaa acccgggccc gttggtccag gca | 1773 | |

<210> SEQ ID NO 64
<211> LENGTH: 1781
<212> TYPE: DNA
<213> ORGANISM: Pantoea citrea

<400> SEQUENCE: 64

| | | |
|---|---|---|
| atggccagtg taatgaaaaa aacagatgca gtgattgtcg gtttcggctg ggccggggct | 60 | |
| atcatggcaa aagagctgac agaagccggg ctgaatgttg ttgcgctgga acgtggacca | 120 | |
| cagcgtgata cttatccgga cggtgcttac ccgcagtcta ttgatgagct gacttacaac | 180 | |
| atccgtaaga agctgttcca ggatttatca aaaagtacgg tcactgttcg ccacaatcca | 240 | |
| tcacagaccg ccgtgcctta tcgccagtta atgcgttcc tgcctggaac cggtaccgga | 300 | |
| gcgccgggct gcactggtca ggggttcatt ttcgtgttga tccggctgaa cttcgcctgc | 360 | |
| gtagccacta tgaagagcgc tatggtaaag acttatccc tcaggggatg accatccagg | 420 | |
| attttggtgt cagttacgat gaactggagc cattctttga tcaggcagaa aaggtctttg | 480 | |
| gtacatccgg aaccgcctgg acagtgaaag gtgagttggt cgggaaaggt aaaggggcca | 540 | |
| acccgtttgc acctgatcgt tccagtgact ttcctctgaa agcacagaaa cgtacttatt | 600 | |
| cagcgcaatt gtttgcagag gctgcggagt ctgtaggcta tcatccgtat gatatgccgt | 660 | |
| ctgctaacac ttctggtcct tacaccaata cttatggtgc tcagatgggg ccgtgtaatt | 720 | |
| tctgcgata ttgcagtggt tatgcctgct atatgtactc gaaggcttcg ccaaacgtca | 780 | |
| atatattgcc agccttacgt caggaaccta aatttgaatt gcgcaatgat tcctatgtgc | 840 | |

```
tgcgggttaa tctgaccgat gataagaaac gcgctaccgg agtcacctat gtcgatgcca      900
gcggtcgtga gtttgaacag cctgctgacc tggtcattct gtctgcgttc cagtttcaca      960
atgtccatct gatgctgctt tccggtatcg gtaaaccctg taacccggtg actaatgaag     1020
gggttgttgg gcgtaacttt gcttaccaga acatttctac tctgaaggct ttgttcgaca     1080
aaaatatcac aaccaatccg tttatcggtg cgggtggtgc gggtgtcggg gtggatgatt     1140
tcaatgccga taactttgac catggtccgc acggttttgt cggcggatcg ccgttatggg     1200
taaaccaggc cggtgttaaa ccaatctccg gactgccgac tcctaccgga actccggcct     1260
ggggtagcga atggaaagcc gctgtcgcag acacttatac ccatcatgta tcgatggatg     1320
cgcacggtgc tcaccagtct taccgtacta actatctcga tcttgacccct aactacaagg     1380
atgtccacgg acaacccttg ctgcgcatga cttttgactg gcaagagaac gacatcaaaa     1440
tgtcgcagtt tatggtgtcg aaaatgcaca acatcgcaca ggccatgaac ccgaaaatga     1500
tcatgggtgg gccaaagacc gccgtacgc attttgatac caccgtgtat cagaccactc     1560
atatgaatgg cggcgccatt atgggtgaag atccgaaaac cagtgcgatc aaccgctatc     1620
tgcagagttg ggatgtgtcg aatgtgtttg taccaggggc ttctgcgttc ccgcaggggt     1680
tgggttataa cccgaccggg atggtcgctg cactgaccta ttggtcagca aaaaccatcc     1740
gggaagttta cctgaaaaat ccgggtccgt tggtacaggc a                         1781
```

<210> SEQ ID NO 65
<211> LENGTH: 1758
<212> TYPE: DNA
<213> ORGANISM: Pantoea citrea

<400> SEQUENCE: 65

```
atgacaaaaa aactccctgc cactgatgtg gtgattgttg gcctcggctg ggccggttca       60
attttagcca aagaactctg cgatcagggt ctgaatgtga ttggtctgga acgtggcccg      120
tggcgcgata ctgccaaaga ttttaacgta gccaccgcgc cggatgaatt gcgttacaac      180
gcccgcgagg aactgatgct ccggccggca cagaacacct gtaccatgcg taataaccct      240
tcagaaactg cactgccaat gcggttctgg ggctcttttcc acccgggtaa cggtaccggt      300
ggcgccggta accactgggc gggtattact ttccgctatc agcctgccga tttccggctg      360
gcgagccatc tgcgtgagcg ctacggcaaa gaagttgatc cggctctgac cttacaggac      420
tggggggatca cctgggaaga gatggaaccc ttttatgact cttttgaacg ggttgccgga      480
atttcaggga aagccggtaa catcaaaggc agtattatcg aaggcggaaa cccgttcgaa      540
ggtccgcgcg cccgtgatta tccaaatccg ccaaatattc agaccattgc gcaaacattc      600
tttgccaaaa ctgccaccga aatgggttac aaaccttttta acgttccttc tgcactggcc      660
tctcagggtt ataccaacca gtatggtgtg acgatgggcc cttgtaccta ttgtggtttc      720
tgtaccaact acgctgcgc caactattcg aaagccagtg ctatcgttaa cgttttaccg      780
gcagtagtca gcatgcccaa cttttgaagca cgcaccaact gtgaagtcat ggaagttctg      840
aaagacagca gcggcaaaaa ggctaccgga gtggtgtata tcgacagtaa tggcgaacgt      900
tatgaacagc cagcgtctat cgtgattgtg gccgccttta cttttgaaaa cgtgcgtctg      960
atgctgctgt cgaatgttgg tgtgccttat gaccctgtca ccggcaaagg aactaccggc     1020
cgtaactact gttaccagac agcgaatggt gtccgtctgt tcttcaaaga tcaaatcttc     1080
aacccgtttta tcgcggtgg cgccatcggg atgggaatcg acgaattcaa caacgacaac     1140
tttgatcact ccggattagg gtttgttggc ggtggttcta cccgggtgac acctatcggt     1200
```

-continued

| | |
|---|---|
| gctgcaccta ttgcttcgcg tccggtgccg ccgggcactc cgcgctgggg atcggcctgg | 1260 |
| aagaaagcaa ccgtggaaca ttatctgacc aatatgagta ttggttgcga ggccagcagc | 1320 |
| tatccgcagc gcaccaacta tctgtcgctc gatccaaact ataccgaccc gcatggccgg | 1380 |
| ccgttattac ggataacgtt tgatttcccg gacaatgata tgcggatggc acagtatgtc | 1440 |
| accaataaag ttggtgaaat tgccttacgt atgaatccgg tgcaaatcca gaaacaacca | 1500 |
| cgtactgccc cgtgggccaa caacgactac cagtcatctc acgtggttgg cggctttgtg | 1560 |
| atgggcgctg acccgtctac cagtgcggtc aataagtttt gccaggtctg ggatattcca | 1620 |
| aatctgttcg tggtgggtgg ttctgcggtt ccaaataacc ccgggtataa cccgaccggt | 1680 |
| actgttggcg cccttgcctt ccgtaccgct cactatatcc gtactcagta cctcaaacag | 1740 |
| cccggggaga tgatggta | 1758 |

<210> SEQ ID NO 66
<211> LENGTH: 1770
<212> TYPE: DNA
<213> ORGANISM: Pantoea citrea

<400> SEQUENCE: 66

| | |
|---|---|
| atgagcaaaa tcaggccaaa ggccgacgca gtgattgtgg gcctgggatg ggcaggatcg | 60 |
| ttaatggcaa atgaactgac ccaggccggg ttaaatgttg ttgccattga aggggggtca | 120 |
| tggcgtgaca ccagtaccga tttcccaacc tcaattgata ctgacgaatt acgtttcgtc | 180 |
| agccgcagag caataatgca gcccactgct gtagaaacta tgaccttcag gaataatcct | 240 |
| ctgcagcagg ctcttccact gcgtgagttt aatacctatc agtttggtat gaatgtcggc | 300 |
| ggtgccggta cacactggaa cgccatgaca tggcgctttt tacctaatga cttccagaca | 360 |
| tacaccaata ctgttgaacg ttacggtaaa acaaattcc tggaagggat gcaggttcag | 420 |
| gactggggcg tgacctatga tgaccttgaa ccttttatg ataaatttga gcgctttgca | 480 |
| ggaacttcag gaaaagccgg aaatattaaa ggcgaaaaaa tcgacggcgg aaatgtattt | 540 |
| gaaggaccgc gcagcaggga ctatccgttc ccaccactga acgcactca gttatcgatg | 600 |
| atatttgaca aagcgacccg cgaaatgggg ctacacccgt tgcggtacc tgccggaaat | 660 |
| acttcagggg cttataccaa tactctgggc attaatatgg cccttgtac ttattgtggg | 720 |
| ttctgtgaat ttttcggttg tggtaactgg tcgaaaagta gtccgaacgc ctgtattttg | 780 |
| ccagcagtga tgcaacgcag taatttctca gtgatcaccg agtcggaagt gttacgggtg | 840 |
| aataaagcgg cagacggcaa gaccgccacc ggtgtcactt ttatcggaag cgatggtgtt | 900 |
| gagtgggaac aacctgccga tatcgtgatc atttctgcct accagtttga taatgtccgt | 960 |
| ctgatgttac tgtcaggaat tggcgagcct tataactata aaaccggcac tggtgtggtt | 1020 |
| ggccgtaatt acgcttatca gactatctct ggtgcaggtg tattctttga aaatgaaaat | 1080 |
| ctgaatccat ttattggtgc tggtgcactg gctcaggcag tggatgatta caacagcgat | 1140 |
| aacttcgatc actcaaacct ggactttatc ggaggcggtg tggccctggt tcactccagc | 1200 |
| aatggtcgcc cgattgcatt atccggtgcg gtgcctccgg aacaccaaa atggggttct | 1260 |
| aaatggaagc aggctgctca gcagagttac cagaattaca actccgtcta tgtgatgggc | 1320 |
| aacagctatc cacatcgtga tgtttttcctc gatctcgacc ccgaatataa agaccgccac | 1380 |
| ggacaaccgc tgctccgggt taccttcgac tggatcgaaa atgataagcg ctcaggccac | 1440 |
| tttatggccg atcgctcggt agaaaattgg catgcgatgg gagcaaaaac cgtagtacgt | 1500 |
| caggaaccta cggcccgtaa tttctcgcca atggacaatc tttcttcgca taccaccgga | 1560 |

-continued

```
ggcgcctgca tgggagatga tcctaagacc agtgcggtta accgttacct ccaaagctgg    1620
gatgtgcata acgttttgt ctgtggtgcc tctgctttcg cgaataatgg cggttacaac     1680
ccaaccggta ccgtaggcgc gttaacttta tgggctgctg aagccatcaa aaatcagtac    1740
ctcaaatctc ccggcccgct ggtgaggatc                                     1770
```

<210> SEQ ID NO 67
<211> LENGTH: 1770
<212> TYPE: DNA
<213> ORGANISM: Pantoea citrea

<400> SEQUENCE: 67

```
atgaataata ttcgtccaaa agctgatgtt gttattgtcg gtctgggatg gtgcggctct    60
ttaattgctg aagaactcac ccgggccgga atgaatgtgg tggctataga acgtggaccc    120
tggtgggaaa ccagcaccga cttcccgcca tccattgata ctgatgagct gcgctgggac    180
acccgtcgtt ccatgttgtt accccgcgg gtcgaaacga caactttccg gaataatact    240
tcacagcaag ccttaccttc ccgtgactgg aacctgaatg aacttggcta taacgtcggt    300
ggatccggta ctcactgggc gggaatggcg tggcgtttta cgccgtttga tttccagccc    360
tattcgcaaa ccgtggcgcg ttacggtaag cagcagattg ttccggggct gattctgcag    420
gactgggggg tgagttatga tgaactggag cctttctatg atcggtttga gaaaatagcc    480
ggagtttccg gaaaggccgg taagtcaaat ggcaacgtgg tgccggaagg taatccgttt    540
gagggtaacc ggagcagtga gtatccactg ccgccgctgg aaagtacccg gctaaccgat    600
ctgtttgagc aggggcaaa atctctcggg ctcaatccgt ttatggttcc tgccggtcag    660
gcttcccgtg cctatgttaa cccgttaggg gttcgcatgg ggccgtgcac ctattgtggt    720
tattgtttgt actatggctg cgggaacttc tctaaatcca gccgaatgc ctgtgttatt    780 cccgcactga tgcagcgcga aaactttact gtgcttactg attctgccgt tgtgaaggtt    840
aataaggcag aggacggtaa gacggctacc ggtgtgacgt ttattgataa aaacaataag    900
cagtgggagc aaccggcaga cattgtcatc ctgtccgcat tccagatgca gaatgtgcgg    960
ttgctgttgc tgtctcagat tggtcagcct tataacccgc agacaaagca aggggtggta    1020
gggcgggctt acagcttcca gactgtctca ggagccagcc tgttcttcaa agatgagtac    1080
ctgaatcagt acatcggtgc cggagcgctt tcacagcagg ttgatgactt taacggtgat    1140
aattttgacc ataccggtaa agggtttatc ggcggtgccg ggattctggt cgttgcccgt    1200
ggagccaggc caataggtaa tgccgatact ctgccaccgg gaactcctcg ctggggaaa    1260 gaatggaagc aggcatatac ccatgccttc cagaatgcga cctttatctt tggtcagggc    1320
accagttatt cccatgaaga ttattatctg gacctggatc cggaatacaa agataagtac    1380
ggattgccgt tacttcgggt gacgtttgac tacaacgata tgaccggcg ttcggccaaa    1440 tttgtcgaac agcgcagtgt ggaaatcggt aaagcgatgg gagctgagcg ggttttggc    1500 actaactccg cttccggcca ttactcaccg tacaatttcg ccagcgatca cactatcggc    1560
ggagccgtca tggaaccgga tccccggacc agtgtgttaa atcgctacca gcagagctgg    1620
gatgtgcaca atgtgttcgt gctgggtgct tcttcttcc cgaataatgc cggatataac    1680
ccgacaggca ccatcggtgc tcttagctta tggactgcga aagcgattat tgagcagtac    1740
agaaagaatc ctggcccgct ggtgaaggtg                                     1770
```

<210> SEQ ID NO 68
<211> LENGTH: 1770
<212> TYPE: DNA

<213> ORGANISM: Pantoea citrea

<400> SEQUENCE: 68

```
atgaattaca ccagacctaa agcagatgcc gttattatcg gcctcggctg ggccggctct    60
ttgatggccg aagaactgac ccgcgccgga ttaaatgtgg ttgcgattga acgcggcccc   120
tgggaacaga cccagagcaa tttctccccc gccattgctg ccgatgaact acgttatggc   180
gtacgccgcg aaatactgaa accgccccgt gtagaaaccc tgacttttcg taacgacagc   240
agccagaaag cactgccagc ccgcgactgg aatgcctttc agatgggcta cagtgtaggt   300
ggtgccggta acactgggc agccaatgcc tggcgtttta acccttctga tttcgagatg   360
gcgacccgtc acaaagagcg ctataacaat atgccgctgg ccgacggcct gatccttcag   420
gactggggg ttagctatgc agagctggaa cctttctatg atcgtgtgga aaaaattgcc   480
ggtatttccg gtaaagcagg tgtgcttaac ggctccactc aggaaggcgg aaatccgttt   540
gaaggcaacc gtaccagtga gtacccgaca ccgccattaa tccgttcgca ctggaacgat   600
accttccata atatcaccac taaaatgggc taccaccgt tccctattcc ggcaggaacc   660
atcggtgcag cgtttaccaa cccgttaggc attaacctgg cccttgtac ctattgcggc   720
tattgcggtt tttacggatg tggtaactgg tctaaatctt caccgaatat ctgtgtggtt   780
ccggcactga tggatcgcac caactttacc ctgctgaccg aatgtaccgc gctgtacatt   840
aataaagctg acgatgaaaa aaccgtcacc ggtgtgacct tccgtgattc tgatggtaac   900
accggcttcc agccggcaga catcgtttgc ctgtcggcgt atcagttaga caacgtgcgc   960
ctgctgttac tgtcgaaaat cggtaaagcc tacgaccacg ccacaggcga aggtacactc  1020
ggtcgcgcct ataactacca gaccatgtcg atgggatatc tgtattacga aaatgaatac  1080
atgaacccgt tcatctctac cggcgcgtta tccacccaga ttgatgattt caatggcgat  1140
aacttcgacc acaccgggct tggattcctg ggaggtgccg gaattcaggc gctgtcagat  1200
caggggactc cgttaagtat gactgaccgc ctgcctgccg gcagcaaaat gtggggctcg  1260
gcgtggaaaa aagcgttccg ccacagttat cagaactatg ccaaaattca gggccaggga  1320
acctcgtatt cacaccgtga ttcctatctg tcactggacc cgaattacac tgacgagaac  1380
ggacagcctc tgctgcgtct gaccttcgac tacaaccaga atgatcgtct gatggcgcgt  1440
tttattcgtg accggattga agatatctgt aaagtctccg cgccagcag ctggataacc  1500
gaagcgttcc ctgactccca caactcaccg ttccgtgcct atgacagttc tcataccatt  1560
ggcggtgccg tgatggggct tgatccgaaa acctcggtac tgaatcgcta ccagcaacac  1620
tgggatgcac acaatctgtt tgtgctcggg gcctcatctt acccgaataa tggcggttat  1680
aacccgacca tcactctcag tgccctgacg ttatggactg cgcaccatat cgttaatgac  1740
tacctgaaaa atccgggttc gctggtacga                                    1770
```

<210> SEQ ID NO 69
<211> LENGTH: 1638
<212> TYPE: DNA
<213> ORGANISM: Pantoea citrea

<400> SEQUENCE: 69

```
atgagtcaga ataacgtaga tgcagaagta attattattg gttccggagt gatgggcggg    60
ctactggcga ctcagctgtc tgctgccgga aaatcagtga ttattgttga ggcgggccca   120
cgtgttacac gccagcaaat cgttgaccgt ttcagaaact caccgttcaa gatgtcactc   180
actaatatga aattgcaggg tgtcggctcg ccgtatcctg atttacctca tgtaccttcc   240
```

```
acttacggca actacctgca acaggtcggg ccggtaaaat acccgactaa atacctgcgt      300
gtcgttggcg gaaccacatg gcactttggt tccgctttgt ggcggatgat tccaaacgat      360
tttaaattga agacgttgta cggacatggc agagactggc cgtttggtta cgacgaactg      420
gaaccctggt attgcgaagc agagcatgca ctgggagtgt caggagtcga tggacaggac      480
gagagcgggc acggtggtaa accctggcct ccacgctcta aacctttccc gatgccgggc      540
ttacctacca gttatatgtt tgaccggctg agcgagttgc ttggtaaagg cggttataac      600
ccggtgctgg aaccaaatgg cagggcgacc cgcccctggg gcaatcgtcc ggtatgtgca      660
ggcaataata actgcaaccc ggtgtgcccg attggtgcca aatatgatgg ttcaatgcat      720
atcgatcagg cagaacggct gggtgctaag ctgctggaca attcggtggt gtataaaata      780
gaagcggatg acaacggtaa aatcacccgt atctggtata aaaagcctga tggttctgag      840
cattccctga cagcaaatct gtttattgtg gctgcctatg ggattgaatc accgaaatta      900
ttgctgatgt ctacctcaga aaaatatccg aatggtattg ccaactcttc tgatcaggtc      960
ggccgtaatc tgatgggtca caccggcatt agtatgaact ttatgatggc cgaggatgtc     1020
tggccggggc agggaccaac agaattactg gtctatctaa acaaccgtga tggtgagttc     1080
agaaaaacgt tcccgagcta taaaatcaaa gtgcgtaata ccgtgccaac cgctgattat     1140
gcttccgggc tgattagtaa agggtatta ggttcagaac tggatgagca actgcgtaag     1200
ctgtcagccc gttcgctgaa cttcgccatt gattttgaga cagtgccatt gccggaaaac     1260
cgggtcgttc ccagtaaaac caaaactgat gcaattggaa ttccgctacc ggaaatatcg     1320
tacagcgtga ccgattactg gcaggcaggg aaagaagcag ggctgaaaga ttttgcgaat     1380
tttgcaaaat tactgggggg cgatgtgctg aaaatcgaca ccaattatca ggatcgccag     1440
catattatgg gaaccaccat catgggcgat gacccgaaaa attcggtggt gaattctgat     1500
tgccggaccc atgatcaccc gaacctgtac attgccggaa ccagcgtgat gccttcggca     1560
tcctgtatga atccaactct caccgggggct gcgttaagtt tgcggctggc aaatcatctg     1620
ttgaaaaacg tactggtt                                                   1638
```

<210> SEQ ID NO 70
<211> LENGTH: 1620
<212> TYPE: DNA
<213> ORGANISM: Pantoea citrea
<400> SEQUENCE: 70

```
atggctaata ctactttaga tttcgactac gttatcgtcg gctcaggcgt taccggagca       60
ctgattgcct ggcaattgtc ccgtcatggt aaacgggttt gtatgattga ggccggcgat      120
cacattcaac gctggaaagc gatagagcat taccgcagtt tgccggataa aagcatcgcc      180
aataattcac cctaccctaa tctggagtgg gcacccaatc ccattggcgg gcattatctg      240
gaacaaaagg gcccggtaaa ttatgcgacg acttatatca gaatggtggg gggaactacc      300
tggcactggg actctgcgac ctggagactg ttaccgtcag attttgaact aaaacccgc       360 tatggcgtag gccgcgactg gccgattggt tacgaagtgc tggaaccctg gtatcagaaa      420
gctgaagagc aactgggggt caatggctgg gatactgaag atcagagtgg ccagggcaaa      480
gatcattacc ctccacgttc acaacccctat cctactccgg ccacccgtt cagttgggga      540 caacaggttg ttgccggtaa acttgaggcg gcgggttact ctgccattca tgaacccaat      600
gccaggcttt ctgtggctac cgccgaacgt ccggcctgtg ccggaaataa tacctgtgac      660
cctatttgcc ccatcggcgc taaatatacc gctgactttc atgtgcaaaa agcgctcgac      720
```

```
catggctgta cattgctttc taactcggtg gtttaccgtg tcgaggccgg agatgatggt    780
aaaattaccg ctgtgcattt ccgtcggccg gataagtcaa cgggaacagt tagcgggaaa    840 gttttgtga ttgctgctaa tgcaattgag acgcctaaat tgctgctgat gtccgtatcg    900
gagcgctatc ctcagggtat tgctaataca tcaggtcagg tcgggcgaaa tctgatggat    960
cacaccggac tgggctttaa tctggtgacc gaagatgaag tctggccagg taccgggcct   1020
aatgccttgc tggtgatgct caatgcccgt gaagggaaat tcagagccga aagagcgtct   1080
tataaaacta aatttcgtaa taccgccgtc aattttgccg tcactaagtc cctgattaaa   1140
cagggaatca tgggtaatga gctctaccgg caaattaaat atcagtctgc ccgtcagtta   1200
tctattgccg tcgatctgga aactttgcct aacccgcaga atcgtattgt cccaagtaaa   1260
gatcggactg acagcctggg gatccctgtc ccggaaatcc actacgatgt ggatgattac   1320
tggaataaag ggcgcgatgc tgctatcgct gacgtacaaa atatcgcaaa aattctgaac   1380
gcaaagattg tggcaacgga taccaataaa caaaaccgcg aacatatttt gggaaccatg   1440
attatgggta actcacccac tgattcggtg gtggataaaa attgccggac tcacgatcat   1500
cccaatttat atatcgccgg gaccagtgtc tttccggccg tcggctgtgt taatccgacc   1560
ctgacaggtg cagcattagc tttacgcatt gccgacacgt tgttacagga tccagtgact   1620
```

<210> SEQ ID NO 71
<211> LENGTH: 1602
<212> TYPE: DNA
<213> ORGANISM: Pantoea citrea

<400> SEQUENCE: 71

```
atgaaaacca cacattctgc caccgttgtt atcatcggtt caggcatcgc aggctcacag     60
atagcccaaa aattacaaaa agctggcatt gatactctga tgctggaagc aggttcacgg    120
attgagcgct ggaaaattgt agaaaactac cgtaattcgc catttaaaac tgattttcag    180
tcaccgtatc caccgacccg tcatgcgcca cacccgcaat actcgccgga agataacggc    240
tactttattc agtatggtcc ggagccttat aaagcgggct acctgcgtgt cgctggtgga    300
accacctggc actggtctgc tcaggcctgg cgtttactgc caaatgatat gcgtctgaaa    360
acactgtatg gcgtcgggcg tgactggccg atcagttatg acgatctgga accgtattac    420
tatgaatctg aagttgaaat gggtgttggc ggcccggaag acaccggttc accacggagt    480
aaaccttatc cacatccgcc gttgccttg tctgattttg acaaggcctt caaaaatgtg    540
gtggataaaa acggctatca cctgattacc gaaccggcag cccgtaatac tgaaccgttt    600
gacggtcgcc cggcctgctg tggcaacagt aactgcatgc ctatttgtcc tattgaagcg    660
cagtacaccg gtgaaaccgc ggttcgtaaa gctgaacgtg ccggatctct gctggttccg    720
gatgccgtgg tctataaaat agagcacgat gccaaaggca atatcacttc tgttctgtat    780
aaagatccaa acggggaaag tttccgtgtc acagggaaaa tcttcgtact ggcggctaat    840
gccatcgaaa ctccgaagct gatgctgatt tcccgatctg acaaatatcc aaatggtatt    900
ggcaacacga ctgataacgt tggccgtcac ctgatggatc atcctggaac ttcagtttac    960
ttcctgagta agaaccgat gtggccgggc cgtgggccta tgcgtttaag ttgcattaac   1020 aactgcgcg atggtgattt ccgttcagaa cattcggcga tgaaaatcaa cctgggcaac   1080
tattctccaa cgctggcggt gagtaattac ctgctgagta aaggggtttc cggcaaagat   1140
ctgccggcga tggtgcgtga ttatgcgtca cgctgggtag cagtgaatac cttcttcgat   1200
atcctgcctg acagagataa ccggattgtg gcggtagact cgcaaaaaga tgcaatgggt   1260
```

| | |
|---|---:|
| attcctaaac caggcgtgca ttaccacatc aacgattaca ttaataaagc gcgtgatgtc | 1320 |
| gcccaccagc acttcgacca tattgccggt ctgtttggcg gtacggaagt gcgtcatgat | 1380 |
| gataagtact tcaacaataa ccacatcatg ggcaccctaa ttatgggtaa tgatcccaac | 1440 |
| gactccgtgg tggatgctga tttacgtacc cacgatcacc agaatctgtt tgtggcgtcc | 1500 |
| agtggtgtta tggccagtgc cggaaccgtt aactgcaccc tgacattatc agcgctggcg | 1560 |
| atgagactgg cagacaaatt aatcgcggag tgccaacatt ta | 1602 |

<210> SEQ ID NO 72
<211> LENGTH: 1590
<212> TYPE: DNA
<213> ORGANISM: Pantoea citrea

<400> SEQUENCE: 72

| | |
|---|---:|
| ttggctacag aatttgatgc agatgtgatt gtcgtagggt caggagcctg tggctctaac | 60 |
| ctggcaaacg aactggcggt aaaagggaaa tcggtgattc tgctggaagc aggtgccaat | 120 |
| gtgccgcgct ggaaaatcct cgaaaacttc cgtaattcag gccgccatta tgaccggaat | 180 |
| aatgcatacc caaataatcc gtggtctccg accagtaata cccccggcta tatagagaac | 240 |
| gttggtgaat tcgtgaaca gcctggcatg ctaaaactgg tgggtggcac cacatggcac | 300 |
| tggggtggcg ccacctggcg gtacattcca aatgatttta aactgaagac tatgtacggt | 360 |
| gtgggtcgcg actggccgat cagttacagc gatctggaac ccttctatac ccgtgccgaa | 420 |
| tatgctatcg gggttgccgg ctcagacaca gaagaccagt caggtcagaa cccggggatc | 480 |
| tcttttcctc cacgttccaa agcttaccct gtagatccgg aagctgatat ctacagtaac | 540 |
| gccaaactta agcagcact gttaccgcat ggccatagcg tagtacacga acccacagtg | 600 |
| cgtatccatc gcccttatga tggtcgtccg ggatgccagg ggaataataa ctgtgaccag | 660 |
| gtctgtccaa taggtaccctt gtataacggt tcagttcatg cagataaagc cgtgcgtaac | 720 |
| ggcgcaaaac tgattaccga tgcggtagta cacaaaatta ccaagggtga acaaggtaaa | 780 |
| atcacttctg tcagttacct gaccccctgct ggtgaagaac acacgctgac tgctaaaatat | 840 |
| tttgttctgg cggcacacag tttcgaaact tcaaagctga tgctgatgaa cgatatcggt | 900 |
| aactcctctg atatggtggg tcgtaatctg atggaccata ttggcctgag tatgaatttc | 960 |
| cttgccgatg aaccaatgtg ggcaggacgc ggcccggtgc agcaggcgac tattatgacc | 1020 |
| tggcgtgacg gtgattttcg ttccaaatat tcagccaaca agcactcttt agccaataac | 1080 |
| aacccacaaa tcgatatcgc ccaacgtgct attaacgagg gattgatggg taagagctg | 1140 |
| gatgctcgta tccttgactg gtcatcccgc tggatgtcga tctatagctt tctggaacca | 1200 |
| ttgcctaatc cggctaaccg tgtacagccg aacccggcct ggaaagacag ccttggttta | 1260 |
| cctggtatca aagtgacctt tgatgtcgat gactatacca aactgggtgc taagcacatg | 1320 |
| gtcgaacaat ataagcagat tgccgggctg atgaacggtc aaatcattga tttaaatact | 1380 |
| gcgttcgaaa accatgacca cctgatgggc accatgatta tgggtgataa tcctaaggac | 1440 |
| tccgtggtta accatgaatg ccgcagccac gaccatccga acctgtttat tgcatcagtt | 1500 |
| ggcgtaatcc ctgctgccgg tgtcgttaac ccgacactga ccggtgtggc tctggcaatc | 1560 |
| cgttctgctg acatcattgc aaaggaggtg | 1590 |

<210> SEQ ID NO 73
<211> LENGTH: 1599
<212> TYPE: DNA
<213> ORGANISM: Pantoea citrea

<400> SEQUENCE: 73

```
atgtctgatt cattaagcgc cgacgttgtt gttatcggag ccgggattgc cggttcactg    60
gcagcactaa aaatggctaa agcgggtgcc tctgtcttaa tccttgaatc cggtccggaa   120
attaagcgtg acgaagcggt gaactatttt cgcaactcgc catttaaagg cgattttacc   180
gaaccgtatc cgccggaacc ctgggcacct cagcctaaat ttattccgac tgataacaat   240
tatctgatcc agaaaggtcc ggacccttat cgtgcccagt atttacgtgg catcggtggt   300
accacctggc actgggccgg tcaggcgttt cgtctgctgc aaacgatat gaagatcaat    360
accctgtacg tgttggtcg tgactggcca atcagctatg aggacttaga gccttactac   420
agcgatgcgg aataccagat gggagtttcc ggtgatgatg atttaaattc gccgcgctca   480
cgtccttacc cgttaccagg cattccgtta ccttacggtt ttgagcgcct gaaacagcgc   540
cttagcccgc ttggctatca ggtgggtatc ggtccgcagg cacgtaacag tattccttat   600
cagggacgcc cggcctgctg tggtaataac aactgtatgc ctgtttgtcc tatcgatgct   660
cagtaccacg gcgggatctc tgcccgcaaa gcagtggatg ccggggtaaa aattatcgcc   720
aatgccgtgg tttaccgcat cgaagcagat gatcatggcg tgatccaggc tgtacattat   780
ctggatcaaa acaaagcgac tcaccgcgtg accggtaaac agtttgttct gaccgcaaac   840
ggcgttgaaa gcccgaaaat tctgctgctg tcgacctcag atcgctatcc aaacggtatt   900
gctaacagct ccgggatggt aggacgtaac ctgatggacc acccgggcac ctccgtcgag   960
ttttatgctg acgagccaat ctggtttggt cgtggtccga tcgtccgggg cagtatcaac  1020
aacatgcgtg acggtagctg gcgtagcgag cgttccgcat tgcgtatcga cctggctaac  1080
acctcgccgg tgcgttatct gaccgagcgt ctggtacgtc agggttatta cggcaaagcg  1140
ctgaacgaca aactggcctt ccaggccgag cgttttgtac agctgaaatg cctgctggaa  1200
atgctgccgg atccggaaaa ccgcttagtc ctcagcaaaa ctgagaaaga tgcctggggt  1260
atcccgcgtc ttgaggtgta ttacaaattc cctgaatacg tgcatgccgg ttatgaccag  1320
tctatgtctg acttccggaa aattgttcag cagatgggtg gaaccgagcc gctatatagc  1380
cagcgtggtg tctacgacaa caaccagcat atcaccggca ccatgattat gggcagcgat  1440
cctaagaact ccgtcgttga cggtaactgt cgtacccatg accatccgaa cctgtttatt  1500
gccggtaccg gaatcatgcc ttcggcgtca accgttaact ccactttaac ggggacggct  1560
ctggcgttgc gtatggccga ctatgtgctg aaaagcctg                         1599
```

<210> SEQ ID NO 74
<211> LENGTH: 1629
<212> TYPE: DNA
<213> ORGANISM: Pantoea citrea

<400> SEQUENCE: 74

```
atgtctgaac aatatagcgc agatgtggta gttgttggtg gcggtatttg tggtggaacc    60
gtggcaaaag agctggcaga agctggttta tccgtactgg tactggatgc aggccctcgc   120
tgggaaagag gggaagtggt agagaactgg cgaaatctgc cgccagtgaa taaatctgaa   180
tctgattacg caacgccata tccggcggaa ccgtgggcag ttcatccgca gctctatcca   240
tataataatt atccggaagt ttccggtccg atgcttctg catttcgtca gggtatgatc    300
aaaggcgtcg gcgggacaac ctggcactgg gcagcttcct gctggcgttt cctgcctgca   360
gatatgcagc tccagaccac ttatggtgtg ggcgtgact gggtggtgac ttatgacgaa    420
atggaagatt attactatcg tgccgaggtg ctgattggtg ttaatggccc taacgacaca   480
```

| | |
|---|---|
| tcactgaagt acgttgctcc acgtaaaaag ccattcccga tggagccaat gccatacggt | 540 |
| ccggccgatc gtcggtttac cgaagtcgtg gcaactgccg gttatgaaaa cacccggta | 600 |
| ccccagggac gtaacagccg gccatatgac gggcgtccgc agtgctgcgg taacaataac | 660 |
| tgtatgccta tctgtccaat cggcgccatg ttcaatggta ttcacagtat tattaaagcc | 720 |
| gaaaaagcag gtgctaaggt tctgccaaat gcggtggtct ataagtttga taccgacgaa | 780 |
| aacaacaaca ttacagcgtt gtactactac gatccggaca aaaactcgca ccgcgtaaca | 840 |
| gcacggactt ttgtgctggc aggtaacggt atcgaaacac cgaaactgct gctaatggcg | 900 |
| gctaatgacc gtaacccgaa tggtatcgcg aacagttcag gaatggtggg gcggaatatg | 960 |
| atggatcacc cgggtattct gatgagcttc cagtcagcag agcctatctg gaccggcggt | 1020 |
| ggttcggtac agatgagttc aatcactaac tatcgtgatg gtgatttccg tcgtgagcat | 1080 |
| tcggcaattc agatcgggat gaacaatact tctcagaacc ataaagccgg ggtgaaagcg | 1140 |
| ctgcaaatgg ggctggtagg taagaaactg gatgaggaga ttcgtcgccg ggccgcctgt | 1200 |
| ggaatggata tctatgttaa ccacgatatt ctggccaatc cggacaaccg tctgacactc | 1260 |
| agcaccgtgc ataaagataa actgggtatc ccatacccgc atgttaccta tgatgtgggt | 1320 |
| gattatgtgc gtaaggccgc ggtttcatcc cgtgagcatc tgatgactat tgccaaactg | 1380 |
| tttggcgcga ccgaaatcga atgactccg tattttaacc cgaacaacca cattatgggc | 1440 |
| gggactatcg ggggacatga tccgaaagat tcagtggtcg ataaatggat gcgaacccac | 1500 |
| gatcatcaga acctgtatat cgcttccggt ggtgtgatgg cagccgcagg gactgttaac | 1560 |
| tcaaccctga gtatggtggc gttatctttg cgcgctactg acagtatcaa acgcgatctg | 1620 |
| caacacggt | 1629 |

<210> SEQ ID NO 75
<211> LENGTH: 1623
<212> TYPE: DNA
<213> ORGANISM: Pantoea citrea

<400> SEQUENCE: 75

| | |
|---|---|
| atgaatgcag atgtgattgt ggttggcacc gggggttgtcg gttgcctgat tgctgaacag | 60 |
| ttactcgata gtggccactc cgttgtgatg ctggaagctg gcccgcgggt cgaacgttgg | 120 |
| cagattgtcg aaaactaccg aaatttacca ccggtttccc ggttacattt taatgcccct | 180 |
| tatccaccgg agccctgggc tcctcatctg atgtcggcca cgcctgagca ggccgctgaa | 240 |
| tatctgcaac tggaaggtcc taatgcccgg gcctatcagc agggatatgt tcgttatgcc | 300 |
| ggcggagcaa catggcactg ggctggaatt tgttggcggt taactccgga agatatgcag | 360 |
| ctaaaaacgc tctacggtgt tggccgtgac tgggcttttg attatgccac cctggaacct | 420 |
| tattcaccc gtgccgaata tgctcttggg gtctgtggac cttctgagcc ggaactgcaa | 480 |
| tggcccccgg ttcgttccaa accttatccg atgggccgtc tgccttcgg gccgggtgag | 540 |
| caacgcttta ccgacgcggc tgcctctatt ggcctgacaa atctgccttc agctcaggcg | 600 |
| cgtaatagcg gtattgctta cggggatcgt cctgcctgtt gcggtaataa taactgcatt | 660 |
| ccggtctgcc cgattggtgc gaagtacgat gcagcaactt cactgacacg tattgaatcc | 720 |
| aaaggcggca aaattcagcc aaatgcggtg gtctataaaa tagaaaccgg tgcggataat | 780 |
| aaagtccagg cagttcacta ttttgacaat aacaaacaga ctcaccgggt gaccgggtct | 840 |
| gtctttgtta ttgcctgtaa cggtattgaa actccgaaac tactactgat gtctgcggac | 900 |
| agcagaaacc cgcacggtgt agcaaacagc tcagatcagg tgggacgcaa tatgatggac | 960 |

-continued

```
caaccgaagc tggtagtaga acttgagctg gctgaacccg cctggaccgg cgttggaccg      1020
gtgcagggaa gcagtattat ggaaacctct cagggcagtt tccgttctga atattgcggg      1080
gcgttgttcc gtttcaacaa tatggctcgc agccggattg gtgctatggc ggcgctggaa      1140
aaaggtctgg tgggtaaagc actggatact gaaattcgtc gtctgtcagc ctgtaccacc      1200
gaaattgcta ttgaacatga gctgatgccg gatgccaata accgcttaac tttatcggct      1260
aaaaaagact ggctgggatt acctaaaccc aacatttact acgatgtcgg tgactatgta      1320
cgccagggat cgcagcgcca ttctttacct atcgcccgcc aactggcaaa agcgatggga      1380
gcgaccaaag tagatatttc gaccgaatat accaacagtg accatattat gggcggctgc      1440
attatgggga ccgatcctgc agtctcggtg gtggatgtgg attgccgggc tcatgaccat      1500
gaaaacctgt ttttaccggg tggagctgcg atgactaccg gaggatgtgg taacagtacc      1560
ctgacaatgt ctgccttagc actgaaagcc gcagatgcca ttcatgcaca attagggaaa      1620
gca                                                                   1623
```

<210> SEQ ID NO 76
<211> LENGTH: 1602
<212> TYPE: DNA
<213> ORGANISM: Pantoea citrea

<400> SEQUENCE: 76

```
atgtctgaga ctatttctac tgacatcgtc gtgattggtt ccggcgttgt aggttcgtta       60
acagccagaa aactggcttt ggcaggacgt aaagttctga tgctggaagc aggtccgcgt      120
attcagcgtg accagattgt cagcaatttt cgccattcgg cacgtaaaga cgattttatc      180
gccccgtacc caaactctga atcgcacca tttcctgact ataagccgga agataacggc      240
tatttagacc agacagggcc taaagattac aagccggaat atttgcgtgt tgtcggtggc      300
accagctggc actgggcagc tcaggcctgg cgcctggttc gaatgatttt tcgactgaaa      360
tcacagtatg gcgtgggtcg tgactggccg atcagttatg aagatctgga accctattat      420
tatgaagccg agattttgtg gggtgttttc ggtcctgcag aaatggctaa atactcgccg      480
cgcaagcatc cctatccgat ggaagggtg aaaatgtctt atcttgaaca acgggtcacc      540
gcgcgactgg cacccaaata tgaagttctg accaacacca ccggtcgtaa ctccgttcct      600
tatgacggtc gtccacagtg ttgcggcaat aataactgta tgccaatctg cccgattgat      660
gcacagtatc acggcggtat tgctgctgct gccgctgaga ttgccggggt taaactgatc      720
cctcaggcag ttgtttataa gcttgaacat aacagtcacg gtaaaattac tgctctgcac      780
tactatgact ggaataaaca atcgcatcgt gtcgaagctg aaatcttcgt gatggcggct      840
aacgctgtcg aaaccccacg tattctgatg ctgtcagccg atgataaaaa cccgaatggg      900
ttatgcaata actatgatca gctgggacgt aatctgatgg atcacccgtc gaattccgca      960
actttctacg tagacgagcc tctctggcca ggtcgtggac cgatgagccc ttcatctatc     1020
cagcaattgc gtgatggtgc attccgttca gagtcagcgg ctttccgtat tgatatctct     1080
aactcctcac gggttgccgg tgttactgcc ggagcgatta agaaggcct gaccggagcc      1140 gatctggaca gcgctattct gtatcgcgcc tcacatgaac tgagcattaa aaacgttctg     1200
gagcagttac ctgatccgaa aaaccgcacc atgctgagca cccgtaaaaa agatgccctc     1260
ggtctgccgg ttcctgcgtt ctcgtactct tttgatgaat atatcgagaa aggcatgcag     1320
cactcgctgg aagtctatgc cgatatcgcc cgcatgctgg gtgccacgaa tgtccgttat     1380
tcgactccgg gtgtgtatag caacaaccaa cacatcaccg gaaccctggc aatgggcacc     1440
```

```
gatgaaaaaa cctcagtgac cgaccatgtg ggtaaagcct gggaatacga caacctgtat      1500
atggtgtcta ccggggtgat gccaacagtg gccactgcta actccacgct gaccgcctgt      1560
gctctgggct tacgcaccgc tgacgccatt cttggcaaaa tc                         1602

<210> SEQ ID NO 77
<211> LENGTH: 1659
<212> TYPE: DNA
<213> ORGANISM: Pantoea citrea

<400> SEQUENCE: 77
atgatgatga aaaaaccaga atttactccg ggtggcgatg cctccgcgga tattgttatt        60
gtgggctccg gtattgttgg tggactgatt gcagacagac tggtcagtca gggatattcc      120
gtactgatac ttgaagcagg gttacgaatc agccgtgcac aggcagtaga aaactggcgt      180
aatatgccgt ttgctaaccg tgccggttca gattttcagg cttatatcc gcagtcacca       240 ctggcgcctg ccccgctcta ttttccgccg aacaactatg tcaatgtcac cggaccaagc      300
gccggcagct tccagcaagg ctatctgcga actgtcggag gcaccacctg gcactgggcg      360
gcttcctgct ggcgccacca tccaagtgac tttgtgatga aaagcaaata cggtgtcggc      420
cgcgactggc ctatctctta tgacgagatg gagccatggt attgtgaagc gaatatgaa       480 attggtgtgg ccgccccgag cgacccgtcc atgcagtcac cgagtgaacg tagccgtcct      540
tatccgatgg atatggtgcc atttgctcac ggtgatactt attttgccag cgtggttaac      600
ccgcatggtt ataacctggt gccaatcccg cagggtcgta gtaccgtcc gtgggaagga       660 cgcccggttt gctgcggtaa caataactgc cagcctatct gcccaatcgg tgcaatgtat      720
aacggtatcc accatataga gcgtgctgaa agcaaaggtg cggtggttct ggcagaatca      780
gtggtctaca agattgatac tgatgataat aaccgtgtta ctgcggtgca ctggctggac      840
aaccagggcg catcacacaa agcgaccggt aaagcgttcg cactggcctg taacgggatt      900
gaaaccccgc gtctgctatt acaagcagcc aataaggcta cccgaccgg gattgccaac       960 agctcagaca tggttggccg taacatgatg gaccactccg gcttccattg cagcttcctg     1020
accgaagagc ctgtgtggct gggtcgtggc ccggctcaga gtagctgtat ggtcggcccg     1080
cgtgacggtg ccttccgtag cgaatattcg gctaacaaaa tgatcctgaa taatatttca     1140
cgggttgttc cagccaccaa acaggctctg gctaaaggac tggtcggcaa agctctggac     1200
gaagagattc gttatcgttc tattcatggt gtcgatcttt ccatcagtct ggaaccgtta     1260
ccagacccgg aaaaccgtct gactctcagc aagactcgta agatccaca tggcctggcc      1320 tgtccggata ttcattacga cgtgggagat tatgtgcgta aggggcgac tgcggctcat      1380 gaacaactgc aacacatcgg ttctctgttt aatggtaaag agttcaatat cacgactgcc     1440
ctgaacgcca ataaccacat tatgggcgga accatcatgg gtaaaagcgc caaagatgcc     1500
gtggtcgatg gtaactgccg gacctttgac catgagaatt tatggttgcc tggcggcgga     1560
gccattcctt cagccagtgt ggtgaacagt actctgagca tggcagcact gggcctgaaa     1620
gctgcacacg atatttctct gcgcatgaag gagttcgca                             1659

<210> SEQ ID NO 78
<211> LENGTH: 1275
<212> TYPE: DNA
<213> ORGANISM: Pantoea citrea

<400> SEQUENCE: 78
atgaaaaaga tgacatttaa gcgcctgtta ctggcgaata ctgtagttct ggcctgcggg        60
```

-continued

```
ctggctggcg cggtacaggc ggccgatgca ccgaatcagg atcaactggt aaaacagggt    120
gaatatctgg cacggctggg agattgtatg gcttgccata cgacctccgg gcggcctgat    180
tattcgggcg gtctggcgat aaaatcggat ctcgggacta tttactccac caatatcacc    240
ccggacaaac agtacgggat aggtaattac accgagcaac agtttgccga tgcagtgcgc    300
aaaggggtgc gtccggatgg cagtttcctc tatccggcca tgccttatcc ggattatgcc    360
aaaaccagtg atgcggatat tcatgccctg tacagctact ttatgcacgg tgtgaccgcc    420
agcaacagtc agccgccgca gaccgacctc agcttcccgt tcagtcagcg ttggggcatg    480
cgtttctgga acatggtgtt tacctccgat aagccattcc agccgattgg cggagcttca    540
gagcaggtta accgtggggc ttatattgtt gagtctctgg gccactgtag cagctgccat    600
acgccgcgtg gtgtggcaat ggaagagaaa gcgctggaca gcagtgacag caacttcctt    660
tctggcggca acctcaatgg ctgggatgtc ccttcattac ggggtattgc ccgctggagc    720
ccggatgaga ttgtcgatta cctgcaaagc ggacgtaacg acaaggccgg tgtcgccggt    780
gagatgacct cggtcgtgaa aaattcgacc tcgcacatga ccgatgccga cctgcaggcg    840
attgccgcct atctgaaatt ccttggtggc aacccgccat gcaggcctta tgatcagcag    900
aaaaatcagg ccactaccgc taaactgacc gcggcggtgg atctgactga aggccagacg    960
ctctacctga caactgtgg tgcctgccat tttgttaacg ggctggatgc tgcacgggca   1020
ttcccacagt tggatcaggc atcggttgtt aatgccaaag atccgcaggg gctgatccat   1080
atcatcctgc agggtgcgca gttaccggca actgagaagt cgccatcaat gctgaaaatg   1140
cctggcttcg acaccgtttt atctgacgac caggtggcta aactggcaac cttcgtacga   1200
cagggctgga gtaacgatgc atcggcagtg actgctgatc aggtgaaaaa agttcgtgag   1260
gggctggagc agcac                                                     1275
```

<210> SEQ ID NO 79
<211> LENGTH: 1308
<212> TYPE: DNA
<213> ORGANISM: Pantoea citrea

<400> SEQUENCE: 79

```
atgaaaacaa tttttgtgaa acttctgcct cttgccataa tgtcagttat tggcgttatc     60
gggctgaagc aggcttatgc tgacagcaat gatagtgcag acctgataaa acaaggtgca    120
tacctggctc gcgccggaga ctgtacagcc tgccatactg aagctggcgg caaaccctttt   180 gccggtggtc tggctatcag gagtccgatg ggagtcattt actcaactaa tatcactccg    240
gataaaaatg ccggaatcgg cagttacacc gaacaacagt ttgcagaggc ggttcgtaaa    300
ggagtccgtc gggatggcag taatctgtac ccggcaatgc cttatcctga ctatagcggt    360
attaccgata aagacattca tgccctgtat gtgtacttta tgcacggtgt agccccggtg    420
agtgtaaaag caccacaaac ctccctgact ttccgttca gcctgcggtg gggaatgaaa     480
ttctggaata ttgccttcgc gtccggaaac agctatccac cagctccaac aactcagtca    540
gacagtgctg atgctcaggc attaagccgg ggcagatatc tggtcgatac tttaggtcac    600
tgtagcagtt gtcatactcc acgaggtatc gggatgcagg aaaaagcgtt gaacgacagt    660
gatagtcgct ttctgtctag cggcatgctt aatgactgga cagtgccttc gttgagaaat    720
cctgacggat ggtctgtgaa tgatattgca gaatacctgt ctacagggcg caatgacttc    780
gccagtgtcg gtggtgaaat gacgggcgtg gtgcaacaca gcatgcaaca tatgaaccag    840
gccgatttac atgccattgc tctgtacctt aaatcattac ctgccagtac taaacagcag    900
```

| | |
|---|---:|
| cataatgtga aacccgatct gcagaatgac actcagaaaa cggtggatac tctgacgctc | 960 |
| ggcaaaaatc tcaactctgg tcagatgctt tacctgaaca actgtgaagc atgtcacctg | 1020 |
| accgatggcg gaggagctaa aaagatttc ccacgtctga atggggccag tatagtgctt | 1080 |
| gctgataacc cgacagggct gatatcggtg atgcttaaag gtgcgcagac cccttctacg | 1140 |
| gcaaatgcac cgtcagtaca gtttatgccc ggatttgagc aacggctcaa tgatcagcaa | 1200 |
| attgctgagc tcgccagttt tgtccgcagc ggctggggaa ataatgcgcc accagtatca | 1260 |
| gcagcagatg tggctaaggt ccgtgccagt cttaatacca gtcagaaa | 1308 |

<210> SEQ ID NO 80
<211> LENGTH: 1320
<212> TYPE: DNA
<213> ORGANISM: Pantoea citrea

<400> SEQUENCE: 80

| | |
|---|---:|
| atgaaaaaaa taacattatt gtactcagcc gtgctggcgg tctgctggg ctgtaccgtg | 60 |
| gcacaggctg atgacagtgg cggacaactg gtcgcccggg gagaatatct ggcgactgcg | 120 |
| ggagattgtg tggcctgcca taccgccagc ggtccggctt ttaccggagg gttgaaaatg | 180 |
| accactccgg tcggcgctat ctattcgacc aatattaccc cggataaaca gaccggaatt | 240 |
| ggtgattaca cctatgatga cttgcccgc gcattacgcc agggtattgc ccgcgatggc | 300 |
| cgtcatctgt atccggcaat gccttatacg gaatatgcga aggtcaatga tgacgatatg | 360 |
| catgccctgt atgcatactt tatgcatggt gttaccgcgg tacatcagcc aaataaaccg | 420 |
| tcagatattc cctggccgtt aaatatgcgc tggccactgg cggtctggaa taagttgttc | 480 |
| ctcgacaata ctccgttcaa aaacgacccg gcacaaagtg ctgagtggaa ccgtggggct | 540 |
| tacctggtcc aggggcttga gcactgtggt gcctgtcata caccgcgtgg tattgcattt | 600 |
| caggaaaagg cttcagatga aagggagct gacttcttaa ccggtggaac actggaaggc | 660 |
| tggcatgcgc cggatctgac cggaaatgta aaatccggat tagggcgctg gagcaccggg | 720 |
| gatttgcaga cgttcctgaa aaccgggcgc aatgaccaga gcgcggcatt tggttcgatg | 780 |
| agtgaagcca tcgggcacag tacccagcac ctgaccgatg cggatttaca tgctatggcg | 840 |
| gtctatatta aatcgctaaa atcttctgat ccagaggcac agcctccggc gaccaccgac | 900 |
| agcactacgg cggcgttaat cagaggagat ctgagccaga ccggtgcgga agaatatatg | 960 |
| gataactgtg cagcctgcca ccgtctggat ggcaaagggt atgccaaaac cttcccgaca | 1020 |
| ctggccggta acccggtatt actgagtgat gatccttcct cactgattag cattgtcctg | 1080 |
| acaggcggaa agatgccggt gactcagcaa tcggtgaccg gactgaccat gcctgatttc | 1140 |
| ggctggcggc tcagtgacca gcaggtcgct gatgtggtca gctttatccg cagcagttgg | 1200 |
| ggtaataatg ccggtaaagt agaggctaag caggtagcag acattcgcaa gctaatgccg | 1260 |
| gtaccgaatc aggcagataa tccgcaggta aaggccgaaa agccggatcc cgctaagaaa | 1320 |

<210> SEQ ID NO 81
<211> LENGTH: 1347
<212> TYPE: DNA
<213> ORGANISM: Pantoea citrea

<400> SEQUENCE: 81

| | |
|---|---:|
| atgaaagcta ttaaaggaat catcgttgtg atactggtgt tggtcattat ccttctggcc | 60 |
| tacgctctgt ggccgaccaa aacagcatcg cttcgccgt tacctgcgga taactcccct | 120 |
| cagttggcct cactggtcag ccagggtcag tatcttgcga ctgccggtga ctgtgcggcc | 180 |

-continued

| | |
|---|---|
| tgccatactc agccgggcgg taaaccgttg gccgggggac tgccgattcg cagcccgatt | 240 |
| ggggttattt acaccactaa tatcactccg gataaacaga cggggatagg taattactct | 300 |
| ctggatgatt ttgaacgcgc agtacgccac ggcattttgc caaatggcga caccttgtat | 360 |
| ccggccatgc cttatccgtc ctatgcaaaa atcagcgatg atgatgtacg ggccttgtat | 420 |
| gcctggttta tgcatggggt ccaaccggtc agccagcaga accgtgccag cgacatcccg | 480 |
| tggccactct cgatgcgcct gccactggcg gtgtggcgca agatgttttgc gccggatccg | 540 |
| gctaacaccg gttttacagc agataaatac cagagcgcca gcctggctcg cggcgcttat | 600 |
| ctggttcagg gccttggcca ttgcggtacc tgccatactc ctcgcgccgg caccttgcag | 660 |
| gaaaaagcgc tggatgattc cggacagcag tatcttgcgg gtggtcaggt gattgacggc | 720 |
| tggctggcgg taaatctgcg cggtgataaa gccgacggtc tgggtaactg gacagaacag | 780 |
| gatattatcg acaccctgcg caccgggcat aacgtcagcc atactgtggt ggggcagcca | 840 |
| atggcagagg ttgtggctaa aagcaccagt catatgagtg atgccgattt ggcggccatt | 900 |
| gccgcatata tcaaatcact gcctgcaggc cagggttcaa aagcatcgta cacggaatca | 960 |
| tcacaaacag cagacatgct ggcccgtggt gaaaaccta ccccgggtgc gcagttgtat | 1020 |
| gtagataact gttctgcctg tcatcagacc agcggtaaag gtgttcagca tatcttccct | 1080 |
| gcgatggccg ataaccccgac aatactggcc gacaatccgg tgtcggtgat tcatctgatt | 1140 |
| cttgacggta gccgcctgcc agccacacct cagtccccgt cagcactggc aatgcctggc | 1200 |
| ttcggctggc gtttgtcaga taaacaggtc gccgatttaa gtaacttttat tcgcaacagt | 1260 |
| tggggtaata aagcgacaga agtgaccgaa cagcaggtga acaggtccg ggcagattat | 1320 |
| ccgccgaaag gcgagaataa ggatccg | 1347 |

<210> SEQ ID NO 82
<211> LENGTH: 1320
<212> TYPE: DNA
<213> ORGANISM: Pantoea citrea

<400> SEQUENCE: 82

| | |
|---|---|
| atgaaaaaaa gcatattagc gctggtgttt ggttcactgg cttttttctgc catggccgag | 60 |
| gataacagtg gtcaggattt agtgaagcgg ggcgagtatc tggcgcgggc aggtgactgt | 120 |
| gttgcctgcc ataccagcga aggcggtcag ccttttgccg gtggattgcc gatggcaaca | 180 |
| cctatcggaa agatctattc gaccaatatt actcccgata agacttacgg catcggagat | 240 |
| tatacttatg acgatttcca gaaagcggta cgccacgggg tagcgaaaaa tggtgagaca | 300 |
| ttgtatccgg caatgcctta tccgtcgtac gcagtggtca gtgatgacga catgcacgct | 360 |
| ctctacgcct attttatgca gggtgtgaaa cctgtcagcc agcctaatca cgccactgat | 420 |
| attccatggc ctctgtcaat gcgttggccg ctggctatct ggcggggaat gtttgctccg | 480 |
| gcagtaaaac ctgccacagc acagccagga gaagatccgg tgctggcgcg tggacgctat | 540 |
| ctggttgaag ggttaggcca ctgtggtgct tgccatactc ctcgtagcat caccatgcag | 600 |
| gagaaggcgc ttaacaatag cgaaggtacc gattatctgt ctggcagcag tgctccgatt | 660 |
| gatggctgga cagccattaa tctgcgcggc gacgatcgtg atggtctggg ccgctggtcg | 720 |
| accagcgata ttgcacaatt cctgcgttat ggacgaaatg atcggaccgc cgtatttggt | 780 |
| ggcatgaccg atgtggtaca gcatagcctg caatacctga gtgatgacga tattaacgcg | 840 |
| atagcacgtt accttaagtc tctgtcacca cgggatagcc atcagccggt atttaaggcg | 900 |
| gatgattctg tctcgcaggc attatggaaa ggtaatgatc agcgaaccgg ggctgctgag | 960 |

```
tatgttgaca gttgtgcagc ctgccataag accgatggta gcgggtacac ccgcttcttc   1020
ccggcgctga aaggcaaccc ggtggtactg gcagaagatc caacctcact tatccatatt   1080
gttctgacag gggatacgtt acccggagtt cagggcgcgc catcggcgat cactatgccg   1140
gcatttggct ggcggcttaa tgatcagcag gtagcaaatg tcgtgaactt tatccgtagc   1200
agttggggaa ataccagcac tgcggcggta tcggcagatc aggtggctaa gttgagaaaa   1260
tcagccgatg tgcagggaaa aatgggtgat gcatcagtag agaaattacc taaacagcct   1320
```

<210> SEQ ID NO 83
<211> LENGTH: 1323
<212> TYPE: DNA
<213> ORGANISM: Pantoea citrea

<400> SEQUENCE: 83

```
atggctaaaa aaacacgacg cgttatctcc gtggtcgctg cggtagtcat tgccggtgca     60
ctcggttata ccgcctatga acagtacggt attcataaaa actatccaca aaccgtcagc    120
ctggagacgg gcccggcact gcaggaccag attaaacggg gcgaatatat tgcccgtctt    180
tctgactgta cggcctgtca taccgctgaa ggtggccagc catttgccgg ggctatgct     240 ctgcaaacgc cgttcgggaa aattctgtca tcaaacatca cctctgaccg ggaaaccggt    300
attggtggat ggactcagga acagtttgat aaagctgttc gtcatggtgt tggttctcac    360
ggctatctgt atgcagccat gccttatccg gcgtactcac ggctgaccga tgcagacctg    420
accgatttat gggcctatat ccgtaacctg ccagcggtta accataaagt ggtagaaaac    480
cagctgccat tcccgttcaa tcagcgctgg acgctggcgg gctggaatat gctgttcttt    540
aaagatgcgg catttacccc taatccacag gccagcgaac aggttaaccg tggccagtat    600
ctggtcgatg gaccagggca ctgtgcttcc tgccatactg ccaaaaatat gctgggcggt    660
gacagctctg cttatctgca gggcggagca ttgcagggtt ggtatgcacc ggacctgacg    720
ccggatcctc attccggttt aggcaactgg agtaatgccg atattgtcag ctacctgcgt    780
tccggcagta accgtatcac cgcctcctca ggcccgatga ccgaagcggt agagaattca    840
acgcagtata tgaatgataa tgatttgaac gcgattgcgg cttatctgaa atctattcct    900
gcctctcacc cacaggttcc gacagctctg acggctgatg accagcaaat ggtctccggc    960
aagaaagtgt ttgaatctca gtgcagtgcc tgtcacgttt ctgatggtgc agggattcgc   1020
aacatgatcc cggcactggc aggcaatcca caggtaaatt ctgcagatcc gtccagcctg   1080
ctaaacgtgg tactgaatgg cagcgaggga ccgtttaccc atgcgaatcc gacggctgca   1140
ggtatgccat cgttcggctg gaaactgtct gacgctaata ttgcagaggc cctgacctat   1200
atccgtaaca gctggggcaa cgccgctccg gccgtcacgg ctgaccaggt gagcgcagcc   1260
cgtaaagcaa ccggagcaaa aagctggctg ggagattcca tcgcctctca ggacagcggt   1320
aaa                                                                 1323
```

<210> SEQ ID NO 84
<211> LENGTH: 1323
<212> TYPE: DNA
<213> ORGANISM: Pantoea citrea

<400> SEQUENCE: 84

```
atgaaaaaga caacaatagc cattgctgtt gcggggatcg tcgtggtcgg cgcactcgct     60
gcattatgga tgaacggcag cacgcgggca gacgatgtag ccggagacca ggtgcagacc    120
agccagccgg tgtctgcaga agacagtgcg gcggtgaaac ggggtgaata catcgcagta    180
```

```
gccggtgact gtgtcgcctg ccatactgcc ccgggaagta aaacccccgtt cagtggcgga      240 tatgggattg atacgccgtt tgggaccatt tatgccagta atatcacgcc tgataaccag      300
accggaattg gccagtggac cgaacgtgat ttctaccggg cagttcgtca cggtattggc      360
cggcagggcg aaaatctcta cccggcgatg ccctataatg cctacgtgaa ggtcagtgat      420
caggatatgc atgatctgtg gatgtatatg cgtacggtta aaccggtgaa tcagcagccg      480
ccggaaactc acctgccgtt cccttataat atccgactgg caatgcgtgg ctggaatctg      540
ctgtttttta aaaatagtgg atttgatgcg aatagcagtc agtcagcaga gtggaaccgc      600
ggggcttatc tggttcaggg gcttgagcac tgtgctgcct gccacacgcc gaaaaatatg      660
ctgggtggag atacgtcagc gtatctgcaa ggtagcagcc tcggacagtg gcatgcaccg      720
gaaattaccg gcaacaccta taccggtatt ggccagtgga gtgagcaaca ggtggttgat      780
tacctgaaaa gcggcagcaa tcaggttgca gtagcttccg gaccgatggc cgaagcggtg      840
accaattcga ctcaacatct gacggatgct gatctgcggg ccattgcagt ctatctgaaa      900
tcccagccgg gttcggcaaa ccaaaagcca gcggctttgg cagcaaccag cccgttgatg      960
caacagggag cgaatgttta tcaggcaaac tgtagtgcct gtcataacag cgatggccgg     1020 ggaataccte agctggctgc cgggttgcgg gataacccgg gaataatggc ggccgacagc     1080
tcatcggtca ttactactat tcttgaaggc gggcgcggcg cggtgaccct gaacaatccg     1140
accagtggtg ctatgccctc gttcgcatgg aaactgtctg atcagcaaat tgccgcggta     1200
tcttcctata ttcgcaacag ctggcaaaat gcggccccgg cagtgacttc acaacaggtg     1260
gctgcaatgc gtaagcaact gaaactgacc cctcagttac cagataacgg agagccggca     1320
cat                                                                   1323

<210> SEQ ID NO 85
<211> LENGTH: 1308
<212> TYPE: DNA
<213> ORGANISM: Pantoea citrea

<400> SEQUENCE: 85
atgacgatta aaaaatatat tgcttcagtt gtcggagtgg ctgtagtggc cggactcgga       60
ttcactggct ggaaatgctg gcataacgct catcaggatc acagttttgt agcccctgca      120
tctgccgggg ataccggcag cacgcgcgatt gcacgtggta atatctggc cacggccggg      180 gattgtgttg cctgtcacac tgcgcctggc ggtaagcctt atgcgggtgg actgggactc      240
aatacgccgt ttggtaccat ctatgcgacc aatatcaccc cggataaaga gaccggaatt      300
ggcggctgga ctgatcagca gtttatgaac gctgttcgta acggtaaagg tgctaacggt      360
gagaatctct atccggcaat gccttataat gtttatgctc aggtcagcga tcaggatctg      420
aaagatatta agcctatct ggacagcgta ccggcagtac attcaccgg accaaaaaca      480 gatttaccat ttccgtataa tatccggctg atgatgatgg gctggaacct gctgttcctg      540
aataccgcag cgttcaaagc tgaccctgca caatctgccc agtggaaccg tggcgcttac      600
ttagttgaag gctcgggca ttgtacttcc tgtcacacac caaagaatat gctgggtgcg      660
gataaaatgg gggttcatct gcaaggtggt gagctggaag ggtggctggc tccggaaatt      720
accggcaaca cgcgtcaggg aatcggtggc tggagtgatg atgaattagt gcattacctg      780
aaaaccggag caaacgataa aacggttgct gcaggtccaa tggctgaagc ggttcataat      840
tcactgcaac atttgaacga tcaggactta acggcaatgg caacttacct gaaaagcttg      900
ccaggcagtg aagacaaatc agttgctctg agtggaatgg atgatgtgat ggcccgcgga      960
```

```
cagagtattt atcaggcgaa ctgctctgcc tgccatcagt cggatggtgc tggtgtccgg    1020
gatatggtgc cggcgttaag gggtaacaac gggctacagg catttgaacc gaccaacgtg    1080
ttgcatgtac tgatgattgg ggcacagggc gcagccaccg ccagcaatcc taccagcgcg    1140
gcgatgccag agtttggctg gaaactgact gaccagcaaa tggcagatgt cagtacttat    1200
gtccgtaaca gttggggaaa taaggcgcca gctgtcaccg catcacaggc ggcggctgca    1260
cggaaactgc tgtcaggttc accggcattg cataatccag cggcaaac                1308

<210> SEQ ID NO 86
<211> LENGTH: 1224
<212> TYPE: DNA
<213> ORGANISM: Pantoea citrea

<400> SEQUENCE: 86
atgatgaaaa agttaatgct gactgccggc agtttactgt tgctgacagc cggttacgca      60
catgctgaca gcggtggcga ttcctgggac ctggtaagta aaggccgtta cattgcgcaa     120
ctgggtgact gtaccgcctg tcatacagag ccgggacatc ctctgttttc ggcggggtc     180 gcgattgaga cacctttggg aaaactggta ggcgcgaata ttacccctga tccgaaaacc     240
ggcattggta aatggacctt tgaagacttc cagaacgcga tgcgtaaagg ccacagccgt     300
gacggtcagt tgctttacgg tgccatgcct ttcacggcct acaccaaagt aactaccgac     360
gataaccggg cactgtggtc ttatctgcaa actgttcagc cggtaaaccg ggtggttaac     420
accaaccagt tgccattccc gttcaatatc cgtacttcac tgcatgtctg ggatatgctg     480
aattttaccg aaggtgaata taagccggac cctaaacaat cagccgaatg gaaccggggc     540
gcttatctgg ttcagggtct ggggcattgc agtacctgcc atacacctaa aaatatgctg     600
ggtggtgata agacagcaa gttcctgcaa ggcggctcac tgggtgtctg gtttgctccg     660
gatattaccg ccaataccca cagcggtatt ggtcagtgga cccagcagga aattgtcgaa     720
tacctgaaaa ccggtgctaa taaatacgat atcgcttcag gtccgatggc tgaagctgta     780
gagcattcga ctcagtactg gaaagatgaa gacctgaatg cggctgcggt gtacctgaaa     840
tcgctgaaaa acgatagtag ccaaccacaa cctctggcgg cggataatgg ccagatggtg     900
aatggtaaag cgatttacgc ggaccgttgc agtgcctgcc atgtgtcaca aggtcaggga     960
gtctcacatc tgttcccgca actggctaat gcaccactgg ttaatgcagt cgaccctgca    1020
tcactgattc atgtagtgct ggcgggcagt cgcgccggag ggaccgctgc ggctccaacg    1080
gctcctgcta tgcctgcatt tggctggaac atgacggatc agaacgtcgc cgatgtgctg    1140
acctatattc gtaacagttg ggggaatgca gcaccgtctg tcaccgccag cgatgtgaag    1200
aatatgcgca gtactttaga gaag                                           1224

<210> SEQ ID NO 87
<211> LENGTH: 1300
<212> TYPE: DNA
<213> ORGANISM: Pantoea citrea

<400> SEQUENCE: 87
atgcagaaat taagggtgtt taccccgttg gctattatgc tggctgggtt ttgtggctct     60
gtttacgctg ataacagtcc tgcctcgtca gacagcacat cgctttcccg cggagaatat    120
ctggccagag ccggcgactg tgttgcctgc catacagcag aaggaggcaa accttttgcc    180
ggtggattga aaatgacgac gccggtaggg gccatctatt caacaaatat cactccggat    240
aaagataccg ggatcggtaa ttacagttac gatgactttg tcaaagctgt acgccaggga    300
```

```
gtcagtaaat ccggatcaac cctctatccg gcgatgccgt atgcttcttt taccaggata    360
tcagaccagg atatgcatga tctgtataac tattttatgc agcaggttaa accggtcagc    420
cagcagaata aagcctctga tatcccctgg cctttgagta tgcgctggcc actggcattc    480
tggcgctgga catttaccga tgataagcgt tttcagcctg tcgaaggtaa atcggcagaa    540
tggcaacggg gggcgtatct ggtcgagggg ctggaacatt gcggagcctg ccacactccg    600
agaggtatag cattccagga gaaagcactt gatcaaagtg atccggttta tctgacgggt    660
aacacactgg aaggatggta tgcaccggat ctcaccggca cgcaatctga tggtctgggt    720
cgctggtcac aacaggacat tgtcagtttc ctgaaaaatg gtgtaacggc acaaagctct    780
gcctttggtt ccatgtcaga ggtggttcat gacagtacca gctatcttac cgacagtgat    840
cttcaggcaa ttgcagtcta tctgaaatcg ctgcctgcgg cacaccagac gcaggcgcca    900
gccagtaata atgctaccgc tcaggcactt tttaaaggcg atgtttctgc tacgggtgca    960
caggtttatc tggataactg ttctgcctgt catcgctcgg atggtaaagg gtatgataaa   1020
acgttcccgt cactggcagg caattccgca gtactgaaca gtgacccttc atcagtgatt   1080
catattatct tgcaggggg acaacgcgca gtgacaccag atatgccgac cggattaacc   1140
atgccggact ttggttggcg gttatcggat cagcaggtcg cggatgtcgc cacctttatc   1200
cgtcagggat gggggaataa tgctgctgcg gtcacagcca gtcaggttgc cgatatccgc   1260
aagctaatcc cgaaacccgc ttctcaggct gctaagtagc                         1300

<210> SEQ ID NO 88
<211> LENGTH: 1404
<212> TYPE: DNA
<213> ORGANISM: Pantoea citrea

<400> SEQUENCE: 88
atgagcagga gtgtaaaagt gagaccaacg agtctggctt taattatcgg gctctcggtg     60
ttctcgggga aagctgtgca ggctgcagac accccttcag catcgacgat aattgagcaa    120
ggaaaatatt tatcagtggc cgcggactgt ggagcctgtc ataactcccc gacaagcgga    180
gctgctatgc gggggggcta tgcgattgcc tcaccaatgg gcaatattat cgccagcaac    240 attacccccgt cagtgacagc cggcattggt aattataccg aacaacaatt tgcccgggcg    300
gtcagagagg gagttaacgc acagggcgac catctttatc cggcaatgcc ttataccctcg    360 tacagtaaaa tgactgacag tgatattcat gcgctgtatc agtattttat gcacggggtt    420
cagccggttg atactccggc tccggccaca aagcttccgt ttccgttctc aattcgtagc    480
agtatggcgt tgtggaatat gctgtttgcc agccagcagc gtttcactcc ggatagccag    540
aaatcagctc agctaaaccg gggtgattac ctggtcaatg tgctggagca ctgtgatgcc    600
tgccatactc ctcgtaattt cctgatgggt cagaaaaatg acctggcttt atccggcggg    660
caggtgggta gctggtatgc tcctaatatc acttctgata aaactgccgg tattggtagc    720
tggagcgatg accagctgtt tcagtacctg aaaacaggtc atgttgccgg taaagctcag    780
gccgcgggcc ctatggcaga agccattgag aacagcctgc aacaccttag cgatgatgat    840
ttgcatgcca ttgttgcctg gctgaaacag gttcccgcct cggcgccac agctacggaa    900 tcacgtttta ctcagggtgc gccttcgac agtgaggccg ccatgcgcgc gaccgatcat    960
ccggatgccg gctgggtcgt gttcagtaac agctgtgcta actgccacca ggccaacggt   1020
gaaggcagcc agttttatcc ttcgttattc cacaacagtg caaccggtgc cgcacagccg   1080
gacaacctga ttgcgaccat tctgtttggt gtccgccgtc acgccgacgg ccagtatgtt   1140
```

```
gcgatgccag cattcggacc tgcagcttcg tttgttgacc ggctcaatga tcagcaagtt   1200
gcagatgtgg ctaactatgt cttaaaaaat tacggaaatg cctcactgac tgtcactgcc   1260
gatcaggtga aaacagttcg tgaaggcggg cctgtaccgg ccattgctta tctgtcaaat   1320
ccggcagtgt tagctatcgg tgcattgatt gtgctggtga ttctgggcct gatcgtgact   1380
gcagttcgca gaaggggggaa aaaa                                          1404
```

<210> SEQ ID NO 89
<211> LENGTH: 1485
<212> TYPE: DNA
<213> ORGANISM: Pantoea citrea

<400> SEQUENCE: 89

```
gtgaaacaac aacacaagct aaacgcgcat aaagccgcag gtttccgccg aaagctactg     60
agtctttgtc tgggactgag tgcattaagc gcggttcctg tgatggcagc tgagcaggtg    120
ccggtcagtc agccttctgt ggataacagt gctgatgcat tgttgaaaca ggggcattat    180
ctggccattg ctgctgactg tgccgcctgt cataccgatc tcaaaccaa aaagactttc    240 gccggtggtt acgccattca ctctccaatg ggggtgattt attccaccaa catcactcct    300
tcacggcagt atggtatcgg ttcctacagc gaagctcagt ttgaacaggc agttcgccat    360
ggtattcgcg gtgacgggag ccacctgtat ccggccatgc catacacttc ctattcgggt    420
ctgaccgatc aggatattca tcgttgtat tactatttca ctcacggcgt acaaccggta    480
gaacaggcta atcgtccgac agaactcagc tttccgttta atatccgcga agctatgtgg    540
ggctggaatt tactgttcct gaaacaaaaa cctttccgtg acgacccctc ccaaagcccg    600
caatggaacc gtggtaagta tctggtcgcg aaccttgaac actgtggaga gtgtcacacc    660
ccacgtaata cattgatggg cagcgaaacc gggtcggcac agtatagcgg tgcagccctg    720
ggaagctggt ttgcaccaaa tctgacttct gaccagcaga gcggtctggg cagctggcaa    780
cgtgatcagc tcatcaccta tctgaaaaca ggtcatgttg ccggtaaagc tcaggctgcc    840
ggaccgatgg cggaagctgt caccaatagc ctgcaatatc tgagtgatga tgatatcggg    900
gccattgtga cgtatttgca aagtctgcca ccggtcagtg aaccagacca ggcgaaagct    960
accggtgatt tcggcagttc cgctggtaac agttcagatt ctgaggttcg tggtactcag   1020
cctatgggat ctgtactgcc ggacgacatt accggtaaag cccctttacga cacaacctgt   1080 gccagctgcc atcagtcttc cggagcgggt actacggata atttctatcc atcactgttc   1140
cacaacactg ccaccggcgg aaatacccccg aacaatctgg tctccgcgat tctgtttggt   1200
gtgcaacgtg aagtgaacgg caagcaggta ctgatgccag cctttggtcc gggatcagac   1260
gtgcaatcgc tgaatgatga gcaggtagca aaacttagta attacatctt caaacaattc   1320
ggcaatccac aactgtcggt gactgctgat caggtaaaaa cactacgtga aggcggccca   1380
cagccgttcc tcgccaaata cgctgcatca ggatcggcea tgggtggtgt gatcctgtta   1440
ctgattattg tgctgattat tgtccgcatt tcgcgcaaac gtcgc                    1485
```

<210> SEQ ID NO 90
<211> LENGTH: 1413
<212> TYPE: DNA
<213> ORGANISM: Pantoea citrea

<400> SEQUENCE: 90

```
atgaaatgcg cttatttatc tttactgata agtacgctgc tgtatgccgg tttttcgccc     60
gccactcagg ctgaaacacc cgcgacagca gaaactctgc ttgcacaagg aaaatattta    120
```

```
tctgtggctg cagactgtag cgcctgccat gacagtcccg atcaccatgt catggctggc    180
ggaaacagta taaattcccc actgggcaag attgttgcca gtaacattac cccgtcagtg    240
cactatggca ttggcagtta taccgagcag caattttcgg atgcggttcg aaaaggtatt    300
aatgctcagg gcgaaaacct ctaccctgca atgccttaca cctcttacag ccagctcacc    360
gacagcgata tccacgcgtt gtattactat tttatgcatg gtgtaactgc tgtcgatcgc    420
gccgctgggg ccacacagct gcccttccg tttaacctgc gtatcagcat gaaactgtgg    480
aatgctctgt atgcggacaa caagccgttc cgtccttcat cctcgcaaac cgatcaggtt    540
aaccgcggca actatctgat ttacggggttg gctcattgtg atacctgcca tacaccgcga    600
aatgccctga tggccgaaaa atctgaccag tctctctccg ggggatcact cggccaatgg    660
tatgcaccca atatcacctc agataagtcc tctggtatcg gtaactggag cgatcagcaa    720
ctgtaccagt atctgaagac cggacatgct gtcggcaaag cccaggctgc cgggccaatg    780
gcagaagcta ttgaacacag cctgcaatac ctgtctgatg atgacctgca tgcgattgta    840
gccagccttc gtctaaccag accggtgaat actgcatccg cagatcgcgg gatgcagggt    900
aaagcaatat ctgatgaaaa cagtatccgt ggtaccaaag ttgccagcgg agagccggtt    960
tccggcccaa tgtcaggggc aattctgtac tcaggtaact gtgctgcctg ccatacgcct   1020
tccggtgccg gatcctacag ccagaattat ccgtcactgg tacacaacac cactgtaggg   1080
agcaccgatc ccactaatct gattgccact ctgttatttg gcgttcaccg taccgttgat   1140
caacaaagca tcacaatgcc cgcctttggg ccacaaggct ataccgaccg tcttagctttg   1200 gcagagattg ccacactggc gacctatgtc cggcagactt atggcgccgg aggtgaagct   1260
gtcagcgaac aacaggtaga gcaggtttac caggtgggc ctaagccgct gattggctgg   1320
ctggccgacg aagaatacag gcttttaatc gttgtagtgc tgttgctgtt ggctggcctg   1380
attatcaccg tagtgcgcaa agggagaaaa gca                                  1413

<210> SEQ ID NO 91
<211> LENGTH: 1422
<212> TYPE: DNA
<213> ORGANISM: Pantoea citrea

<400> SEQUENCE: 91
atgaaaaaac atgccataaa gttttccctg tcgctaatgt ttgccggaag catgttgtgg     60
gctggttccg ctgcagccgc aactggcgat gccgcggcgg ccattagccg tggtgaatat    120
ctggcgacgg cttcggactg tgctgcctgt catactgata aggcggtct gccgtttgcc     180 ggtggattaa aaattgaatc cccggtcggg acgattattg ccagtaatat tactccctcc    240
ttaaccgctg ggattggtca ttatactgaa cagcagtttg cggatgcggt gcgtaaaggg    300
attcgtgccg atggtgctaa cctttacccg gccatgcctt atacagcgta ctcggtgatg    360
acagatcagg atattcatga tctgtaccag tactttatgc agggcgtaaa accggtggat    420
catccggccg cggagactga gttaccgttc ccgatgaaca tccgcatgat gatgaaggcc    480
tggaatttac tgttcctcaa cgataaacca ttcagcccgg atgcatcaca aagcgctgcg    540
tggaaccggg gtaaatatct ggtaactggt gcagcgcact gtagtacctg tcatacaccc    600
agagggccac tgatggaaga ggaaagcagt cagttcctga gcggtggtca ggtcgggca    660 tggtacgcgc caaatattac ttcggatcca cagtcaggga ttggccgctg agccaggct    720 gatattgtac agtatctgcg cactggtaat ctgccaggta agcccaggc tgccggtagt    780 atgggagaag cggtagagca tagcttccag catctgacag atgatgacct gaatgcgatt    840
```

```
gctacctata ttcgtaccgt gaagccagtg gcaacgcccg aaaacgccgg ttcaagattt       900
atgcagggtg acagccacga tgctaccgga aaaattcgtg gtctgagtca gcaacaggtc       960
actgatgcta acagcaagg gctggcgttg ttccagggca attgtgcctc ctgtcatgaa      1020
gctggcgggc agggaagcag ggatagttat tatccgagcc tgttccacaa ttcagtgacc      1080
ggcgcagaga acagtaataa cctgattgct accattctga atggcgttaa ccgtaccacc      1140
cgggacggtc aggtatttat gccaggtttt ggtcatcatc caaatgatat caataatctg      1200
actgacgagc agatagcgtc gctggcaaac tatgtgctca caacctatgg taaaccgtcg      1260
aaaccggtga ctgcggcgat ggttgccacc gtacgccagg gagggccggg ttccagtctg      1320
gtgcttctcg cccggtttgg aatagctgcc ggagtggtag ttgttttgat tctgctggga      1380
ttctgggtgg ttcgccgcaa aaaaaacgtc agggatccgt cg                         1422

<210> SEQ ID NO 92
<211> LENGTH: 1353
<212> TYPE: DNA
<213> ORGANISM: Pantoea citrea

<400> SEQUENCE: 92
atgaaaaaac tgctttccct gtgtatcgcg ggtgccctgg ccgggatcat gctgaatagt        60
gccgccatgg ctgaagacag caatgctcag agcctgatcg caaaaggaca gtatctttcg       120
gtagccggtg actgtgctgc ctgtcatacc accagcggag gaaaaccttt tgccggcggt       180
ctggctattg ccacaccgat tggcaagata ttctccacca atatcactcc gtcaaaaacc       240
tccggcattg gcgattactc gctgcaggag tttgaaaaag cggttcgtca gggagtaaga       300
aaagacggcg ccaatctcta tccggcgatg ccttacactt cttatgccaa aatttccgat       360
gaggatatgc aggctctgta tgcttatttc atgcatggcg ttgcgcctgt ggatgagaaa       420
ggcccgcaaa ctgccctgcc attcccgttc aatattcgtc tgtcgatggc gggctggaac       480
ctgattttgg ccggagacaa accatttacg ccagacagta accagtcagc agaatggaac       540
cgcggcgctt atctggttca gggtctggct cactgctcca cctgccatac cccgcgtaat       600
gctttgatgg ctgaagagtc tggccaggcg ctggctggtg cttctctcgg tacctggttt       660 gcaccaaaata ttaccccgga tgcccatgca gggattggca atggtcagc cagtgattta      720 gccacttatc tgtctaccgg tcgttcaccg aacggttctc aggctggcgg cccgatgctg       780
gaagctatcg ataaaagctt tagtaaactt tctcagtcag atattaatgc gatagtgacc       840
tatgtgcgtt ccgtgaagcc tcagtcagcc aatgccgctc cgggccaggt acctgccagt       900
gccccggtag tgtccgattt tgcgctgatg aatggaacag cttctgatgg cgcgaagctg       960
tatgaagctc actgctccac ctgccaccag gcctctggtc agggcagcaa tggcttaccg      1020
gctttatatg gtaacgccgc gctgcatcgt ccggtagcgg ataacgcagt catggctatc      1080
ctggacggcc tgactccgac tcagggccag gctatgccgt cgtttaaaac tgccatgaat      1140
gatcaacaga ttgccaccct gaccaactac ctgtttaaaa cctttggcga tgccggtgtt      1200
cagaccaccg cagacagagt taaggtatta cgggaaggtg gagcaccatc tccgttactg      1260
gcgattgcca aaggcgggat gatagctgcg gtgatcgtgg tattactgct gatagtgggc      1320
ggagtgatgg ttaaatcgcg gcgtaaacgc cgt                                  1353

<210> SEQ ID NO 93
<211> LENGTH: 1428
<212> TYPE: DNA
<213> ORGANISM: Pantoea citrea
```

<400> SEQUENCE: 93

```
atgaaaaaat actcagctct tctgactttg tcagctgcat tcctgttctc cccctcgct      60
ctggcggcca ccagcagcaa tagcgattta gtcagtcgcg gtgaatatct ggcgcgggcc    120
ggtgactgta ctgcatgcca cactgccgca ggtggtgccg aatatgccgg cgggtataaa    180
tttaatatgc ctatgggcac tatcgtagca ccgaatatta cctcttcagt gcaatacggt    240
attggtaact ggtctgaagc cgattttgcc aaagcagtaa ggcaaggggt acgcctgat     300
ggttctcatc tctatccggc aatgccatat acctcttacg ccacagttac cgatgaagat    360
atgcaggcgt tatatgcttt cttcaaaacc gttccggcag tagataaagc cccggcagat    420
aaaaacgacc tgaaatttcc gtttaacctg ccaggcctga tggggatctg aatgctttg     480
tttgccagtg atgcgccatt taaagccgat ccggcattaa ctgctgagca aaaccggggg    540
aaatatctgg ccgaagggct ggctcactgt tcaacctgtc acagtccacg caatcagatg    600
atggccgaga atactcatca gttgcttgca ggcaatcatg tggatggctg ctggcacca    660
aacataacct ctgatgctgt cagcggcatc ggtggctgga gccagcagga actgaccgaa    720
tatctgaaaa ccggccatgt ggaagggaaa gctcaggccg gtggtcctat ggctgatgcc    780
atcgagcaca gtttcagtca cttatcagac agtgatttag ccagtattgc cacatggctg    840
aaaacagtac cagccatccg cactccgggc cagacacaac cttcatgggc tgccgcgcca    900
gccagtaagg tagactggac aagttatcaa accgggggcg ggaagaataa ttctccggcg    960
taccgtgact cgtccactac cgacggagcc gtactgtttg acagcagttg tgcggcctgc   1020
catcaatcga gtggccaggg ttcagacgac cattacttcc cgtctctgac ccataacagt   1080
gcggttggtg cagcggaccc gtcaaatctg gttatggcga ttgttgatgg tattcaccgt   1140
aaaacccggg agggtgaagc ggttatgcca gcgttctctt cagaaactca ggccattcac   1200
tcatggctga ataatgatca gattgcggca gtgactaact acgtcaccga aaaatttggt   1260
cacggaaatg ccggtctgac cggtgccgat gttgagaaaa tccgtaacgg caacagcaat   1320
gttccgttcc tgattaaaaa tgcaggcggc ctgaccattg cgggatagt gattgtcgtt   1380
attatcatta ttgcgttact ggcggcacgc agccgtaaaa acgtcga                1428
```

<210> SEQ ID NO 94
<211> LENGTH: 1311
<212> TYPE: DNA
<213> ORGANISM: Pantoea citrea

<400> SEQUENCE: 94

```
atgaaagctg tgataattcg atcggccatc gcgttagctc tgatgcatgg cagcctggca     60
ctggcggcag atgataatgc tgacttaatt aaacgcggag aatatctggc aactgccagt   120
gactgtaccg cttgtcatac ggcccctggt ggtccggcat atggcggtgg ttacccggta   180
gcgactccgt tcggtaaaat ctggggaagt aatatctcct cagataaaca atttggtatt   240
ggtagctgga ccgacgatca gtttgtcgcg gcggtccgtc agggtgtcgg taaaaacggc   300
gagcagctgt atccggcgat gccgtatgac gcatttacca agatgaaacg cgacgatgtt   360
ctggccatca aagcctacct gatgtcatta ccggctgtgc ataaagccgc accagaaacc   420
tctctgccgt tcccgttcaa ccagcgttgg gggatgcgtt tctggaaaat gtttaacctg   480
actgaaggcg aactgaaaaa tgaccctcag cagagcccac aatggaacaa tggtcgttac   540
ctggtagagg cactggcaca ctgtaccacc tgccatacac cgcgtaatct gaccatggga   600
atggatacca gcaaaccgct atccggcggg gatttaggcg actggattgc ctttaatatt   660
```

```
accccgggta aatcaggaat cggcgactgg tcgagtcagg atatcgtgac ctacctgaaa      720
accggttacc tggcaggcaa agcctcagca tcaggcccga tggccgaagc gattgagcac      780
agcctgcaat atctgccgga ttcagatttg caggatatag ccacttacct gaaatcggta      840
aaaccggtgg atgatgagaa gcagagcgtg ccacgggaca gccagggaca gccgtcggat      900
gccattatcc gcctgcgggg tgctgatgca gccactctac agtcacaacc cggcgctgtg      960
gtatttgaag caactgttc gacctgtcac ggtgctgaag gtgccggatc aggccaggga     1020
ttccacgcct atccgtcact gttccaccac tccagcaccg gagccatcga tcctaaaaac     1080
gtggtatcgg tgatactgaa cggtgttaac cgccatatgc aacagggtga tattttatg      1140 ccatcctttg ctccgcagtt aaacgatcag caggtggctg atgtggcgaa ctttgtgatg     1200
cagaaatttg gcaatccggc ggctgaaaaa gtagacacca gccaggtttc caaagcacgg     1260
aaaaatgcca gtctgccgtt accgccaacc tttgcagacg gtgctaatcc g             1311
```

<210> SEQ ID NO 95
<211> LENGTH: 1458
<212> TYPE: DNA
<213> ORGANISM: Pantoea citrea

<400> SEQUENCE: 95

```
atgattcgtt catcttttaa gcgctcacgg aattttctgc cgttggccgg gctgttgttt       60
tgtgctgcgg gctatgcgca aaccggatca gctcaacctg atccggtggc aacacaaccc      120
actccgactc agccagcggc cgctgccggt acgcagggaa cgaccctgat tcagcagggt      180
gagtatctgg cgaaagccgc ggactgtgaa gtttgtcata cggctaccgg cgggcagacc      240
ttcgctggtg ggcttgggtt taaaaccccg ttttggcacca ttttttcatc gaacatcacc      300
ccggataaaa cccacgggat tggtcagtgg agtgagaagc agttcagtga tgcgctacgt      360
tatggcatcc gtgctgatgg caagaatctg tacccggcaa tgcctataca ctcttattct      420
aagctgacgg atgcagacat acatgccatg tatgccttct ttatgtcgct gaaaccggtc      480
gccaccgatc ccccggaaaa taagatgggc ttcccgtaca atcagcgtat tgccctgaaa      540
ggctggaatc tgatcaattt ccattaccag ccgtttaagc aggatcctga tcagtcggcc      600
gaatggaacc ggggtcacta cctggcaacg gcgctgggac actgtgaaga gtgccatact      660
ccacgtaacc tggcgatggg cctgagcgat aagtcctatg ccggtgcgat ggtggatggc      720
tgggaagcat ttaacatctc ttcggataat acttccggga ttggtcgttg gagccacgct      780
gatctgatgc agtacctgaa aaccggttct gtaccaggtg tggctaccac gggcggaggt      840
atggctgatg ttatttctca cagtctgcgt ttcctgagca atgatgacct cagtgcactg      900
gcaacctata tcaagagtgt tccgccgcag aaaactgcgt cacaaaaccg ctccggatac      960
ggcgacaatg ttcagagtga tattactcag gcggttcgcg gcatgccaat tgatgattcc     1020
gcaccttctg gtgccgtatt atttaacggc aactgtgcca gctgtcacgg gaccaaaggt     1080
caggggatag gtgaaaaccg ttactatccg tcactgtcaa ataacagtgt ggtcggtgcg     1140
gataaagcca ataacctggt tcaggtgatt ctgtatggta tcgatcgtac caacggcaaa     1200
ggcgaacata tcgtgatgcc tggctttggt gacgaactga ccgacagtca gattgcgacc     1260
ctgactaact atctgcgcac caatttcggc actaatcctg cgccggttga tgccgcacag     1320
gtgaaagcgc tgcgggaaaa taacgtgatg gttattccgg gctacctgct gattttgggc     1380
ggagtcatcg gtgtcatcat ccttgttgcc atcattatgt acttccgtcg cagaaaagct     1440
gcgcgcaacc acgcgggc                                                   1458
```

<210> SEQ ID NO 96
<211> LENGTH: 1425
<212> TYPE: DNA
<213> ORGANISM: Pantoea citrea

<400> SEQUENCE: 96

| | | | | | |
|---|---|---|---|---|---|
| atgaaacgat | tctcgcgggt | aaagcttacc | ttactggggt | tgttgtgcgg | cggtctgact | 60 |
| tcactggcgg | caaatgcagc | tgacattgac | caggcgctat | tgcaacaagg | tgaacaggtg | 120 |
| gcaacagcct | ctgactgtca | ggcttgtcac | accgcaccag | gcagtaaaac | cgcattcagt | 180 |
| ggtggttatg | caattgcttc | tccgatggga | gcaatatatt | caaccaacat | cactccggat | 240 |
| ccggcaacag | gtatcggcaa | atacaccgag | cagcagttta | tcgaggcggt | tcgtcatggt | 300 |
| gttcgggccg | atggtgccca | actgtatccg | gccatgcctt | atacttcgta | ccggatgatg | 360 |
| actgacagtg | acatccatgc | gctgtattac | tactttatgc | atggtgtgaa | accggtcgac | 420 |
| cagcagaata | cagaaactca | gctctccttc | ccgttcaaca | tgcgttttag | catgaagttc | 480 |
| tggaatctgc | tctatgccga | cactaagact | ttccaacagg | atccgcaaaa | gagcgcggaa | 540 |
| tggaatcgcg | gaaattatct | ggtcaatggc | cttgcgcact | gtgacacctg | tcatacacca | 600 |
| cgtggcttta | tgatgaatga | acagaccgac | cagccgctgg | caggtgctcc | tctgggaagc | 660 |
| tggtatgcac | cgaacattac | ttcagataag | gtcagtggta | ttggcggctg | gagtaacgat | 720 |
| gagatagttc | agtacctgaa | aactggccgt | gcagcaggta | aaaaccaggc | ggctggcggg | 780 |
| atggcagaag | ccgtggaaca | cagtctgcaa | tatctgccgg | acagtgattt | acaggctatt | 840 |
| gccacttatc | tgaagcaaac | cacaccgatc | cgcaccccgg | gcgagactca | gcggcatac | 900 |
| agctatggct | cgtcttcgac | caatgttgat | gatcaggtcc | gtggaatggc | accaaataat | 960 |
| gcccgtgact | cattaaccag | cggagctgct | ttattcagcg | gaagctgtgc | cagctgtcac | 1020 |
| cagccagacg | gtgcaggaag | caagaatcag | acttatcctt | cgctgttcaa | taacacggcg | 1080 |
| accggcatga | ttcacccgca | aaacctgatt | gcaactatcc | tgtttggtgt | ccaacgtaac | 1140 |
| actaaagacc | atcaggtgct | gatgccaggt | ttcggtgctt | caacctccta | tgtggatagc | 1200 |
| ctgaccgatc | aacagattgc | ggatatcagt | aactatgtac | tgcataatta | cggtaatcct | 1260 |
| gcggttacag | tgaaagcagg | cgatgtggcg | tgggttcgta | aaggcgggca | tccgccggca | 1320 |
| ctggttgcgc | tgcagcctta | tatgattccg | gcaattgcgg | tcggggtcat | tatcattatc | 1380 |
| ctgctgctgg | tagcattcag | acttcgtcgt | agccgacgca | aaagt | | 1425 |

<210> SEQ ID NO 97
<211> LENGTH: 735
<212> TYPE: DNA
<213> ORGANISM: Pantoea citrea

<400> SEQUENCE: 97

| | | | | | |
|---|---|---|---|---|---|
| atgtcagaac | agaacaaagg | gcagtctcgc | agggatttt | tactaaaaac | gatcactta | 60 |
| gcacctgcaa | tggctgtcgg | aagcaccgct | ataggttcac | ttgctcttag | cccggcagta | 120 |
| caggccgccg | atactcaaac | cagcggcccg | caaaaggccc | gggattatca | gccaaactgg | 180 |
| tttaccaaag | aagagtttgc | atttatcact | gctgctgtgg | cgaaactgat | tccagcagat | 240 |
| tcccgtggcc | cggagccct | tgaggcgggt | gtacctgaat | acatcgaccg | gcaaatggat | 300 |
| actccttatg | ccactggttc | aaactggtat | atgcaaggcc | cgtttgcccc | cgatacgccg | 360 |
| aaagaactgg | gttatcagtt | accgctggtg | ccgcggcaaa | tttatcgtct | gggactggcc | 420 |
| gatgcagata | atttctgcaa | acaacaatat | ggtcacgtgt | tgctgagct | cagcgatgat | 480 |

| | |
|---|---|
| cagcaggtca ctgcactgaa agcttttgaa tctggtcagg ctaaattcac tcagcttcct | 540 |
| gccacactgt tttttccta tttactacag aacaccgcg aaggtttctt cagcgatccg | 600 |
| atccacggcg gcaatcaggg tatggctggc tggaaactga ttggtttccc tggtgcccgg | 660 |
| gctgacttta tggactgggt cgaacgtggt gaacattatc cgttcccacc agtatcaatt | 720 |
| cgcggagaaa gggca | 735 |

<210> SEQ ID NO 98
<211> LENGTH: 726
<212> TYPE: DNA
<213> ORGANISM: Pantoea citrea

<400> SEQUENCE: 98

| | |
|---|---|
| atgaaaaata cgccccggag taaggactcc accggcagac gacttttttt acaacgttct | 60 |
| ctatcgctaa tccctttagt tgcagccaca ggtactcctt ttgccaccag ccaggctgcc | 120 |
| gaaaaaaaaa ctccggcagt cactcaggat tacgtaccgc aatttttga ccctcagcaa | 180 |
| tgggcgttta ttaatgccgc agttgatcgg ctaattccgg aagatcagaa cggggcggga | 240 |
| gctgtcagtg aaggtgttcc ggtctacatc gatcgtcaga tggaactccc ttatggttac | 300 |
| ggacacctct ggtatatgca gccccctttc gcatcccaca gcgacccgac cctgggctac | 360 |
| cagtcccctc tggtgcctcg tgagctttat cgccaggga ttgcactcac tgagcactac | 420 |
| tgccagcaaa catttcataa gtcgtttgct caactcacca ccgaccagca ggatcaggta | 480 |
| ttacagttac tcgaaaagaa taccctgacg gataacaatc tgagtggttc gttattttt | 540 |
| gagcaactgc tggataacac caaggaaggc taccttgcag acccggtaca tggaggcaat | 600 |
| cagactttgg cttcatggaa actgattggt tacccgggg ctcgtgcaga ttataccgac | 660 |
| accgtagcac agccaaatgt cccatacccg ttgggccctg tgagtatttc cggtaaaagg | 720 |
| agtgtc | 726 |

<210> SEQ ID NO 99
<211> LENGTH: 732
<212> TYPE: DNA
<213> ORGANISM: Pantoea citrea

<400> SEQUENCE: 99

| | |
|---|---|
| atgtcagata aaccttccca ttccaggcgt gatttcctgc tgaaatcact cactctgatc | 60 |
| cctgcggttt ccgtaggagg tgctattacc agcggtatcg caggaccggg caatgctcag | 120 |
| gcggccgaaa cctctgctac agccgcgaca gcgcagactc cctattcccc cgtatttttc | 180 |
| aaacctgacg agtgggcatt tgtgaaagca gcctgcgccc ggctgatacc tgccgatgat | 240 |
| atggggtctg gcgcgttgga ggccggggtg cctgaatttc tcgatcgtca cctgcagacc | 300 |
| ccttatgcca acggttctgt ctggtatacc caggggccat tgttgaggc aggaccggaa | 360 |
| tttggctatc agggtcgtaa aacgctgagt gagatcattg ttcagggat ccgtggtgtt | 420 |
| atcggctgga cgcagagcaa taaacagcag acgttcgatg ccctgaccca tgcagaacag | 480 |
| gaagaaatat tggtggcatt ggaaaaaggc aagatccatc tggaagagat ggatgccaaa | 540 |
| accttcttcg actacttcct gggtgaagtg cgcaatggct ctttgctga tccttcctac | 600 |
| ggaggcaaca aagggatggt tggctggaag ctgatcggct tcccgggcat gcgtgccgat | 660 |
| tacatagatt tcattaccgt ccgcgataaa ccttatccgc tcggaccggt agatttggca | 720 |
| gggaacaggg gt | 732 |

<210> SEQ ID NO 100

<211> LENGTH: 717
<212> TYPE: DNA
<213> ORGANISM: Pantoea citrea

<400> SEQUENCE: 100

| | | | | | |
|---|---|---|---|---|---|
| atgaaagaaa | attctcaacc | gccggcagca | tcgcggcgaa | aattttttaca | gacagccctg | 60 |
| gccattattc | cttctaccgc | tctggccacc | agtgtcgtgc | ctgctgctct | ggcggccgaa | 120 |
| cagaccaaaa | atcccacccg | tgattatgtg | ccggtctttt | ttaaagacga | tgagtggcgg | 180 |
| tttattatcg | cggccaccga | tgtgctgatc | ccggggggatg | aatatggccc | tggcgccgtg | 240 |
| agtgaaggag | ttccggtgtt | tatcgaccgg | cagatgaaaa | tgccttatgg | ctacggtcag | 300 |
| ttgtggtaca | tgaaaccgcc | ttttcaggaa | ggatctccac | tgctgggtta | ccagaaaaac | 360 |
| ctgactccac | gggatatcta | tcgacggggg | atcgccgccc | tgaataaagc | ctgccagacc | 420 |
| acttatcagc | atccgttcgc | ctcactggcg | acagcagata | agttcaggt | aatggaagat | 480 |
| ttggaatccg | aaagctggt | gaccgaagac | gttgacggca | aactgttttt | tgcacagtta | 540 |
| ctggaaaata | ccaaagaagg | ataccttgcc | gatccgattc | acgggggcaa | tcagacaatg | 600 |
| gcctcctgga | aaatgattgg | tttccctggc | gcccgcgccg | attacgttca | ggtcatggat | 660 |
| aatcccggaa | aaccttatct | tccgggcccg | gtcagtattt | ccggtaaata | tggtgct | 717 |

<210> SEQ ID NO 101
<211> LENGTH: 729
<212> TYPE: DNA
<213> ORGANISM: Pantoea citrea

<400> SEQUENCE: 101

| | | | | | |
|---|---|---|---|---|---|
| atgaaacaaa | gtggtatcgg | gaggcgtccg | tttattatcg | gatctctgat | tggtattgct | 60 |
| tcattaggca | tgaagtgtgg | tgtaagtagt | gttttttgcag | ctgtcacctc | cccactggat | 120 |
| gaacttaaca | gttatcagcc | cgttttttttt | aaacccgaag | agtggcaatt | catcatggct | 180 |
| gcctgcgatc | gtctcatccc | acaggatgag | gaagggcctg | gcgcacttga | aacacatgta | 240 |
| cctgtttttta | ttgataaaca | gatgctaaca | ccttacggga | aaggtgagga | ctggtatatg | 300 |
| gaaggcccctt | ttaatgcgca | tgccagcaca | ttatttggct | accagttacc | ttttccattg | 360 |
| caggttatgt | atcaaagagg | aattaaagcc | accaacagct | ataccgcct | ccatttcaat | 420 |
| caggattttg | cagcattaac | tgcggcacag | caggatgctg | tcttatcagc | actggaagaa | 480 |
| aataagatca | ctttctcaga | gttttcagag | cctgacttat | cagcctcata | tttctttacc | 540 |
| cggttgctgg | aaaataccaa | agaaggttat | ctgtctgatc | ctaaatatgg | tggaaataaa | 600 |
| ggcatggcag | cctgggtaat | gatcaacttc | cctggtgccc | gcgccagttt | ccctacatgg | 660 |
| ataaaaattc | acaacgtcaa | atatccatta | ggaccggtag | ctttgaatgg | tgatgttgcc | 720 |
| caatcctct | | | | | | 729 |

<210> SEQ ID NO 102
<211> LENGTH: 747
<212> TYPE: DNA
<213> ORGANISM: Pantoea citrea

<400> SEQUENCE: 102

| | | | | | |
|---|---|---|---|---|---|
| atgtctgatc | cttcatcgaa | agggattagc | cggcgacggc | tgctctctgg | ctctgccgca | 60 |
| ggtttaaccg | ttgccgcggt | aagcagtgct | aatgccacca | ctatcaccgg | catccctcgc | 120 |
| tgatgctgt | ttgaccataa | cagccccatc | actcccacca | gccccggcct | taagttcctg | 180 |
| actcaggaag | aagcgactga | agtggatgct | atcgtcagtc | agttgatccc | tgcggatgag | 240 |

| | |
|---|---|
| ttgtcggtga gcggtaaaga tgccggttgt acggtattta tcgaccggca actggctggc | 300 |
| agctatggcg atgccagccg caactatatg cgtggcccctt tccgggaagg aactccggcc | 360 |
| cagggtgatc agtctccgtt agtaccccgc gagcgttacc gtcttggact ggcgggcttg | 420 |
| agtgactatt gccagcaaaa ataccagaaa ctgttcagcc aactggacag cgcaacccgg | 480 |
| gatgaagtgt tgaccggact ggaacaggga aaaatcaatc ttaccggcat cagcggcaag | 540 |
| atgttttttg atcaggttct aaccaacacc atggagggct tcttctccga tccggtgtat | 600 |
| ggcggcaacc gcaatatggt cagctggaaa atgattggtt ccctggcgc tcgttatgac | 660 |
| tatcgcgact atctgaccaa aaccgatcag aaactggatt tagtcccgat ttccatcatg | 720 |
| ggcagcaccg cctggaacgc gaaggta | 747 |

<210> SEQ ID NO 103
<211> LENGTH: 714
<212> TYPE: DNA
<213> ORGANISM: Pantoea citrea

<400> SEQUENCE: 103

| | |
|---|---|
| atgaagcgaa gagagtttct gtcatcaatg gctgcgtttg gtgctgcctc ggcgatcccg | 60 |
| ctgaccaatg ctgccgaaat tctctggcgg cagccctggc cgcctggtca ggtgagcctg | 120 |
| cctccgggct tgccgagaaa aggcggatta cagtttttta cccgccatca actggaaacc | 180 |
| gtcggagcaa ttgctgagcg gtttattccc gccgatgaat taagtatcag tggtaaagag | 240 |
| gccggctgcg caatttttat cgatcgccaa ctggcagggg attttggcca ggctgtcacg | 300 |
| gtgtaccggc tgggccggtt tgttaaaggc actcctgagc aggggccaca gtcacctctc | 360 |
| accccggcag atcaatatcg tctgggcctg aatgcgctgg acagctattg ccagcagcag | 420 |
| tttcaccata actttactga gttgaccggt gatcagcagg accaggtttt gcagggcatg | 480 |
| gaaaccggga aaatcagcct ggctgaaaac tttgacagta aggtgttttt tgaactgtta | 540 |
| ctgcaaaacg tccgtgaagg ttttctgtcc gatcccctgt atggcggcaa caaagatatg | 600 |
| gccagctgga aaatgattgg ttttcccggt gcccgttatg acttccgcga tgttatcgcc | 660 |
| aaaaaaggcc aaaaattaaa cattattcct accagcctga ttgataacaa cctt | 714 |

<210> SEQ ID NO 104
<211> LENGTH: 726
<212> TYPE: DNA
<213> ORGANISM: Pantoea citrea

<400> SEQUENCE: 104

| | |
|---|---|
| atgcttttgc aaaaaaacac cacgcgccgc aaattcctgc tcggttcgct gatggctttg | 60 |
| ccactcaccg aactggtgct taagggtctg actgcggcac aggcagccga tatggctgca | 120 |
| cctgaactta ccagctataa accggccttt ttcaccgctg acgaatggca gtttattctg | 180 |
| gctgcgaccg accgcattat tcctgcgggc ggaccgggta aagccccggg cgcgctggaa | 240 |
| actaatgtgc cgatatttat cgaccagcaa ctccatgatg agcatttcgg taaggaaatc | 300 |
| tacatggaag gccgtttaa cccgcatgcc ccggccacta tggggtatca ggtgcctctc | 360 |
| tatccacaac agatttatca gaccggtatc cggctgacta atcagtggag ccagcaaaac | 420 |
| ctgcagaaac ctttccatca gttatcggaa gcagataaag acaaggtgct gacgggatta | 480 |
| cagaaaaaca ctctcgactt cgcagccctg ggtgaaaaca ccctgaaggg ctcgttgttc | 540 |
| ttcagtcagt tgctcggaga aaccaaacac ggttatctcg ccgacccgat gtatggcggc | 600 |
| aataaaggga tgaaagcgtg gattgcgatt ggttttcccg ggcccgcgc cagttatctg | 660 |

-continued

```
gaatgggtaa acaacataa tgtgaagtat ccctcgggc cggtcagcct gctgggcgag    720
actgcg                                                             726

<210> SEQ ID NO 105
<211> LENGTH: 735
<212> TYPE: DNA
<213> ORGANISM: Pantoea citrea

<400> SEQUENCE: 105
atgcaacgtc gtaaatttat caagaccgga ttaatcctgg cagggaccgg aactgcagca    60
tcagtattta aaccagcggg tgctgcggcg cgcgataata tactgaatgg cggaaaactg   120
tggaaagcta agaaacacc accgccgact ccggctgatc aaccaaacg tctctatctg    180 accgaacagg aatatgccca gatcaccgcg atttttaacc ggctgatccc tgcagatgaa   240
ctgactgtca gcgcctccga tgcgggctgt gttgttttta tcgataacca gttagccgga   300
aattatggta aagccagctg gcgctataat gttggcccgt ttgaaaatgg tacgccttcc   360
cagggtaacc agcagcctta cactccggct cagatttacc gtattggttt ggccgaaata   420
gaaaaagact gtcagagtaa attttcaaaa tccttcagcg aactaactaa tgatcagcag   480
gataaatatc tggaacagat ggaagccgac cagattaaat accctaccct gtcatccaaa   540
gatgtattta gtcagttctt atccaatgta caggaaggtt ttcttgccga cccgatatat   600
ggtggtaacc gcaatatgat tggctggaaa atgattggtt cccgggagc acgttatgac   660 tatcgtgatt atgccccact gaaaggaact aaattaaata tcgaaccggt cagcattatt   720
caactcctga aagca                                                   735

<210> SEQ ID NO 106
<211> LENGTH: 717
<212> TYPE: DNA
<213> ORGANISM: Pantoea citrea

<400> SEQUENCE: 106
gtgaagcgca ggcgtttttt ggcttctctc ggagtattgc ttatcagcac tgctctgaaa    60
gttaaagcaa agattattc cggcggtatg ccgtgggtcg tgcatgctgt taagccaccg   120
caaccagtag tcgcggggga atggcagttt tttacaccag aagaagtggc gataattgaa   180
gctattgctg accggataat ccctcaggat gaactgagta ttggcggaaa agaagcgggt   240
tgcgcattat ttctcgaccg ccagttagcg ggagattacg gcaaagcagt cagtatatat   300
cgtcttggac cgtttattca gaatggttta ccggaggcgg gcccgcaata taagagatgtc   360 cctgcagaac gttaccggtt gggtctggcg tcagtaaatg aaatcagcca ggccaaatac   420
aatggtaaaa agttcaatga atcagtgaa gaacaacagg atgatttact gggtaaaatc   480
gaatcgggag tattaccact caccggagtc gacggtaagt tattttttga tcagttggtc   540
ataaatatgc gtgaaggatt ttttgccgat ccattatatg gcggaaataa agatatggct   600
ggctggaaaa tgctcggttt tcccggcgcg caatatgatt tccgtgatgt gattgataaa   660
cgaggcgaag aattgaatat caagccggtc agcatggtaa ctaacaacga tcaatct     717

<210> SEQ ID NO 107
<211> LENGTH: 531
<212> TYPE: DNA
<213> ORGANISM: Pantoea citrea

<400> SEQUENCE: 107
atgacagcaa ataatcgcca tccttccggg gtttcacgcc gtcgtctgct gcagggtatg    60
```

```
ggcattctgt cggttgccgg gttatgtggt tcactgtttc cttcttttcg tgcagcagca    120
gcagaactgc aggacagtgg ttttatcccg ttatctgaat ttctggttaa tcgccgggtg    180
aacccaattc tggctcagcg ttactacgat gcattgcatc gccatgatga aaaatttgat    240
cagaagctgg cattgcttaa acaggatatt cagccaggaa agtatcaaaa cattgatgat    300
tttcttcaaa aaaatgccgt cggaacagat ttacgacagg cagcaggtca ggtcatttct    360
gcctggtaca ccgagtggt aggcaacgac gagaaactgg aacttatcgc atatgcagac    420
gcgatgatgt atgtgcccac cagtggcgtt cttgtggttc caacctatgg cagtggcccg    480
atttcctggg ctgccgttga caataaaccc gcacaccagg ggccggctgt a            531
```

<210> SEQ ID NO 108
<211> LENGTH: 546
<212> TYPE: DNA
<213> ORGANISM: Pantoea citrea

<400> SEQUENCE: 108

```
atgaaactca cagatactat ttcgacagat cgccgaaaac tgattaagtc attatcgttg    60
ctgaccgtat tctctgtgag tgggttacgt ctggtgacct gtccggcatt tgctggcggt   120
ttgcctgcca gtgcggattt tcatgaattc tcaacctttg ttattggccg ccagtagat    180 cctgttttat caggccgtta ttttgccgca ttgcaggctg cagacggaca tttcattcaa    240
caactgaatc aggcgatggt tgccagtgtc ccgtttcgca gtcagggat tgatacgatg    300 ctggcatcac tccctcacga cagtgacatc tttaataccc ttaaaaaaat cacctcagcc    360
tggtatctgg aatcgtcgg cgaaggcgcc ggggcgactc tgatcgcctt ccatgacgca    420
ctgatgttcc agccaacccg tgaatacgtt tttgttcccg gttatggcgg gggccctgac    480
agttgggtct cacttaaaca tcccgactta ctgagcgaag ataccgagca ggaacagaaa    540
aatggc                                                               546
```

<210> SEQ ID NO 109
<211> LENGTH: 546
<212> TYPE: DNA
<213> ORGANISM: Pantoea citrea

<400> SEQUENCE: 109

```
atgaaaaatg aaattattcg ggatgactct cctgctgaat acaatttgtc ccgcagaaag    60
gtgctgcttg gtggtcttat tttattaggc agtagttatc tgggcccatc gcttccggcc   120
tgggcagata cgttaaatga ccaggctacc atcgaccagt ttatgcagtt atcacaatta    180
cttgttaatc atcagcttga tccggtaaca gggcagcgtc tggctgctgc gatgatcagt    240
ggcaacatga ttacacggca acagataacc agtctgctgg ctgtagctca ggcccgtcag    300
gcaaaagtgg ttgaggattt tttctcagat attccacagg gtgagctgaa aaatgcggct    360
ctcagcatta tctctgcctg gtataaaggt gtactgattg atgcacccgg ggctgaggtg    420
tttgcttatg aaaaagcctt aatgtatcag ccgactatcg atgtgatgac cattccgacc    480
tatgccatta ccggccctaa tggctggagc tcccatgcag ctccgctggc cgatatgccg    540
gacttc                                                               546
```

<210> SEQ ID NO 110
<211> LENGTH: 501
<212> TYPE: DNA
<213> ORGANISM: Pantoea citrea

<400> SEQUENCE: 110

```
atgattgata tgttaaatat gatatcgcgc aggcgcatat tgcagggat gggggcattg      60 gccgccacaa cattacttcc gtctggtatt ttaccggcat tcgcggatac tcctgcaaac    120 agcgactta acgatatatc caggttgtta accggccgca atactttatc ggctgaattt    180
agtagcgcgc tttttctgc cttcacgaaa attgatagcc gcttcccaca gcaactggct    240
cgcctgaaac agtggatcac tgctaattcc gtcccggcag ctgacctgca gaaacgtctg    300
accgccgaca gctctgtcgc ggatctggcc ggattaccgg cactgattct gaccggctgg    360
tatctgggta ttgccggcag cggcgacaaa gctgtctgcg tcacctatgt cgatgctctg    420
gcaaatcagg aagttgcatc ggtgctgaac ccgcctacct acgcctatgg cgcctatggc    480
agttgggcca caaaaccttt t                                              501

<210> SEQ ID NO 111
<211> LENGTH: 585
<212> TYPE: DNA
<213> ORGANISM: Pantoea citrea

<400> SEQUENCE: 111
atgaataacc ataatgcacc tgaaacacag cctgagctga gtgaagaggg gttgcgtcgc      60
cgaaagctgt tcggacagac gggcgggttg gtggcttcct tcgccattgg ctccgcaata    120
gctggcagca cactcagtaa tggtgccaat gcagcaacca cttctgccgg gcctgatact    180
cagaccctga atcagtttat gaaaaacctcc cgtcttctta ccggccatca gaacctcgat    240
cttaccctgg gtcaacgtct gtacgtggca ttcagcgaga aggacccaca gttcattacc    300
cagctgtcag ccttgaatca gtggattgcc gataaacaac cggcagatgt agaggccctt    360
gacagccagt tgtcaggaca gccgctgcat gccctgatga tgtcggtgat taaaggctgg    420
tatctcggag tcattgatga cagtcaccat gccaaagtct atgcctatca gaatgccctg    480
atgtaccagg taccgcgtga tggcatggtc atccctacct atgcgcataa cggaccggac    540
tactggactg cagatccacc accggtcgat cgacttctga acttc                    585

<210> SEQ ID NO 112
<211> LENGTH: 540
<212> TYPE: DNA
<213> ORGANISM: Pantoea citrea

<400> SEQUENCE: 112
atgaataagg ctacacctgt cagccccggt gaaagacgac gctttattaa gttgttagca      60
gcatcaacgg tggcgggaac agtcagcagt ttattgccgg ccagatagc ctgggcaatt     120 gatgccgggc agccggcggt cgccggtttt ccggcattta tgacggtatc tgaaattatt    180
tgcggctatc cgactctgga taatgcactg ggcaaacgta ttttcagcct gatcagtgct    240
gagcacggtg atgcttctca gagtattgcc gagctgcaaa agcaactgaa tgcagatatg    300
tcctctgccg aaatgcaggc ggcgttgaaa acactggata ccccggcaca acagctgttc    360
agtgaaattt tgcgcggctg gcaaattggt attgtcggta gcggtaagca atcacaggtc    420
gtggcttatg agtacgcact gatgtacgcg ccgatttcag atgttgtcgt cctgccgacg    480
tttgcccgtg gtgaaccca ttactgggca taccctcctg tgattaagac cggaaagctg    540

<210> SEQ ID NO 113
<211> LENGTH: 552
<212> TYPE: DNA
<213> ORGANISM: Pantoea citrea

<400> SEQUENCE: 113
```

```
atgaaatttg ttatagatca ggaatctgat acaggggaaa tctctgcatc acgccgtagt        60
ttcctgataa aaataactgc attattagcc tcattcacct tgattccggc acatgctgtt       120
attaccactc cagctgacgt tggtgcatca gtgatatcgc agttacagac aaccgctcaa       180
ttcttaaccg aaagccagca ggatcctcaa ctgattatcc gtgcagctaa cgccctgcta       240
aaagttaaca gtaattttgc cggtgatctg caacagcttt cttcattgat tgcagacaat       300
cacatagcca acttaaaaga cctcaaaacc tcaaatcttt tgagggcaa accacagcaa        360 accgcgaaag acattttgtc tgccttatat cttggctatg ccggaacacc ggtgatgttg       420
tcatcggaag ataatgtcgt gtttgttgcc tatgcccagg cacgcacgta tcagctcacc       480
aaagatttca ccccggtccc cagctactcc cgctggaaaa gtggctactg ggcgcatttg       540
ccggcaggcg tt                                                           552
```

<210> SEQ ID NO 114
<211> LENGTH: 522
<212> TYPE: DNA
<213> ORGANISM: Pantoea citrea

<400> SEQUENCE: 114

```
atgaatctta cacgccgccg gttgctgacc ggctcggcgg ggctgatagt ggctggcgta        60
ttgtcgcaga ctctgtcagg ccgctatgcg ctggccagtc cgccactggc ttccgcagtc       120 gcccctccg ccggatttaa cacattatcg gtactgatta ccggtcagga taagcccgat        180
gccctgctgg cgcagcgcct gtacagctgg ttagcagccc atacttccgg tctggacagt       240
cagttggaga cgctgagctc actgctgcaa caacactctg atgctaatgg cagcaccctg       300
cttagcctga tgaaatcgca gccagaaaat attaatacac tctatcagtc actggtgtct       360
ggctggtatc tcggtgttgt cgggccactg ccgcgtccgg actgcatcgc cttcgaaaat       420
attgtcagct accaactgct caaacaatct gtgttaccgc caagctacgc gccgggccaa       480
ccaggattct gggtgcagcc acctgcgggg agagtacatg tc                          522
```

<210> SEQ ID NO 115
<211> LENGTH: 567
<212> TYPE: DNA
<213> ORGANISM: Pantoea citrea

<400> SEQUENCE: 115

```
atgaagcaaa tatttgagca aagtcatacc gatctaccgg aaaatggaac cggttccagt        60
cgcagaggat ttattaagtc cgctctggta ttaactgcca gtggtctggt cgcgtctctg       120
ccattgcgta gtttcgccag cagtgtggtt catggtggcg ataccactca ggactttatc       180
agtgtttcgc aggcaatcac cgaacacaaa catatcaacc cacagttagc cgctcatttc       240
ctgagtgcgt ttatcaaaag ggataatcag ttcagcagca aaattacccg acttgcgcag       300
ctctaccaga cgggtgatac agctattgta tttaaaaaca aagcggtagc cgccgggctt       360
ggcgattttc tgcagcagat cctgaccgcc tggtataccg aacgattggg tgatgactac       420
aaaggcactc tggtcgctta caaagaagcg ctgatgtacg acaccgtgag cgatggctta       480
gtggtcccga cctattgcgg caatggcccg ctttggtgga cagtgccggt ccccgaccca       540
ctcgatcctg aactgatcaa caacctg                                           567
```

<210> SEQ ID NO 116
<211> LENGTH: 20
<212> TYPE: DNA
<213> ORGANISM: Artificial Sequence
<220> FEATURE:

<223> OTHER INFORMATION: primer

<400> SEQUENCE: 116
agttagccgc tcatttcctg                                           20

<210> SEQ ID NO 117
<211> LENGTH: 17
<212> TYPE: DNA
<213> ORGANISM: Artificial Sequence
<220> FEATURE:
<223> OTHER INFORMATION: primer

<400> SEQUENCE: 117
agccgcctgg tttttac                                              17

<210> SEQ ID NO 118
<211> LENGTH: 24
<212> TYPE: DNA
<213> ORGANISM: Artificial Sequence
<220> FEATURE:
<223> OTHER INFORMATION: primer

<400> SEQUENCE: 118
gcgtctctgc cattgcgtag tttc                                      24

<210> SEQ ID NO 119
<211> LENGTH: 21
<212> TYPE: DNA
<213> ORGANISM: Artificial Sequence
<220> FEATURE:
<223> OTHER INFORMATION: primer

<400> SEQUENCE: 119
gggtgcggat cggtgtggtt t                                         21

<210> SEQ ID NO 120
<211> LENGTH: 24
<212> TYPE: DNA
<213> ORGANISM: Artificial Sequence
<220> FEATURE:
<223> OTHER INFORMATION: primer

<400> SEQUENCE: 120
aaagttggaa cctcttacgt gccg                                      24

<210> SEQ ID NO 121
<211> LENGTH: 24
<212> TYPE: DNA
<213> ORGANISM: Artificial Sequence
<220> FEATURE:
<223> OTHER INFORMATION: primer

<400> SEQUENCE: 121
caacagtact gcgatgagtg gcag                                      24

<210> SEQ ID NO 122
<211> LENGTH: 21
<212> TYPE: DNA
<213> ORGANISM: Artificial Sequence
<220> FEATURE:
<223> OTHER INFORMATION: primer

<400> SEQUENCE: 122
cggtactgag gcaatgtcat g                                         21

<210> SEQ ID NO 123

```
<211> LENGTH: 21
<212> TYPE: DNA
<213> ORGANISM: Artificial Sequence
<220> FEATURE:
<223> OTHER INFORMATION: primer

<400> SEQUENCE: 123
acggagagcc ggatattaca t                                              21

<210> SEQ ID NO 124
<211> LENGTH: 21
<212> TYPE: DNA
<213> ORGANISM: Artificial Sequence
<220> FEATURE:
<223> OTHER INFORMATION: primer

<400> SEQUENCE: 124
gcagccgcta cgcagataaa a                                              21

<210> SEQ ID NO 125
<211> LENGTH: 24
<212> TYPE: DNA
<213> ORGANISM: Artificial Sequence
<220> FEATURE:
<223> OTHER INFORMATION: primer

<400> SEQUENCE: 125
ctcggcgaaa aagaaccaga caag                                           24

<210> SEQ ID NO 126
<211> LENGTH: 20
<212> TYPE: PRT
<213> ORGANISM: Pantoea citrea

<400> SEQUENCE: 126

Gly Glu Tyr Leu Ala Arg Leu Gly Asp Cys Met Ala Cys His Thr Thr
 1               5                  10                  15

Ser Gly Arg Pro
         20

<210> SEQ ID NO 127
<211> LENGTH: 20
<212> TYPE: PRT
<213> ORGANISM: Pantoea citrea

<400> SEQUENCE: 127

Gly Gln Tyr Leu Ala Thr Ala Gly Asp Cys Ala Ala Cys His Thr Gln
 1               5                  10                  15

Pro Gly Gly Lys
         20

<210> SEQ ID NO 128
<211> LENGTH: 20
<212> TYPE: PRT
<213> ORGANISM: Pantoea citrea

<400> SEQUENCE: 128

Gly Arg Tyr Ile Ala Gln Leu Gly Asp Cys Thr Ala Cys His Thr Glu
 1               5                  10                  15

Pro Gly His Pro
         20

<210> SEQ ID NO 129
<211> LENGTH: 19
<212> TYPE: PRT
```

-continued

<213> ORGANISM: Pantoea citrea

<400> SEQUENCE: 129

Gly Glu Tyr Leu Ala Thr Ala Gly Asp Cys Val Ala Cys His Thr Ala
1               5                   10                  15

Ser Gly Pro

<210> SEQ ID NO 130
<211> LENGTH: 20
<212> TYPE: PRT
<213> ORGANISM: Pantoea citrea

<400> SEQUENCE: 130

Gly Glu Tyr Ile Ala Val Ala Gly Asp Cys Val Ala Cys His Thr Ala
1               5                   10                  15

Pro Gly Ser Lys
            20

<210> SEQ ID NO 131
<211> LENGTH: 20
<212> TYPE: PRT
<213> ORGANISM: Pantoea citrea

<400> SEQUENCE: 131

Gly Ala Tyr Leu Ala Arg Ala Gly Asp Cys Thr Ala Cys His Thr Glu
1               5                   10                  15

Ala Gly Gly Lys
            20

<210> SEQ ID NO 132
<211> LENGTH: 20
<212> TYPE: PRT
<213> ORGANISM: Pantoea citrea

<400> SEQUENCE: 132

Gly Glu Tyr Ile Ala Arg Leu Ser Asp Cys Thr Ala Cys His Thr Ala
1               5                   10                  15

Glu Gly Gly Gln
            20

<210> SEQ ID NO 133
<211> LENGTH: 20
<212> TYPE: PRT
<213> ORGANISM: Pantoea citrea

<400> SEQUENCE: 133

Gly Glu Tyr Leu Ala Arg Ala Gly Asp Cys Val Ala Cys His Thr Ser
1               5                   10                  15

Glu Gly Gly Gln
            20

<210> SEQ ID NO 134
<211> LENGTH: 20
<212> TYPE: PRT
<213> ORGANISM: Pantoea citrea

<400> SEQUENCE: 134

Gly Glu Tyr Leu Ala Arg Ala Gly Asp Cys Val Ala Cys His Thr Ala
1               5                   10                  15

Glu Gly Gly Lys
            20

```
<210> SEQ ID NO 135
<211> LENGTH: 20
<212> TYPE: PRT
<213> ORGANISM: Pantoea citrea

<400> SEQUENCE: 135

Gly Lys Tyr Leu Ala Thr Ala Gly Asp Cys Val Ala Cys His Thr Ala
 1               5                  10                  15

Pro Gly Gly Lys
         20

<210> SEQ ID NO 136
<211> LENGTH: 20
<212> TYPE: PRT
<213> ORGANISM: Pantoea citrea

<400> SEQUENCE: 136

Gly Lys Tyr Leu Ser Val Ala Ala Asp Cys Gly Ala Cys His Asn Ser
 1               5                  10                  15

Pro Thr Ser Gly
         20

<210> SEQ ID NO 137
<211> LENGTH: 20
<212> TYPE: PRT
<213> ORGANISM: Pantoea citrea

<400> SEQUENCE: 137

Gly His Tyr Leu Ala Ile Ala Ala Asp Cys Ala Ala Cys His Thr Asp
 1               5                  10                  15

Pro Gln Thr Lys
         20

<210> SEQ ID NO 138
<211> LENGTH: 20
<212> TYPE: PRT
<213> ORGANISM: Pantoea citrea

<400> SEQUENCE: 138

Gly Glu Tyr Leu Ala Arg Ala Gly Asp Cys Thr Ala Cys His Thr Ala
 1               5                  10                  15

Ala Gly Gly Ala
         20

<210> SEQ ID NO 139
<211> LENGTH: 20
<212> TYPE: PRT
<213> ORGANISM: Pantoea citrea

<400> SEQUENCE: 139

Gly Glu Gln Val Ala Thr Ala Ser Asp Cys Gln Ala Cys His Thr Ala
 1               5                  10                  15

Pro Gly Ser Lys
         20

<210> SEQ ID NO 140
<211> LENGTH: 19
<212> TYPE: PRT
<213> ORGANISM: Pantoea citrea
```

```
<400> SEQUENCE: 140

Gly Lys Tyr Leu Ser Val Ala Ala Asp Cys Ser Ala Cys His Asp Ser
1               5                   10                  15

Pro Asp His

<210> SEQ ID NO 141
<211> LENGTH: 20
<212> TYPE: PRT
<213> ORGANISM: Pantoea citrea

<400> SEQUENCE: 141

Gly Glu Tyr Leu Ala Lys Ala Ala Asp Cys Glu Val Cys His Thr Ala
1               5                   10                  15

Thr Gly Gly Gln
            20

<210> SEQ ID NO 142
<211> LENGTH: 20
<212> TYPE: PRT
<213> ORGANISM: Pantoea citrea

<400> SEQUENCE: 142

Gly Glu Tyr Leu Ala Thr Ala Ser Asp Cys Thr Ala Cys His Thr Ala
1               5                   10                  15

Pro Gly Gly Pro
            20

<210> SEQ ID NO 143
<211> LENGTH: 19
<212> TYPE: PRT
<213> ORGANISM: Pantoea citrea

<400> SEQUENCE: 143

Gly Glu Tyr Leu Ala Thr Ala Ser Asp Cys Ala Ala Cys His Thr Asp
1               5                   10                  15

Lys Gly Gly

<210> SEQ ID NO 144
<211> LENGTH: 20
<212> TYPE: PRT
<213> ORGANISM: Pantoea citrea

<400> SEQUENCE: 144

Gly Gln Tyr Leu Ser Val Ala Gly Asp Cys Ala Ala Cys His Thr Thr
1               5                   10                  15

Ser Gly Gly Lys
            20

<210> SEQ ID NO 145
<211> LENGTH: 20
<212> TYPE: PRT
<213> ORGANISM: Pantoea citrea

<400> SEQUENCE: 145

Leu Gly His Cys Ser Ser Cys His Thr Pro Arg Gly Val Ala Met Glu
1               5                   10                  15

Glu Lys Ala Leu
            20
```

```
<210> SEQ ID NO 146
<211> LENGTH: 20
<212> TYPE: PRT
<213> ORGANISM: Pantoea citrea

<400> SEQUENCE: 146

Leu Gly His Cys Gly Thr Cys His Thr Pro Arg Ala Gly Thr Leu Gln
1               5                   10                  15

Glu Lys Ala Leu
            20

<210> SEQ ID NO 147
<211> LENGTH: 14
<212> TYPE: PRT
<213> ORGANISM: Pantoea citrea

<400> SEQUENCE: 147

Leu Gly His Cys Ser Thr Cys His Thr Pro Lys Asn Met Leu
1               5                   10

<210> SEQ ID NO 148
<211> LENGTH: 20
<212> TYPE: PRT
<213> ORGANISM: Pantoea citrea

<400> SEQUENCE: 148

Leu Glu His Cys Gly Ala Cys His Thr Pro Arg Gly Ile Ala Phe Gln
1               5                   10                  15

Glu Lys Ala Ser
            20

<210> SEQ ID NO 149
<211> LENGTH: 14
<212> TYPE: PRT
<213> ORGANISM: Pantoea citrea

<400> SEQUENCE: 149

Leu Glu His Cys Ala Ala Cys His Thr Pro Lys Asn Met Leu
1               5                   10

<210> SEQ ID NO 150
<211> LENGTH: 20
<212> TYPE: PRT
<213> ORGANISM: Pantoea citrea

<400> SEQUENCE: 150

Leu Gly His Cys Ser Ser Cys His Thr Pro Arg Gly Ile Gly Met Gln
1               5                   10                  15

Glu Lys Ala Leu
            20

<210> SEQ ID NO 151
<211> LENGTH: 14
<212> TYPE: PRT
<213> ORGANISM: Pantoea citrea

<400> SEQUENCE: 151

Pro Gly His Cys Ala Ser Cys His Thr Ala Lys Asn Met Leu
1               5                   10

<210> SEQ ID NO 152
<211> LENGTH: 20
<212> TYPE: PRT
<213> ORGANISM: Pantoea citrea
```

```
-continued

<400> SEQUENCE: 152

Leu Gly His Cys Gly Ala Cys His Thr Pro Arg Ser Ile Thr Met Gln
1               5                   10                  15

Glu Lys Ala Leu
            20

<210> SEQ ID NO 153
<211> LENGTH: 20
<212> TYPE: PRT
<213> ORGANISM: Pantoea citrea

<400> SEQUENCE: 153

Leu Glu His Cys Gly Ala Cys His Thr Pro Arg Gly Ile Ala Phe Gln
1               5                   10                  15

Glu Lys Ala Leu
            20

<210> SEQ ID NO 154
<211> LENGTH: 14
<212> TYPE: PRT
<213> ORGANISM: Pantoea citrea

<400> SEQUENCE: 154

Leu Gly His Cys Thr Ser Cys His Thr Pro Lys Asn Met Leu
1               5                   10

<210> SEQ ID NO 155
<211> LENGTH: 15
<212> TYPE: PRT
<213> ORGANISM: Pantoea citrea

<400> SEQUENCE: 155

Leu Glu His Cys Asp Ala Cys His Thr Pro Arg Asn Phe Leu Met
1               5                   10                  15

<210> SEQ ID NO 156
<211> LENGTH: 15
<212> TYPE: PRT
<213> ORGANISM: Pantoea citrea

<400> SEQUENCE: 156

Leu Glu His Cys Gly Glu Cys His Thr Pro Arg Asn Thr Leu Met
1               5                   10                  15

<210> SEQ ID NO 157
<211> LENGTH: 15
<212> TYPE: PRT
<213> ORGANISM: Pantoea citrea

<400> SEQUENCE: 157

Leu Ala His Cys Ser Thr Cys His Ser Pro Arg Asn Gln Met Met
1               5                   10                  15

<210> SEQ ID NO 158
<211> LENGTH: 15
<212> TYPE: PRT
<213> ORGANISM: Pantoea citrea

<400> SEQUENCE: 158

Leu Ala His Cys Asp Thr Cys His Thr Pro Arg Gly Phe Met Met
1               5                   10                  15
```

```
<210> SEQ ID NO 159
<211> LENGTH: 15
<212> TYPE: PRT
<213> ORGANISM: Pantoea citrea

<400> SEQUENCE: 159

Leu Ala His Cys Asp Thr Cys His Thr Pro Arg Asn Ala Leu Met
1               5                   10                  15

<210> SEQ ID NO 160
<211> LENGTH: 15
<212> TYPE: PRT
<213> ORGANISM: Pantoea citrea

<400> SEQUENCE: 160

Leu Gly His Cys Glu Glu Cys His Thr Pro Arg Asn Leu Ala Met
1               5                   10                  15

<210> SEQ ID NO 161
<211> LENGTH: 15
<212> TYPE: PRT
<213> ORGANISM: Pantoea citrea

<400> SEQUENCE: 161

Leu Ala His Cys Thr Thr Cys His Thr Pro Arg Asn Leu Thr Met
1               5                   10                  15

<210> SEQ ID NO 162
<211> LENGTH: 15
<212> TYPE: PRT
<213> ORGANISM: Pantoea citrea

<400> SEQUENCE: 162

Ala Ala His Cys Ser Thr Cys His Thr Pro Arg Gly Pro Leu Met
1               5                   10                  15

<210> SEQ ID NO 163
<211> LENGTH: 15
<212> TYPE: PRT
<213> ORGANISM: Pantoea citrea

<400> SEQUENCE: 163

Leu Ala His Cys Ser Thr Cys His Thr Pro Arg Asn Ala Leu Met
1               5                   10                  15

<210> SEQ ID NO 164
<211> LENGTH: 25
<212> TYPE: PRT
<213> ORGANISM: Pantoea citrea

<400> SEQUENCE: 164

Asp Leu Thr Glu Gly Gln Thr Leu Tyr Leu Asn Asn Cys Gly Ala Cys
1               5                   10                  15

His Phe Val Asn Gly Leu Asp Ala Ala
            20                  25

<210> SEQ ID NO 165
<211> LENGTH: 25
<212> TYPE: PRT
<213> ORGANISM: Pantoea citrea
```

```
<400> SEQUENCE: 165

Asn Pro Thr Pro Gly Ala Gln Leu Tyr Val Asp Asn Cys Ser Ala Cys
1               5                   10                  15

His Gln Thr Ser Gly Lys Gly Val Gln
            20                  25

<210> SEQ ID NO 166
<211> LENGTH: 25
<212> TYPE: PRT
<213> ORGANISM: Pantoea citrea

<400> SEQUENCE: 166

Gln Met Val Asn Gly Lys Ala Ile Tyr Ala Asp Arg Cys Ser Ala Cys
1               5                   10                  15

His Val Ser Gln Gly Gln Gly Val Ser
            20                  25

<210> SEQ ID NO 167
<211> LENGTH: 25
<212> TYPE: PRT
<213> ORGANISM: Pantoea citrea

<400> SEQUENCE: 167

Ser Leu Gln Thr Gly Ala Glu Glu Tyr Met Asp Asn Cys Ala Ala Cys
1               5                   10                  15

His Arg Leu Asp Gly Lys Gly Tyr Ala
            20                  25

<210> SEQ ID NO 168
<211> LENGTH: 25
<212> TYPE: PRT
<213> ORGANISM: Pantoea citrea

<400> SEQUENCE: 168

Leu Met Gln Gln Gly Ala Asn Val Tyr Gln Ala Asn Cys Ser Ala Cys
1               5                   10                  15

His Asn Ser Lys Gly Arg Gly Ile Pro
            20                  25

<210> SEQ ID NO 169
<211> LENGTH: 25
<212> TYPE: PRT
<213> ORGANISM: Pantoea citrea

<400> SEQUENCE: 169

Asn Leu Asn Ser Gly Gln Met Leu Tyr Leu Asn Asn Cys Glu Ala Cys
1               5                   10                  15

His Leu Thr Asp Gly Gly Gly Ala Lys
            20                  25

<210> SEQ ID NO 170
<211> LENGTH: 25
<212> TYPE: PRT
<213> ORGANISM: Pantoea citrea

<400> SEQUENCE: 170

Gln Met Val Ser Gly Lys Lys Val Phe Glu Ser Gln Cys Ser Ala Cys
1               5                   10                  15

His Val Ser Asp Gly Ala Gly Ile Arg
            20                  25
```

```
<210> SEQ ID NO 171
<211> LENGTH: 25
<212> TYPE: PRT
<213> ORGANISM: Pantoea citrea

<400> SEQUENCE: 171

Asp Gln Arg Thr Gly Ala Ala Glu Tyr Val Asp Ser Cys Ala Ala Cys
 1               5                  10                  15

His Lys Thr Asp Gly Ser Gly Tyr Thr
            20                  25

<210> SEQ ID NO 172
<211> LENGTH: 25
<212> TYPE: PRT
<213> ORGANISM: Pantoea citrea

<400> SEQUENCE: 172

Val Ser Ala Thr Gly Ala Gln Val Tyr Leu Asp Asn Cys Ser Ala Cys
 1               5                  10                  15

His Arg Ser Asp Gly Lys Gly Tyr Asp
            20                  25

<210> SEQ ID NO 173
<211> LENGTH: 25
<212> TYPE: PRT
<213> ORGANISM: Pantoea citrea

<400> SEQUENCE: 173

Val Met Ala Arg Gly Gln Ser Ile Tyr Gln Ala Asn Cys Ser Ala Cys
 1               5                  10                  15

His Gln Ser Asp Gly Ala Gly Val Arg
            20                  25

<210> SEQ ID NO 174
<211> LENGTH: 23
<212> TYPE: PRT
<213> ORGANISM: Pantoea citrea

<400> SEQUENCE: 174

Pro Asp Ala Gly Trp Val Val Phe Ser Asn Ser Cys Ala Asn Cys His
 1               5                  10                  15

Gln Ala Asn Gly Glu Gly Ser
            20

<210> SEQ ID NO 175
<211> LENGTH: 26
<212> TYPE: PRT
<213> ORGANISM: Pantoea citrea

<400> SEQUENCE: 175

Asp Asp Ile Thr Gly Lys Ala Leu Tyr Asp Thr Thr Cys Ala Ser Cys
 1               5                  10                  15

His Gln Ser Ser Gly Ala Gly Thr Thr Asp
            20                  25

<210> SEQ ID NO 176
<211> LENGTH: 26
<212> TYPE: PRT
<213> ORGANISM: Pantoea citrea
```

```
<400> SEQUENCE: 176

Ser Thr Thr Asp Gly Ala Val Leu Phe Asp Ser Ser Cys Ala Ala Cys
1               5                   10                  15

His Gln Ser Ser Gly Gln Gly Ser Asp Asp
            20                  25

<210> SEQ ID NO 177
<211> LENGTH: 26
<212> TYPE: PRT
<213> ORGANISM: Pantoea citrea

<400> SEQUENCE: 177

Ser Leu Thr Ser Gly Ala Ala Leu Phe Ser Gly Ser Cys Ala Ser Cys
1               5                   10                  15

His Gln Pro Asp Gly Ala Gly Ser Lys Asn
            20                  25

<210> SEQ ID NO 178
<211> LENGTH: 26
<212> TYPE: PRT
<213> ORGANISM: Pantoea citrea

<400> SEQUENCE: 178

Gly Pro Met Ser Gly Ala Ile Leu Tyr Ser Gly Asn Cys Ala Ala Cys
1               5                   10                  15

His Thr Pro Ser Gly Ala Gly Ser Tyr Ser
            20                  25

<210> SEQ ID NO 179
<211> LENGTH: 26
<212> TYPE: PRT
<213> ORGANISM: Pantoea citrea

<400> SEQUENCE: 179

Ser Ala Pro Ser Gly Ala Val Leu Phe Asn Gly Asn Cys Ala Ser Cys
1               5                   10                  15

His Gly Thr Lys Gly Gln Gly Ile Gly Glu
            20                  25

<210> SEQ ID NO 180
<211> LENGTH: 26
<212> TYPE: PRT
<213> ORGANISM: Pantoea citrea

<400> SEQUENCE: 180

Gln Ser Gln Pro Gly Ala Val Val Phe Glu Gly Asn Cys Ser Thr Cys
1               5                   10                  15

His Gly Ala Glu Gly Ala Gly Ser Gly Gln
            20                  25

<210> SEQ ID NO 181
<211> LENGTH: 26
<212> TYPE: PRT
<213> ORGANISM: Pantoea citrea

<400> SEQUENCE: 181

Ala Lys Gln Gln Gly Leu Ala Leu Phe Gln Gly Asn Cys Ala Ser Cys
1               5                   10                  15

His Glu Ala Gly Gly Gln Gly Ser Arg Asp
            20                  25
```

```
<210> SEQ ID NO 182
<211> LENGTH: 23
<212> TYPE: PRT
<213> ORGANISM: Pantoea citrea

<400> SEQUENCE: 182

Asp Gly Ala Lys Leu Tyr Glu Ala His Cys Ser Thr Cys His Gln Ala
 1               5                  10                  15

Ser Gly Gln Gly Ser Asn Gly
            20
```

MULTIMERIC OXIDOREDUCTASES

SEQUENCE LISTING

The sequence listing submitted via EFS, in compliance with 37 C.F.R. §1.52(e), is incorporated herein by reference. The sequence listing text file submitted via EFS contains the file "30809US-C1C3_SEQLIST.txt" created on Apr. 2, 2013, which is 292,079 bytes in size.

FIELD OF THE INVENTION

The present invention relates to isolated naturally occurring and recombinant multimeric oxidoreductase complexes. More specifically the invention relates to the identification and use of multimeric oxidoreductase complexes isolated from *Pantoea citrea* wherein the complexes include a cytochrome C subunit and a dehydrogenase subunit.

BACKGROUND OF THE INVENTION

The synthesis and manufacture of L-ascorbic acid (AsA, vitamin C) has received considerable attention due to its relatively large market volume and high value as a vitamin and antioxidant. A chemical route, the Reichstein-Grussner method, from glucose to AsA, was first disclosed in 1934 (*Helv. Chim. Acta* 17:311-328). More recently bioconversion methods for the production of AsA intermediates have been disclosed and reference is made to Lazarus et al. (1989), Vitamin C: Bioconversion via a Recombinant DNA Approach", GENETICS AND MOLECULAR BIOLOGY OF INDUSTRIAL MICROORGANISMS, American Society for Microbiology, Washington D.C. edited by C. L. Hershberger; Crawford et al., (1980) *Advances in Carbohydrate Chemistry and Biochemistry* 37: 79-155 (1980); Anderson et al., (1985) *Sci.* 230: 144-149; and Sugisawa et al. (1990) *Agric. Biol. Chem.* 54:1201-1209.

A typical process for the manufacture of AsA is shown in FIG. 15. In general, the process begins with a metabolite used by a microorganism, e.g. D-glucose. Through enzymatic conversions, which may include D-glucose dehydrogenase, D-gluconate dehydrogenase, and 2-keto-D-gluconate dehydrogenase, the D-glucose undergoes a series of oxidative steps to yield 2,5-diketo-D-gluconate (2,5-DKG). Further the 2,5-DKG may be reduced to 2-keto-L-gulonic acid (2-KLG). This process may be carried out in microorganisms such as *Gluconobacter, Acetobacter, Erwinia* or *Pantoea*. Reference is made to various U.S. Patents disclosing parts of this overall conversion such as U.S. Pat. Nos. 3,790,444; 3,922,194; 3,959,076; 3,998,697; 4,245,049 and 5,008,193. Because of the commercial market for AsA, AsA intermediates independent of AsA, have become a material of economic and industrial importance and for that reason it would be desirable to increase microbial efficiency for enzymatic conversion of carbon substrates into AsA intermediates.

Compared to other bacterial organisms, the gram-negative Enterobacteria, *Pantoea citrea* has the ability to efficiently convert glucose and other sugars into different aldo and keto-sugar derivatives and particularly into the AsA intermediates 2,5-DKG and 2-KGL. In this invention, the genome of *Pantoea citrea* was analyzed to determine if there were unique properties of the microorganism that contributed to efficient sugar conversion. Analysis of the genome revealed that while the *Pantoea* genome is similar to other Enterobacteria, such as *Salmonella, Klebsiella* and *E. coli*, in certain respects, it contains a number of different genes, which provide additional sugar metabolism capabilities.

This invention is directed to the discovery that the *Pantoea citrea* genome includes a family of genes that code for membrane bound three-component oxidoreductase complexes. Specifically, it was discovered that the *P. citrea* genome includes 19 operons that code for membrane bound three-component oxidoreductase complexes and each of these complexes include a cytochrome C homologue subunit and a subunit having dehydrogenase activity. This is in contrast to other known microbial genomes, such as *Bacillus subtilis, E. coli* and *Pseudomonas aeruginosa. B. subtilis* and *E. coli* are not known to include multimeric oxidoreductase enzyme complexes containing cytochrome C homologs and *P. aeruginosa* is known to comprise one three-component multimeric complex containing a cytochrome C homologue.

SUMMARY OF THE INVENTION

In a first aspect, the invention is directed to isolated polynucleotides encoding cytochrome C (CytC) proteins and the CytC proteins encoded by said polynucleotides. Preferred CytC proteins include the amino acid sequences illustrated in FIGS. 4A-4B and 5A-5B.

In a second aspect, the invention is directed to isolated polynucleotides encoding dehydrogenases and the dehydrogenase proteins encoded by said polynucleotides. Preferred dehydrogenases include the amino acid sequences illustrated in FIGS. 2A-2C and 3A-3B.

In a third aspect, the invention is related to polynucleotides encoding multimeric oxidoreductase complexes, wherein the complex comprises a CytC subunit and a dehydrogenase subunit, and the multimeric complexes encoded by said polynucleotides.

In a fourth aspect, the invention is related to polynucleotides encoding multimeric oxidoreductase complexes comprising an operon including three subunits said subunits including a CytC subunit, a dehydrogenase subunit and a third subunit designated the gamma subunit.

In a fifth aspect, the invention is directed to an operon encoding an oxidoreductase complex, said operon comprising three coding regions, wherein the coding regions are the regions illustrated by the 19 operons in FIGS. 1A and 1B. In one embodiment of this aspect, the operon comprises the open reading frames (orfs) of orf 3653, orf 3652 and orf 3651. In a second embodiment of this aspect, the operon comprises the orfs of orf 2418, orf 2419 and orf 2420. In a third embodiment of this aspect, the operon comprises the orfs of orf 1840, orf 1841 and orf 1842. In a fourth embodiment of this aspect, the operon comprises the orfs of orf 2035, orf 2036 and orf 2037. In a fifth embodiment of this aspect, the operon comprises the orfs of orf 3687, orf 3688 and orf 3689.

In a sixth aspect, the invention concerns a vector comprising a polynucleotide encoding a CytC subunit, a dehydrogenase subunit or a multimeric oxidoreductase complex as defined herein. Further the invention is directed to host cells transformed with a vector of the invention. Preferred host cells include *Pantoea, Klebsiella* and *E. coli* cells.

In a seventh aspect, the invention is directed to a method of enhancing enzymatic oxidation of a carbon substrate in a host cell comprising transforming the host cell with a polynucleotide encoding a CytC subunit, a dehydrogenase subunit or a multimeric oxidoreductase complex as defined herein to obtain an altered host cell, wherein the polynucleotide is expressed; culturing the altered host cell under suitable culture conditions and allowing the oxidation of the substrate wherein said oxidation is enhanced compared to a corresponding unaltered host cell. In a preferred embodiment of this aspect the substrate is a polyol.

In an eighth aspect, the invention is directed to a method of enhancing enzymatic reduction of a carbon substrate in a host cell comprising transforming the host cell with a polynucleotide encoding a CytC subunit, a dehydrogenase subunit or a multimeric oxidoreductase complex as defined herein to obtain an altered host cell, wherein the polynucleotide is expressed; culturing the altered host cell under suitable culture conditions and allowing the reduction of the substrate wherein said reduction is enhanced compared to a corresponding unaltered host cell. In a preferred embodiment of this aspect the substrate is a polyol.

In a ninth aspect, the invention is directed to a method for enhancing the production of an AsA intermediate in a host cell. One embodiment of this aspect comprises introducing into a host cell a polynucleotide encoding a multimeric oxidoreductase complex including at least two subunits as defined herein to obtain an altered host cell, wherein the polynucleotide is expressed; culturing the altered host cell under suitable culture conditions and allowing the production of an AsA intermediate. In a second embodiment of this aspect, the AsA intermediate is preferably 2-KDG or 2,5-DKG. In another embodiment of this aspect, the polynucleotide encodes a multimeric oxidoreductase complex selected from the group consisting of a) SEQ ID NOs. 41, 5, and 23
b) SEQ ID NOs. 42, 4 and 22;
c) SEQ ID NOs. 39, 6 and 24;
d) SEQ ID NOs. 40, 3 and 29;
e) SEQ ID NOs. 57, 19 and 38;
f) sequences having at least 95%, 96%, 97%, 98% and 99% sequence identity to each of the sequences of a)-e) above; and
g) combinations of each of the sequences of a)-f) above.

BRIEF DESCRIPTION OF THE DRAWINGS

In FIG. 1A the order of the gamma, alpha and CytC subunits is preserved in the operon and this group of 10 operons is referred to herein as family 1. In FIG. 1B the order of the gamma, alpha and CytC subunits is not always preserved and this group of operons is referred to herein as family 2. The bold arrows indicate flanking genes in the same region of the respective open reading frame (off).

Figure 1A:
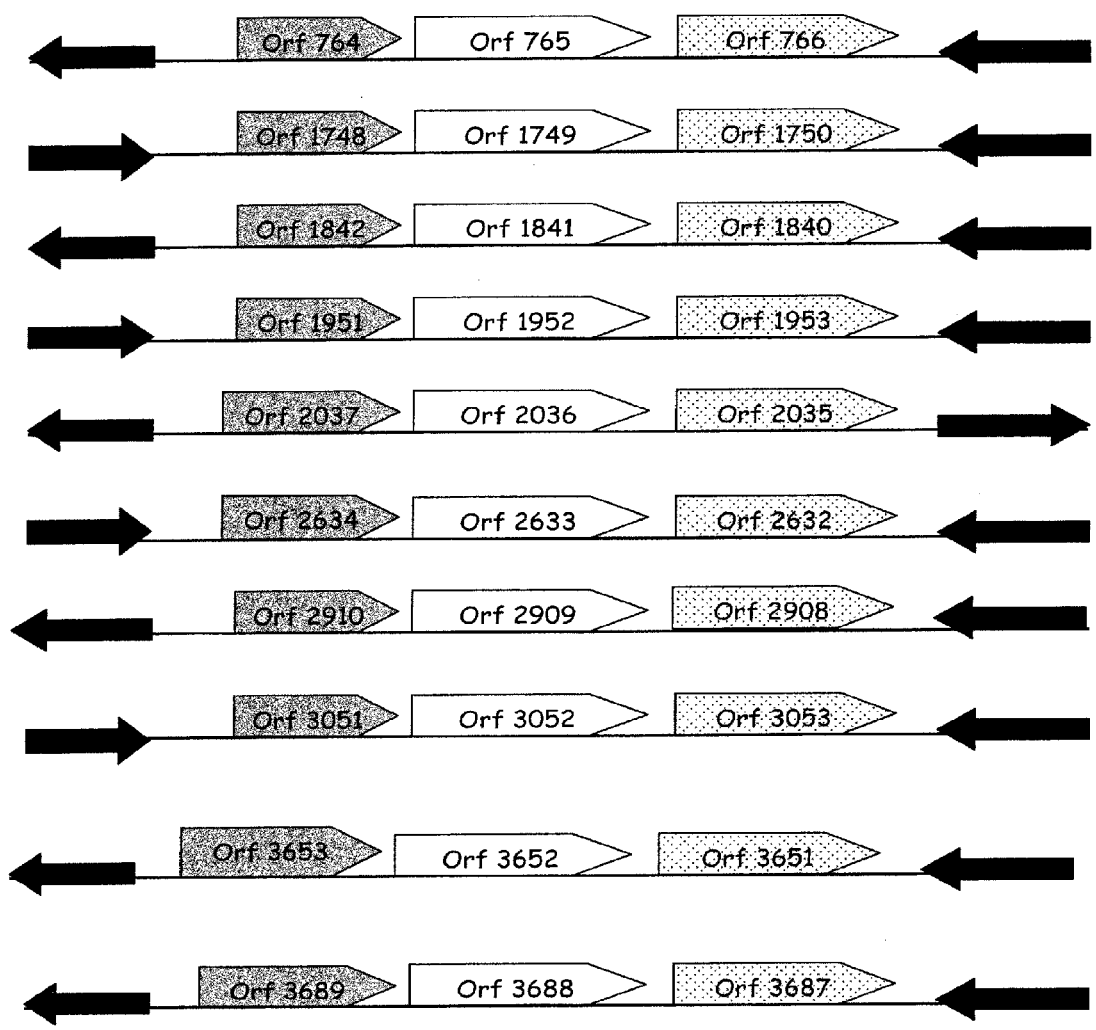
FIGS. 1A and 1B show a schematic representation of the 19 operons identified and sequenced according to the invention. Each operon is characterized by at least three open reading frames (Orfs) generally designated as the gamma subunit (shaded symbol), the alpha subunit (blank symbol) and the cytochrome C (CytC) subunit (stippled symbol). The alpha subunit has dehydrogenase activity.

Orf 764 corresponds to the amino acid sequence of SEQ ID NO: 46;
Orf 765 corresponds to the amino acid sequence of SEQ ID NO: 1;
Orf 766 corresponds to the amino acid sequence of SEQ ID NO: 20;
Orf 1748 corresponds to the amino acid sequence of SEQ ID NO: 48;
Orf 1749 corresponds to the amino acid sequence of SEQ ID NO: 8;
Orf 1750 corresponds to the amino acid sequence of SEQ ID NO: 27;
Orf 1842 corresponds to the amino acid sequence of SEQ ID NO: 41;
Orf 1841 corresponds to the amino acid sequence of SEQ ID NO: 5;
Orf 1840 corresponds to the amino acid sequence of SEQ ID NO: 23;
Orf 1951 corresponds to the amino acid sequence of SEQ ID NO: 44;
Orf 1952 corresponds to the amino acid sequence of SEQ ID NO: 7;
Orf 1953 corresponds to the amino acid sequence of SEQ ID NO: 28;
Orf 2037 corresponds to the amino acid sequence of SEQ ID NO: 42;
Orf 2036 corresponds to the amino acid sequence of SEQ ID NO: 4;
Orf 2035 corresponds to the amino acid sequence of SEQ ID NO: 22;
Orf 2634 corresponds to the amino acid sequence of SEQ ID NO: 45;
Orf 2633 corresponds to the amino acid sequence of SEQ ID NO: 9;
Orf 2632 corresponds to the amino acid sequence of SEQ ID NO: 26;
Orf 2910 corresponds to the amino acid sequence of SEQ ID NO: 43;
Orf 2909 corresponds to the amino acid sequence of SEQ ID NO: 2;
Orf 2908 corresponds to the amino acid sequence of SEQ ID NO: 21;
Orf 3051 corresponds to the amino acid sequence of SEQ ID NO: 47;
Orf 3052 corresponds to the amino acid sequence of SEQ ID NO: 10;
Orf 3053 corresponds to the amino acid sequence of SEQ ID NO: 25;
Orf 3653 corresponds to the amino acid sequence of SEQ ID NO: 39;
Orf 3652 corresponds to the amino acid sequence of SEQ ID NO: 6;
Orf 3651 corresponds to the amino acid sequence of SEQ ID NO: 24;
Orf 3689 corresponds to the amino acid sequence of SEQ ID NO: 40;
Orf 3688 corresponds to the amino acid sequence of SEQ ID NO: 3;
Orf 3687 corresponds to the amino acid sequence of SEQ ID NO: 29;
Orf 1219 corresponds to the amino acid sequence of SEQ ID NO: 52;
Orf 1220 corresponds to the amino acid sequence of SEQ ID NO: 18;
Orf 1221 corresponds to the amino acid sequence of SEQ ID NO: 34;
Orf 1982 corresponds to the amino acid sequence of SEQ ID NO: 55;
Orf 1983 corresponds to the amino acid sequence of SEQ ID NO: 14;
Orf 1984 corresponds to the amino acid sequence of SEQ ID NO: 35;
Orf 1957 corresponds to the amino acid sequence of SEQ ID NO: 53;
Orf 1956 corresponds to the amino acid sequence of SEQ ID NO: 31;
Orf 1955 corresponds to the amino acid sequence of SEQ ID NO: 16;
Orf 2418 corresponds to the amino acid sequence of SEQ ID NO: 57;
Orf 2419 corresponds to the amino acid sequence of SEQ ID NO: 19;
Orf 2420 corresponds to the amino acid sequence of SEQ ID NO: 38;

Orf 2448 corresponds to the amino acid sequence of SEQ ID NO: 12;
Orf 2447 corresponds to the amino acid sequence of SEQ ID NO: 50;
Orf 2446 corresponds to the amino acid sequence of SEQ ID NO: 32;
Orf 3043 corresponds to the amino acid sequence of SEQ ID NO: 54;
Orf 3042 corresponds to the amino acid sequence of SEQ ID NO: 13;
Orf 3041 corresponds to the amino acid sequence of SEQ ID NO: 37;
Orf 3397 corresponds to the amino acid sequence of SEQ ID NO: 58;
Orf 3398 corresponds to the amino acid sequence of SEQ ID NO: 56;
Orf 3399 corresponds to the amino acid sequence of SEQ ID NO: 15;
Orf 3400 corresponds to the amino acid sequence of SEQ ID NO: 36;
Orf 3676 corresponds to the amino acid sequence of SEQ ID NO: 51;
Orf 3675 corresponds to the amino acid sequence of SEQ ID NO: 17;
Orf 3674 corresponds to the amino acid sequence of SEQ ID NO: 33;
Orf 3820 corresponds to the amino acid sequence of SEQ ID NO: 30;
Orf 3819 corresponds to the amino acid sequence of SEQ ID NO: 49; and
Orf 3818 corresponds to the amino acid sequence of SEQ ID NO: 11.

FIGS. 2A-2C illustrate the amino acid sequences of the alpha subunits corresponding to the family 1 operons including SEQ ID NOs: 1-10.

FIGS. 3A-3B illustrate the amino acid sequences of the alpha subunits corresponding to the family 2 operons including SEQ ID NOs: 11-19.

FIGS. 4A-4B illustrate the amino acid sequences of the CytC subunits corresponding to family 1 operons, including SEQ ID NOs: 20-29.

FIGS. 5A-5B illustrate the amino acid sequences of the CytC subunits corresponding to family 2 operons, including SEQ ID NOs: 30-38.

FIGS. 6A-6B illustrate the amino acid sequences of the gamma subunit corresponding to family 1 operons, including SEQ ID NOs: 39-48.

FIG. 7 illustrates the amino acid sequences of the gamma subunit corresponding to family 2 operons, including SEQ ID NOs: 49-57.

FIG. 8 illustrates the amino acid sequence of Orf 3397 corresponding to SEQ ID NO: 58.

FIGS. 9A-9J illustrate the nucleic acid sequences (SEQ ID NOs. 59-68) encoding the amino acid sequences of the family 1 alpha subunits illustrated in FIGS. 2A-2C.

FIGS. 10A-10H illustrate the nucleic acid sequences (SEQ ID NOs. 69-77) encoding the amino acid sequences of the family 2 alpha subunits illustrated in FIGS. 3A-3B.

FIGS. 11A-11H illustrate the nucleic acid sequences (SEQ ID NOs 78-87) encoding the amino acid sequences of the family 1 CytC subunits illustrated in FIGS. 4A-4B.

FIGS. 12A-12H illustrate the nucleic acid sequences (SEQ ID NOs. 88-96) encoding the amino acid sequences of the family 2 CytC subunits illustrates in FIGS. 5A-5B.

FIGS. 13A-13E illustrate the nucleic acid sequences (SEQ ID NOs. 97-106) encoding the amino acid sequences of the family 1 gamma subunits illustrated in FIGS. 6A-6B.

FIGS. 14A-14C illustrate the nucleic acid sequences (SEQ ID NOs. 107-115) encoding the amino acid sequences of the family 1 alpha subunits illustrated in FIG. 7.

Figure 15:
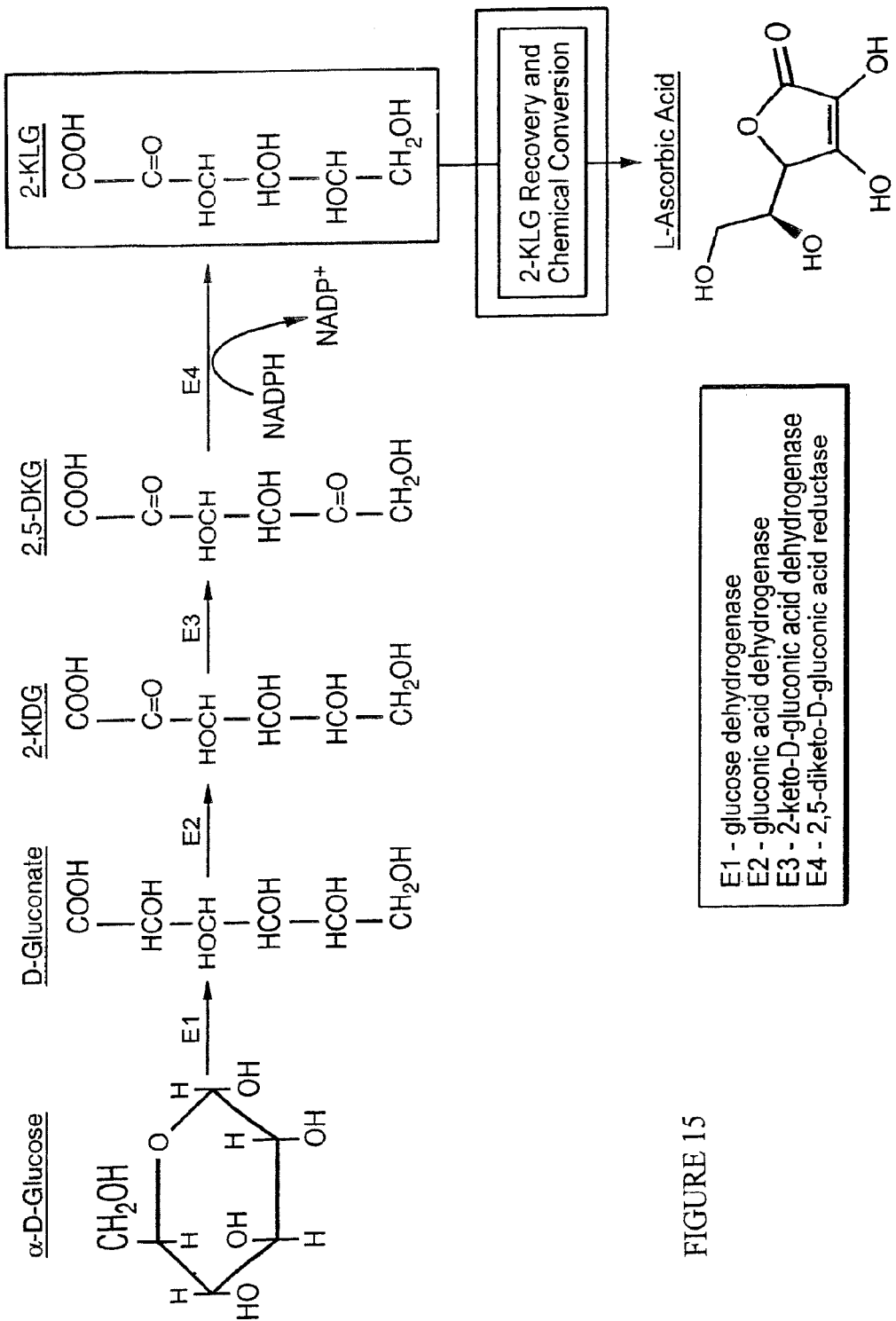

FIG. 15 is a schematic representation of a pathway to AsA intermediates. In this representation, the enzyme that converts glucose (GL) to gluconate (GA) is glucose dehydrogenase (GDH); the oxidative enzyme that converts GA to 2-KDG is gluconate dehydrogenase (GADH); the oxidative enzyme that converts 2 KDG to 2,5-DKG is 2-keto-D-gluconate dehydrogenase (KDGDH) and the reducing enzyme that converts 2,5-DKG to 2-KLG is 2,5-diketo-D-gluconic acid reductase (DKGR). The 2-KLG may then be recovered and chemically converted to L-Ascorbic Acid (AsA).

Figure 16A:

FIGS. 16A and 16B depict the three heme binding sites found in the CytC proteins illustrated in FIGS. 4 and 5 and corresponding to Orfs 766, 1840, 1953, 2035, 2632, 2908, 3053, 3651, 3687, 1750, 3820, 1956, 1984, 2420, 2446, 3041, 3400, 3674 and 1221.

DETAILED DESCRIPTION OF THE INVENTION

The practice of the present invention will employ, unless otherwise indicated, conventional techniques of molecular biology (including recombinant techniques), microbiology, cell biology and biochemistry, which are within the skill of one in the art. Such techniques are explained fully in the literature, such as MOLECULAR CLONING: A LABORATORY MANUAL, 2$^{nd}$ Ed. (Sambrook, J. et al., 1989) Cold Spring Harbor Laboratory Press; CURRENT PROTOCOLS IN MOLECULAR BIOLOGY (F. M. Ausubel et al., eds., 1987 and annual updates); OLIGONUCLEOTIDE SYNTHESIS (M. J. Gait ed., 1984); PCR: THE POLYMERASE CHAIN REACTION (Mullis et al., eds., 1994); MANUAL OF INDUSTRIAL MICROBIOLOGY AND BIOTECHNOLOGY, 2$^{nd}$ Ed. (A. L. Demain et al., eds 1999); MANUAL OF METHODS FOR GENERAL BACTERIOLOGY (P. Gerhardt et al., eds) pp. 210-213, American Society for Microbiology, Washington D.C., and BIOTECHNOLOGY: A TEXTBOOK OF INDUSTRIAL MICROBIOLOGY, 2$^{nd}$ Ed. (T. D. Brock, 1989) Sinauer Associates, Inc. Sunderland, Mass.

It is to be understood that this invention is not limited to the particular methodology, protocols and reagents described, as these may vary.

All patent and publications, including all sequences disclosed within such patents and publications, referred to herein are expressly incorporated by reference.

The headings provided herein are not limitations of the various aspects or embodiments of the invention, which can be had by reference to the specification as a whole.

A. Definitions

Unless defined otherwise herein, all technical and scientific terms used herein have the same meaning as commonly understood by one of ordinary skill in the art to which this invention pertains. Singleton, et al., DICTIONARY OF MICROBIOLOGY AND MOLECULAR BIOLOGY, 2D ED., John Wiley and Sons, New York (1994) and Hale & Marham, THE HARPER DICTIONARY OF BIOLOGY, Harper Perennial, N.Y. (1991) provide one of skill with general dictionaries of many of the terms used in this invention.

The following abbreviations apply as used herein: glucose (GL); D-gluconate (GA); 2-keto-D-gluconate (2-KDG); 2,5-diketo-D-gluconate (2,5-DKG), 2-keto-L-gulonic acid (2-KLG), L-idonic acid (IA), 5-keto-D-gluconate (5-KDG), ascorbic acid (AsA), glucose dehydrogenase (GDH), gluconate dehydrogenase (GADH), 2-keto-D-gluconate dehydrogenase (2-KDGDH), and 2,5-diketo-D-gluconate reductase (DKGR).

The term "AsA intermediate" encompasses any product in the pathway to AsA including but not limited to GA, 2-KDG, 2,5-DKG, 5-KDG, IA and 2-KLG.

Four stereoisomers of AsA are possible: L-ascorbic acid (AsA), D-araboascorbic acid (erythorbic acid), which shows vitamin C activity; L-araboascorbic acid, and D-xyloascorbic acid.

As used herein "GDH" or "a protein having GDH activity" refers to a protein which is capable of catalyzing the conversion of glucose (GL) stereoselectively to (GA).

The term "GADH" or "a protein having GADH activity" refers to a protein which is capable of catalyzing the conversion of GA stereoselectively to 2-KDG. For example, the multimeric oxidoreductase complexes comprising the operons selected from the group of a) orfs 1842, 1841 and 1840;
b) orfs 2037, 2036 and 2035;
c) orfs 3653, 3652 and 3651; and
d) orfs 3689, 3688 and 3687 have GADH activity.

The term "2-KDGDH" or "a protein having 2-KDGDH activity" refers to a protein which is capable of catalyzing the conversion of 2-KDG stereoselectively to 2,5-DKG, and 2,5-diketo-D-gluconate reductase (DKGR) refers to a protein capable of catalyzing the conversion of 2,5-DKG stereoselectively to 2-KLG.

An "oxidoreductase protein" as used herein broadly refers to an oxidation-reduction (redox) enzyme or electron-transferring protein that is involved in the transfer of electrons from an electron donor (the reducing agent or reductant) to an electron acceptor (the oxidizing agent or oxidant) such as molecular oxygen.

There are generally five different groups of oxidoreductase proteins:

a) Pyridine-linked dehydrogenases, which require either nicotinamide adeninedinucleotide (NAD) or nicotine adeninedinucleotide phosphate (NADP) as a coenzyme and catalyze the reversible transfer of electrons from a donor to the coenzyme to form either NADH or NADPH;

b) flavin-linked dehydrogenases, which contain flavin adenine dinucleotide (FAD) or flavin mononucleotide (FMN) as a prosthetic group;

c) iron-sulfur proteins, which contain two to eight atoms of iron and an equal number of acid-labile sulfur atoms wherein the iron atoms undergo Fe(II)—Fe(III) transitions;

d) cytochromes which contain iron-porphyrin prosthetic groups; and e) ubiquinone also known as coenzyme Q, a lipid soluble coenzyme.

Examples of pyridine-linked dehydrogenase systems include NAD linked glyceraldehyde 3-phosphate dehydrogenases; lactate dehydrogenases; glycerol 3-phosphate dehydrogenases; glutamate dehydrogenases and ethanol dehydrogenases, and NADP linked glucose 6-phosphate dehydrogenases and isocitrate dehydrogenases. Examples of flavin-linked dehydrogenase systems include NADH dehydrogenases, which contain FMN and catalyze the transfer of electrons from NADH; succinate dehydrogenases; dihydrolipoyl dehydrogenases; α-ketoglutarate dehydrogenases; acyl-CoA dehydrogenases; glucose oxidases and aldehyde oxidases. Examples of iron-sulfur proteins include NADH dehydrogenases; succinate dehydrogenases and ferredoxins. At least five different types of cytochromes have been identified based upon absorption spectral data and these include Cytochromes a, $a_3$, b, c, and $c_1$.

A "multimeric oxidoreductase complex" as used herein means at least two polypeptide subunits operably linked to one another having oxidoreductase activity. In one preferred embodiment, the multimeric oxidoreductase complex comprises three subunits organized in a single transcriptional unit known as an operon. A multimeric oxidoreductase complex according to the invention encompasses an oxidoreductase enzyme or protein within any one of the five oxidoreductase groups referred to above.

The term "subunit" as used herein generally refers to a discrete continuous part of an amino acid sequence that is equated with a particular function and is used interchangeably with the term domain.

The term "cytochrome C (CytC)" or "CytC protein" as used herein refers to an oxidoreductase having one or several heme c groups bound to the protein by one, or more commonly two, thioether bonds involving sulphydryl groups of cysteine residues. The fifth heme iron ligand is always provided by a histidine residue (Pettigrew et al. (1987) CYTOCHROMES C. BIOLOGICAL ASPECTS, Springer Verlag, Berlin; Moore et al. (1990) CYTOCHROMES C: EVOLUTIONARY, STRUCTURAL AND PHYSIOCHEMICAL ASPECTS, Springer Verlag, Berlin; and Ambler (1991), *Biochim. Biophys. Acta* 1058:42-47).

The term "CytC subunit" refers to a component of a multimeric oxidoreductase as referred to above, which has the structure and function of a CytC as defined above.

The term "dehydrogenase" as used herein refers to an enzyme that catalyzes an oxidoreductase reaction involving removal of hydrogen from one substrate and its transfer to another molecule, usually to a coenzyme or cofactor, such as NAD, NADP and FAD. Preferred dehydrogenases according to the meaning herein fall under the group designated pyridine-linked dehydrogenases which require either NAD or NADP as a coenzyme and catalyze the reversible transfer of electrons from a donor to a coenzyme to form either NADH or NADPH. and flavin-linked dehydrogenases, which contain flavin adenine dinucleotide (FAD) or flavin mononucleotide (FMN) as a cofactor.

The term "dehydrogenase subunit" used interchangeably with the term "alpha subunit" refers to a component of a multimeric oxidoreductase as referred to above, which has the structure and function of a dehydrogenase as defined above.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand.

As used herein the term "polypeptide" refers to a compound made up of amino acid residues linked by peptide bonds. "Amino acid" refers to all naturally occurring L-α-amino acids and includes norleucine, ornithine and homocysteine. The amino acids are identified by either the single-letter or three-letter designations. The term "protein" as used herein is synonymous with the term "polypeptide" and may also refer to two or more polypeptides. Thus the terms "protein", "peptide" and "polypeptide" are used interchangeably. It will be understood that, as a result of the degeneracy of the genetic code, a multitude of nucleotide sequences encoding a given protein may be produced.

A polynucleotide or polypeptide having a certain percentage (for example 80%, 85%, 90% or 95%) of sequence identity to another sequence means that, when aligned, that percentage of nucleotide bases or amino acid residues in a candidate sequence are identical with the nucleotide bases or amino acid residues of the reference sequence.

The term "operon" as used herein means a cluster of two or more structural genes which are transcribed as a single transcriptional unit from a common promoter. The genes of the operon code for proteins with related metabolic function. The genes comprising an operon may be adjacent genes.

The term "gene" means the segment of DNA involved in producing a polypeptide chain, that may or may not include regions preceding and following the coding region, e.g. 5' untranslated (5' UTR) or leader sequences and 3' UTR or "trailer" sequences as well as intervening sequences (introns) between individual coding segments (exons).

The term "open reading frame (orf)" is defined herein as a region of a gene that contains the coding sequence for a protein.

A "vector" refers to a nucleic acid construct designed for transfer of nucleic acid sequences into host cells. An "expression vector" refers to a vector that has the ability to incorporate and express heterologous DNA fragments in a foreign cell. Many prokaryotic and eukaryotic expression vectors are commonly available. Selection of appropriate expression vectors is within the knowledge of those having skill in the art. An expression vector is generally generated recombinantly or synthetically with a series of specific nucleic acid elements that permit transcription of a particular nucleic acid in a host cell. The expression vector may be incorporated into a plasmid, chromosome, mitochrondrial DNA, plastid DNA, virus or nucleic acid fragment. In the present specification "plasmid" and "vector" are often used interchangeably. Typically a vector includes among other sequences, a nucleic sequence to be transcribed and a promoter.

A "promoter" as used herein refers to a nucleic acid sequence that functions to direct transcription of a downstream gene or genes. The promoter will generally be appropriate to the host cell in which the desired gene is being expressed. The promoter together with other transcriptional and translational regulatory nucleic acid sequences are necessary to express a given gene. In general, the transcriptional and translational regulatory sequences include but are not limited to promoter sequences, ribosomal binding sites, transcriptional start and stop sequences translational start and stop sequence and enhancer or activator sequences.

The term "operably linked" means the nucleic acid is placed in a functional relationship with another nucleic acid sequence. For example, a promoter is operably linked to a coding sequence if it affects the transcription of the sequence. Generally, "operably linked" means the DNA sequences being linked are contiguous, and, in the case of a secretory leader, contiguous and in reading phrase. However, enhancers do not have to be contiguous. Linking may be accomplished by ligation at convenient restriction sites. If such sites do not exist, the synthetic oligonucleotide adaptors or linkers are used in accordance with conventional practice.

The terms "isolated" and "purified" as used herein refer to any enzyme, nucleic acid, protein, peptide or cofactor that is removed from at least one component which it is naturally associated.

"Chromosomal integration" is a process whereby an introduced nucleic acid is incorporated into a host chromosome. The process preferably takes place by homologous recombination.

"Recombinant host cells", "host cells", "cells" and "cell culture" are used interchangeably to designate individual cells, cell lines, cell cultures and harvested cells which have been or are intended to be transformed with a vector or construct of the invention. The term also includes the progeny of the cells originally receiving the vector or construct.

As used herein the term "recombinant" refers to a host cell that has a modification of its genome, e.g., as by the addition of nucleic acids not naturally occurring in the host organism or by a modification of nucleic acid naturally occurring in the host cell.

An "altered host cell" refers to a host cell comprising one or more introduced polynucleotides encoding a CytC subunit, a dehydrogenase subunit or a multimeric oxidoreductase complex according to the invention.

A "corresponding unaltered host cell" is a host cell which does not include the introduced polynucleotide encoding a CytC subunit, a dehydrogenase subunit or a multimeric oxidoreductase complex and is generally compared to an altered bacteria host when both are grown under essentially the same culture conditions.

The term "enhanced" refers to a level of activity, production or accumulation of an enzyme, substrate or product in an altered host cell compared to a corresponding unaltered host cell.

The term "polyol" means an alcohol molecule with numerous hydroxyl radicals. A keto-polyol derivative is a polyol that includes one or more keto groups in the polyol molecule. Non-limiting examples of polyols include glucose, gluconate, arabinose, arabitol, xylose, xylulose, xylitol, sucrose, sorbose, fructose, mannose, mannitol, meso-erythritol, L-erythrulose, idonate, cellobiose, lactose, idose, galactose, ribose, altose, maltose, erythrose, sorbitol, glycerol, 2-KDG, 5-keto-D-gluconic acid, 2-KLG, methanol, and erythorbic acid.

A "polyol dehydrogenase" is an enzyme which catalyzes an oxidoreductase reaction and uses a polyol substrate.

The term "carbon substrate" encompasses carbohydrates, including but not limited to glucose, gulose, lactose, sorbose, fructose, idose, galactose, mannose, ribose, xylose, arabinose, glycerol and dihydroxyacetone in either D or L form, or a combination of carbohydrates, such as glucose and fructose, and 6-carbon sugar acids, such as but not limited to 2-KLG, GA, idonic acid, 6-phosophogluconate, 2-KDG, 5-keto-D-gluconic acid, 2,3-L-diketogulonic acid, dehydroascorbic acid, erythorbic acid and mannonic acid. In some preferred embodiments the carbon substrate is a hexose or a pentose. The terms polyol and carbon substrate may be used interchangeably herein.

A "desired product" herein refers to a compound which is enzymatically derived from the carbon substrate. In particularly preferred embodiments, the desired product is an organic acid (i.e. gluconic acid and other AsA intermediates, succinic acid, citric acid, lactic acid.

As used herein, the family "Enterobacteriaceae" refers to bacterial strains having the general characteristics of being gram negative and being facultatively anaerobic. One embodiment of preferred Enterobacteriaceae strains are those that are able to produce 2,5-diketo-D-gluconic acid from D-glucose solutions. Included in the family of Enterobacteriaceae are the genus *Erwinia, Enterobacter, Gluconobacter, Klebsiella, Escherichia* and *Pantoea*.

In the present invention, a preferred Enterobacteriaceae strain is a *Pantoea* species. *Pantoea* include *P. agglomerans, P. dispersa, P. punctata, P. citrea, P. terrea, P. ananas* and *P. stewartii*. Particularly preferred are strains of *Pantoea citrea*. *Pantoea citrea* can be obtained from ATCC (Manassas, Va.) having ATCC accession number 39140, for example. *Pantoea citrea* has sometimes been referred to as *Erwinia citreus* or *Acetobacter cerinus*. Thus, it is intended that the genus *Pantoea* include species that have been reclassified, including but not limited to *Erwinia citreus* or *Acetobacter cerinus*.

In another embodiment, a preferred bacterial host strain is a strain from the Pseudomonadacea family. These bacterial strains are gram-negative and generally non-sporing. Included in this family are *P. aeruginosa, P. alcaligenes, P. fluorescens, P. denitrificans, P. putida, P. species* (sp), *P. syringae, P. oleovorans, P. mendocina, P. pseudoalcaligenes*.

Other preferred bacterial host cells are *Bacillus* cells. *Bacillus* includes all members known to those of skill in the art, including but not limited to *B. subtilis, B. licheniformis, B. lentus, B. brevis, B. stearothermophilus, B. alcalophilus, B. amyloliquefaciens, B. clausii, B. halodumas, B. megaterum, B. coagulans, B. circulans, B. lautus* and *B. thuringiensis*.

The term "heterologous" as used herein refers to nucleic acid or amino acid sequences not naturally occurring in the host cell. As used herein, the term "endogenous" refers to a nucleic acid naturally occurring in the host.

The term "expression" as used herein refers to the process by which a polypeptide or protein is produced based on the nucleic acid sequence of a gene. The process includes both transcription and translation. The term "overexpression" means an increased number of copies of the same gene product in a host cell.

The term "introduced" in the context of inserting a nucleic acid sequence into a cell, means "transformation", "transduction" or "transfection" and includes reference to the incorporation of a nucleic acid sequence into a prokaryotic cell where the nucleic acid may be incorporated into the genome of the cell (for example, chromosome, plasmid or mitochondrial DNA), converted into an autonomous replicon, or transiently expressed (for example, transfected mRNA or DNA).

The term "culturing" refers to fermentative bioconversion of a carbon substrate to a desired product within a culture vessel. In particularly preferred embodiments, culturing involves the growth of a bacterial organism under suitable conditions for the production of the desired products.

The term "enzymatic conversion" refers to the modification of a carbon substrate to a desired product by contacting the carbon substrate with an oxidoreductase enzyme complex or dehydrogenase enzyme encompassed by the invention. In some embodiments, contacting comprises exposing the carbon substrate to an altered bacterial host cell that expresses the multimeric oxidoreductase complex. In some embodiments the enzymatic conversion of a carbon substrate is an oxidation and may be part of an oxidative pathway yielding a desired product. In a nonlimiting example, gluconate is an oxidative product of the enzymatic conversion of glucose. In a further nonlimiting example the enzymatic conversion of glucose to 2-KDG and 2,5-DKG includes two or three enzymes in an oxidative pathway. In some embodiments the enzymatic conversion of a carbon substrate is a reduction.

It is well known in the art that many compounds mentioned in the present specification, such as gluconate may exist in a variety of ionization states depending upon the surrounding media. The use of the term, such as, for example gluconic acid, to designate such molecules is intended to include all ionization states of the organic molecule referred to. Thus, for example, both "D-gluconic acid" and D-gluconate" refer to the same organic moiety and are not intended to specify particular ionization states or chemical forms.

As used herein the term "comprising" and its cognates are used in their inclusive sense; that is, equivalent to the term "including" and its corresponding cognates. "A" "an" and "the" include plural references unless the context clearly dictate otherwise.

B. Embodiments

Polypeptides and Polynucleotides

Provided herein are isolated novel proteins, multimeric oxidoreductase complexes and nucleic acids. Also provided herein are the use of said isolated proteins, multimeric complexes and nucleic acids. Further provided are methods for the production of said proteins, multimeric complexes and nucleic acids in host cells. Moreover, in one aspect of the invention, the multimeric complexes have been identified as belonging within the family of oxidoreductases and include three subunits which are designated a cytochrome C subunit, a dehydrogenase subunit and a gamma subunit, said gamma subunit having an unidentified function.

CytC possesses a wide range of properties and functions in a large number of different redox reactions. (Pettigrew et al., CYTOCHROMES C. BIOLOGICAL ASPECTS, Springer Verlag, Berlin, Heidelberg, N.Y. (1987). While not meant to limit the invention in any manner, it is believed that one role of CytC is to provide substrate recognition specificity. Some properties of several CytCs are described herein:

class 1, having 1-2 heme groups with a redox potential of 0 to +500 mV;

class IIa, having 1 heme group with a redox potential of 0 to +150 mV;

class IIb with 1 heme group having a redox potential of 0 to +500 mV;

class III, having 3 to 16 heme groups with a redox potential of −400 to 0 mV;

class IV having 4 heme groups with a redox potential of −80 to +400 mV;

class $c_1$ having 1 heme group with a redox potential of +200 to +290 mV; and class c554 with various subgroups having between 1 and 2 heme groups with a redox potential of −276 to +47 mV.

Further proteins belonging to the CytC family include the following heme consensus sequence Cys-X-X-Cys-His wherein the His residue is one of the two axial ligands of the heme iron and X represents any amino acid residue (Mathews, F. S. (1985) *Prog. Biophys. Mol. Biol.* 45:1-56). Reference is also made to the PROSITE database of protein families and domains. In a preferred embodiment of the invention the CytCs have between 1 and 4 heme groups, that is at least 1, at least 2, at least 3, and at least 4 heme groups. In one preferred embodiment the CytCs of the invention have 3 heme groups. Reference is made to FIGS. 16A and 16B wherein 3 heme consensus sequences are illustrated for each of the CytC orfs.

In one embodiment, an isolated CytC will comprise any one of the amino acid sequences illustrated in FIGS. 4A-4B and 5A-5B (SEQ ID NOs. 20-38) and amino acid sequences having at least 90%, 93%, 95%, 96%, 97%, 98% and 99% identity to the amino acid sequences thereof.

In one preferred embodiment an isolated CytC comprises the amino acid sequence of any one of SEQ ID NOs. 20-29 (FIGS. 4A-4B) and amino acid sequences having at least 90%, 93%, 95%, 96%, 97%, 98% and 99% identity thereto. In one preferred embodiment an isolated CytC will comprise the amino acid sequence of SEQ ID NO. 22 and amino acid sequences having at least 90%, 93%, 95%, 96%, 97%, 98% and 99% identity thereto. In a second preferred embodiment an isolated CytC will comprise the amino acid sequence of SEQ ID NO. 23 and amino acid sequences having at least 90%, 93%, 95%, 96%, 97%, 98% and 99% identity thereto. In a third preferred embodiment an isolated CytC will comprise the amino acid sequence of SEQ ID NO. 24 and amino acid sequences having at least 90%, 93%, 95%, 96%, 97%, 98% and 99% identity thereto. In a fourth preferred embodiment an isolated CytC will comprise the amino acid sequence of SEQ ID NO. 29 and amino acid sequences having at least 90%, 93%, 95%, 96%, 97%, 98% and 99% identity thereto.

In another preferred embodiment an isolated CytC comprises the amino acid sequence of any one of SEQ ID NOs. 30-38 (FIGS. 5A-5B) and amino acid sequences having at least 90%, 93%, 95%, 96%, 97%, 98% and 99% identity thereto. More preferably an isolated CytC will comprise the amino acid sequence of SEQ ID NO. 38 and amino acid sequences having at least 90%, 93%, 95%, 96%, 97%, 98% and 99% identity thereto.

A further embodiment of the invention includes polynucleotides encoding a CytC according to the invention. Preferred polynucleotides include those having any one of the nucleic acid sequences illustrated in FIGS. 11A-11H and 12A-12H (SEQ ID NOs. 78-96) and nucleic acid sequences having at least 85%, 90%, 93%, 95%, 96%, 97%, 98% and 99% identity thereto.

In one embodiment the nucleic acid sequences which encode a CytC are any one of the sequences illustrated in SEQ ID NOs. 78-87 and nucleic acid sequences having at least 90%, 93%, 95%, 96%, 97%, 98% and 99% identity thereto. Preferably the nucleic acid sequence encoding a CytC is the sequence illustrated in SEQ ID NO. 80 and sequences having at least 90%, 93%, 95%, 97%, 98% and 99% identity thereto. Preferably the nucleic acid sequence encoding a CytC is the sequence illustrated in SEQ ID NO. 81 and sequences having at least 90%, 93%, 95%, 96%, 97%, 98% and 99% identity thereto.

Preferably the nucleic acid sequence encoding a CytC is the sequence illustrated in SEQ ID NO. 82 and sequences having at least 90%, 93%, 95%, 96%, 97%, 98% and 99% identity thereto. Also preferably the nucleic acid sequence encoding a CytC is the sequence illustrated in SEQ ID NO. 87 and, sequences having at least 90%, 93%, 95%, 96%, 97%, 98% and 99% identity thereto.

In another embodiment the nucleic acid sequences which encode a CytC are any one of the sequences illustrated in SEQ ID NOs. 88-96 and nucleic acid sequences having at least 90%, 93%, 95%, 96%, 97%, 98% and 99% identity thereto. Preferably the nucleic acid sequence encoding a CytC is the sequence illustrated in SEQ ID NO. 96 and sequences having at least 90%, 93%, 95%, 96%, 97%, 98% and 99% identity thereto.

In a further embodiment the invention includes a polynucleotide encoding a CytC having an amino acid sequence of any one of SEQ ID NOs. 20-38 or an amino acid sequence having at least 95%, 96%, 96%, 98% and 99% sequence identity thereto.

The CytC sequences having said identity can be identified by substantial nucleic acid and/or amino acid sequence homology to the CytC sequences outlined herein. Such homology can be based upon the overall nucleic acid or amino acid sequence, and is generally determined as outlined below, using either homology programs or hybridization conditions. Homology as used herein is in reference to sequence identity. Homology will be determined using standard techniques known in the art, including, but not limited to, the local homology algorithm of Smith & Waterman, (1981) *Adv. Appl. Math.* 2:482, by the homology alignment algorithm of Needleman & Wunsch, (1970) *J. Mol. Biol.* 48:443, by the search for similarity method of Pearson & Lipman, (1988) *PNAS USA* 85:2444-2448 by computerized implementations of these algorithms (GAP, BESTFIT, FASTA, and TFASTA in the Wisconsin Genetics Software Package, Genetics Computer Group, 575 Science Drive, Madison, Wis.), and the Best Fit sequence program described by Devereux, et al. (1984), *Nucl. Acid Res.* 12:387-395, preferably using the default settings, or by inspection. Also reference is made to the multiple sequence alignment program CLUSTRAL W (Thompson et al. (1994) *Nucleic Acid Research* 22: 4673-4680).

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, (1987) *J. Mol. Evol.* 35:351-360; the method is similar to that described by Higgins & Sharp (1989) *CABIOS* 5:151-153. Useful PILEUP parameters include a default gap weight of 3.00, a default gap length weight of 0.10, and weighted end gaps.

In a preferred embodiment, multiple sequence analysis is done using the Lasergene program suite from DNASTAR. DNASTAR uses the Clustal algorithm in the Megalign program version 3.12. Default multiple alignment parameters include a gap penalty of 10 and a gap length penalty of 10. Pairwise alignment default parameters include Ktuple of 1, a gap penalty of 3; a window of 5 and diagonals saved of 5.

Another example of a useful algorithm is the BLAST algorithm, described in Altschul, et al. (1990), *J. Mol. Biol.* 215, 403-410 and Karlin, et al. (1993), *PNAS USA* 90:5873-5787. A particularly useful BLAST program is the WU-BLAST-2 program which was obtained from Altschul, et al., *Methods in Enzymology* 266: 460-480 (1996); WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

An updated BLAST algorithm, is described in Altschul, et al. (1997), *Nucleic Acid Res.* 25, 3389-3402. A particularly useful BLAST program is Basic BLAST. Preferred parameters are Lambda K H 0.318, 0.135, 0.401 and gapped Lambda K H 0.27, 0.0470, 0.23, Matrix: BLOSUM62, gap penalties: existence 11, extension 1.

In one embodiment, nucleic acid encoding a CytC having at least 90%, 93%, 95%, 96%, 97%, 98% and 99% identity with a nucleic acid illustrated in any one of SEQ ID NOs. 78-96 is determined through hybridization studies. One embodiment involves nucleic acids which hybridize under high stringency conditions to the nucleic acid sequences identified in FIG. 11 or 12 or a complement thereof.

High stringency conditions are known in the art and see for example, Maniatis, et al., MOLECULAR CLONING: A LABORATORY MANUAL, 2d Edition (1989) and SHORT PROTOCOLS IN MOLECULAR BIOLOGY, ed Ausubel et al. Stringent conditions are sequence dependent and will be different in different circumstances. Longer sequences hybridize specifically at higher temperatures.

An extensive guide to the hybridization of nucleic acids is found in Tijssen, TECHNIQUES IN BIOCHEMISTRY AND MOLECULAR BIOLOGY—HYBRIDIZATION WITH NUCLEIC ACID PROBES, Overview of Principles of Hybridization and the Strategy of Nucleic Acid Assays (1993). Generally stringent conditions are selected to be about 5 to 10 degrees lower than the thermal melting point Tm for the specific sequence at a defined ionic strength and pH. The Tm is the temperature (under defined ionic strength, pH and nucleic acid concentration) at which 50% of the probes complementary to the target, hybridize to the target sequence at equilibrium. Stringent conditions will be those in which the salt concentration is less than about 1.0M sodium ion, typically about 0.01 to 1.0M sodium ion concentration (or other salts) at pH 7.0 to 8.3 and the temperature is at least 30° C. for short probes (e.g. for 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

Polymerase chain reaction PCR may also be used to screen for homologous sequences and reference is made to Chen et al., (1995) *Biotechniques* 18(4):609-612. Other methods include protein bioassay or immunoassay techniques which include membrane-based, solution-based or chip-based technologies for the detection and/or quantification of the nucleic acid or protein.

The invention also provides a method of using the polynucleotides which encode a CytC or dehydrogenase subunit as defined herein as probes for detecting other CytC or dehydrogenase proteins in microbial organisms. In one embodiment at least 10, 15, 20, 15, 30, 40, 50 or more contiguous bases from any one of SEQ ID NOs. 59-77 (for a dehydrogenase protein) or from any one of SEQ ID NOs. 78-96 (for a CytC protein) may be used as a probe. Further oligonucleotide probes useful in the present invention may comprise a nucleic acid sequence encoding a polypeptide having at least 5, 10, 15, 20, 25, 30 or more contiguous amino acid residues of any one of SEQ ID NOs. 1-19 (for a dehydrogenase protein) and any one of SEQ ID NOs. 20-38 (for a CytC protein). Hybridization studies as indicated above would be further used to identify CytC and dehydrogenase proteins in various microbial organisms and specifically in *Pantoea* species.

In another embodiment, the invention is directed to an isolated dehydrogenase comprising any one of the amino acid sequences illustrated in FIGS. 2A-2C and 3A-3B (SEQ ID NOs. 1-19) and amino acid sequences having at least 90%, 93%, 95%, 96%, 97%, 98% and 99% identity to the amino acid sequences thereof. In one embodiment the dehydrogenase is a flavin-linked dehydrogenase and in another embodiment the dehydrogenase is a pyridine-linked dehydrogenase. In a further embodiment the dehydrogenase exhibits polyol dehydrogenase (PDH) activity and reference is made to Nordling et al. (2002) *Eur. J. Biochem.* 269:4267-4276. The PDH family of dehydrogenases includes sorbitol dehydrogenases (Saito et al., (1997) *Appl. Environ. Microbiol.* 63:454-460).

In another embodiment an isolated dehydrogenase comprises the amino acid sequence of any one of SEQ ID NOs. 1-10 (FIGS. 2A-2C) and amino acid sequences having at least 90%, 93%, 95%, 96%, 97%, 98% and 99% identity thereto. Preferably an isolated dehydrogenase will comprise
a) the amino acid sequence of SEQ ID NO. 3 and amino acid sequences having at least 90%, 93%, 95%, 96%, 97%, 98% and 99% identity thereto;
b) the amino acid sequence of SEQ ID NO. 4 and amino acid sequences having at least 90%, 93%, 95%, 96%, 97%, 98% and 99% identity thereto;
c) the amino acid sequence of SEQ ID NO. 5 and amino acid sequences having at least 90%, 93%, 95%, 96%, 97%, 98% and 99% identity thereto; and
d) the amino acid sequence of SEQ ID NO. 6 and amino acid sequences having at least 90%, 93%, 95%, 96%, 97%, 98% and 99% identity thereto.

In another preferred embodiment an isolated dehydrogenase according to the invention comprises the amino acid sequence of any one of SEQ ID NOs. 11-19 (FIGS. 3A-3B) and amino acid sequences having at least 90%, 93%, 95%, 96%, 97%, 98% and 99% identity thereto. Preferably an isolated dehydrogenase will comprise the amino acid sequence of SEQ ID NO. 19. In one preferred embodiment the dehydrogenase is a flavin-linked dehydrogenase.

A further embodiment of the invention includes isolated polynucleotides encoding a dehydrogenase according to the invention. Preferred polynucleotides include those having any one of the nucleic acid sequences illustrated in FIGS. 9A-9J and 10A-10H (SEQ ID NOs. 59-77) and nucleic acid sequences having at least 85%, 90%, 93%, 95%, 96%, 97%, 98% and 99% identity thereto.

In one embodiment the nucleic acid sequences which encode a dehydrogenase are any one of the sequences illustrated in SEQ ID NOs. 59-68 (FIGS. 9A-9J) and nucleic acid sequences having at least 85%, 90%, 93%, 95%, 96%, 97%, 98% and 99% identity thereto. Preferably the nucleic acid sequence encoding a dehydrogenase is
a) the sequence illustrated in SEQ ID NO. 61 and sequences having at least 90%, 93%, 95%, 96%, 97%, 98% and 99% identity thereto;
b) the sequence illustrated in SEQ ID NO. 62 and sequences having at least 90%, 93%, 95%, 96%, 97%, 98% and 99% identity thereto;
c) the sequence illustrated in SEQ ID NO. 63 and sequences having at least 90%, 93%, 95%, 97%, 96%, 98% and 99% identity thereto; and
d) the sequence illustrated in SEQ ID NO. 64 and sequences having at least 90%, 93%, 95%, 96%, 97%, 98% and 99% identity thereto.

In another embodiment the nucleic acid sequences which encode a dehydrogenase according to the invention are any one of the sequences illustrated in SEQ ID NOs. 69-77 (FIGS. 10A-10H) and nucleic acid sequences having at least 85%, 90%, 93%, 95%, 96%, 97%, 98% and 99% identity thereto. One preferred embodiment comprises the nucleic acid sequence having the sequence illustrated in SEQ ID NO. 77.

In a further embodiment the invention includes a polynucleotide encoding a dehydrogenase having an amino acid sequence of any one of SEQ ID NOs. 1-19 or an amino acid sequence having at least 95%, 96%, 96%, 98% and 99% sequence identity thereto.

Sequence identity is generally determined as outlined above for CytC sequences using either homology programs or hybridization conditions.

Dehydrogenase assays are well known and may be adopted from the methods described in Bouvet et al. (1989) *Int. J. Syst. Bacteria* 39:61-67 using cells grown on MGY supplemented with 2-KDG. Reference is also made to Shinagawa and Ameyama (1982) *Meth. Enzymol.* 89:194-198.

Oxidoreductase Complexes:

In one embodiment of the invention an isolated multimeric oxidoreductase complex includes at least two subunits and the complex is coded for by an operon comprising at least two genes. The subunits include a CytC subunit and a dehydrogenase subunit as defined herein. In another embodiment the multimeric oxidoreductase complex comprises three subunits of different molecular weights which are coded for by an operon comprising at least three genes. The subunits include a CytC subunit, a dehydrogenase subunit and a third subunit which is defined by a nucleic acid encoding an amino acid sequence as set forth in any one of SEQ ID NOs. 39-57 (FIGS. 6A-6B and 7) or an amino acid sequence having at least 95%, 96%, 97%, 98% and 99% identity thereto.

Preferred isolated multimeric oxidoreductase complexes include (a) a CytC subunit having an amino acid sequence of any one of SEQ ID NOs. 20-38 (FIGS. 4A-4B and 5A-5B)

and amino acid sequences having at least 90%, 93%, 95%, 96%, 97%, 98% and 99% identity to the amino acid sequences thereof and (b) a dehydrogenase subunit having an amino acid sequence of any one of SEQ ID NOs. 1-19 (FIGS. 2A-2C and 3A-3B) and amino acid sequences having at least 90%, 93%, 95%, 96%, 97%, 98% and 99% identity thereto. In one preferred embodiment the CytC subunit of the multimeric oxidoreductase complex will comprise an amino acid sequence selected from the group consisting of SEQ ID NO. 22, SEQ ID NO. 23, SEQ ID NO. 24, SEQ ID NO. 29, SEQ ID NO. 38, and an amino acid sequence having at least 95%, 96%, 97%, 98% and 99% identity thereto. In another preferred embodiment the dehydrogenase subunit of the multimeric oxidoreductase complex will comprise an amino acid sequence selected from the group consisting of SEQ ID NO. 3, SEQ ID NO. 4, SEQ ID NO. 5, SEQ ID NO. 6, SEQ ID NO. 19 and an amino acid sequence having at least 95%, 96%, 97%, 98%, 99% sequence identity thereto.

In another embodiment the isolated multimeric oxidoreductase complex further comprises a third subunit having an amino acid sequence of any one of SEQ ID NOs. 39-57 (FIGS. 6A-6B and 7) and an amino acid sequence having at least 90%, 93%, 95%, 96%, 97%, 98% and 99% identity thereto. In one embodiment the third subunit will comprise an amino acid sequence from any one of SEQ ID NOs. 39-48 and an amino acid sequence having at least 90%, 93%, 95%, 96%, 97%, 98% and 99% sequence identity thereto. According to this embodiment, the third subunit will comprise about 220-265 amino acid residues, also about 225-255 amino acid residues and about 235 to 250 amino acid residues. In another preferred embodiment the third subunit will comprise an amino acid sequence from any one of SEQ ID NOs. 49-57 and an amino acid sequence having at least 90%, 93%, 95%, 96%, 97%, 98% and 99% sequence identity thereto. According to this embodiment, the third subunit will comprise about 155 to 215 amino acid residues, also about 165 to 205 amino acid residues and about 170 to 200 amino acid residues. In a preferred embodiment, the third subunit of the multimeric oxidoreductase complex will comprise an amino acid sequence selected from the group consisting of SEQ ID NO. 39, SEQ ID NO. 40, SEQ ID NO, 41, SEQ ID NO. 42, SEQ ID NO. 57 and an amino acid sequence having at least 90%, 93%, 95%, 96%, 97%, 98% and 99% sequence identity thereto.

In another embodiment of the invention an isolated multimeric oxidoreductase complex is encoded by a) a first polynucleotide coding for a CytC subunit having an amino acid sequence of anyone of SEQ ID NOs. 20-38 and amino acid sequences having at least 90%, 93%, 95%, 96%, 97%, 98% and 99% identity to the amino acid sequences thereof and (b) a second polynucleotide coding for a dehydrogenase subunit having an amino acid sequence of any one of SEQ ID NOs. 1-19 and amino acid sequences having at least 90%, 93%, 95%, 96%, 97%, 98% and 99% identity thereto. The isolated multimeric oxidoreductase may further be encoded by a third polynucleotide coding for a third subunit having an amino acid of any one of SEQ ID NOs. 39-57 and amino acid sequence having at least 90%, 93%, 95%, 96%, 97%, 98% and 99% identity thereto. In one preferred embodiment the first polynucleotide will encode a CytC subunit having the amino acid sequence of SEQ ID NO. 24, SEQ ID NO. 38 or an amino acid sequence having at least 98% identity thereto. In another preferred embodiment the second polynucleotide will encode a dehydrogenase subunit having the amino acid sequence of SEQ ID NO. 6, SEQ ID NO. 19 or an amino acid sequence having at least 98% sequence identity thereto.

In yet another embodiment the isolated multimeric oxidoreductase complex will be encoded by a) a first polynucleotide encoding a CytC subunit, said polynucleotide having a nucleic acid sequence set forth in any one of SEQ ID NOs. 28-96 and nucleic acid sequences having at least 90%, 93%, 95%, 96%, 97%, 98% and 99% identity thereto and b) a second polynucleotide encoding a dehydrogenase subunit, said polynucleotide having a nucleic acid sequence set forth in any one of SEQ ID NOs. 59-77 and nucleic acid sequences having at least 90%, 93%, 95%, 96%, 97%, 98% and 99% identity thereto. Further the multimeric oxidoreductase complex will be encoded by c) a third polynucleotide encoding a third subunit, said third polynucleotide having a nucleic acid sequence set forth in any one of SEQ ID NOs. 97-115 (FIGS. 13A-13E and 14A-14C) and nucleic acid sequence having at least 90% 93%, 95%, 96%, 97%, 98% and 99% sequence identity thereto.

In one embodiment the CytC subunit represents the last gene in the multimeric oxidoreductase complex operon. In another embodiment, the dehydrogenase subunit is represented by the subunit having the greatest molecular weight in the multimeric oxidoreductase complex.

Other preferred isolated multimeric oxidoreductase complexes comprise any one of the 19 operons identified in FIGS. 1A and B. More specifically,
(1) SEQ ID NOs: 46, 1 and 20;
(2) SEQ ID NOs: 48, 8 and 27;
(3) SEQ ID NOs: 41, 5 and 23;
(4) SEQ ID NOs: 44, 7 and 28;
(5) SEQ ID NOs: 42, 4 and 22;
(6) SEQ ID NOs: 45, 9 and 26;
(7) SEQ ID NOs: 43, 2 and 21;
(8) SEQ ID NOs: 47, 10 and 25;
(9) SEQ ID NOs: 39, 6 and 24;
(10) SEQ ID NOs: 40, 3 and 29;
(11) SEQ ID NOs: 52, 18 and 34;
(12) SEQ ID NOs: 55, 14 and 35;
(13) SEQ ID NOs: 53, 31 and 16;
(14) SEQ ID NOs: 57, 19 and 38;
(15) SEQ ID NOs: 12, 50 and 32;
(16) SEQ ID NOs: 54, 13 and 37;
(17) SEQ ID NOs: 58, 56, 15 and 36;
(18) SEQ ID NOs: 51, 17 and 33;
(19) SEQ ID NOs: 30, 49 and 11; and
(20) operons having subunits with at least 90%, 93%, 95% 96%, 97%, 98%, and 99% sequence identity to the subunits of operons (1)-(19).

In one preferred embodiment the multimeric oxidoreductase complex has 2-KDGDH activity and comprises operon (14) FIG. 1, which includes the subunits having the amino acid sequences of SEQ ID NO. 57, SEQ ID NO. 19 and SEQ ID NO. 38 and sequences having at least 95%, 96%, 97%, 98% and 99% identity thereto.

In another preferred embodiment the multimeric oxidoreductase complex has GADH activity and comprises an operon selected from the group consisting of
a) operon (3) which includes the subunits having an amino acid sequence of SEQ ID NOs: 41, 5 and 23;
b) operon (5) which includes the subunits having an amino acid sequence of SEQ ID NOs: 42, 4 and 22;
c) operon (9) which includes the subunits having an amino acid sequence of SEQ ID NOs: 39, 6 and 24;
d) operon (10) which includes the subunits having an amino acid sequence of SEQ ID NOs: 40, 3 and 29; and
e) operons having subunits with at least 95%, 96%, 97%, 98%, and 99% sequence identity to each of the subunits of operons (3), (5), (9), or (10).

In yet another preferred embodiment of the multimeric oxidoreductase complex, the subunits comprising the operons of operon (3), operon (5), operon (9) and operon (10) may be mixed to from new operons. For example, SEQ ID NO. 6 which represents the dehydrogenase subunit of operon (9) could be combined with a) SEQ ID NO. 23, which represents the CytC subunit of operon (3); b) SEQ ID NO. 22, which represents the CytC subunit of operon (5) or c) SEQ ID NO. 29, which represents the CytC subunit of operon (10).

The isolated multimeric oxidoreductase complexes described above are preferably encoded by polynucleotides having the nucleic acid sequences set forth as follows:
(1) SEQ ID NOs: 104, 59 and 78;
(2) SEQ ID NOs: 106, 66 and 85;
(3) SEQ ID NOs: 99, 63 and 81;
(4) SEQ ID NOs: 102, 95 and 86;
(5) SEQ ID NOs: 100, 62 and 80;
(6) SEQ ID NOs: 103, 67 and 84;
(7) SEQ ID NOs: 101, 60 and 79;
(8) SEQ ID NOs: 105, 68 and 83;
(9) SEQ ID NOs: 97, 64 and 82;
(10) SEQ ID NOs: 98, 61 and 87;
(11) SEQ ID NOs: 110, 76 and 92;
(12) SEQ ID NOs: 113, 72 and 93;
(13) SEQ ID NOs: 111, 89 and 74;
(14) SEQ ID NOs: 115, 77 and 96;
(15) SEQ ID NOs: 70, 108 and 90;
(16) SEQ ID NOs: 112, 71 and 95;
(17) SEQ ID NOs: 114, 73 and 94;
(18) SEQ ID NOs: 109, 75 and 91;
(19) SEQ ID NOs: 88, 107 and 69:
and sequences having at least 90%, 93%, 95% 96%, 97%, 98%, and 99% sequence identity to the sequences of (1)-(19).

Preferred multimeric oxidoreductase complexes include complexes having identical or similar activity to known GADHs (Matsushita, et al. (1982) METHODS IN ENZYMOLOGY 89: 187-193; Yum et al. *J. of Bacteriol.* (1997) 179:6566-6572; Matsushita et al. (1979), *J. Biochem.* 85:1173; and Kulbe et al. (1987), Ann. N.Y. Acad. Sci. 506:552) and to known 2-KDGDHs (Shinagawa et al. (1982) *Methods in Enzymology* 89: 194-198; Pujol et al. (2000) *J. Bacteriol.* 182:2230-2237 and Stroshane (1977) *Biotechnol. BioEng* 19:459).

Figure 1B:
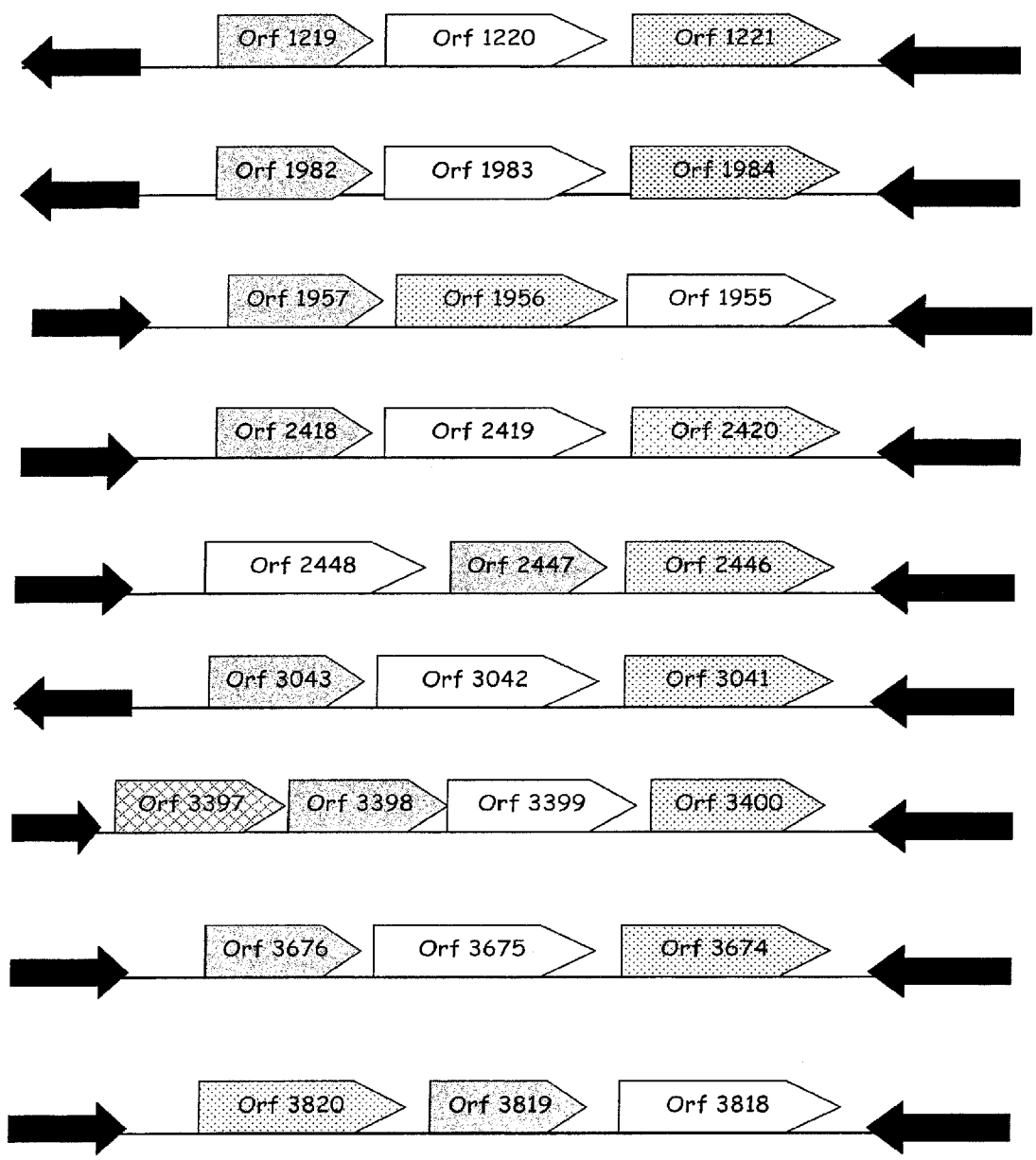

The various orfs of the operons as listed in FIGS. 1A and 1B may be subject to in vitro recombination, wherein fragments of the genes provide a means of generating new oxidoreductase proteins having improved enzyme activity, stability or altered substrate specificity, for example. In vitro recombination may be accomplished by various well known means such as by DNA shuffling and variations of this technique (Stemmer W. P. (1994) *PNAS* USA 91:10747-10751; Stemmer W. P. (1994) *Nature* 370:389-391; Zhao et al., (1999) *Protein Eng.* 12: 47-53; Zhao et al., (1998) *Nucleic Acids Res.* 26: 681-683 and Arnold et al. (1997) *Adv. Biochem. Eng. Biotechnol* 58: 1-14.). DNA shuffling relies on homologous recombination during PCR reassembly of gene fragments from multiple parent sequences. Sequence crossovers are generated at points of high sequence identity.

Other in vitro recombination techniques include those described in Wells et al., (1985) *Gene* 34: 315-323 and Wang and Malcom (1999) *Biotechniques* 26: 680-682. Those skilled in the art are also aware of non-homologous random recombination to generate new gene variants and reference is made to Bittker et al., (2002) *Nat. Biotech.* 20:1024-1029).

Vectors:

Further the invention pertains to host cells transformed with a vector comprising a polynucleotide encoding a CytC subunit, a dehydrogenase subunit or a multimeric oxidoreductase complex as described herein. Plasmids which can be used as vectors in bacterial organisms are well known and reference is made to Maniatis et al., MOLECULAR CLONING: A LABORATORY MANUAL, 2nd Ed. (1989); Sambrook et al. MOLECULAR CLONING: A LABORATORY MANUAL 2nd Ed. (1989) and Bron, S. Chapter 3, Plasmids in MOLECULAR BIOLOGY METHODS FOR BACILLUS, Eds. Harwood and Cutting (1990) John Wily & Sons Ltd.

One preferred plasmid for the introduction of polynucleotides encoding non-naturally occurring proteins into a strain of Enterobacteriaceae is RSF1010, a moblizable, but not self transmissible plasmid which has the capacity to replicate in a broad range of bacterial hosts, including gram negative and gram positive bacteria (Frey et al., (1989), The Molecular Biology of IncQ Plasmids, In: Thomas (Ed.) PROMISCUOUS PLASMIDS OF GRAM NEGATIVE BACTERIA, Academic Press, London pp. 79-94 and Frey et al. (1992) *Gene* 113:101-106).

Promoters useful with the polynucleotides encoding the CytC subunit, the dehydrogenase subunit, a multimeric oxidoreductase complex or any of the operons disclosed herein include the native promoter of the operon. However, both synthetic promoters and hybrid promoters may also be useful. One example of a useful hybrid promoter is a tac promoter, which is a hybrid of the trp and lac promoters. Promoters are well known in the art and reference is made to Sommer et al. (2000) *Microbiol.* 146:2643-2653; Brosius et al., (1985) *J. Biol. Chem.* 260:3539; Russell and Bennett (1982) *Gene* 20: 231; Mulligan et al., (1985) *J. Biol. Chem.* 260: 3529; Deuschle et al., (1986) *EMBO J.* 5:2987-2994; Amann et al. (1983) *Gene* 5: 167-178 and Amore et al. (1989) *Appl. Microbiol. Biotech.* 30:351-357. In addition to a functioning promoter sequence, an expression vector may also include an efficient ribosome binding site and a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

Gene Transfer:

Gene transfer techniques for bacterial cells are well known and these techniques include transformation, transduction, conjugation and protoplast fusion. Gene transfer is the process of transferring a polynucleotide, gene or genes to a cell wherein exogenously added DNA is taken up by a bacterium. General transformation procedures are taught in CURRENT PROTOCOLS IN MOLECULAR BIOLOGY (Vol. 1 Ausubel et al. Eds., John Wiley and Sons, Inc. 1987, Chapter 9). These techniques include calcium chloride methods, transformation using DEAE-Dextran and electroporation. Also reference is made to U.S. Pat. No. 5,032,514; Potter, H. (1988) *Anal. Biochem.* 174:361-373; Sambrook, supra and Ferrari et al., Genetics pgs 57-72 in BACILLUS, Harwood et al., Eds. Plenum Publishing Corp. Transformation of a host cell can be detected by the presence/absence of selective marker gene expression.

Host Cells:

Bacterial cells are the preferred host cells according to the invention and particularly preferred bacterial host cells are Enterobacteriaceae cells. More specifically the cells of *Erwinia, Enterobacter, Gluconobacter, Klebsiella, Escherichia* and *Pantoea* and most preferably *Pantoea* sp. *Klebsiella* sp. and *E. coli* cells. Particularly preferred *Pantoea* cells are *P. citrea* and *P. agglomerans*, and reference is made to U.S. Pat. No. 5,032,514; Truesdell et al., (1991) *J. Bacteriol.* 173: 6651-6656 and ATCC accession number 39140. Other preferred bacteria host strains include strains of Pseudomonadaceae. *Bacillus* strains may also serve as host cells.

In one embodiment a host cell is transformed with a vector comprising any one of the 19 operons illustrated in FIGS. 1A and 1B. Preferably a host cell may be transformed with a polynucleotide encoding the sequences set forth in
a) SEQ ID NO. 3 and SEQ ID NO. 29;
b) SEQ ID NO. 4 and SEQ ID NO. 22;
c) SEQ ID NO. 5 and SEQ ID NO. 23;
d) SEQ ID NO. 6 and SEQ ID NO. 24 and
e) sequences having at least 95%, 96%, 97%, 98% and 99% sequence identity to the sequences of a)-d).

Also a host cell may be transformed with a polynucleotide encoding the sequences set forth in SEQ ID NO. 19 and SEQ ID NO. 38 or sequences having at least 95%, 96%, 97%, 98% and 99% sequence identity to either SEQ ID NO. 19 or 38.

In another embodiment a bacterial host cell may be transformed with an isolated polynucleotide which codes for a multimeric oxidoreductase complex having an amino acid sequence comprising an alpha subunit, a gamma subunit and a cytochrome C subunit, wherein the alpha subunit has dehydrogenase activity and is selected from the sequences of SEQ ID NOs: 1-19 and sequences having at least 95%, 96%, 97%, 98% and 99% sequence identity thereto; the gamma subunit is selected from the sequences of SEQ ID NOs: 39-57 and sequences having at least 95%, 96%, 97%, 98% and 99% sequence identity thereto; and the cytochrome C subunit is selected from the group of sequences of SEQ ID NOs: 20-38 and sequences having at least 95%, 96%, 97%, 98% and 99% sequence identity thereto.

As stated above, bacterial host cells may be recombinant host cells. Modification to host cells may have been realized prior to, simultaneously with, or after introduction of a polynucleotide encoding a CytC, a dehydrogenase or a multimeric oxidoreductase complex as defined according to the invention. Recombinant host cells may include chromosomal inactivations, such as deletions or interruptions of endogenous chromosomal genes, modifications resulting in increased expression of endogenous chromosomal genes, and inclusion of heterologous genes.

In another embodiment, the host cells may be engineered to include genes encoding enzymes known to effect the conversion of glucose or other ordinary metabolites to 2-KDG or 2-KLG. Non-limiting examples of the enzymes effecting the conversion of an ordinary metabolite to 2-KDG or 2-KLG are D-glucose dehydrogenase (Adachi, O. et al., (1980) *Agric. Biol. Chem.*, 44:301-308; Ameyama, M. et al., (1981) *Agric. Biol. Chem.* 45:851-861; Smith et al. (1989) *Biochem. J.* 261:973; and Neijssel et al., (1989) *Antonie Van Leauvenhoek* 56(1):51-61); D-gluconate dehydrogenase (McIntire, W. et al., (1985) *Biochem. J.*, 231:651-654; Shinagawa, E. et al., (1976) *Agric. Biol. Chem.* 40:475-483; Shinagawa, E. et al., (1978) *Agric. Biol. Chem.* 42:1055-1057; and Matsushita et al. (1979), *J. Biochem.* 85:1173); 5-keto-D-gluconate dehydrogenase (Shinagawa, E. et al., (1981) *Agric. Biol. Chem.*, 45:1079-1085 and Stroshane (1977) *Biotechnol. BioEng.* 19(4) 459); and 2,5-diketo-D-gluconic acid reductase (U.S. Pat. Nos. 5,795,761; 5,376,544; 5,583,025; 4,757,012; 4,758,514; 5,008,193; 5,004,690; and 5,032,514).

Recovery and Detection of Redox Products:

Methods useful for the detection of oxidoreduction reaction products include the use of high-performance liquid chromatography (HPLC) using anion exchange (*J. Chrom.* 1980, 196:163); electro-redox procedures (Pachia, 1976, *Anal. Chem.* 48:364); thin-layer chromatography; column chromatography and mass spectrometry. The skilled artisan will be well aware of appropriate controls to be applied in utilizing these detection methods. Specifically methods for detection of AsA intermediates and AsA stereoisomerisms include the use of redox-titration with 2,6 dichloroindophenol (Burton et al. 1979, *J. Assoc. Pub. Analysts* 17:105) or other suitable reagents.

Once produced, the products of oxidoreductase reactions and specifically keto-polyol derivatives such as AsA intermediates can be recovered and/or purified by any means known to those of skill in the art, including, lyophilization, crystallization, spray-drying, and electrodialysis.

Cell Cultures and Fermentations:

Methods suitable for the maintenance and growth of bacterial cells are well known and reference is made to the MANUAL OF METHODS OF GENERAL BACTERIOLOGY, Eds. P. Gerhardt et al., American Society for Microbiology, Washington D.C. (1981) and T. D. Brock in BIOTECHNOLOGY: A TEXTBOOK OF INDUSTRIAL MICROBIOLOGY, 2nd ed. (1989) Sinauer Associates, Sunderland, Mass.

Cell Precultures—Typically cell cultures are grown at 25 to 32° C., and preferably about 28 or 29° C. in appropriate media. Exemplary growth media useful in the present invention are common commercially prepared media such as but not limited to Luria Bertani (LB) broth, Sabouraud Dextrose (SD) broth or Yeast medium (YM) broth. These may be obtained from for example, GIBCO/BRL (Gaithersburg, Md.). Other defined or synthetic growth media may be used and the appropriate medium for growth of the particular bacterial microorganism will be known by one skilled in the art of microbiology or fermentation science. Suitable pH ranges preferred for the fermentation are between pH 5 to pH 8. Preferred ranges for seed flasks are pH 7 to pH 7.5 and preferred ranges for the reactor vessels are pH 5 to pH 6. It will be appreciated by one of skill in the art of fermentation microbiology that a number of factors affecting the fermentation processes may have to be optimized and controlled in order to maximize the ascorbic acid intermediate production. Many of these factors such as pH, carbon source concentration, and dissolved oxygen levels may affect enzymatic processes depending on the cell types used for ascorbic acid intermediate production.

The production of various desired products, such as AsA intermediates can proceed in a fermentative environment, that is, in an in vivo environment, or a non-fermentative environment, that is, in an in vitro environment; or combined in vivo/in vitro environments. The fermentation or bioreactor may be performed in a batch process or in a continuous process.

In Vivo Biocatalytic Environment:

Biocatalysis begins with culturing a bacterial host cell according to the invention in an environment with a suitable carbon source ordinarily used by Enterobacteriaceae or other bacterial strains. Suitable carbon sources include 6 carbon sugars, for example, glucose, or a 6 carbon sugar acid, or combinations of 6, carbon sugars and/or 6 carbon sugar acids. Other carbon sources include, but are not limited to galactose, lactose, fructose, or the enzymatic derivatives of such.

In addition, fermentation media must contain suitable carbon substrates which will include but are not limited to monosaccharides such as glucose, oligosaccharides such as lactose or sucrose, polysaccharides such as starch or cellulose and unpurified mixtures from a renewable feedstocks such as cheese whey permeate, cornsteep liquor, sugar beet molasses, and barley malt. While it is contemplated that the source of carbon utilized in the present invention may encompass a wide variety of carbon containing substrates and will only be limited by the choice of organism, the preferred carbon substrates include glucose, fructose and sucrose and mixtures thereof. Fermentation media must also contain suitable minerals, salts, vitamins, cofactors and buffers suitable for the growth or the cultures and promotion of the enzymatic pathway necessary for ascorbic acid intermediate production.

Batch and Continuous Fermentations:

The present invention may employ a batch fermentation process, a modified batch fermentation process, called Fed-batch or a continuous fermentation process. A classical batch fermentation is a closed system where the composition of the media is set at the beginning of the fermentation and not subject to artificial alterations during the fermentation. At the beginning of the fermentation the media is inoculated with the desired bacterial organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of desired product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in T. D. Brock in BIOTECHNOLOGY: A TEXTBOOK OF INDUSTRIAL MICROBIOLOGY, Second Edition (1989) Sinauer Associates, Inc. Sunderland, Mass.

In one embodiment, the concentration of a carbon substrate in the feed solution is from about 55% to about 75% on a weight/weight basis. In other embodiments, the concentration is from about 60 to about 70% on a weight/weight basis.

Continuous fermentation is an open system where a defined fermentation media is added continuously to a bioreactor and simultaneously an equal amount of conditioned media is removed for processing. Continuous fermentation generally maintains the cultures at a constant high density where cells are primarily in log phase growth. Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

In one embodiment, the invention concerns a method of enhancing the enzymatic conversion of a polyol or carbon substrate in a bacterial host cell which comprises contacting a bacterial cell which has been altered to include a polynucleotide encoding a multimeric oxidoreductase complex or a polynucleotide encoding a dehydrogenase subunit or a cytochrome c subunit encompassed by the invention with a polyol or carbon substrate under suitable culture conditions, wherein the polynucleotide is expressed in the altered bacterial host cell and allowing the enzymatic conversion of the polyol or carbon substrate to a desired product wherein, the enzymatic conversion of said polyol or carbon substrate is enhanced compared to the enzymatic conversion of the polyol or carbon substrate from a corresponding unaltered bacterial host cell exposed to substantially the same culture conditions. In some preferred embodiments, the enzymatic conversion of the polyol or carbon substrate is an oxidative conversion, such as the conversion of glucose to an organic or sugar acid or a keto-derivative. Examples of sugar acids include aldonic acids, uronic acids and aldonic acids. More specifically, sorbitol, gluconic acid, glucaric acid, glucuronic acid and also 2-KDG, 5-KDG and 2,5-DKG. In other embodiments, the enzymatic conversion of the polyol or carbon substrate is a reductive conversion.

In yet other embodiments, the invention includes a method for producing a desired product, such as a sugar acid described above comprising, contacting an altered bacterial host cell with a polyol or carbon substrate (for example, with glucose or fructose) under suitable culture conditions, wherein the altered bacterial host cell is obtained by the transformation of a bacterial host cell with a vector including a polynucleotide encoding a multimeric oxidoreductase complex, a dehydrogenase, or a cytochrome C protein according to the invention and producing the desired product from an enzymatic conversion of the polyol or carbon substrate.

The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

6. EXAMPLES

Example 1

Sequencing of the *Pantoea citrea* Genome

Approximately 95% of the *P. citrea* genome was sequenced by constructing a representative library using standard protocols as described in Birren B. et al., (1999) GENOME ANALYSIS: A LABORATORY MANUAL., Vol. 3 Cold Spring Harbor Laboratory Press, New York. Briefly *P. citrea* genomic DNA was physically sheared by sonication to produce random fragments with an average size of 0.6 to 1.0 kilobases. The DNA fragments were blunt-ended and cloned into pUC18 (New England BioLabs, Beverly, Mass.). Once the quality of the library was assessed by sequencing 50-100 randomly picked colonies, random clones from the library were picked and amplified by PCR (Dunham et al. (1999) Bacterial Cloning Systems, pages 41-57 in GENOME ANALYSIS: A LABORATORY MANUAL. Vol. 3 Birren B. et al., (1999) Cold Spring Harbor Laboratory Press NY) and the product of the PCR reactions were used for sequencing. Sequencing was performed using Applied Biosystems 3700 DNA sequencers (Perkin-Elmer, Foster City, Calif.). Each of the clones was sequenced from both ends using standard and reverse pUC18 primers. An average of 400-500 base pairs were obtained from each template. With this approach, 68,389 reads were performed and the reads totaled 34,788,222 base pairs (bp). These sequences were assembled in 224 contiguous sequences that yielded 4,439,491 bp in total.

The TBLAST program was used to translate the submitted DNA into Orfs and at least 19 operons comprising three (3) Orfs were initially annotated as sorbitol dehydrogenases based on their similarity to the sorbitol dehydrogenase sequence reported by Saito et al., (1997) *Appl. Environ. Microbiol.* 63:454-460.

The size of the Orf designated as the gamma subunit was used to divide the 19 operons into 2 families. Family 1 includes 10 members with a gamma subunit of about 238 to 249 amino acids and reference is made to FIG. 1A. Family 2 includes 9 members with a gamma subunit of about 174 to 195 amino acids and reference is made to FIG. 1B. The observation that each of the 19 operons contains orfs suggests that in the natural environment of *P. citrea*, all these genes are under pressure to stay functional. Additionally analysis of the DNA sequences upstream of the genes, showed that all the genes are preceded by appropriate ribosome binding sites (data not shown).

Example 2

Determination that Orfs 2418-2420 (Corresponding to SEQ ID NO. 115, SEQ ID NO. 77 and SEQ ID NO. 96) Encode a 2-KDGDH Operon Having SEQ ID NO. 57, SEQ ID NO. 19 and SEQ ID NO. 38 by Inactivation of the Operon Cloning of the 2-KDGDH Operon:

Strain 139-2a/Ps- was used for cloning the 2-KDGDH operon. This strain is a derivative of strain 139-2a having ATCC accession number 39140 wherein the cryptic plasmid (pS) is removed by the methods disclosed in WO 98/59054. Reference is also made to Truesdell et al., (1991) *J. Bacteriol.* 173:6651-6656.

Using two PCR primers, KDGF1 and KDGR1 a 2.8-kb DNA fragment encompassing the 2-KDGDH operon from the chromosome of *P. citrea* 139-2a/Ps- strain was amplified using standard techniques (Sambrook et al., MOLECULAR CLONING: A LABORATORY MANUAL, Cold Spring Harbor Laboratory Press (1989) 2nd Ed.).

```
KDGF1
                                    (SEQ ID NO. 116)
5'AGTTAGCCGCTCATTTCCTG 3'

KDGR1
                                    (SEQ ID NO. 117)
5'AGCCGCCTGGTTTTTAC 3'
```

The DNA fragment was cloned into the pZeroBlunt vector having a lac promoter (lacP) (Invitrogen, Carlsbad Calif.) using *E. coli* TOP10 cells as the host. This resulted in plasmid pKDG2 (6.32-kb). On LA+Kan50 plates, (LB media solidified with 1.5% agar plus 50 ppm kanamycin) three $Kan^R$ transformants were obtained. When checked by digesting with appropriate restriction enzymes (EcoRI, ScaI+SpeI, SalI+SpeI), all three transformants were found to have inserts, and the transcriptional directions were opposite to the orientation of the lacP.

Construction of the Knockout Plasmid Used to Delete the 2-KDGDH Operon from the *P. citrea* Chromosome:

In general, the strategy used to inactivate genes by homologous recombination with a plasmid has been delineated before and reference is made to Miller et al., (1988) *J. Bacteriol.* 170:2575-2583. This general approach was used to inactivate the 2-KDGDH operon.

The pKDG2 plasmid obtained according to the example above, was digested with HpaI+ScaI enzymes to eliminate a 0.993-kb region from the middle to C-terminus of the alpha subunit. The plasmid was then inserted with a cat cassette (1.080-kb) flanked by two loxP sites (Palmeros et al., (2000) *Gene* 247:255-264) resulting in plasmid pKDGCat1 (6.41-kb; cat runs opposite to 2-KDGDH operon). This plasmid was verified by digestion with NotI, SacI and XbaI enzymes. The 1.5-kb AatII+SpeI fragment containing the ColE1 Ori region was removed from plasmid pKDGCat1, and then ligated with the 502-bp AatII+SpeI DNA fragment that contains the minimal R6K origin of replication (ori) region. The R6K ori DNA was obtained by PCR using plasmid pGP704 (Miller et al., (1988) *J. Bacteriol.* 170:2575-2583) as PCR substrate with primers. Thus the final knockout plasmid pKDGCatR6 (5.37-kb) was obtained. *E. coli* PIR1 strain (Invitrogen, Carlsbad, Calif.) was transformed using the procedure described in Sambrook et al. MOLECULAR CLONING: A LABORATORY MANUAL, Cold Spring Harbor Laboratory Press (1989) 2nd Ed. In this final knockout construct, a 960-bp and a 840-bp region of homology are available at the 5'- and 3'-ends of the 2-KDGDH operon to allow homologous recombination in *P. citrea* chromosome.

Transformation into a *P. citrea* Strain:

After the final knockout plasmid pKDGcatR6 (5.37 kb) was verified with HindIII digestion, the plasmid was electroporated (Sambrook et al., MOLECULAR CLONING: A LABORATORY MANUAL, Cold Spring Harbor Laboratory Press (1989) 2nd Ed.) into *P. citrea* 139-2a/Ps- (pKD46) competent cells and selected for chloramphenicol-resistant (CmR) transformants on LA+Cm10 plates (LA is LB plus agar plates with 10 ppm Cm) using well known techniques. To distinguish between single and double crossover recombination events, the CmR transformants were checked on LA+Kan3 plates for kanamycin sensitivity (KanS). Nine of the 13 CmR transformants were KanS, implying that they had undergone a double crossover recombination event that inactivated the 2-KDGDH operon. Four transformants, Nos. 4, 5, 8 and 9 were checked by PCR with both internal and external primers as described below.

PCR Verification of the Knockout Strains:

For verifying the 2-KDGDH operon deletion, two outside primers will amplify the same size band both in the wild type containing a functional KDGDH operon and putative mutants (altered strains) wherein the 2-KDGDH operon was deleted. (Reference is made to the example above wherein 0.993-kb was exchanged with 1.08-kb cat-loxP DNA).

Thus one outside primer with one cat-gene-specific primer was used to verify the recombination junctions of the putative mutants. With cat3+KDGR2 primers, all four transformants amplified the expected 1.14-kb band as compared to the unaltered strain wherein there was no amplification. With KDGF2+cat4 primers, the transformants amplified the expected 1.17-kb band. This result revealed that the four transformants had undergone a double crossover recombination event at the KDG locus as expected thereby inactivating the operon.

```
KDGF2
                                    (SEQ ID NO. 118)
5'GCGTCTCTGCCATTGCGTAGTTTC 3'

KDGR2
                                    (SEQ ID NO. 119)
5'GGGTGCGGATCGGTGTGGTTT 3'

CAT3
                                    (SEQ ID NO. 120)
5'AAAGTTGGAACCTCTTACGTGCCG 3'

CAT4
                                    (SEQ ID NO. 121)
5'CAACAGTACTGCGATGAGTGGCAG 3'
```

Removal of the pKD46 Plasmid:

Since the altered strains still contained plasmid pKD46 plasmid (Datsenko and Wanner (2000) *Proc. Natl. Acad. Sci.* 97:6640-6645) they were cured of the plasmid as follows. Cells were grown in liquid medium without Carbenicillin (Carb) at 30° C. for 3 passages (3 days) followed by plating and isolation of single colonies. All single colony isolates lost the pKD46 plasmid when tested for Carb sensitivity on LA+Carb200 plates (Datsenko and Wanner, supra and Palmeros et al. (2000) *Gene* 247:255-264). Furthermore, no plasmid was detected in any of the single colony isolates when plasmid DNAs were isolated using standard protocols Sambrook et al., supra. *Pantoea* cells that were cured of plasmid pKD46 were obtained and designated WKDG4.

Fermentation Experiments with *Pantoea citrea*

All reagents and materials used for the growth of bacterial cells were obtained from Diffco Laboratories (Detroit, Mich.), Aldrich Chemicals (Milwaukee, Wis.) or Sigma Chemical Company (St. Louis, Mo.) unless otherwise specified.

Seed Train: Culture vials which were stored in liquid nitrogen containing the indicated strain WKDG4 were thawed in air and 0.75 mL was added to a sterile 2-L Erlenmeyer flask containing 500 mL of seed medium. Flasks were incubated at 29° C. and 250 rpm for 12 hours. Transfer criteria is an $OD_{550}$ greater than 2.5.

Seed flask medium—A medium composition was made according to the following: $KH_2PO_4$ (12.0 g/L); $K_2HPO_4$ (4.0 g/L); $MgSO4.7H_2O$ (2.0 g/L); Diffco Soytone (2.0 g/L); Sodium citrate (0.1 g/L); Fructose (5.0 g/L); $(NH_4)_2SO_4$ (1.0 g/L); Nicotinic acid (0.02 g/L); $FeCl_3.6H_2O$ (5 mL/L of a 0.4 g/L stock solution) and Trace salts (5 mL/L—of the following solution: 0.58 g/L $ZnSO_4.7H_2O$, 0.34 g/L $MnSO_4.H_2O$, 0.48 g/L $Na_2MoO_4.2H_2O$). The pH of the medium solution was adjusted to 7.0±0.1 unit with 20% NaOH. Tetracycline HCl was added to a final concentration of 20 mg/L (2 mL/L of a 10 g/L stock solution). The resulting medium solution was then filter sterilized with a 0.2µ filter unit. The sterile medium was added to a previously autoclaved flask.

Production Fermentor—Additions to the reactor vessel prior to sterilization included: $KH_2PO_4$ (3.5 g/L); $MgSO_4.7H_2O$ (1.0 g/L); $(NH_4)_2SO_4$ (0.92 g/L); Mono-sodium glutamate (15.0 g/L); $ZnSO_4.7H_2O$ (5.79 mg/L); $MnSO_4.H_2O$ (3.44 mg/L); $Na_2MoO_4.2H_2O$ (4.70 mg/L); $FeCl_3.6H_2O$ (2.20 mg/L); Choline chloride (0.112 g/L) and Mazu DF-204 (0.167 g/L) an antifoaming agent.

The above constituted media was sterilized at 121° C. for 45 minutes. After tank sterilization, the following additions were made to the fermentation, tank: Nicotinic acid (16.8 mg/L); Ca-pantothenate (3.36 mg/L); Glucose (25 g/L) and Fructose (25 g/L).

The final volume after sterilization and addition of post-sterilization components was 6.0 L. The prepared tank and media were inoculated with the entire contents from seed flasks prepared as described to give a volume of 6.5 L.

Growth conditions were at 29° C. and pH 6.0. Agitation rate, back pressure and air flow were adjusted as needed to keep dissolved oxygen above zero. When the sugars initially batched into the medium were exhausted, a fed-batch process was used. The production of 2-KDG obtained after a 30 hour time course with strain WKDG4 (2-KDG conc g/L=300) was significant compared with strain 139-2a/Ps- (2-KDG conc g/L=0). Strain 139-2a/Ps- only makes 2-KDG transiently before it is further converted to 2,5-DKG.

Example 3

Determination that Orfs 3651-3653 are Involved in the Formation of 2-KDG

Cloning of the GADH Operon:

Two PCR primers, GADHF1 and GADHR1 were used to amplify a 3.9-kb DNA fragment containing the GADH operon from the chromosome of *P. citrea* strain 139-2a/Ps-.

```
                                        SEQ ID NO. 122
GADHF1 (5'-P-CGGTACTGAGGCAATGTCATG 3'),
and
                                        SEQ ID NO. 123
GADHR1 (5'-P-aCGGAGAGCCGGATATTACAT,3').,
``` wherein P=phosphate and ATG of SEQ ID No. 123 is the start codon of the oil of the gamma subunit of GADH.

The DNA fragment was digested with restriction enzymes (HindIII, PstI and SalI) to check whether the amplification was correct. The fragment was cloned into the HindIII site of the low-copy number vector pCL1920 containing a lac promoter (lacP) (Lerner et al., (1990) *Nucleic Acid Res.* 18:4631). Among 16 white colonies on LA+Spec50+X-gal+ IPTG plates, (LB plates solidified with 1.5% agar plus 50 ppm spectinomycin plus 40 µg/ml X-gal plus 50 µM IPTG) only two colonies (Nos. 7 and 11) contained the insert. When checked with appropriate restriction enzymes (HindIII, PstI, SpeI+ClaI; and XbaI+BglII), the transcriptional directions of inserts in both plasmids were the same with the plasmid borne lacP. One of these plasmids was named pCLE2-7 (8.45-kb) and used as an overexpression plasmid of the GADH operon and for construction of the knockout plasmid as described below.

Construction of the Knockout Plasmid:

The pCLE2-7 plasmid was digested with Bsu361+ClaI enzymes to remove the 910-bp region from the middle of the dehydrogenase subunit and then the cat cassette (1080-bp) flanked by two loxP sites (Palmeros et al. (2000) *Gene* 247: 255-264) was inserted, resulting in plasmid pCLE2Cat1 (8.62-kb; cat gene runs opposite to the GADH operon). The 4065-bp GADH-cat-loxP gene cluster was amplified by PCR from the above plasmid using the GADHF1 and GADHR1 primers and ligated with the 505-bp HindIII+EcoRV R6K minimal origin of replication (Miller et al. (1988) *J. Bacteriol.* 170:2575-2583 and reference is made to the example above) from plasmid pGP704 to generate the final knockout plasmid pE2CatR6-1 (4.58-kb). This was followed by transformation into *E. coli* PIR1 strain (Invitrogen, Carlsbad, Calif.) using the procedures described in Sambrook, supra. In this final construct, a 1160-bp and a 1825-bp region of homology are available at the 5'- and 3'-sites of the GADH operon to allow homologous recombination in the *P. citrea* chromosome.

Transformation into *P. citrea* Strains and Verification of the GADH Inactivation:

After verifying the final knockout plasmid with appropriate restriction enzymes (AatII+AccI and BglII+SnaBI), the plasmid was transformed as described above into *P. citrea* 139-2a/Ps-, and transformants were selected on LA+Cm12 plates. Hundreds of CmR colonies appeared. Four colonies were checked for deletion of the GADH operon by PCR.

Two outside primers will amplify the same size band both in the wild type and putative mutants (see above, 910-bp coding region was exchanged with 1080-bp cat-loxP DNA). Thus, one outside primer with one cat-gene-specific primer was used to verify the putative mutants. Only No. 2 transformant amplified the expected 2.46-kb band with cat3+E2R1 primers:

```
Primer E2R1
                                    SEQ ID NO. 124
5'-GCAGCCGCTACGCAGATAAAA-3'
```

However, three other transformants (Nos. 1, 3 and 4) amplified the expected 1.64-kb band with E2F1+cat4 primers:

```
Primer E2F1
                                    SEQ ID NO. 125
5'-CTCGGCGAAAAAGAACCAGACAAG-3'
```

This result revealed that only No. 2 transformant had undergone a single crossover recombination event at the 3'-end of the GADH operon, and the other transformants (Nos. 1, 3 and 4) underwent single crossover recombination events at the 5'-end of the GADH operon. Since a single crossover recombination event will not inactivate the operon, we isolated double crossover recombinants from the No. 2 transformant as described below.

The No. 2 transformant was sub-cultured in liquid medium followed by isolation of single colonies. Five out of 5 single colonies isolated had undergone a second cross-over at the 5' end of the GADH operon upon sub-culturing. This resulted in a true GADH inactivated strain in the 139-2a/Ps- background.

To confirm further, PCR products from the above mentioned single colonies were digested with appropriate restriction enzymes. The 1.64-kb product obtained with E2F1+cat4 primers was digested with XbaI enzyme. The 2.46-kb product obtained with cat3+E2R1 primers was digested with PstI enzyme. Both digestions showed the expected patterns for all samples. Thus, the GADH deletion strains were further confirmed by this strategy. One single colony isolate from above was named WTE2-1 and saved.

Fermentation Studies:

Both strains, WTE2-1 (the GADH deletion strain) and 139-2a/Ps- (the wild-type control strain) are basically grown as outlined above for the 2-KDGDH deletion strain and accumulation of gluconate is measured.

---

The invention claimed is:

1. A method for producing a desired product comprising, contacting an altered bacterial host cell with a polyol substrate under suitable culture conditions, wherein the altered bacterial host cell is obtained by the transformation of a bacterial host cell with a polynucleotide coding for a multimeric oxidoreductase complex selected from: SEQ ID NO: 19 and SEQ ID NO: 38 and wherein the polynucleotide encoding the multimeric oxidoreductase complex is expressed in the altered bacterial host cell and producing a desired product from an enzymatic conversion of the polyol substrate by the multimeric oxidoreductase complex to said desired product.

2. The method according to claim 1, wherein the polyol substrate is glucose, gluconate, arabinose, arabitol, xylose, xylulose, xylitol, sucrose, sorbose, fructose, mannose, mannitol, meso-erythritol, L-erythrulose, idonate, cellobiose, lactose, idose, galactose, ribose, altose, maltose, erythrose, sorbitol, glycerol, 2-KDG, 5-keto-D-gluconic acid, 2-KLG, methanol, and erythorbic acid.

3. The method according to claim 1, wherein the desired product is an ascorbic acid (AsA) intermediate.

4. The method according to claim 3, wherein the AsA intermediate is 2-keto-D-gluconate or 2,5-diketo-D-gluconate.

5. The method according to claim 1, wherein the desired product is an organic acid.

6. The method according to claim 1, wherein the host cell is selected from an Enterobacteriaceae strain, optionally a *Pantoea, Klebsiella, Erwinia* or *E. coli* strain or a Pseudomonadacea strain.

7. The method according to claim 1 further comprising recovering the desired product.

8. The method according to claim 2, wherein the polyol substrate is glucose, sorbitol or glycerol.

9. The method according to claim 1, wherein the desired product is a sugar acid.

10. The method according to claim 1, wherein (b) further comprises SEQ ID NO: 57.

* * * * *